(12) United States Patent
Altman et al.

(10) Patent No.: US 11,453,975 B2
(45) Date of Patent: *Sep. 27, 2022

(54) SILK PERFORMANCE APPAREL AND PRODUCTS AND METHODS OF PREPARING THE SAME

(71) Applicant: Evolved by Nature, Inc., Medford, MA (US)

(72) Inventors: Gregory H. Altman, Arlington, MA (US); Enrico Mortarino, Hickory, NC (US)

(73) Assignee: EVOLVED BY NATURE, INC., Medford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/356,536

(22) Filed: Mar. 18, 2019

(65) Prior Publication Data

US 2019/0309467 A1 Oct. 10, 2019

Related U.S. Application Data

(63) Continuation of application No. 14/958,565, filed on Dec. 3, 2015, now Pat. No. 10,301,768, which is a (Continued)

(51) Int. Cl.
*D06M 15/15* (2006.01)
*A41D 31/00* (2019.01)
(Continued)

(52) U.S. Cl.
CPC ......... *D06M 15/15* (2013.01); *A41D 13/0015* (2013.01); *A41D 31/00* (2013.01); (Continued)

(58) Field of Classification Search
None
See application file for complete search history.

(56) References Cited

U.S. PATENT DOCUMENTS 3,424,164 A 1/1969 Bloch et al.
4,521,458 A 6/1985 Nelson
(Continued)

FOREIGN PATENT DOCUMENTS

CN 1732022 A 2/2006
CN 1277584 C 10/2006
(Continued)

OTHER PUBLICATIONS

Machine translation of JPH09188972 (Year: 1997).*
(Continued)

*Primary Examiner* — Shawn Mckinnon
(74) *Attorney, Agent, or Firm* — Morgan, Lewis & Bockius LLP

(57) ABSTRACT

Silk performance apparel and methods of preparing the same are disclosed herein. In some embodiments, silk performance apparel includes textiles, fabrics, consumer products, and other materials that are coated with aqueous solutions of pure silk fibroin-based protein fragments. In some embodiments, coated apparel products exhibit surprisingly improved moisture management properties and increased resistance to microbial growth.

48 Claims, 278 Drawing Sheets

Related U.S. Application Data continuation of application No. PCT/US2015/063545, filed on Dec. 2, 2015.

(60) Provisional application No. 62/086,297, filed on Dec. 2, 2014, provisional application No. 62/192,477, filed on Jul. 14, 2015, provisional application No. 62/245,221, filed on Oct. 22, 2015.

(51) Int. Cl.

| | |
|---|---|
| A41D 13/00 | (2006.01) |
| A61Q 19/00 | (2006.01) |
| D06N 7/00 | (2006.01) |
| A61K 8/64 | (2006.01) |
| A41D 31/18 | (2019.01) |

(52) U.S. Cl.
CPC .............. A41D 31/185 (2019.02); A61K 8/64 (2013.01); A61Q 19/00 (2013.01); D06N 7/00 (2013.01); D06M 2200/50 (2013.01); D06N 2203/02 (2013.01); D10B 2401/02 (2013.01)

(56) References Cited

U.S. PATENT DOCUMENTS

| | | | |
|---|---|---|---|
| 5,089,395 A | 2/1992 | Snyder et al. | |
| 5,142,292 A | 8/1992 | Chang | |
| 5,820,928 A | 10/1998 | Groshens | |
| 5,968,762 A | 10/1999 | Jadamec et al. | |
| 6,902,932 B2 | 6/2005 | Altman et al. | |
| 7,632,873 B2 | 12/2009 | Mougin | |
| 7,635,755 B2 | 12/2009 | Kaplan et al. | |
| 7,674,882 B2 | 3/2010 | Kaplan et al. | |
| 7,727,542 B2 | 6/2010 | DiBenedetto et al. | |
| 8,071,722 B2 | 12/2011 | Kaplan et al. | |
| 8,187,616 B2 | 5/2012 | Wang et al. | |
| 8,288,347 B2 | 10/2012 | Collette et al. | |
| 8,420,077 B2 | 4/2013 | Altman et al. | |
| 8,501,172 B2 | 8/2013 | Kaplan et al. | |
| 8,551,538 B2 | 10/2013 | Qian | |
| 8,614,293 B2 | 12/2013 | Kaplan et al. | |
| 8,623,398 B2 | 1/2014 | Altman et al. | |
| 8,628,791 B2 | 1/2014 | Altman et al. | |
| 8,633,027 B2 | 1/2014 | Altman et al. | |
| 8,674,077 B2 | 3/2014 | Sutherland et al. | |
| 8,685,426 B2 | 4/2014 | Altman et al. | |
| 8,715,740 B2 | 5/2014 | Wang et al. | |
| 8,741,281 B2 | 6/2014 | Van Epps et al. | |
| 8,894,992 B2 | 11/2014 | Van Epps et al. | |
| 8,900,571 B2 | 12/2014 | Van Epps et al. | |
| 8,926,963 B2 | 1/2015 | Van Epps et al. | |
| 10,287,728 B2 | 5/2019 | Altman et al. | |
| 2001/0002417 A1 | 5/2001 | Akkara et al. | |
| 2001/0053931 A1 | 12/2001 | Hess et al. | |
| 2002/0114919 A1 | 8/2002 | Yoneda et al. | |
| 2003/0099630 A1 | 5/2003 | DiBenedetto et al. | |
| 2003/0206897 A1 | 11/2003 | O'Prey et al. | |
| 2004/0191199 A1 | 9/2004 | Mougin | |
| 2004/0199241 A1* | 10/2004 | Gravett .................. | A61L 31/14 623/1.13 |
| 2004/0219630 A1 | 11/2004 | Tsubouchi et al. | |
| 2004/0265260 A1 | 12/2004 | Tsubouchi et al. | |
| 2008/0188152 A1* | 8/2008 | Tsai ..................... | D06N 3/0056 442/79 |
| 2009/0162439 A1* | 6/2009 | Gobin .................. | A01N 25/10 424/486 |
| 2009/0188152 A1 | 7/2009 | Davin | |
| 2009/0234026 A1 | 9/2009 | Kaplan et al. | |
| 2011/0076384 A1 | 3/2011 | Cannizzaro et al. | |
| 2011/0105402 A1 | 5/2011 | Kim et al. | |
| 2011/0223153 A1 | 9/2011 | Lu et al. | |
| 2012/0040907 A1 | 2/2012 | DiBenedetto et al. | |
| 2012/0070427 A1 | 3/2012 | Kaplan et al. | |
| 2012/0076771 A1 | 3/2012 | Vepari et al. | |
| 2012/0123519 A1 | 5/2012 | Lovett et al. | |
| 2012/0171770 A1 | 7/2012 | Numata et al. | |
| 2012/0244143 A1 | 9/2012 | Lo et al. | |
| 2012/0252294 A1* | 10/2012 | Leimer ............ | C07K 14/43518 442/59 |
| 2013/0045278 A1 | 2/2013 | Qian | |
| 2013/0165004 A1 | 6/2013 | Kaplan et al. | |
| 2013/0240251 A1 | 9/2013 | Kaplan et al. | |
| 2013/0287742 A1 | 10/2013 | Kaplan et al. | |
| 2013/0287835 A1* | 10/2013 | Kaplan .................. | A61L 31/10 424/443 |
| 2014/0134240 A1 | 5/2014 | Kaplan et al. | |
| 2015/0038043 A1 | 2/2015 | Kaplan et al. | |
| 2015/0056293 A1 | 2/2015 | Wang et al. | |
| 2015/0183841 A1 | 7/2015 | Lo et al. | |
| 2016/0046679 A1* | 2/2016 | Kluge ..................... | B01J 20/24 435/6.1 |
| 2016/0193293 A1 | 7/2016 | Nishi et al. | |
| 2020/0256009 A1 | 8/2020 | Altman et al. | |

FOREIGN PATENT DOCUMENTS

| | | |
|---|---|---|
| CN | 1920162 A | 2/2007 |
| CN | 102605619 A | 7/2012 |
| CN | 102965934 A | 3/2013 |
| CN | 103041440 A | 4/2013 |
| CN | 102605619 A | 6/2013 |
| EA | 201791221 A1 | 12/2017 |
| EP | 1118705 A2 | 7/2001 |
| JP | H04-100975 A | 4/1992 |
| JP | H04100795 A | 4/1992 |
| JP | H04100975 A | 4/1992 |
| JP | H05-005275 A | 1/1993 |
| JP | H08-27186 | 1/1996 |
| JP | H0816309 B2 | 2/1996 |
| JP | 9188972 A | 7/1997 |
| JP | H09-188972 A | 7/1997 |
| JP | H09188972 * | 7/1997 |
| JP | H10-212456 A | 8/1998 |
| JP | H10212456 A | 8/1998 |
| JP | 2000-328455 A | 11/2000 |
| JP | 2001-262470 A | 9/2001 |
| JP | 2002-080498 A | 3/2002 |
| JP | 2002080498 A | 3/2002 |
| JP | 2002-302874 A | 10/2002 |
| JP | 2002-363861 A | 12/2002 |
| JP | 2003-171874 A | 6/2003 |
| JP | 2003-171875 A | 6/2003 |
| JP | 2003-171876 A | 6/2003 |
| JP | 2003171875 A | 6/2003 |
| JP | 2009-074201 A | 4/2009 |
| JP | 2011-153389 A | 8/2011 |
| JP | 2013-245427 A | 12/2013 |
| KR | 10-2005-0091040 A | 9/2005 |
| WO | 2003/035124 A2 | 5/2003 |
| WO | 2004/060424 A2 | 7/2004 |
| WO | 2006/008163 A2 | 1/2006 |
| WO | 2007/016524 A2 | 2/2007 |
| WO | 2007/038837 A1 | 4/2007 |
| WO | 2008/083908 A1 | 7/2008 |
| WO | 2011/069643 A2 | 6/2011 |
| WO | 2012145739 A2 | 10/2012 |
| WO | 2014011644 | 1/2014 |
| WO | 2014011644 A2 | 1/2014 |
| WO | 2014012099 A2 | 1/2014 |
| WO | 2014/145002 A2 | 9/2014 |
| WO | 2014145002 | 9/2014 |
| WO | 2014145002 A1 | 9/2014 |
| WO | WO2014145002 * | 9/2014 |
| WO | 2012145739 | 10/2014 |
| WO | 2015190292 A1 | 12/2015 |
| WO | 2016/090055 A1 | 6/2016 |
| WO | 2016090055 | 6/2016 |

OTHER PUBLICATIONS

Effect of Various Dissolution Systems on the Molecular Weight of Regenerated Silk Fibroin. Wang et al. Dec. 6, 2012 (Year: 2012).*

(56) References Cited

OTHER PUBLICATIONS

Arai et al.; "Biodegradation of *Bombyx mori* Silk Fibroin Fibers and Films"; Journal of Applied Polymer Science, vol. 91, 2383-2390 (2004).
Chilean Patent Application No. 1404-2017 Office Action dated Nov. 5, 2018.
English translation of Chilean Patent Application No. 1404-2017 Office Action dated Nov. 5, 2018.
European Patent Application No. 16825194.0 Search Report and Written Opinion dated Dec. 10, 2018.
Eurasian Patent Application No. 201791221 Office Action dated Dec. 12, 2018.
English translation of Eurasian Patent Application No. 201791221 Office Action dated Dec. 12, 2018.
Eurasian Patent Application No. 201890289 Office Action dated Dec. 21, 2018.
English translation of Eurasian Patent Application No. 201890289 Office Action dated Dec. 21, 2018.
Columbian Patent Application No. NC2017/0006672 Office Action dated Dec. 20, 2018.
English translation of Columbian Patent Application No. NC2017/0006672 Office Action dated Dec. 20, 2018.
Singapore Patent Application No. 11201800272U Search Report dated Feb. 4, 2019.
Behera et al., "Size recipes for low-humidity weaving of cotton yarn", In J Fibre Textile Res 19:67-70, 1994.
Hardy et al.; "Polymeric materials based on silk proteins"; Polymer 49 (2008) 4309-4327.
Hoffman et al.; "Silk fibroin as an organic polymer for controlled drug delivery"; Journal of Controlled Release 111 (2006) 219-227.
Sielc, "Separation of Potassium, Reverse Elution Order in Separation of Alkali Cation" http://www.sielc.com/compound-potassium.html, Aug. 27, 2013, 5 pages.
Singapore Patent Application No. 11201704494S Search Report and Written Opinion dated Apr. 24, 2018.
European Patent Application No. 15864424.5, Extended European Search Report dated Aug. 23, 2018.
Cetinkaya et al.; "Silk Fiber Mechanics from Multiscale Force Distribution Analysis"; Biophysical Journal, vol. 100, Mar. 2011, 1298-1305.
Cho et al.; "Molecular weight distribution and solution properties of silk fibroins with different dissolution conditions"; International Journal of Biological Macromolecules, 51 (2012) 336-341.
Fan et al.; "Vitamin C-reinforcing silk fibroin nanofibrous matrices for skin care application"; RSC Advances, 2012, 2, 4110-4119.
Fournier; "Quantitative data on the *Bombyx mori* L. silkworm: a review"; Biochimie, 1979, 61, 293-320.
Gilbert et al.; "Dispersity in Polymer Science", Pure Appl. Chem., vol. 1, No. 2, pp. 351-353, 2009.
Hyde et al.; "Molecular Weight of Silk Fibroin"; Journal of Polymer Science, vol. 58, pp. 1082-1088 (1962).
Motta et al.; "Stabilization of *Bombyx mori* silk fibroin/sericin films by crosslinking with PEG-DE 600 and genipin"; Journal of Bioactive and Compatible Polymers, 26(2) 130-143 (2011).
Pandit et al.; "Studies on Silk Fibroin, I. molecular Weight, Sedimentation Coefficient, Viscosity and Optical Rotation of Silk Fibroin from Carbonate-Extracted Silk Fiber"; Archives of Biochemistry and Biophysics 149, 259-268 (1972).
Paula's Choice; "Jar Packaging: A Waste of Good Antioxidants & Money"; The Cosmetics Cop; 3 pages (2012).
Preda et al.; "Bioengineered Silk Proteins to Control Cell and Tissue Functions"; Protein Nanotechnology: Protocols, Instrumentation, and Applications, Methods in Molecular Biology, vol. 996, (2013) Chapter 2, pp. 19-41.
Rockwood et al.; "Materials fabrication from *Bombyx mori* silk fibroin"; Nature Protocols, vol. 6, No. 10, 2011, pp. 1612-1631.
Sah et al.; "Regenerated Silk Fibroin from *B. mori* Silk Cocoon for Tissue Engineering Applications"; International Journal of Environmental Science and Development, vol. 1, No. 5, Dec. 2010.

Wang et al.; "Design and engineering of silk fibroin scaffolds with biometric hierarchical structures"; Chem Commun, 2013, 49, 1431.
Wang et al.; "Effect of Various Dissolution Systems on the Molecular Weight of Regenerated Silk Fibroin"; American Chemical Society, BioMacromolecules 2013, 14, 285-289 (article published Dec. 2012).
Wray et al.; "Effect of Processing on Silk-Based Biomaterials: Reproducibility and Biocompatibility"; J. Biomed Mater Res B Appl Biomater. Oct. 2011; 99(1): 89-101 (author manuscript).
Zhang et al.; "Stabilization of vaccines and antibiotics in silk and eliminating the cold chain"; PNAS, Jul. 24, 2012, vol. 109, No. 30, 11981-11986.
International Patent Application No. PCT/US14/58462, International Search Report, dated Mar. 2, 2015.
International Patent Application No. PCT/US2015/063545 IPRP dated Jun. 6, 2017.
International Patent Application No. PCT/US15/63545, International Search Report, dated Jan. 28, 2016.
International Patent Application No. PCT/US2016/042316 IPRP dated Aug. 16, 2017.
Eurasia Patent Application No. 201791221/28 Official Action, dated May 29, 2018, 4 pages.
English translation of Eurasia Patent Application No. 201791221/28 Official Action, dated May 29, 2018.
Mizutani et al., "A New Apparatus for the Study of Fabric Drape", Textile Res J 75(1):81-87, 2005.
Eurasia Patent Application No. 201791221/28 Official Action, dated Jul. 17, 2019.
English translation of Eurasia Patent Application No. 201791221/28 Official Action, dated Jul. 17, 2019.
Singapore Patent Application No. 11201704494S written opinion dated Feb. 18, 2019.
Brazil Patent Application No. 112017011641-3 technical report and preliminary examination report dated Aug. 27, 2019, 6 pages.
Columbia Patent Application No. NC2017/0006672 office action dated Apr. 29, 2019.
English translation of Columbia Patent Application No. NC2017/0006672 office action dated Apr. 29, 2019.
Written Opinion dated Dec. 20, 2019 for Singapore Patent Application No. 11201704494S.
Yasumoto Nakazawa et al. "Development of Small-Diameter Vascular Grafts Based on Silk Fibroin Fibers from *Bombyx mori* for Vascular Regeneration." Journal of Biomaterials Science 22 (2011) 195-206.
Office Action dated May 28, 2019 for Indonesian Patent Application No. P-00201704289.
Notice of Reasons for Rejection dated Dec. 24, 2019 for Japanese Patent Application No. 2017-529648.
Office Action dated Dec. 17, 2019 for Chinese Patent Application No. 201580075200.6.
Search Report and Written Opinion dated Aug. 27, 2019 for Brazilian Patent Application No. BR112017011641-3.
First Office Action for Colombian Patent Application No. NC2017/0006672.
Second Office Action for Colombian Patent Application No. NC2017/0006672.
Takayuki Arai et al. "Biodegredation of *Bombyx mori* Silk Fibroin Fibers and Films." Journal of Applied Polymer Science, vol. 91, 2383-2390 (2004).
Office Action dated Sep. 6, 2019 for Eurasian Patent Application No. 201890289.
Office Action dated Apr. 29, 2020 for Eurasian Patent Application No. 201890289.
Office Action dated Jun. 3, 2019 for Chilean Patent Application No. 2017-001404.
CL 198200371—AKZO NV. Pub. Feb. 4, 1983 (registro 33669).
Third Party Observations filed Jun. 10, 2020 in European Patent Application No. 15864424.5.
Third Party Observations filed Jun. 10, 2020 in European Patent Application No. 16825194.0.
Notice of Reasons for Rejection dated Jul. 28, 2020 for Japanese Patent Application No. 2018-501372.

(56) References Cited

OTHER PUBLICATIONS

Examination Report dated Aug. 10, 2020 for Australian Patent Application No. 2015358537.
Examination Report dated Aug. 21, 2020 for Indian Patent Application No. 201717022753.
Search Report dated Sep. 11, 2020 for Eurasian Patent Application No. 202090772.
Examination Report dated Sep. 17, 2020 for Saudi Arabian Patent Application No. 517381633 (with partial English summary).
Notice of Reasons for Rejection dated Oct. 20, 2020 for Japanese Patent Application No. 2017-529648 (with English translation).
Examination Report, dated Jun. 18, 2021, for Singapore Patent Application No. 11201704494S.
Examination Report, dated Jun. 18, 2021, for Singapore Patent Application No. 11201800272U.
Office Action dated Jan. 11, 2021 for Chinese Patent Application No. 201680053476.9 (w/ translation).
Xu Yunhui et al. "Preparation and controlled release effect of soybean protein/multicarboxylic acids modified cotton fabric." Chinese Journal of Textile Research, vol. 34, No. 6, pp. 73-78, Jun. 2013 (w/ English abstract).
Wu Huiying. "Study on Modification of Silk Fibroin Solution to Cotton Fabric." Cotton Textile Technology, vol. 42, No. 3, pp. 1-4, Mar. 2014 (w/ English abstract).
Office Action dated Nov. 2, 2020 for Chinese Patent Application No. 201580075200.6 (English translation).
Office Action dated Nov. 9, 2020 for Brazilian Patent Application No. BR112018000699-8 (English translation).
Office Action dated Nov. 24, 2020 for Indonesian Patent Application No. P00201801017 (with partial English summary).
Office Action dated Dec. 29, 2020 for Eurasian Patent Application No. 201890289 (with English translation).
Office Action dated Nov. 18, 2020 for Costa Rican Patent Application No. 2017-0000302 (with English translation).
Office Action, dated Sep. 3, 2021, for Chinese Patent Application No. 201680053476.9 (w/ translation).
Office Action, dated Dec. 21, 2021, for Eurasian Patent Application No. 201890289 (w/ translation).
Office Action, dated Dec. 30, 2021, for Saudi Arabian Patent Application No. 518390735.
Office Action, dated Dec. 24, 2021, for Indonesian Patent Application No. P00201801017.
Examination Report, dated Jul. 2, 2021, for Indian Patent Application No. 201817005205.
Examination Report, dated Jul. 16, 2021, for Peruvian Patent Application No. 000958-2017 (w/ partial translation).
Examination Report, dated Aug. 31, 2021, for Australian Patent Application No. 2016294611.
David N. Breslauer, Susan J. Muller, and Luke P. Lee: "Generation of Monodisperse Silk Microspheres Prepared with Microfluidics", Biomacramolecules 2010 11 (3), 643-647.
Office Action for corresponding Canadian Patent Application No. 2,969,563 dated Feb. 2, 2022, 4 pages.
Office Action for corresponding European Patent Application No. 15 864 424.5 dated Mar. 17, 2022, 9 pages.
Office Action for corresponding Costa Rica Patent Application No. 2017-0000302 dated Feb. 11, 2022, 9 pages.
Office Action dated Mar. 16, 2022 for related Chinese Patent Application No. 201680053476.9 (w/ English translation).
Office Action dated Mar. 25, 2022 for related Korean Patent Application No. 10-2017-7018225 (w/ English translation).
Office Action dated Apr. 28, 2022 for related Eurasian Patent Application No. 202090772 (w/ English translation).
Technical Examination Report for related Application No. BR 11 2018 000699-8 dated Jun. 6, 2022, 6 pages.
Nguyen et al. Biological, Chemical, and Electronic Applications of Nanofibers. Macromol. Mater. Eng. 298:822-867 (2013).
Rabotyagova, O.S. et al. Protein based Block Copolymers. Biomacromolecules, 12(2): 269-289 (2011).
Office Action dated Jul. 8, 2022 for Chilean Patent Application No. 2017-001404.
Office Action dated Jul. 29, 2022 for Saudi Arabian Patent Application No. 521420956.

\* cited by examiner

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 4 Hours | Some undissolved silk | Some undissolved silk | Significant amount of undissolved silk | Significant amount of undissolved silk |

Fig. 5A  Fig. 5B  Fig. 5C  Fig. 5D

| Time Point | Sericin was extracted at 100°C, 30 min | Sericin was extracted at 100°C, 60 min | Sericin was extracted at 90°C, 30 min | Sericin was extracted at 90°C, 60 min |
|---|---|---|---|---|
| 1 Hour | Significant amount of undissolved silk | Significant amount of undissolved silk and debris | Significant amount of undissolved silk, highly viscous | Significant amount of undissolved silk |

Fig. 12A  Fig. 12B  Fig. 12C  Fig. 12D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 4 Hours | Some undissolved silk | Some undissolved silk | Significant amount of undissolved silk, highly viscous | Some undissolved silk |
| | 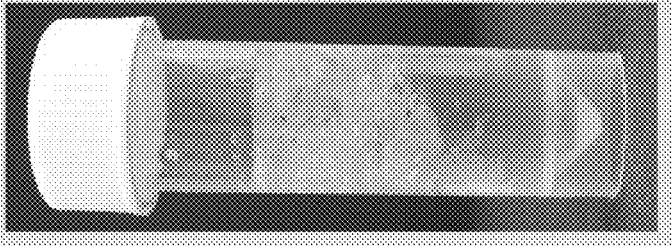 | 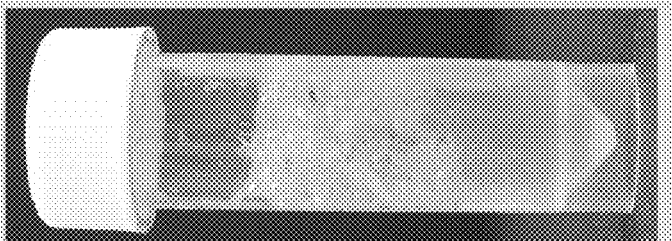 |  |  |
| | Fig. 13A | Fig. 13B | Fig. 13C | Fig. 13D |

| Time Point | Sericin was extracted at 100°C, 30 min | Sericin was extracted at 100°C, 60 min | Sericin was extracted at 90°C, 30 min | Sericin was extracted at 90°C, 60 min |
|---|---|---|---|---|
| 4 Hours | All silk dissolved, some precipitate from bubbles | Completely clear with no precipitate | Some undissolved silk | Some precipitate from bubbles, mostly clear solution |

Fig. 19A    Fig. 19B    Fig. 19C    Fig. 19D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 6 Hours | Some precipitate from bubbles, no undissolved silk | Clear with no precipitate or silk | Some undissolved silk | Clear and no undissolved silk |

Fig. 20A   Fig. 20B   Fig. 20C   Fig. 20D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 4 Hours | Some undissolved silk, cloudy, slightly viscous 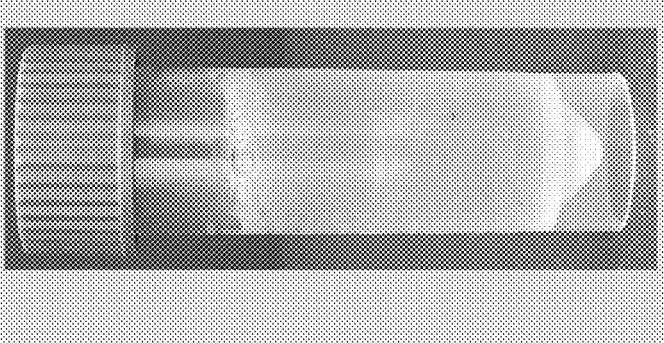 | Very slight amount of silk undissolved, clear with darker color 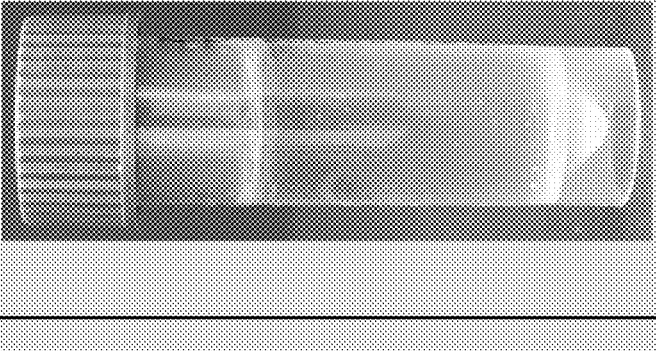 | Some undissolved silk, highly viscous  | Small amount of undissolved silk, not too viscous 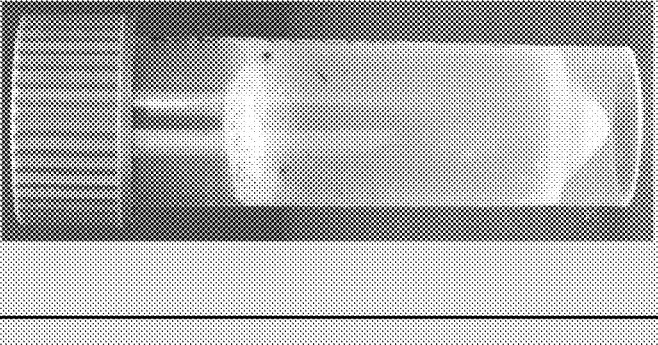 |
| | Fig. 25A | Fig. 25B | Fig. 25C | Fig. 25D |

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 6 Hours | Slightly cloudy with some undissolved silk | Clear with darker color | Some undissolved silk, viscous | Darker color, some undissolved silk, slightly cloudy |

Fig. 26A  Fig. 26B  Fig. 26C  Fig. 26D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 1 Hour | Somewhat cloudy with darker color, some silk particles | Completely clear with dark color, slight amount of silk particles | Cloudy, some undissolved silk, highly viscous | Small amount of undissolved silk, partially cloudy, darker color |

Fig. 27A  Fig. 27B  Fig. 27C  Fig. 27D

| Time Point | Sericin was extracted at 100° C, 30 min | Sericin was extracted at 100° C, 60 min | Sericin was extracted at 90° C, 30 min | Sericin was extracted at 90° C, 60 min |
|---|---|---|---|---|
| 4 Hours | All silk dissolved, slightly cloudy but mostly clear | All silk dissolved, clear, dark | All silk dissolved, cloudy | All silk dissolved, cloudy |

Fig. 31A    Fig. 31B    Fig. 31C    Fig. 31D

Lithium Bromide and Sodium Carbonate Concentration in Silk Protein Solution

| Sample ID | Sample Description | Average Concentration of Na2CO3 (ppm) | Average Concentration of LiBr (ppm) |
|---|---|---|---|
| A | TFF 5kDa | 32.13 | 90.85 |
| B | TFF 10 kDa | 42.91 | 107 |
| C | TFF 10 kDa | 49.06 | 78.55 |
| D | STI 1(TFF-10-0019) | 2.17 | 129.07 |
| E | STI 2(TFF-10-0033) | 2.63 | 196.2 |
| F | STI 3(TFF-10-0034) | 4.18 | 248.93 |

Method: 100C extraction for 60 min, 60C rinse, 100C LiBr in 100C oven for 60 min. Note that TFF could be run for longer and/or at different flow rates (as varied between A-C and D-F) to alter ppm of Na2CO3 and LiBr.

Fig. 34

Lithium Bromide and Sodium Carbonate content in Silk Protein Solution

| Solution Volume | | Sample Weight (mg) | Concentration | |
|---|---|---|---|---|
| Sample ID | Equivalent to (X) Films | | Na2CO3 | LiBr |
| 1 | 6 | 0.171 | ND | ND |
| 2 | 8 | 0.228 | ND | ND |
| 3 | 10 | 0.285 | ND | ND |
| 4 | 12 | 0.342 | ND | ND |
| 5 | Neat | - | ND | ND |

*ND=None Detected

Method: 100C boil for 60 min, 60C rinse, LiBr in 60C oven for 4-6 hours

Fig. 35

Stability of Vitamin C in Solution

| Sample ID | Time (hour) | Actual Conc. (µg/mL) | Area | Concentration Vit C (µg/mL) | Recovered (%) | Stability (%) After 24 hrs. |
|---|---|---|---|---|---|---|
| A | 0 | 82.4 | 4277.9 | 80.53 | 97.73 | |
| B | 26 | 82.4 | 4088.94 | 77.62 | 94.2 | 96.39 |
| Average = | | | 4183.42 | 79.07 | 95.96 | |
| Std. Dev. = | | | 133.62 | 2.06 | 2.49 | |
| % Error | | | 3% | 3% | 3% | |

Method: Vitamin C solution (no silk)

Fig. 36

Molecular Weights of Silk Protein Solutions

| Sample ID | Sample Description | Mn | Mw | Polydispersity (PD) (Mw/Mn) |
|---|---|---|---|---|
| A | TFF 5kDa | 14,497 | 33,874 | 2.3366 |
| B | TFF 10 kDa | 14,542 | 33,455 | 2.3006 |
| C | TFF 10 kDa | 14,972 | 34,026 | 2.2726 |
| D | Silk protein solution in water | 12,055 | 26,531 | 2.2008 |

Fig. 37

Method:
TFF: 100C extraction for 60 min, 60C rinse, 100C LiBr in 100C oven for 60 min.
Silk Protein: 100C extraction for 20 min, RT rinse, LiBr in 60C oven for 4-6 hours

| Sample | LiBr (M) | Avg MW | PD |
|---|---|---|---|
| STI 1(TFF-10-0019) | 9.3 | 15727 | 2.033 |
| STI 2(TFF-10-0033) | 9.3 | 24587 | 2.3669 |
| STI 3(TFF-10-0034) | 9.3 | 25273 | 2.338 |
| STI 9.3 M avg | | 21862 | 2.25 |
| STI 1(TFF-10-0031) | ~7.5 | 29645 | 3.0868 |
| STI 2(TFF-10-0030) | ~7.5 | 26856 | 2.9748 |
| STI 7.5M avg | | 28250.5 | 3.0308 |

* TFF-10-0019 from 2 25g extraction/35g dissolution
* TFF-10-0034 from 100g extraction/ 17-35 g dissolution
* TFF-10-0033 from 100g extraction/ 100 g dissolution

Fig. 39

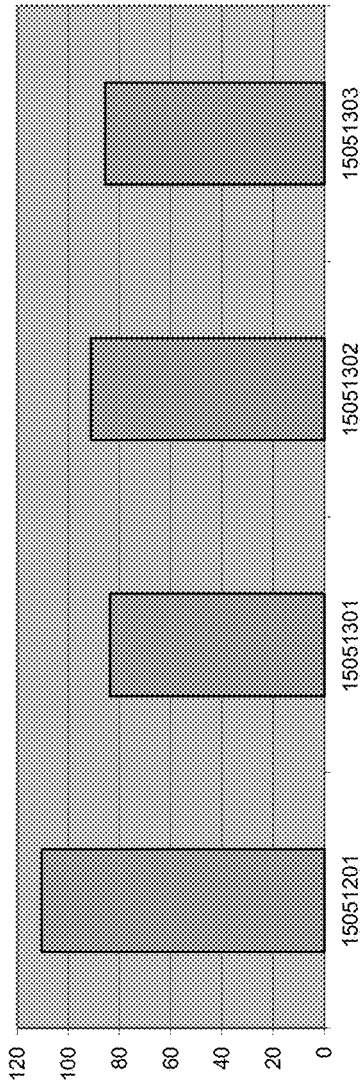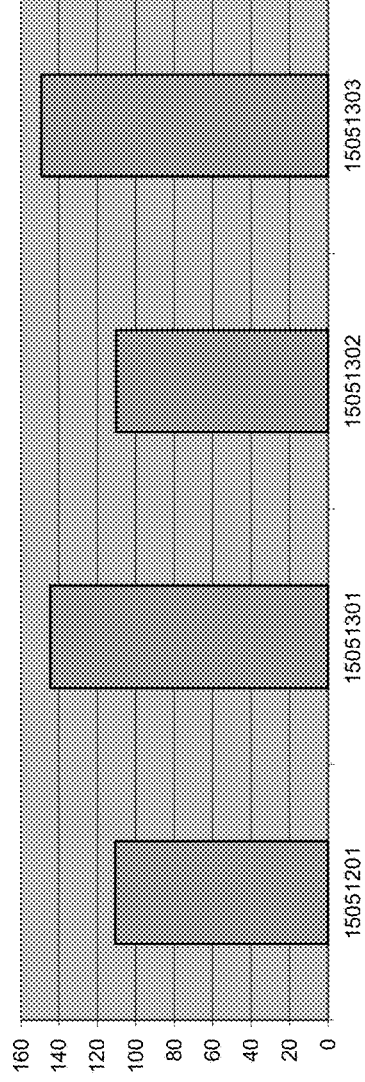

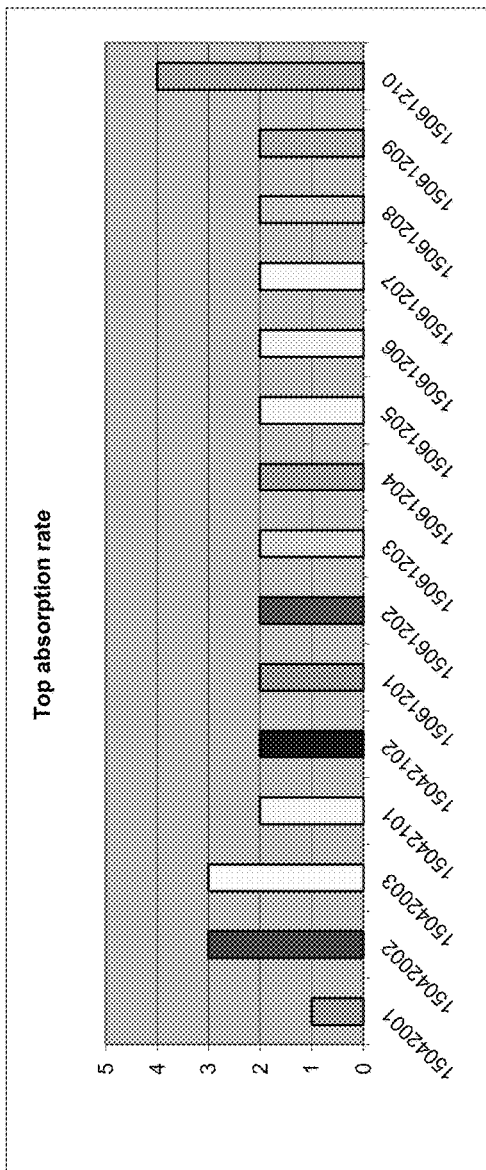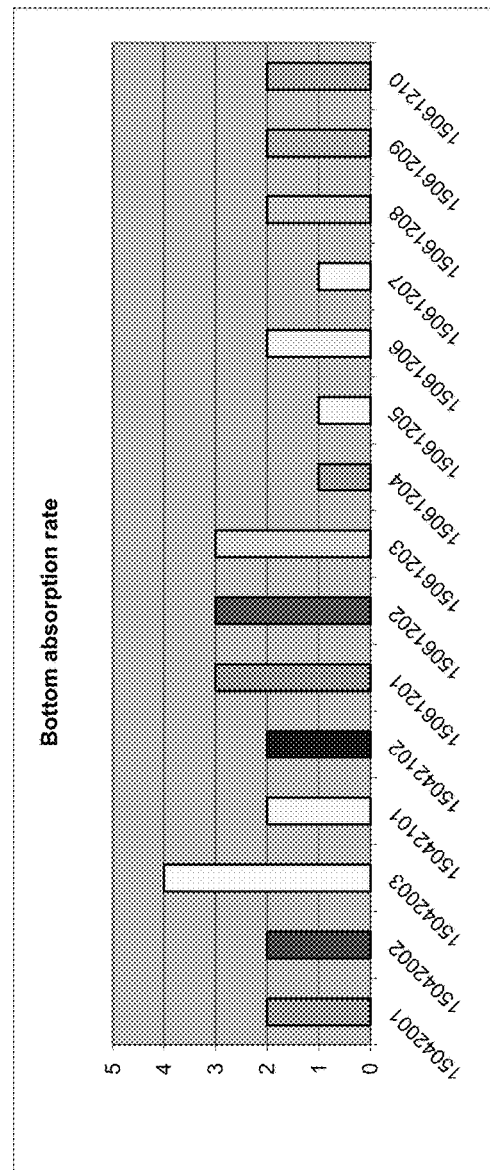

SILK PERFORMANCE APPAREL AND PRODUCTS AND METHODS OF PREPARING THE SAME

RELATED APPLICATIONS

The present application is a continuation of U.S. Nonprovisional Utility application Ser. No. 14/958,565, filed Dec. 3, 2015, which is a continuation of international application no. PCT/US2015/063545 filed Dec. 2, 2015, which application claims the benefit of U.S. Provisional Application No. 62/086,297 filed Dec. 2, 2014 and U.S. Provisional Application No. 62/192,477 filed Jul. 14, 2015 and U.S. Provisional Application No. 62/245,221 filed Oct. 22, 2015. The contents of each of these applications are incorporated herein by reference in their entireties.

FIELD OF THE INVENTION

In some embodiments, the present invention relates to silk performance apparel and products, such as fabrics coated with pure silk fibroin-based proteins or protein fragments.

BACKGROUND OF THE INVENTION

Silk is a natural polymer produced by a variety of insects and spiders, and comprises a filament core protein, silk fibroin, and a glue-like coating consisting of a non-filamentous protein, sericin. Silk fibers are light weight, breathable, and hypoallergenic. Silk is comfortable when worn next to the skin and insulates very well; keeping the wearer warm in cold temperatures and is cooler than many other fabrics in warm temperatures.

SUMMARY OF THE INVENTION

Silk performance apparel and methods of preparing the same are disclosed herein. According to aspects illustrated herein, the present disclosure relates to a product, including, but not limited to, apparel, padding, shoes, gloves, luggage, furs, jewelry and bags, configured to be worn or carried on the body, that is at least partially surface treated with an aqueous solution of pure silk fibroin-based protein fragments of the present disclosure so as to result in a silk coating on the product. In an embodiment, the product is manufactured from a textile material. In an embodiment, the product is manufactured from a non-textile material. In an embodiment, desired additives can be added to an aqueous solution of pure silk fibroin-based protein fragments of the present disclosure so as to result in a silk coating having desired additives.

According to aspects illustrated herein, an aqueous solution of pure silk fibroin-based protein fragments of the present disclosure is available in a spray can for spraying on a product, including, but not limited to, apparel, padding, shoes, gloves, luggage, furs, jewelry and bags, or for directly spraying on the body of a consumer, to impart desired properties to the product. In an embodiment, the product is manufactured from a textile material. In an embodiment, the product is manufactured from a non-textile material. In an embodiment, desired additives can be added to an aqueous solution of pure silk fibroin-based protein fragments of the present disclosure so as to result in a silk coating having desired additives.

In an embodiment, a textile comprising a silk coating of the present disclosure is sold to a consumer. In an embodiment, a textile of the present disclosure is used in constructing action sportswear apparel. In an embodiment, a textile of the present disclosure is used in constructing fitness apparel. In an embodiment, a textile of the present disclosure is used in constructing performance apparel. In an embodiment, a textile of the present disclosure is used in constructing golf apparel. In an embodiment, a textile of the present disclosure is used in constructing lingerie. In an embodiment, a silk coating of the present disclosure is positioned on the underlining of action sportswearlapparel. In an embodiment, a silk coating of the present disclosure is positioned on the shell, the lining, or the interlining of action sportswear/apparel. In an embodiment, action sportswearlapparel is partially made from a silk coated textile of the present disclosure and partially made from an uncoated textile. In an embodiment, action sportswear/apparel partially made from a silk coated textile and partially made from an uncoated textile combines an uncoated inert synthetic material with a silk coated inert synthetic material. Examples of inert synthetic material include, but are not limited to, polyester, polyamide, polyaramid, polytetrafluorethylene, polyethylene, polypropylene, polyurethane, silicone, mixtures of polyurethane and polyethylenglycol, ultrahigh molecular weight polyethylene, high-performance polyethylene, nylon, LYCRA (polyester-polyurethane copolymer, also known as SPANDEX and elastomer), and mixtures thereof. In an embodiment, action sportswear/apparel partially made from a silk coated textile and partially made from an uncoated textile combines an elastomeric material at least partially covered with a silk coating of the present disclosure. In an embodiment, the percentage of silk to elastomeric material can be varied to achieve desired shrink or wrinkle resistant properties and desired moisture content against the skin surface. In an embodiment, a silk coating of the present disclosure is positioned on an internal layer of a shoe (textile or non-textile based). In an embodiment, a silk coating of the present disclosure positioned on an internal layer of a shoe helps maintain optimal feet microenvironment, such as temperature and humidity while reducing any excessive perspiration.

In an embodiment, a silk coating of the present disclosure is visible. In an embodiment, a silk coating of the present disclosure is transparent. In an embodiment, a silk coating of the present disclosure positioned on action sportswear/apparel helps control skin temperature of a person wearing the apparel. In an embodiment, a silk coating of the present disclosure positioned on action sportswear/apparel helps control fluid transfer away from the skin of a person wearing the apparel. In an embodiment, a silk coating of the present disclosure positioned on action sportswear/apparel has a soft feel against the skin decreasing abrasions from fabric on the skin. In an embodiment, a silk coating of the present disclosure positioned on a textile has properties that confer at least one of wrinkle resistance, shrinkage resistance, or machine washability to the textile. In an embodiment, a silk coated textile of the present disclosure is 100% machine washable and dry cleanable. In an embodiment, a silk coated textile of the present disclosure is 100% waterproof. In an embodiment, a silk coated textile of the present disclosure is wrinkle resistant. In an embodiment, a silk coated textile of the present disclosure is shrink resistant. In an embodiment, a silk coated fabric improves the health of the skin. In an embodiment, healthy skin can be determined by visibly seeing an even skin tone. In an embodiment, healthy skin can be determined by visibly seeing a smooth, glowing complexion. In an embodiment, a silk coated fabric decreases irritation of the skin. In an embodiment, a decrease in irritation of the skin can result in a decrease in skin bumps or sores. In an embodiment, a decrease in irritation of the skin can result in a decrease in scaly or red skin. In an embodiment, a decrease in irritation of the skin can result in a decrease in itchiness or burning. In an embodiment, a silk coated fabric decreases inflammation of the skin. In an embodiment, a silk coated textile of the present disclosure has the qualities of being waterproof, breathable, and elastic and possess a number of other qualities which are highly desirable in action sportswear. In an embodiment, a silk coated textile of the present disclosure manufactured from a silk fabric of the present disclosure further includes LYCRA brand spandex fibers (polyester-polyurethane copolymer).

In an embodiment, a textile at least partially coated with an aqueous solution of pure silk fibroin-based protein fragments of the present disclosure is a breathable fabric. In an embodiment, a textile at least partially coated with an aqueous solution of pure silk fibroin-based protein fragments of the present disclosure is a water-resistant fabric. In an embodiment, a textile at least partially coated with an aqueous solution of pure silk fibroin-based protein fragments of the present disclosure is a shrink-resistant fabric. In an embodiment, a textile at least partially coated with an aqueous solution of pure silk fibroin-based protein fragments of the present disclosure is a machine-washable fabric. In an embodiment, a textile at least partially coated with an aqueous solution of pure silk fibroin-based protein fragments of the present disclosure is a wrinkle resistant fabric. In an embodiment, textile at least partially coated with an aqueous solution of pure silk fibroin-based protein fragments of the present disclosure provides moisture and vitamins to the skin.

In an embodiment, the textile at least partially coated with an aqueous solution of pure silk fibroin-based protein fragments of the present disclosure has an accumulative one-way transport index of greater than 140. In an embodiment, the textile at least partially coated with an aqueous solution of pure silk fibroin-based protein fragments of the present disclosure has an accumulative one-way transport index of greater than 120. In an embodiment, the textile at least partially coated with an aqueous solution of pure silk fibroin-based protein fragments of the present disclosure has an accumulative one-way transport index of greater than 100. In an embodiment, the textile at least partially coated with an aqueous solution of pure silk fibroin-based protein fragments of the present disclosure has an accumulative one-way transport index of greater than 80.

In an embodiment, the textile at least partially coated with an aqueous solution of pure silk fibroin-based protein fragments of the present disclosure has an overall moisture management capability of greater than 0.4. In an embodiment, the textile at least partially coated with an aqueous solution of pure silk fibroin-based protein fragments of the present disclosure has an overall moisture management capability of greater than 0.35. In an embodiment, the textile at least partially coated with an aqueous solution of pure silk fibroin-based protein fragments of the present disclosure has an overall moisture management capability of greater than 0.3. In an embodiment, the textile at least partially coated with an aqueous solution of pure silk fibroin-based protein fragments of the present disclosure has an overall moisture management capability of greater than 0.25.

In an embodiment, the textile at least partially coated with an aqueous solution of pure silk fibroin-based protein fragments of the present disclosure has a wetting time of at least 3 seconds. In an embodiment, the textile at least partially coated with an aqueous solution of pure silk fibroin-based protein fragments of the present disclosure has a wetting time of at least 2.5 seconds. In an embodiment, the textile at least partially coated with an aqueous solution of pure silk fibroin-based protein fragments of the present disclosure has a wetting time of at least 2 seconds. In an embodiment, the textile at least partially coated with an aqueous solution of pure silk fibroin-based protein fragments of the present disclosure has a wetting time of at least 1.5 seconds.

In an embodiment, the textile at least partially coated with an aqueous solution of pure silk fibroin-based protein fragments of the present disclosure has a top absorption time of at least 50 seconds. In an embodiment, the textile at least partially coated with an aqueous solution of pure silk fibroin-based protein fragments of the present disclosure has a top absorption time of at least 40 seconds. In an embodiment, the textile at least partially coated with an aqueous solution of pure silk fibroin-based protein fragments of the present disclosure has a top absorption time of at least 30 seconds.

In an embodiment, the textile at least partially coated with an aqueous solution of pure silk fibroin-based protein fragments of the present disclosure has a bottom absorption time of at least 80 seconds. In an embodiment, the textile at least partially coated with an aqueous solution of pure silk fibroin-based protein fragments of the present disclosure has a bottom absorption time of at least 70 seconds. In an embodiment, the textile at least partially coated with an aqueous solution of pure silk fibroin-based protein fragments of the present disclosure has a bottom absorption time of at least 60 seconds. In an embodiment, the textile at least partially coated with an aqueous solution of pure silk fibroin-based protein fragments of the present disclosure has a bottom absorption time of at least 50 seconds. In an embodiment, the textile at least partially coated with an aqueous solution of pure silk fibroin-based protein fragments of the present disclosure has a bottom absorption time of at least 40 seconds.

In an embodiment, the textile at least partially coated with an aqueous solution of pure silk fibroin-based protein fragments of the present disclosure has a spreading speed of at least 1.6 mm/second. In an embodiment, the textile at least partially coated with an aqueous solution of pure silk fibroin-based protein fragments of the present disclosure has a spreading speed of at least 1.4 mm/second. In an embodiment, the textile at least partially coated with an aqueous solution of pure silk fibroin-based protein fragments of the present disclosure has a spreading speed of at least 1.2 mm/second. In an embodiment, the textile at least partially coated with an aqueous solution of pure silk fibroin-based protein fragments of the present disclosure has a spreading speed of at least 1.0 mm/second. In an embodiment, the textile at least partially coated with an aqueous solution of pure silk fibroin-based protein fragments of the present disclosure has a spreading speed of at least 0.8 mm/second.

In an embodiment, the textile at least partially coated with an aqueous solution of pure silk fibroin-based protein fragments of the present disclosure shows less than 2000% microbial growth over 24 hours. In an embodiment, the textile at least partially coated with an aqueous solution of pure silk fibroin-based protein fragments of the present disclosure shows less than 1000% microbial growth over 24 hours. In an embodiment, the textile at least partially coated with an aqueous solution of pure silk fibroin-based protein fragments of the present disclosure shows less than 500% microbial growth over 24 hours. In an embodiment, the textile at least partially coated with an aqueous solution of pure silk fibroin-based protein fragments of the present disclosure shows less than 400% microbial growth over 24 hours. In an embodiment, the textile at least partially coated with an aqueous solution of pure silk fibroin-based protein fragments of the present disclosure shows less than 300% microbial growth over 24 hours. In an embodiment, the textile at least partially coated with an aqueous solution of pure silk fibroin-based protein fragments of the present disclosure shows less than 200% microbial growth over 24 hours.

In an embodiment, the textile at least partially coated with an aqueous solution of pure silk fibroin-based protein fragments of the present disclosure shows less than 2000% bacterial growth over 24 hours. In an embodiment, the textile at least partially coated with an aqueous solution of pure silk fibroin-based protein fragments of the present disclosure shows less than 1000% bacterial growth over 24 hours. In an embodiment, the textile at least partially coated with an aqueous solution of pure silk fibroin-based protein fragments of the present disclosure shows less than 500% bacterial growth over 24 hours. In an embodiment, the textile at least partially coated with an aqueous solution of pure silk fibroin-based protein fragments of the present disclosure shows less than 400% bacterial growth over 24 hours. In an embodiment, the textile at least partially coated with an aqueous solution of pure silk fibroin-based protein fragments of the present disclosure shows less than 300% bacterial growth over 24 hours. In an embodiment, the textile at least partially coated with an aqueous solution of pure silk fibroin-based protein fragments of the present disclosure shows less than 200% bacterial growth over 24 hours.

In an embodiment, the textile at least partially coated with an aqueous solution of pure silk fibroin-based protein fragments of the present disclosure shows less than 2000% fungal growth over 24 hours. In an embodiment, the textile at least partially coated with an aqueous solution of pure silk fibroin-based protein fragments of the present disclosure shows less than 1000% fungal growth over 24 hours. In an embodiment, the textile at least partially coated with an aqueous solution of pure silk fibroin-based protein fragments of the present disclosure shows less than 500% fungal growth over 24 hours. In an embodiment, the textile at least partially coated with an aqueous solution of pure silk fibroin-based protein fragments of the present disclosure shows less than 400% fungal growth over 24 hours. In an embodiment, the textile at least partially coated with an aqueous solution of pure silk fibroin-based protein fragments of the present disclosure shows less than 300% fungal growth over 24 hours. In an embodiment, the textile at least partially coated with an aqueous solution of pure silk fibroin-based protein fragments of the present disclosure shows less than 200% fungal growth over 24 hours.

In an embodiment, the textile at least partially coated with an aqueous solution of pure silk fibroin-based protein fragments of the present disclosure shows less than 2000% growth of *Staphylococcus aureus* over 24 hours. In an embodiment, the textile at least partially coated with an aqueous solution of pure silk fibroin-based protein fragments of the present disclosure shows less than 1000% growth of *Staphylococcus aureus* over 24 hours. In an embodiment, the textile at least partially coated with an aqueous solution of pure silk fibroin-based protein fragments of the present disclosure shows less than 500% growth of *Staphylococcus aureus* over 24 hours. In an embodiment, the textile at least partially coated with an aqueous solution of pure silk fibroin-based protein fragments of the present disclosure shows less than 400% growth of *Staphylococcus aureus* over 24 hours. In an embodiment, the textile at least partially coated with an aqueous solution of pure silk fibroin-based protein fragments of the present disclosure shows less than 300% growth of *Staphylococcus aureus* over 24 hours. In an embodiment, the textile at least partially coated with an aqueous solution of pure silk fibroin-based protein fragments of the present disclosure shows less than 200% growth of *Staphylococcus aureus* over 24 hours.

In an embodiment, the textile at least partially coated with an aqueous solution of pure silk fibroin-based protein fragments of the present disclosure shows less than 2000% growth of *Klebsiella pneumoniae* over 24 hours. In an embodiment, the textile at least partially coated with an aqueous solution of pure silk fibroin-based protein fragments of the present disclosure shows less than 1000% growth of *Klebsiella pneumoniae* over 24 hours. In an embodiment, the textile at least partially coated with an aqueous solution of pure silk fibroin-based protein fragments of the present disclosure shows less than 500% growth of *Klebsiella pneumoniae* over 24 hours. In an embodiment, the textile at least partially coated with an aqueous solution of pure silk fibroin-based protein fragments of the present disclosure shows less than 400% growth of *Klebsiella pneumoniae* over 24 hours. In an embodiment, the textile at least partially coated with an aqueous solution of pure silk fibroin-based protein fragments of the present disclosure shows less than 300% growth of *Klebsiella pneumoniae* over 24 hours. In an embodiment, the textile at least partially coated with an aqueous solution of pure silk fibroin-based protein fragments of the present disclosure shows less than 200% growth of *Klebsiella pneumoniae* over 24 hours.

In an embodiment, an aqueous solution of pure silk fibroin-based protein fragments of the present disclosure is used to coat a textile. In an embodiment, the concentration of silk in the solution ranges from about 0.1% to about 20.0%. In an embodiment, the concentration of silk in the solution ranges from about 0.1% to about 15.0%. In an embodiment, the concentration of silk in the solution ranges from about 0.5% to about 10.0%. In an embodiment, the concentration of silk in the solution ranges from about 1.0% to about 5.0%. In an embodiment, an aqueous solution of pure silk fibroin-based protein fragments of the present disclosure is applied directly to a fabric. Alternatively, silk microsphere and any additives may be used for coating a fabric. In an embodiment, additives can be added to an aqueous solution of pure silk fibroin-based protein fragments of the present disclosure before coating (e.g., alcohols) to further enhance material properties. In an embodiment, a silk coating of the present disclosure can have a pattern to optimize properties of the silk on the fabric. In an embodiment, a coating is applied to a fabric under tension and/or lax to vary penetration in to the fabric.

In an embodiment, a silk coating of the present disclosure can be applied at the yarn level, followed by creation of a fabric once the yarn is coated. In an embodiment, an aqueous solution of pure silk fibroin-based protein fragments of the present disclosure can be spun into fibers to make a silk fabric and/or silk fabric blend with other materials known in the apparel industry.

In an embodiment, a method for silk coating a fabric includes immersion of the fabric in any of the aqueous solutions of pure silk fibroin-based protein fragments of the present disclosure. In an embodiment, a method for silk coating a fabric includes spraying. In an embodiment, a method for silk coating a fabric includes chemical vapor deposition. In an embodiment, a method for silk coating a fabric includes electrochemical coating. In an embodiment, a method for silk coating a fabric includes knife coating to spread any of the aqueous solutions of pure silk fibroin-based protein fragments of the present disclosure onto the fabric. The coated fabric may then be air dried, dried under heat/air flow, or cross-linked to the fabric surface. In an embodiment, a drying process includes curing with additives and/or ambient condition.

According to aspects illustrated herein, methods for preparing aqueous solutions of pure silk fibroin-based protein fragments are disclosed. In an embodiment, at least one pure silk fibroin-based protein fragment (SPF) mixture solution having a specific average weight average molecular weight (MW) range and polydispersity is created. In an embodiment, at least SPF mixture solution having a MW range between about 6 kDa and 16 kDa and a polydispersity range between about 1.5 and about 3.0 is created. In an embodiment, at least one SPF mixture solution having a MW between about 17 kDa and 38 kDa and a polydispersity range between about 1.5 and about 3.0 is created. In an embodiment, at least one SPF mixture solution having a MW range between about 39 kDa and 80 kDa and a polydispersity range between about 1.5 and about 3.0 is created.

According to aspects illustrated herein, there is disclosed a composition that includes pure silk fibroin-based protein fragments that are substantially devoid of sericin, wherein the composition has an average weight average molecular weight ranging from about 6 kDa to about 16 kDa, wherein the composition has a polydispersity of between about 1.5 and about 3.0, wherein the composition is substantially homogenous, wherein the composition includes between 0 ppm and about 500 ppm of inorganic residuals, and wherein the composition includes between 0 ppm and about 500 ppm of organic residuals. In an embodiment, the pure silk fibroin-based protein fragments have between about 10 ppm and about 300 ppm of lithium bromide residuals and between about 10 ppm and about 100 ppm of sodium carbonate residuals. In an embodiment, the lithium bromide residuals are measurable using a high-performance liquid chromatography lithium bromide assay, and the sodium carbonate residuals are measurable using a high-performance liquid chromatography sodium carbonate assay. In an embodiment, the composition further includes less than 10% water. In an embodiment, the composition is in the form of a solution. In an embodiment, the composition includes from about 0.1 wt % to about 30.0 wt % pure silk fibroin-based protein fragments. The pure silk fibroin-based protein fragments are stable in the solution for at least 30 days. In an embodiment, the term "stable" refers to the absence of spontaneous or gradual gelation, with no visible change in the color or turbidity of the solution. In an embodiment, the term "stable" refers to no aggregation of fragments and therefore no increase in molecular weight over time. In an embodiment, the composition is in the form of an aqueous solution. In an embodiment, the composition is in the form of an organic solution. The composition may be provided in a sealed container. In some embodiments, the composition further includes one or more molecules selected from the group consisting of therapeutic agents, growth factors, antioxidants, proteins, vitamins, carbohydrates, polymers, nucleic acids, salts, acids, bases, biomolecules, glycosaminoglycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the added molecule or molecules are stable (i.e., retain activity over time) within the composition and can be released at a desired rate. In an embodiment, the one or more molecules is vitamin C or a derivative thereof. In an embodiment, the composition further includes an alpha hydroxy acid selected from the group consisting of glycolic acid, lactic acid, tartaric acid and citric acid. In an embodiment, the composition further includes hyaluronic acid or its salt form at a concentration of about 0.5% to about 10.0%. In an embodiment, the composition further includes at least one of zinc oxide or titanium dioxide. In an embodiment, the pure silk fibroin-based protein fragments in the composition are hypoallergenic. In an embodiment, the pure silk fibroin-based protein fragments are biocompatible, non-sensitizing, and non-immunogenic.

According to aspects illustrated herein, there is disclosed a composition that includes pure silk fibroin-based protein fragments that are substantially devoid of sericin, wherein the composition has an average weight average molecular weight ranging from about 17 kDa to about 38 kDa, wherein the composition has a polydispersity of between about 1.5 and about 3.0, wherein the composition is substantially homogenous, wherein the composition includes between 0 ppm and about 500 ppm of inorganic residuals, and wherein the composition includes between 0 ppm and about 500 ppm of organic residuals. In an embodiment, the pure silk fibroin-based protein fragments have between about 10 ppm and about 300 ppm of lithium bromide residuals and between about 10 ppm and about 100 ppm of sodium carbonate residuals. In an embodiment, the lithium bromide residuals are measurable using a high-performance liquid chromatography lithium bromide assay, and the sodium carbonate residuals are measurable using a high-performance liquid chromatography sodium carbonate assay. In an embodiment, the composition further includes less than 10% water. In an embodiment, the composition is in the form of a solution. In an embodiment, the composition includes from about 0.1 wt % to about 30.0 wt % pure silk fibroin-based protein fragments. The pure silk fibroin-based protein fragments are stable in the solution for at least 30 days. In an embodiment, the term "stable" refers to the absence of spontaneous or gradual gelation, with no visible change in the color or turbidity of the solution. In an embodiment, the term "stable" refers to no aggregation of fragments and therefore no increase in molecular weight over time. In an embodiment, the composition is in the form of an aqueous solution. In an embodiment, the composition is in the form of an organic solution. The composition may be provided in a sealed container. In some embodiments, the composition further includes one or more molecules selected from the group consisting of therapeutic agents, growth factors, antioxidants, proteins, vitamins, carbohydrates, polymers, nucleic acids, salts, acids, bases, biomolecules, glycosaminoglycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the added molecule or molecules are stable (i.e., retain activity over time) within the composition and can be released at a desired rate. In an embodiment, the one or more molecules is vitamin C or a derivative thereof. In an embodiment, the composition further includes an alpha hydroxy acid selected from the group consisting of glycolic acid, lactic acid, tartaric acid and citric acid. In an embodiment, the composition further includes hyaluronic acid or its salt form at a concentration of about 0.5% to about 10.0%. In an embodiment, the composition further includes at least one of zinc oxide or titanium dioxide. In an embodiment, the pure silk fibroin-based protein fragments in the composition are hypoallergenic. In an embodiment, the pure silk fibroin-based protein fragments are biocompatible, non-sensitizing, and non-immunogenic.

According to aspects illustrated herein, there is disclosed a composition that includes pure silk fibroin-based protein fragments that are substantially devoid of sericin, wherein the composition has an average weight average molecular weight ranging from about 39 kDa to about 80 kDa, wherein the composition has a polydispersity of between about 1.5 and about 3.0, wherein the composition is substantially homogenous, wherein the composition includes between 0 ppm and about 500 ppm of inorganic residuals, and wherein the composition includes between 0 ppm and about 500 ppm of organic residuals. In an embodiment, the pure silk fibroin-based protein fragments have between about 10 ppm and about 300 ppm of lithium bromide residuals and between about 10 ppm and about 100 ppm of sodium carbonate residuals. In an embodiment, the lithium bromide residuals are measurable using a high-performance liquid chromatography lithium bromide assay, and the sodium carbonate residuals are measurable using a high-performance liquid chromatography sodium carbonate assay. In an embodiment, the composition further includes less than 10% water. In an embodiment, the composition is in the form of a solution. In an embodiment, the composition includes from about 0.1 wt % to about 30.0 wt % pure silk fibroin-based protein fragments. The pure silk fibroin-based protein fragments are stable in the solution for at least 30 days. In an embodiment, the term "stable" refers to the absence of spontaneous or gradual gelation, with no visible change in the color or turbidity of the solution. In an embodiment, the term "stable" refers to no aggregation of fragments and therefore no increase in molecular weight over time. In an embodiment, the composition is in the form of an aqueous solution. In an embodiment, the composition is in the form of an organic solution. The composition may be provided in a sealed container. In some embodiments, the composition further includes one or more molecules selected from the group consisting of therapeutic agents, growth factors, antioxidants, proteins, vitamins, carbohydrates, polymers, nucleic acids, salts, acids, bases, biomolecules, glycosamino glycans, polysaccharides, extracellular matrix molecules, metals, metal ion, metal oxide, synthetic molecules, polyanhydrides, cells, fatty acids, fragrance, minerals, plants, plant extracts, preservatives and essential oils. In an embodiment, the added molecule or molecules are stable (i.e., retain activity over time) within the composition and can be released at a desired rate. In an embodiment, the one or more molecules is vitamin C or a derivative thereof. In an embodiment, the composition further includes an alpha hydroxy acid selected from the group consisting of glycolic acid, lactic acid, tartaric acid and citric acid. In an embodiment, the composition further includes hyaluronic acid or its salt form at a concentration of about 0.5% to about 10.0%. In an embodiment, the composition further includes at least one of zinc oxide or titanium dioxide. In an embodiment, the pure silk fibroin-based protein fragments in the composition are hypoallergenic. In an embodiment, the pure silk fibroin-based protein fragments are biocompatible, non-sensitizing, and non-immunogenic.

According to aspects illustrated herein, there is disclosed a gel that includes pure silk fibroin-based protein fragments substantially devoid of sericin and comprising: an average weight average molecular weight ranging from about 17 kDa to about 38 kDa; and a polydispersity of between about 1.5 and about 3.0; and water from about 20 wt. % to about 99.9 wt. %, wherein the gel includes between 0 ppm and 500 ppm of inorganic residuals, and wherein the gel includes between 0 ppm and 500 ppm of organic residuals. In an embodiment, the gel includes between about 1.0% and about 50.0% crystalline protein domains. In an embodiment, the gel includes from about 0.1 wt. % to about 6.0 wt. % of pure silk fibroin-based protein fragments. In an embodiment, the gel has a pH from about 1.0 to about 7.0. In an embodiment, the gel further includes from about 0.5 wt. % to about 20.0 wt. % of vitamin C or a derivative thereof. In an embodiment, the vitamin C or a derivative thereof remains stable within the gel for a period of from about 5 days to about 5 years. In an embodiment, the vitamin C or a derivative thereof is stable within the gel so as to result in release of the vitamin C in a biologically active form. In an embodiment, the gel further includes an additive selected from the group consisting of vitamin E, rosemary oil, rose oil, lemon juice, lemon grass oil and caffeine. In an embodiment, the gel is packaged in an airtight container. In an embodiment, the pure silk fibroin-based protein fragments are hypoallergenic. In an embodiment, the gel has less than 10 colony forming units per milliliter.

According to aspects illustrated herein, there is disclosed a method for preparing an aqueous solution of pure silk fibroin-based protein fragments having an average weight average molecular weight ranging from about 6 kDa to about 16 kDa, the method including the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight ranging from about 6 kDa to about 16 kDa, and wherein the aqueous solution of pure silk fibroin-based protein fragments comprises a polydispersity of between about 1.5 and about 3.0. In an embodiment, the method includes the step of drying the silk fibroin extract prior to the dissolving step. In an embodiment, the amount of lithium bromide residuals in the aqueous solution can be measured using a high-performance liquid chromatography lithium bromide assay. In an embodiment, the amount of sodium carbonate residuals in the aqueous solution can be measured using a high-performance liquid chromatography sodium carbonate assay. In an embodiment, the method includes the step of adding a therapeutic agent to the aqueous solution of pure silk fibroin-based protein fragments. In an embodiment, the method includes the step of adding a molecule selected from one of an antioxidant or an enzyme to the aqueous solution of pure silk fibroin-based protein fragments. In an embodiment, the method includes the step of adding a vitamin to the aqueous solution of pure silk fibroin-based protein fragments. In an embodiment, the vitamin is selected from one of vitamin C or a derivative thereof. In an embodiment, the method further includes the step of adding an alpha hydroxy acid to the aqueous solution of pure silk fibroin-based protein fragments. In an embodiment, the alpha hydroxy acid is selected from the group consisting of glycolic acid, lactic acid, tartaric acid and citric acid. In an embodiment, the method further includes the step of adding hyaluronic acid at a concentration of about 0.5% to about 10.0% to the aqueous solution of pure silk fibroin-based protein fragments. In an embodiment, the method further includes the step of adding at least one of zinc oxide or titanium dioxide to the aqueous solution of pure silk fibroin-based protein fragments.

According to aspects illustrated herein, there is disclosed a method for preparing an aqueous solution of pure silk fibroin-based protein fragments having an average weight average molecular weight ranging from about 17 kDa to about 38 kDa, the method including the steps of: adding a silk source to a boiling (100° C.) aqueous solution of sodium carbonate for a treatment time of between about 30 minutes to about 60 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, wherein the aqueous solution of silk protein fragments comprises sodium carbonate residuals of between about 10 ppm and about 100 ppm, wherein the aqueous solution of pure silk fibroin-based protein fragments comprises fragments having an average weight average molecular weight ranging from about 17 kDa to about 38 kDa, and wherein the aqueous solution of pure silk fibroin-based protein fragments comprises a polydispersity of between about 1.5 and about 3.0. In an embodiment, the method includes the step of drying the silk fibroin extract prior to the dissolving step. In an embodiment, the amount of lithium bromide residuals in the aqueous solution can be measured using a high-performance liquid chromatography lithium bromide assay. In an embodiment, the amount of sodium carbonate residuals in the aqueous solution can be measured using a high-performance liquid chromatography sodium carbonate assay. In an embodiment, the method includes the step of adding a therapeutic agent to the aqueous solution of pure silk fibroin-based protein fragments. In an embodiment, the method includes the step of adding a molecule selected from one of an antioxidant or an enzyme to the aqueous solution of pure silk fibroin-based protein fragments. In an embodiment, the method includes the step of adding a vitamin to the aqueous solution of pure silk fibroin-based protein fragments. In an embodiment, the vitamin is selected from one of vitamin C or a derivative thereof. In an embodiment, the method further includes the step of adding an alpha hydroxy acid to the aqueous solution of pure silk fibroin-based protein fragments. In an embodiment, the alpha hydroxy acid is selected from the group consisting of glycolic acid, lactic acid, tartaric acid and citric acid. In an embodiment, the method further includes the step of adding hyaluronic acid at a concentration of about 0.5% to about 10.0% to the aqueous solution of pure silk fibroin-based protein fragments. In an embodiment, the method further includes the step of adding at least one of zinc oxide or titanium dioxide to the aqueous solution of pure silk fibroin-based protein fragments.

According to aspects illustrated herein, there is disclosed a method for preparing an aqueous solution of pure silk fibroin-based protein fragments having an average weight average molecular weight ranging from about 39 kDa to about 80 kDa, the method including the steps of: adding a silk source to a boiling (100° C.) aqueous solution of sodium carbonate for a treatment time of about 30 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, sodium carbonate residuals of between about 10 ppm and about 100 ppm, fragments having an average weight average molecular weight ranging from about 40 kDa to about 65 kDa, and wherein the aqueous solution of pure silk fibroin-based protein fragments comprises a polydispersity of between about 1.5 and about 3.0. In an embodiment, the method includes the step of drying the silk fibroin extract prior to the dissolving step. In an embodiment, the amount of lithium bromide residuals in the aqueous solution can be measured using a high-performance liquid chromatography lithium bromide assay. In an embodiment, the amount of sodium carbonate residuals in the aqueous solution can be measured using a high-performance liquid chromatography sodium carbonate assay. In an embodiment, the method includes the step of adding a therapeutic agent to the aqueous solution of pure silk fibroin-based protein fragments. In an embodiment, the method includes the step of adding a molecule selected from one of an antioxidant or an enzyme to the aqueous solution of pure silk fibroin-based protein fragments. In an embodiment, the method includes the step of adding a vitamin to the aqueous solution of pure silk fibroin-based protein fragments. In an embodiment, the vitamin is selected from one of vitamin C or a derivative thereof. In an embodiment, the method further includes the step of adding an alpha hydroxy acid to the aqueous solution of pure silk fibroin-based protein fragments. In an embodiment, the alpha hydroxy acid is selected from the group consisting of glycolic acid, lactic acid, tartaric acid and citric acid. In an embodiment, the method further includes the step of adding hyaluronic acid at a concentration of about 0.5% to about 10.0% to the aqueous solution of pure silk fibroin-based protein fragments. In an embodiment, the method further includes the step of adding at least one of zinc oxide or titanium dioxide to the aqueous solution of pure silk fibroin-based protein fragments.

According to aspects illustrated herein, a method is disclosed for producing silk gels having entrapped molecules or therapeutic agents such as those listed in the following paragraphs. In an embodiment, at least one molecule or therapeutic agent of interest is physically entrapped into a SPF mixture solution of the present disclosure during processing into aqueous gels. An aqueous silk gel of the present disclosure can be used to release at least one molecule or therapeutic agent of interest.

According to aspects illustrated herein, pure silk fibroin-based protein fragments from aqueous solutions of the present disclosure can be formed into yarns and fabrics including for example, woven or weaved fabrics, and these fabrics can be used in textiles, as described above.

According to aspects illustrated herein, silk fabric manufactured from SPF mixture solutions of the present disclosure are disclosed. In an embodiment, at least one molecule or therapeutic agent of interest is physically entrapped into a SPF mixture solution of the present disclosure. A silk film of the present disclosure can be used to release at least one molecule or therapeutic agent of interest.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIGS. 5A-5D are photographs showing dissolved silk in room temperature lithium bromide (LiBr) solutions dissolved in a 60° C. oven for 4 hours (sericin extraction temperature and time were varied).

FIGS. 12A-12D are photographs showing dissolved silk in 60° C. LiBr solutions dissolved in a 60° C. oven for 1 hour (sericin extraction temperature and time were varied).

FIGS. 13A-13D are photographs showing dissolved silk in 60° C. LiBr solutions dissolved in a 60° C. oven for 4 hours (sericin extraction temperature and time were varied).

FIGS. 19A-19D are photographs showing dissolved silk in 100° C. LiBr solutions dissolved in a 60° C. oven for 4 hours (sericin extraction temperature and time were varied).

FIGS. 20A-20D are photographs showing dissolved silk in 100° C. LiBr solutions dissolved in a 60° C. oven for 6 hours (sericin extraction temperature and time were varied).

FIGS. 25A-25D are photographs showing dissolved silk in 80° C. LiBr solutions dissolved in a 80° C. oven for 4 hours (sericin extraction temperature and time were varied).

FIGS. 26A-26D are photographs showing dissolved silk in 80° C. LiBr solutions dissolved in a 80° C. oven for 6 hours (sericin extraction temperature and time were varied).

FIGS. 27A-27D are photographs showing dissolved silk in 100° C. LiBr solutions dissolved in a 100° C. oven for 1 hour (sericin extraction temperature and time were varied).

FIGS. 31A-31D are photographs showing dissolved silk in 140° C. (boiling point for LiBr) LiBr solutions dissolved in a 120° C. oven for 4 hours (sericin extraction temperature and time were varied).

FIG. 33 shows peaks from (1) a chemically stabilized sample of vitamin C at ambient conditions and (2) a sample of vitamin C taken after 1 hour at ambient conditions without chemical stabilization to prevent oxidation, where degradation products are visible.

FIG. 34 is a table summarizing the LiBr and Sodium Carbonate ($Na_2CO_3$) concentration in silk protein solutions of the present disclosure.

FIG. 35 is a table summarizing the LiBr and $Na_2CO_3$ concentration in silk protein solutions of the present disclosure.

FIG. 36 is a table summarizing the stability of vitamin C in chemically stabilized solutions.

FIG. 37 is a table summarizing the Molecular Weights of silk protein solutions of the present disclosure.

FIG. 39 is a table summarizing the Molecular Weights of silk dissolved from different concentrations of LiBr and from different extraction and dissolution sizes.

FIG. 60A is a graph illustrating accumulative one way transport index with spray coating.

FIG. 60B is a graph illustrating accumulative one way transport index with stencil coating.

FIG. 63A is a graph illustrating top absorption rate.

FIG. 63B is a graph illustrating bottom absorption rate.

FIG. 80B is a graph illustrating accumulative one way transport index with 0.1% SFS.

FIG. 81A is a graph illustrating overall moisture management capability with 1% SFS.

FIG. 81B is a graph illustrating overall moisture management capability with 0.1% SFS.

FIG. 82A is a graph illustrating summary of wetting time top.

FIG. 82B is a graph illustrating summary of wetting time bottom.

FIG. 83A is a graph illustrating summary of top absorption rate.

FIG. 83B is a graph illustrating summary of bottom absorption rate.

FIG. 84A is a graph illustrating summary of top max wetted radius.

FIG. 84B is a graph illustrating summary of bottom wetted radius.

FIG. 85A is a graph illustrating summary of top spreading speed.

FIG. 85B is a graph illustrating summary of bottom spreading speed.

FIG. 86A is a graph illustrating summary of accumulative one-way transport index.

Figure 86A:
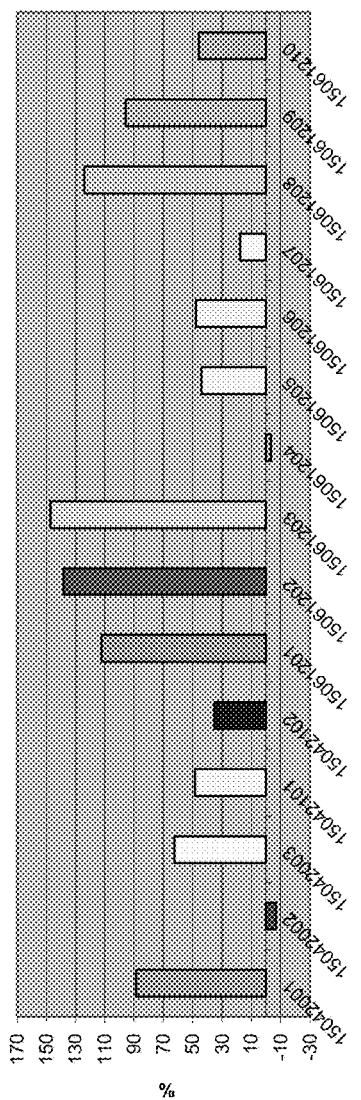
Figure 86B:
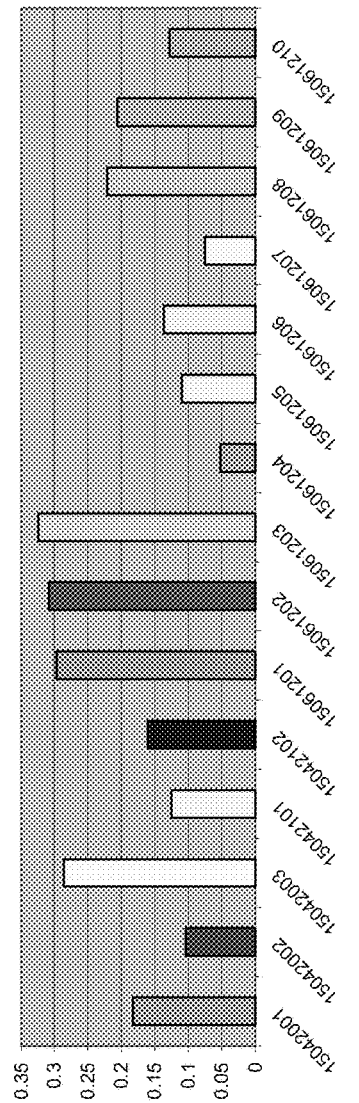

FIG. 86B is a graph illustrating summary of overall moisture management capability.

Figure 87:
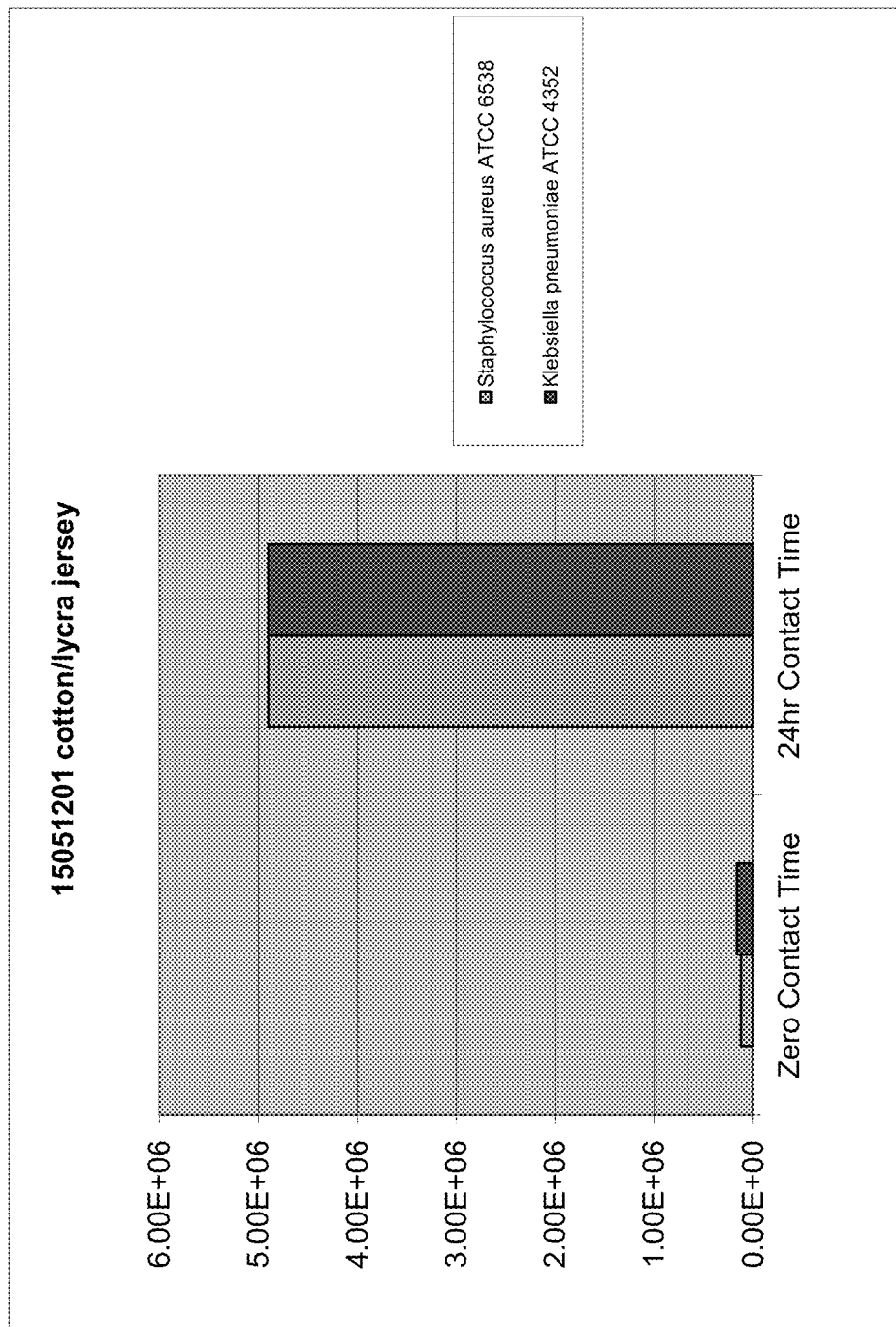

FIG. 87 illustrates bacterial growth results.

Figure 88:
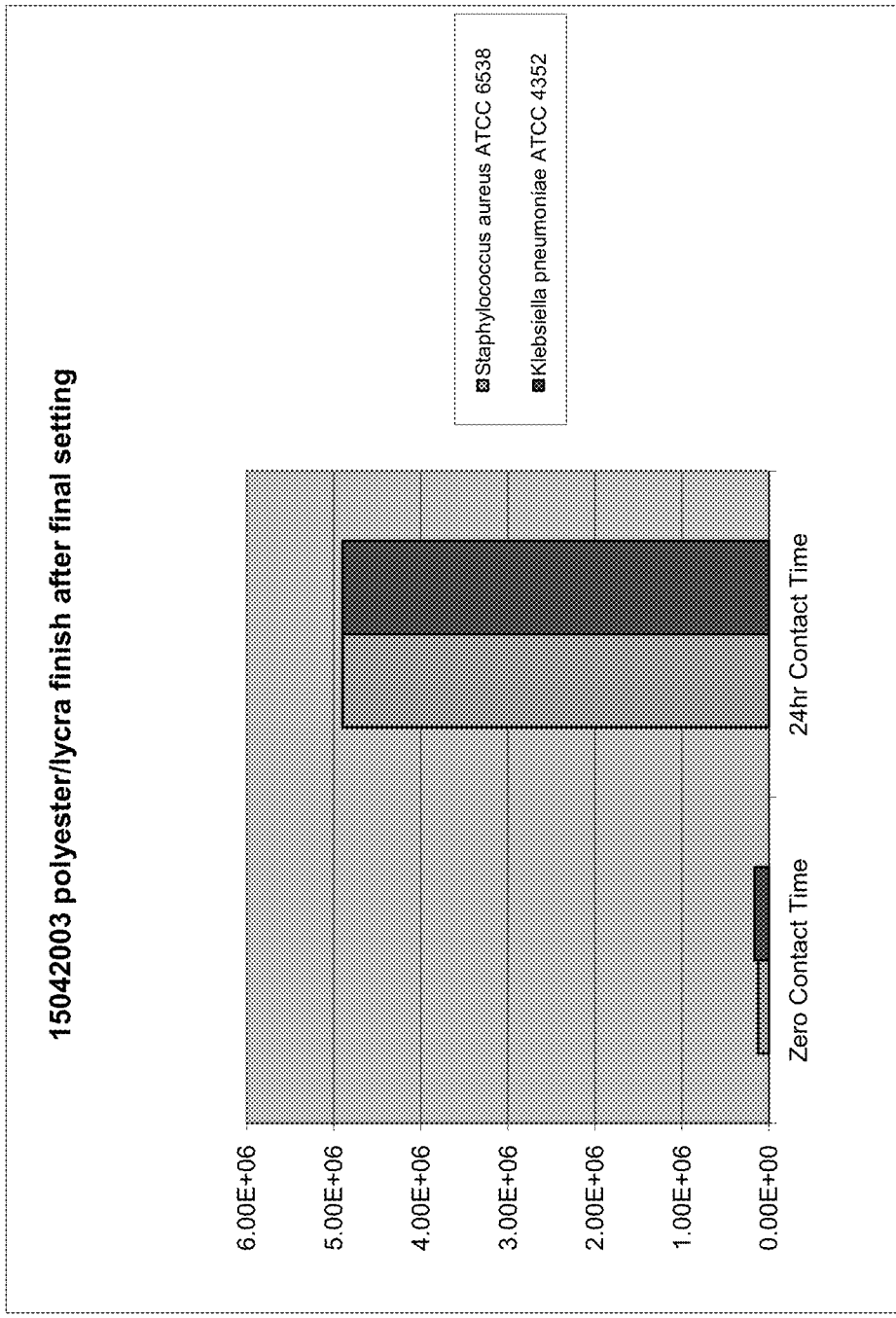

FIG. 88 illustrates bacterial growth results.

Figure 89:
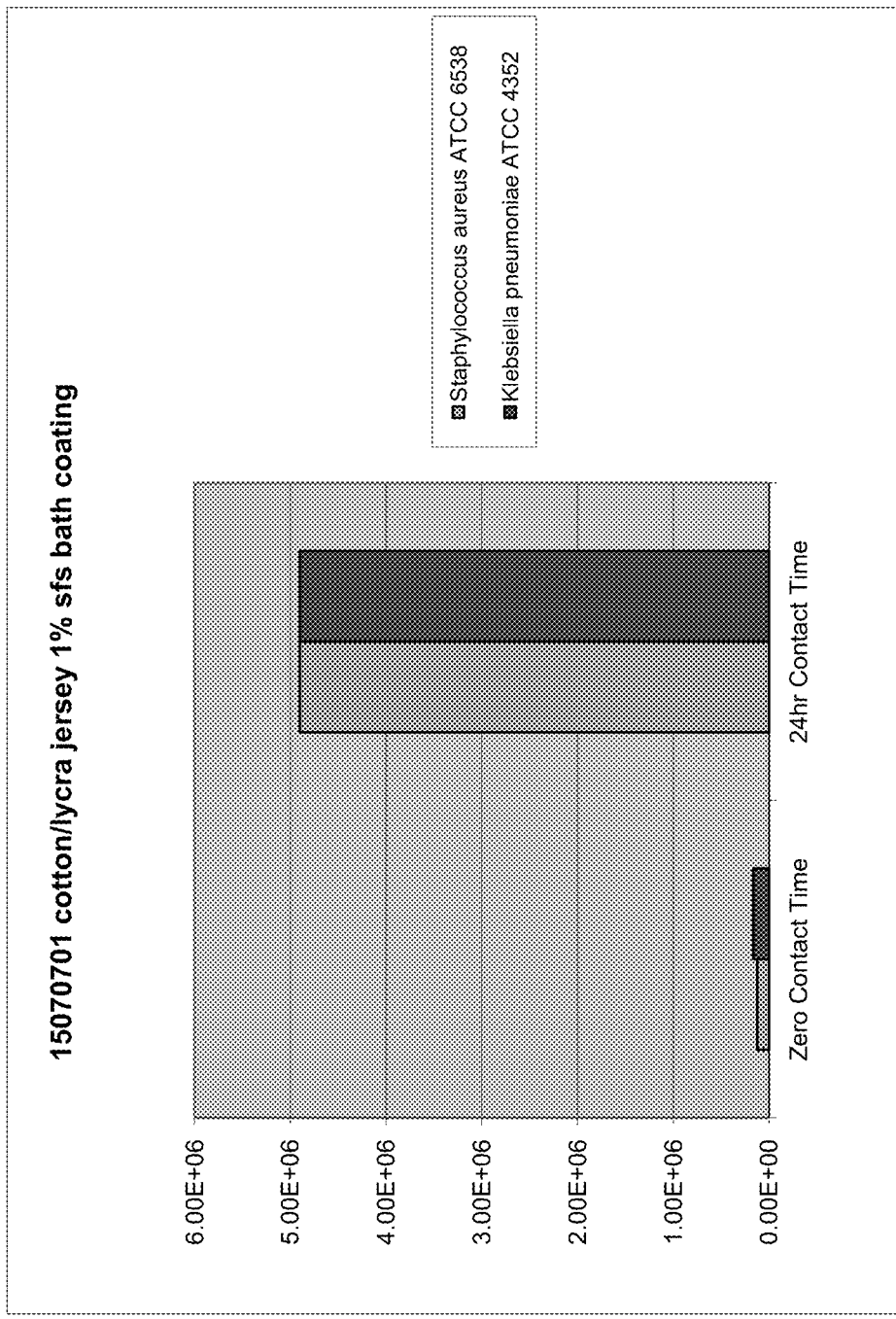

FIG. 89 illustrates bacterial growth results.

Figure 90:
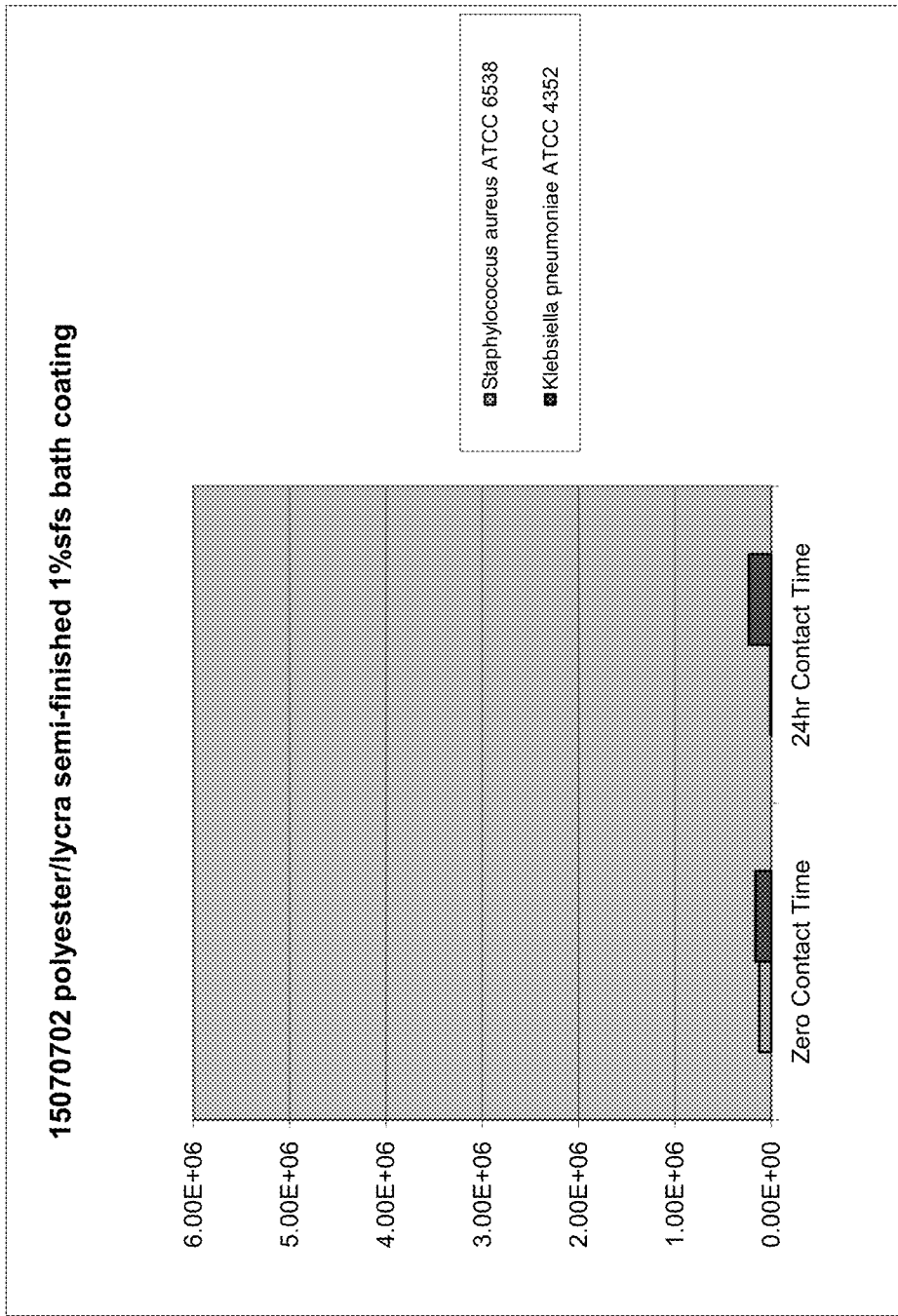

FIG. 90 illustrates bacterial growth results.

Figure 91:
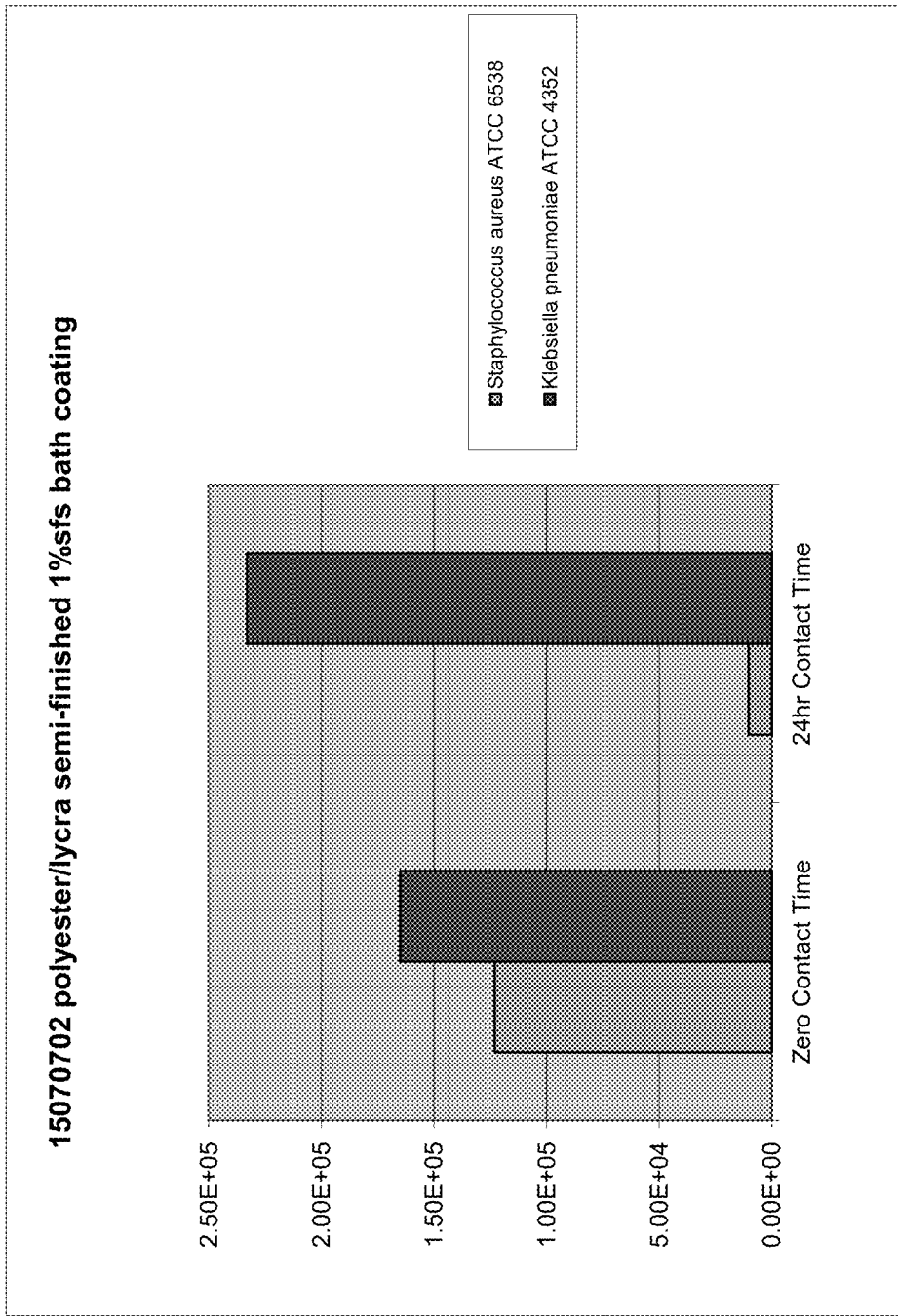

FIG. 91 illustrates bacterial growth results.

Figure 92:
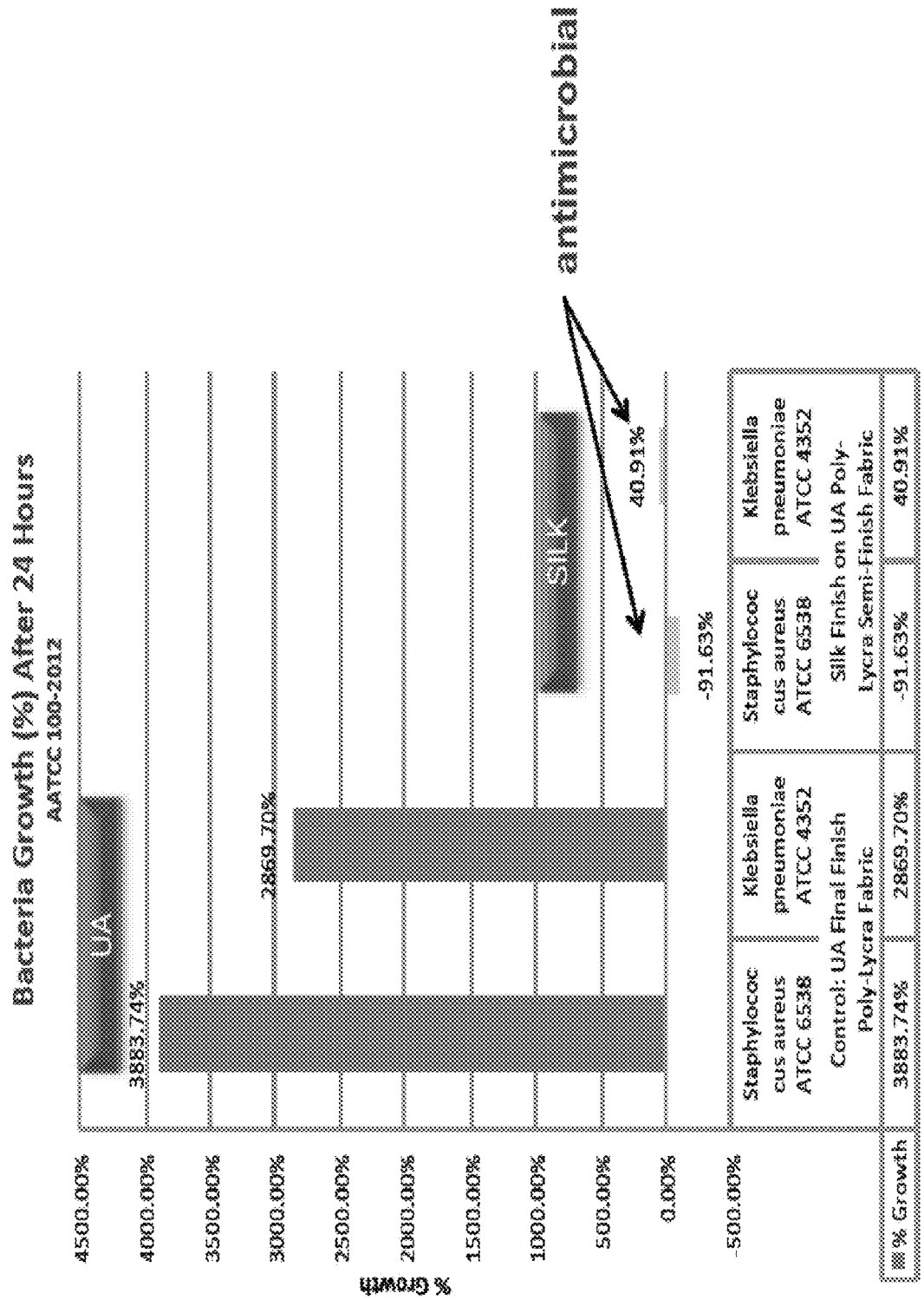

FIG. 92 illustrates bacterial growth results.

Figure 93:
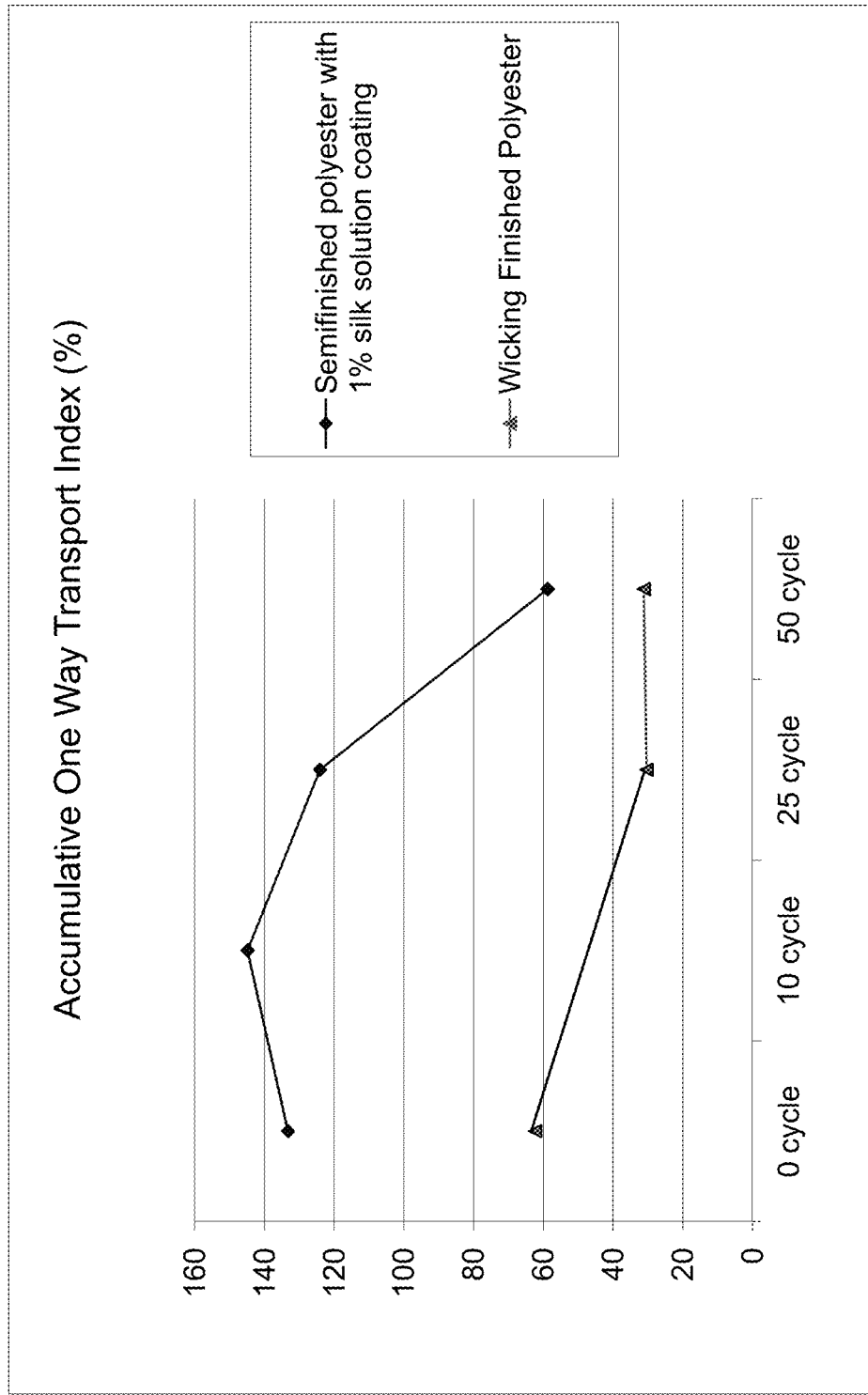

FIG. 93 illustrates accumulative one-way transport index versus fabric washing cycles.

Figure 94:
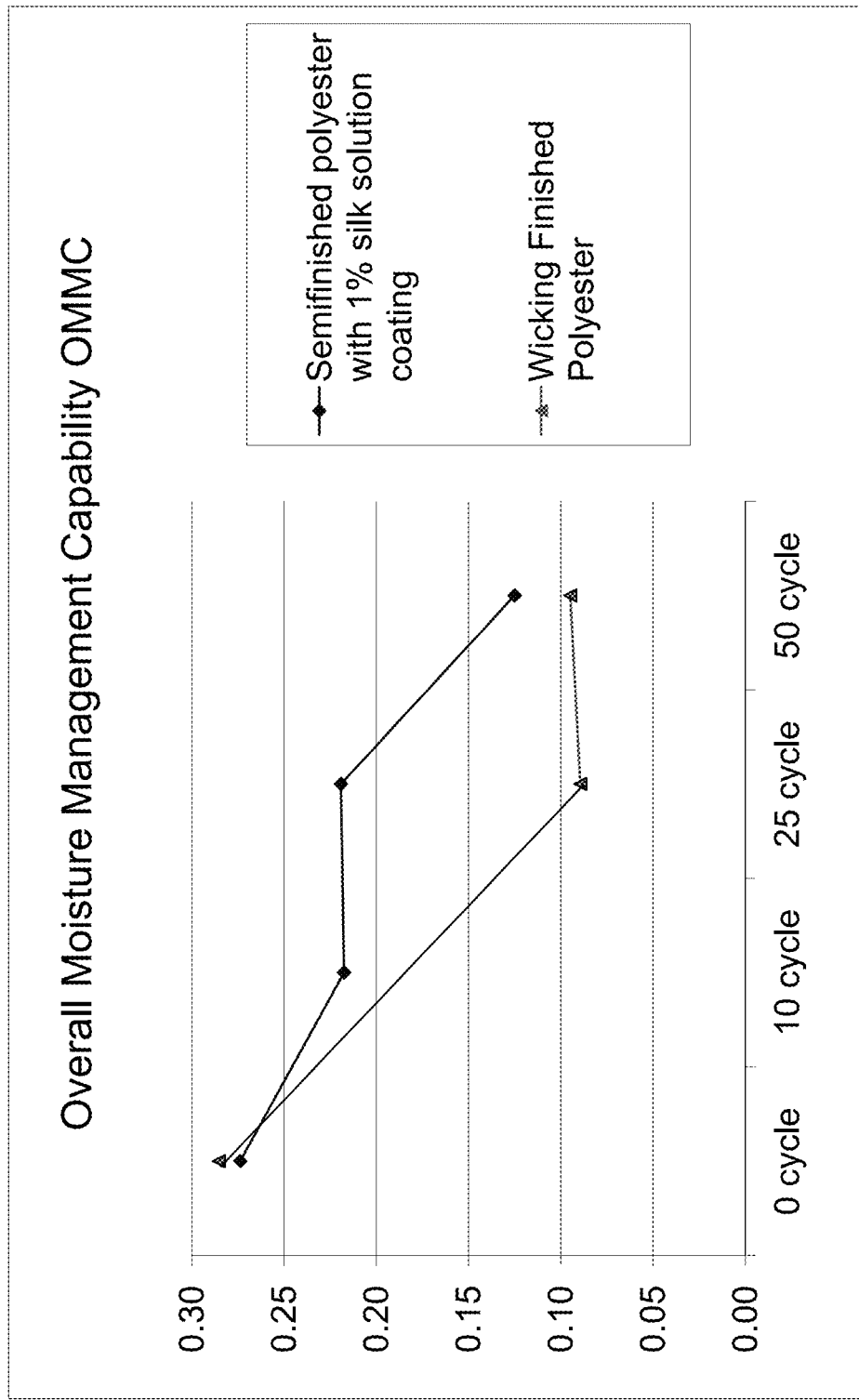

FIG. 94 illustrates overall moisture management capability (OMMC) versus fabric washing cycles.

Figure 95:
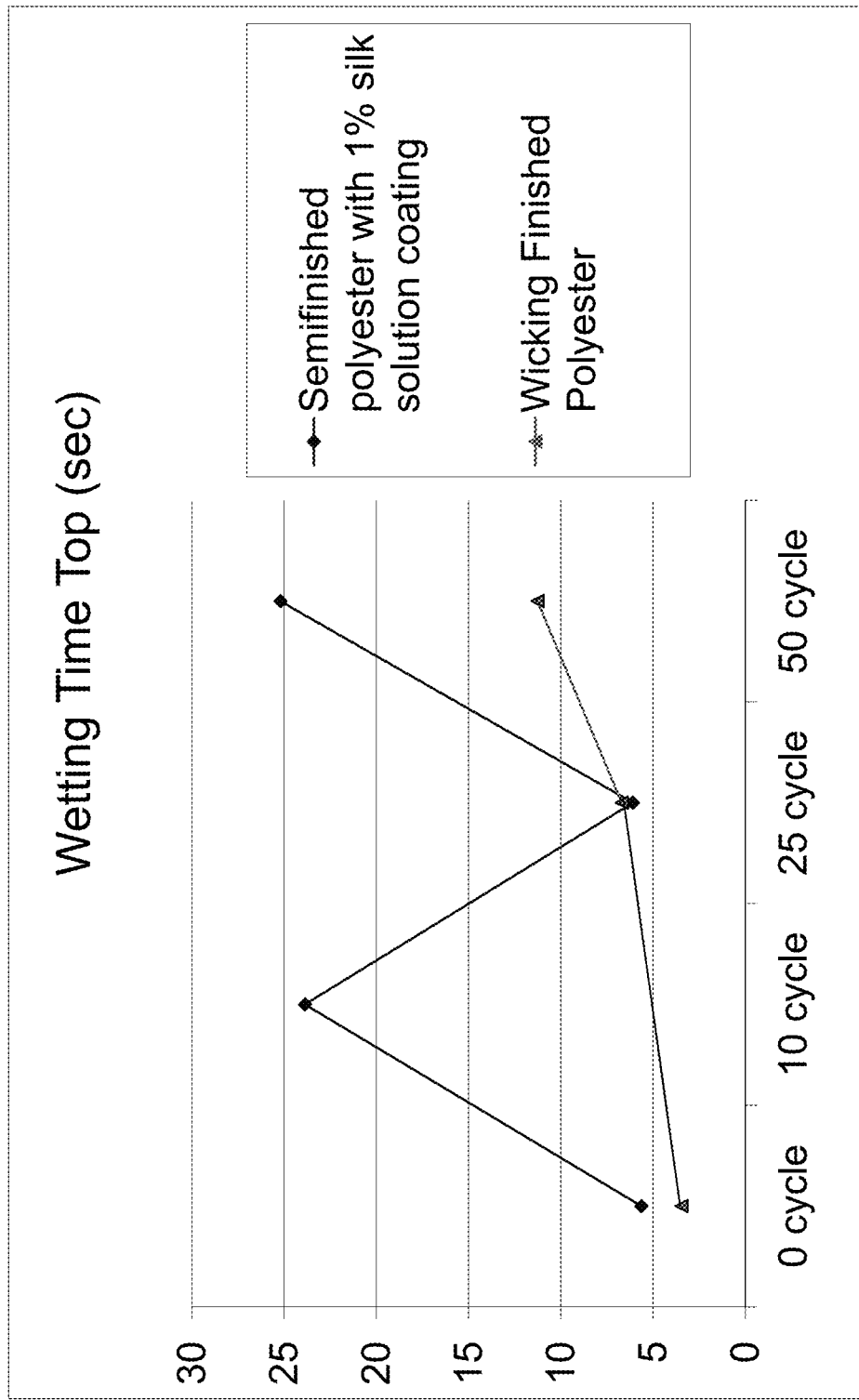

FIG. 95 illustrates wetting time at the top of the fabric versus fabric washing cycles.

Figure 96:
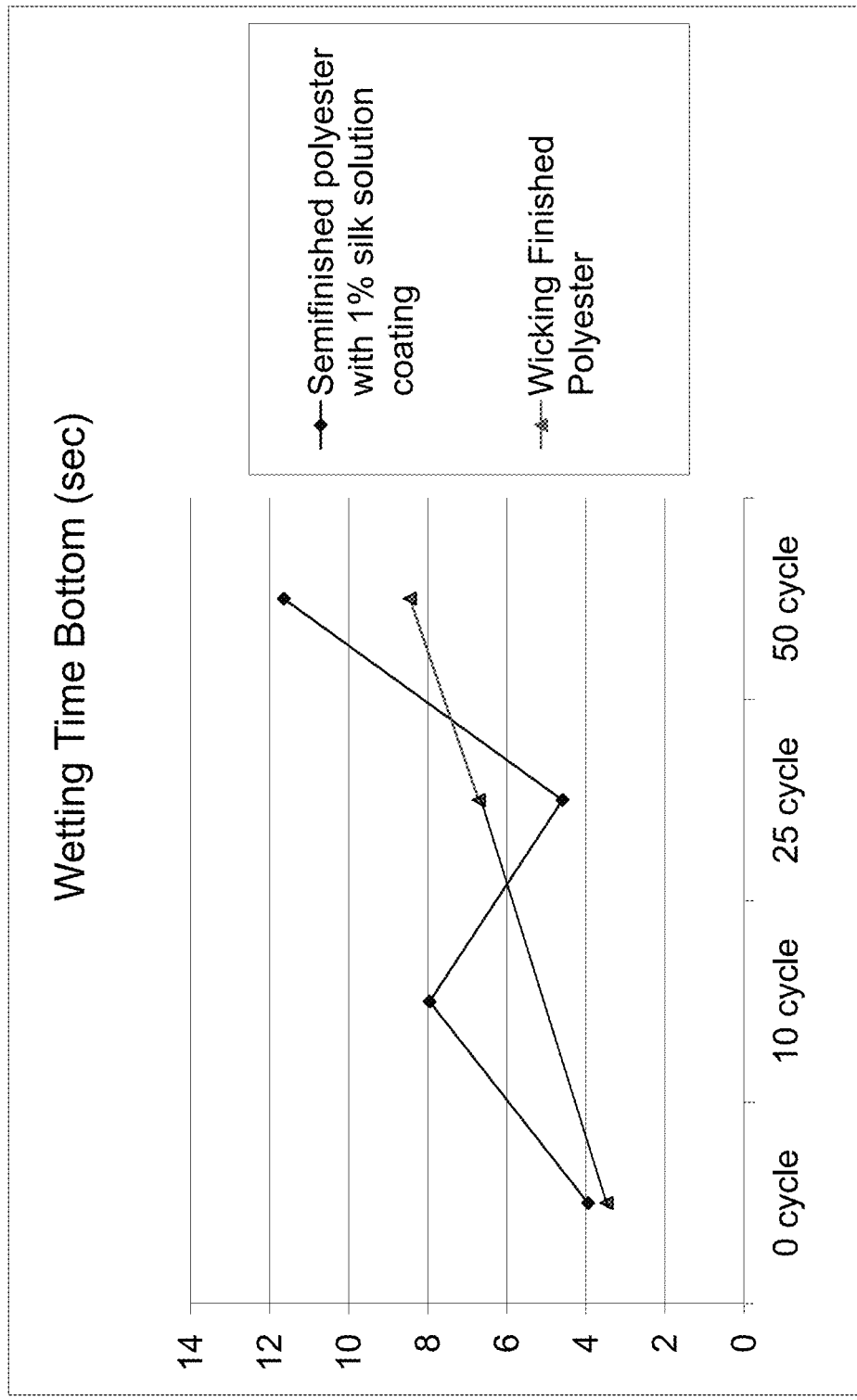

FIG. 96 illustrates wetting time at the bottom of the fabric versus fabric washing cycles.

Figure 97:
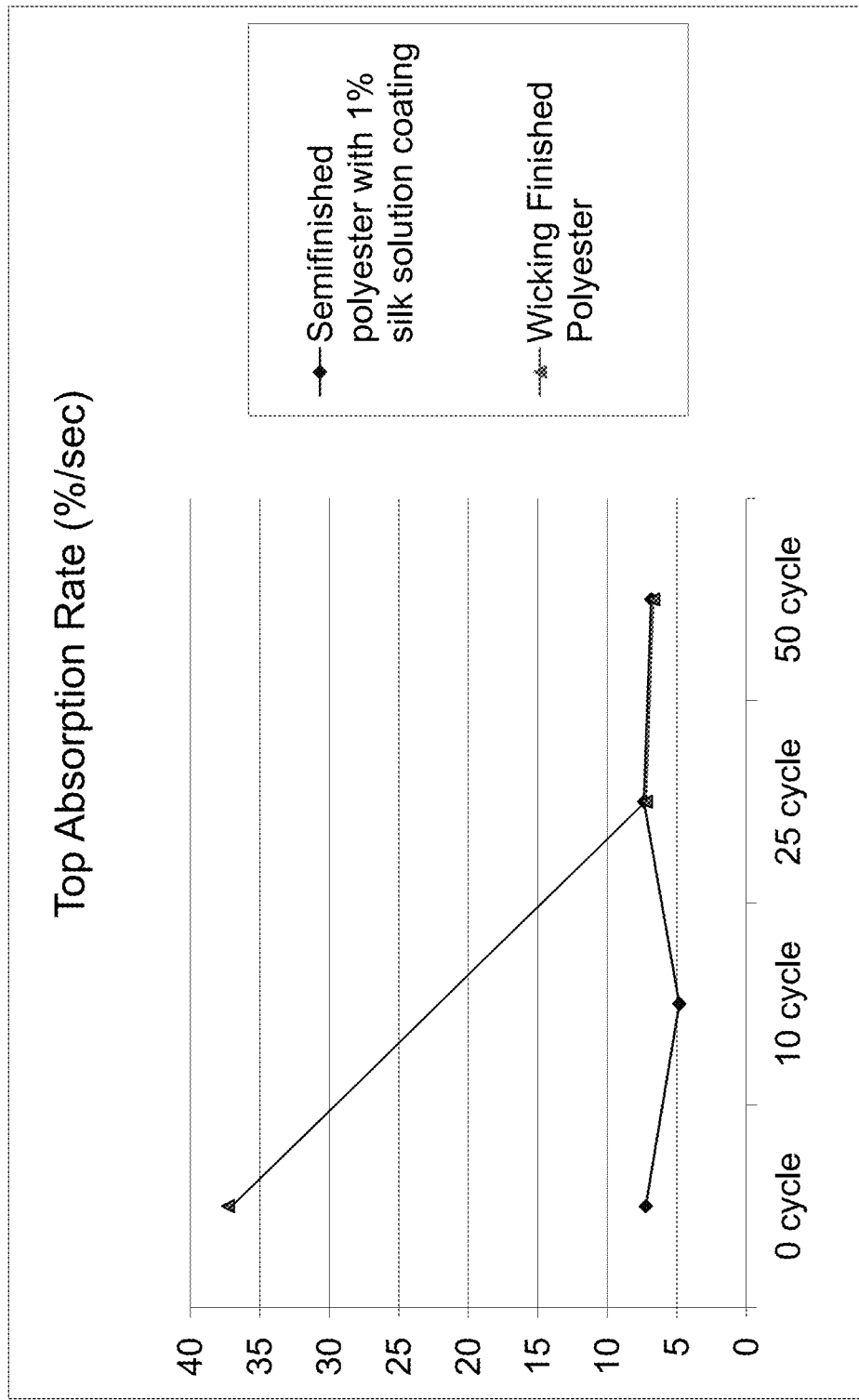

FIG. 97 illustrates absorption rate at the top of the fabric versus fabric washing cycles.

Figure 98:
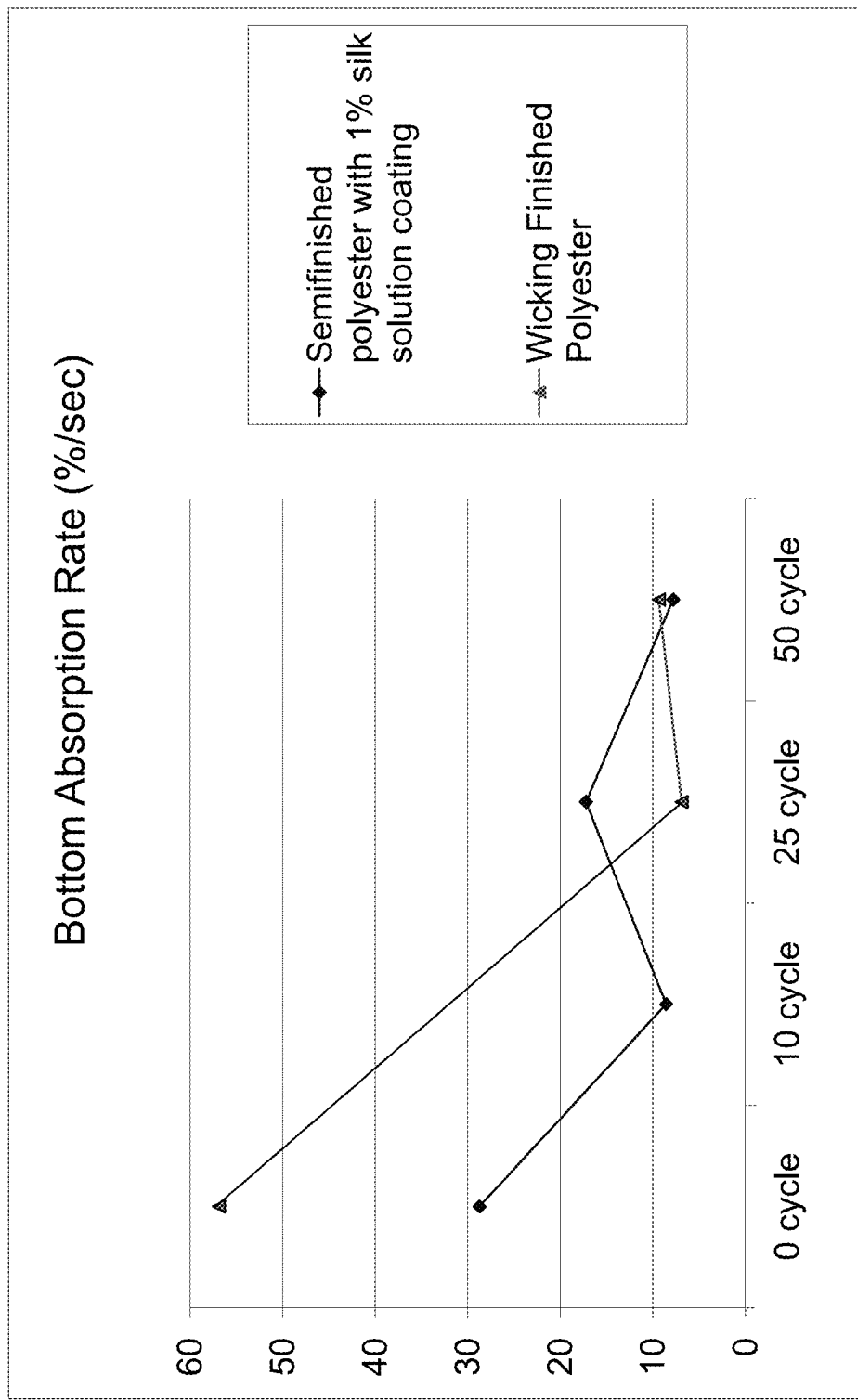

FIG. 98 illustrates absorption rate at the bottom of the fabric versus fabric washing cycles.

Figure 99:
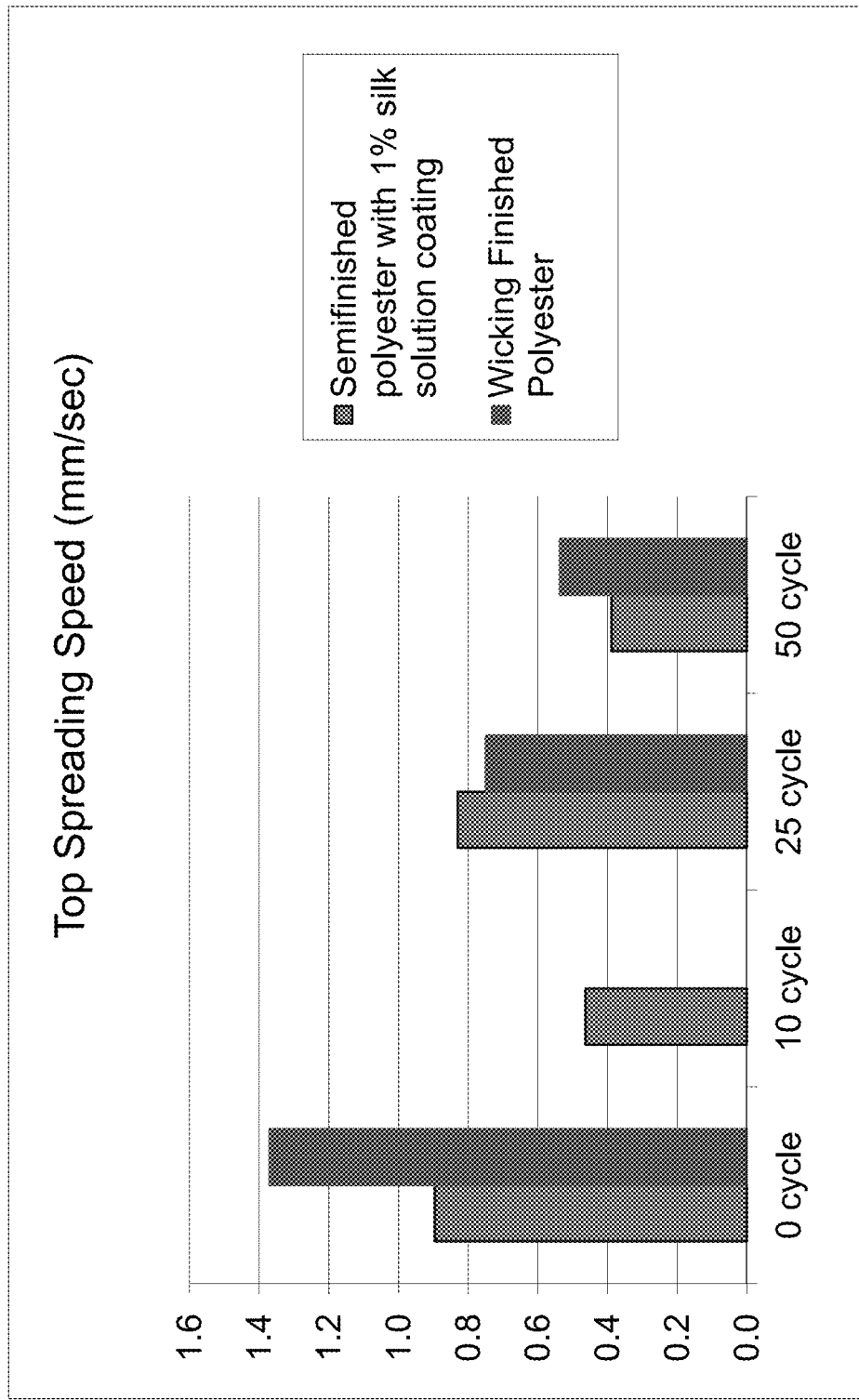

FIG. 99 illustrates spreading speed at the top of the fabric versus fabric washing cycles.

Figure 100:
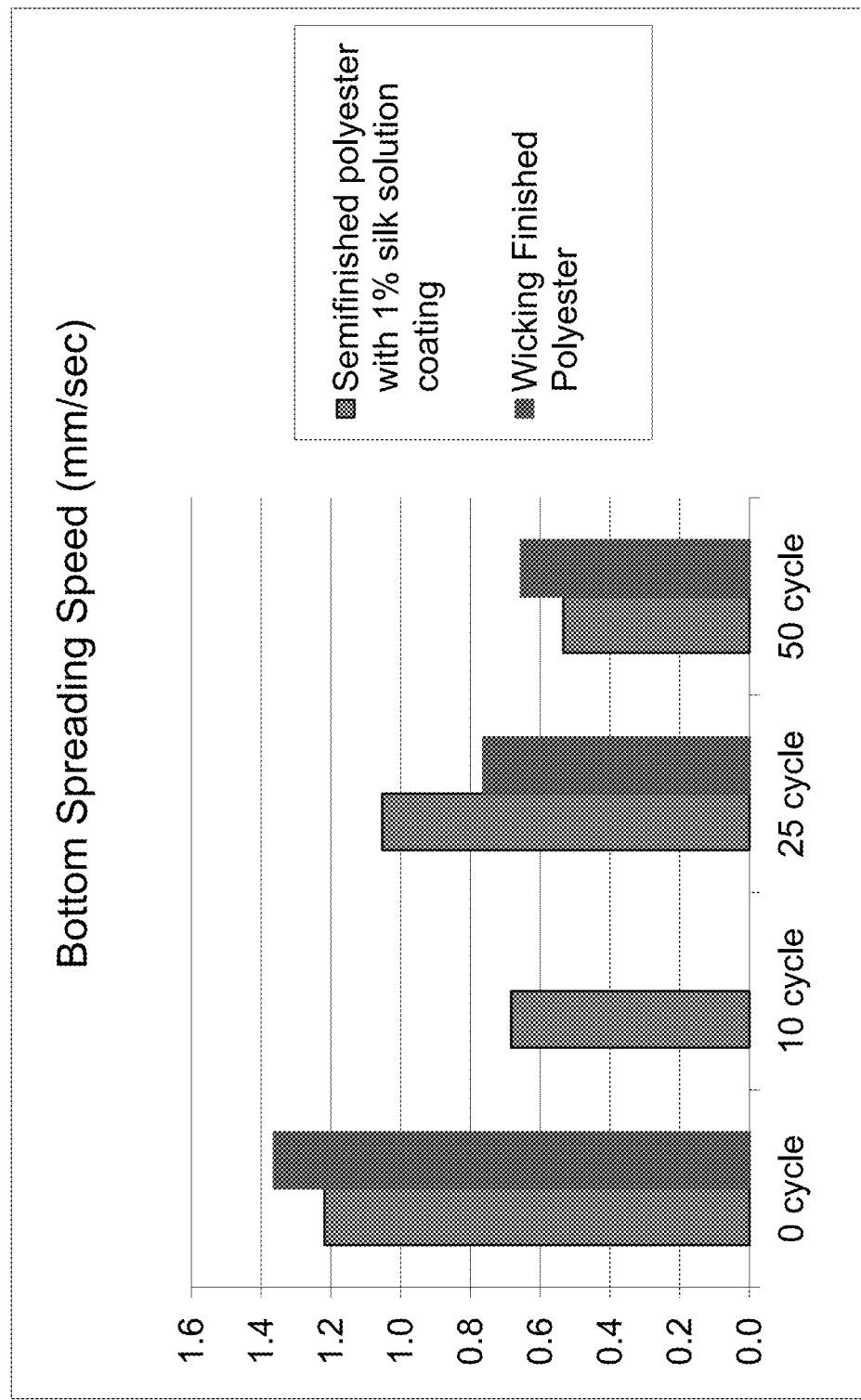

FIG. 100 illustrates spreading speed at the bottom of the fabric versus fabric washing cycles.

Figure 101:
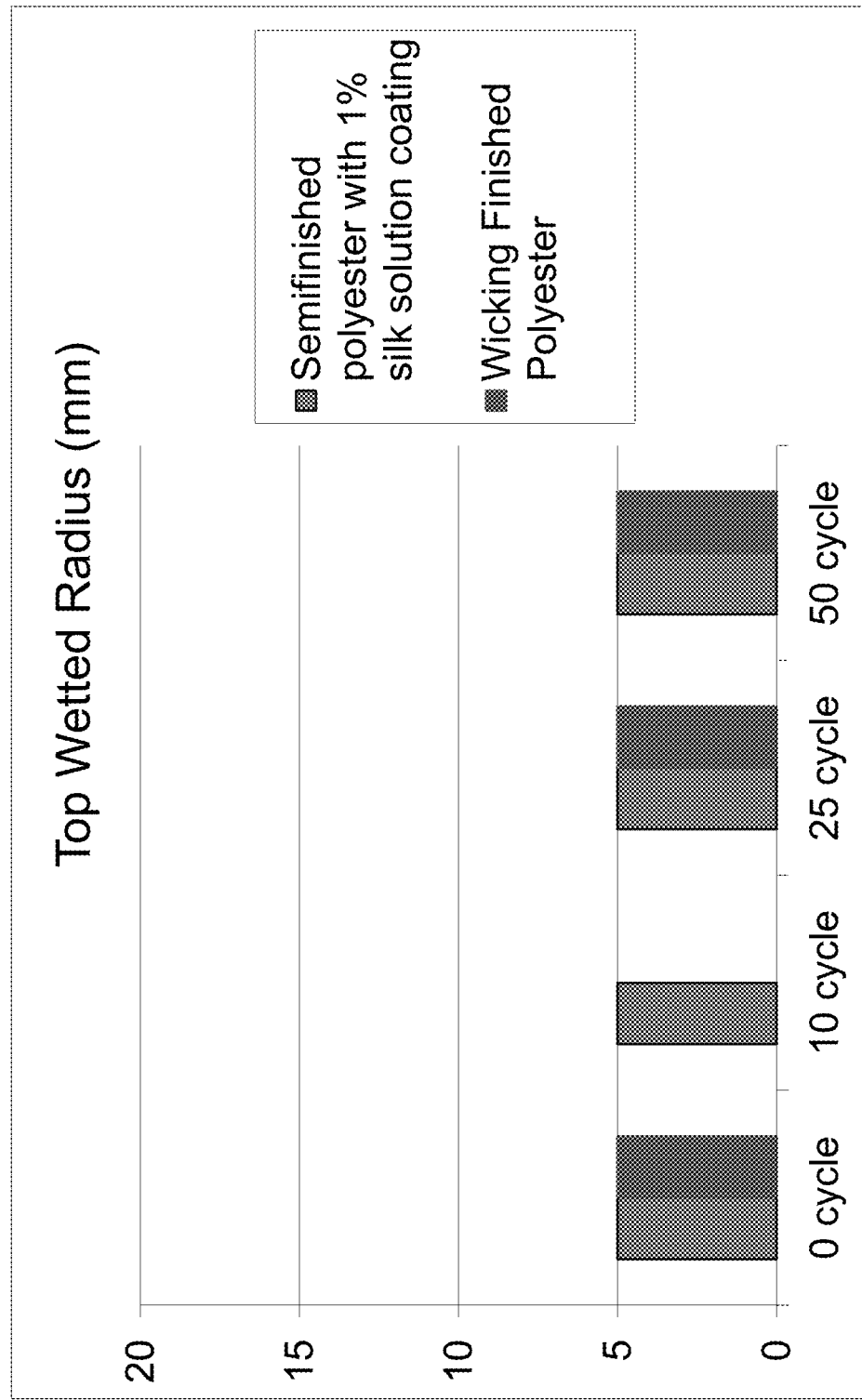

FIG. 101 illustrates wetted radius at the top of the fabric versus fabric washing cycles.

Figure 102:
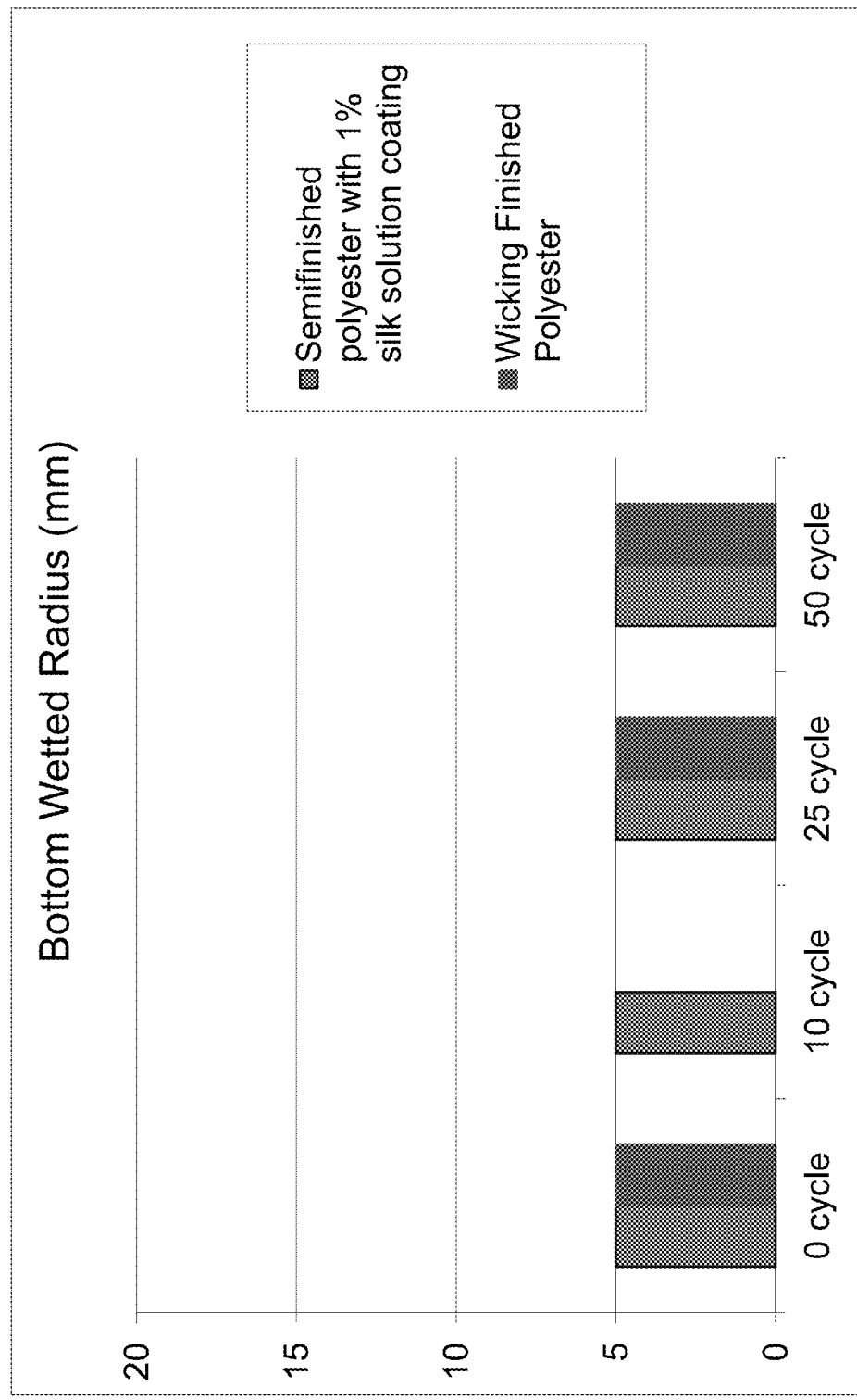

FIG. 102 illustrates wetted radius at the bottom of the fabric versus fabric washing cycles.

Figure 103:
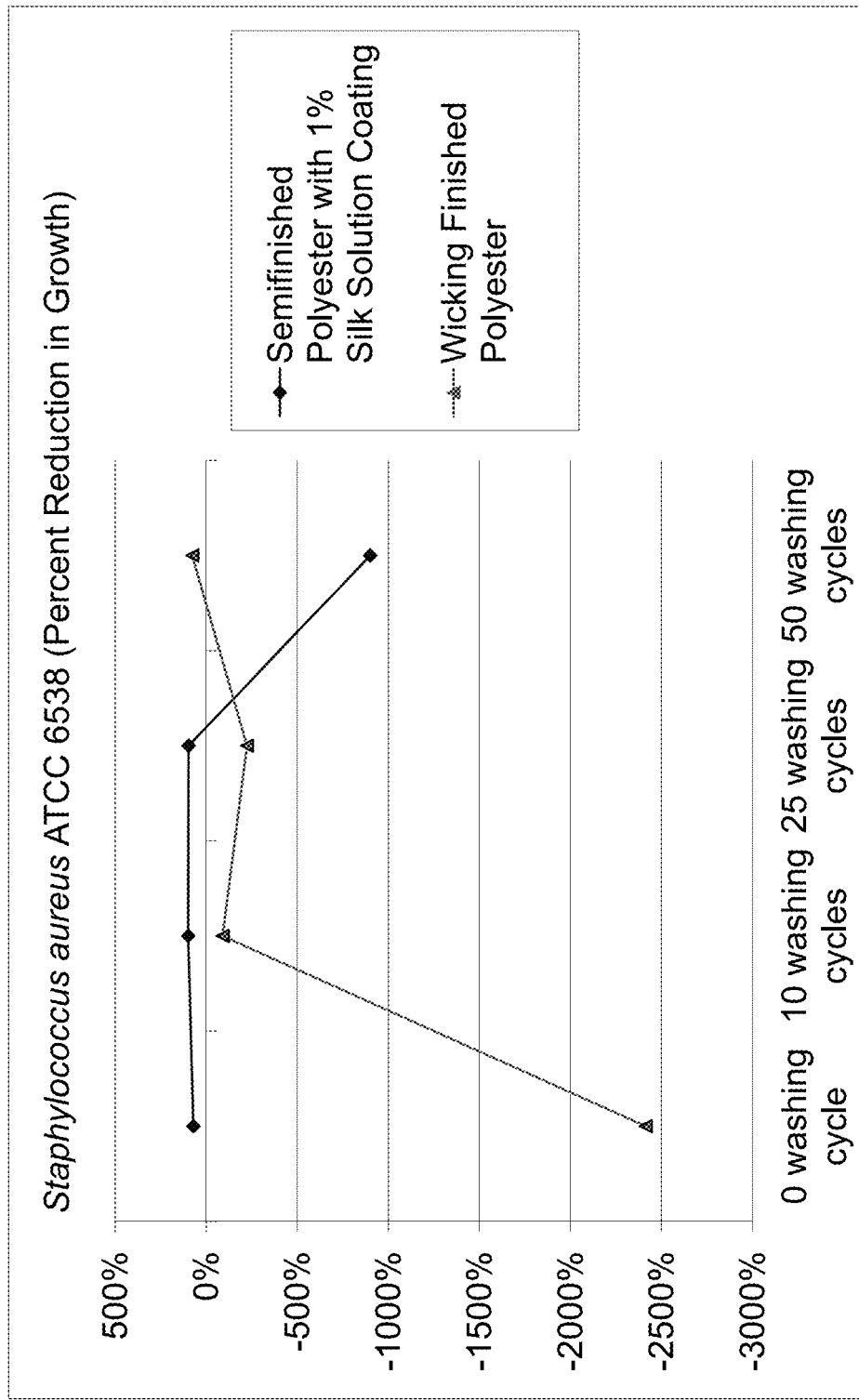

FIG. 103 illustrates percent reduction in growth of *Staphylococcus aureus* ATCC 6538 versus fabric washing cycles.

Figure 104:
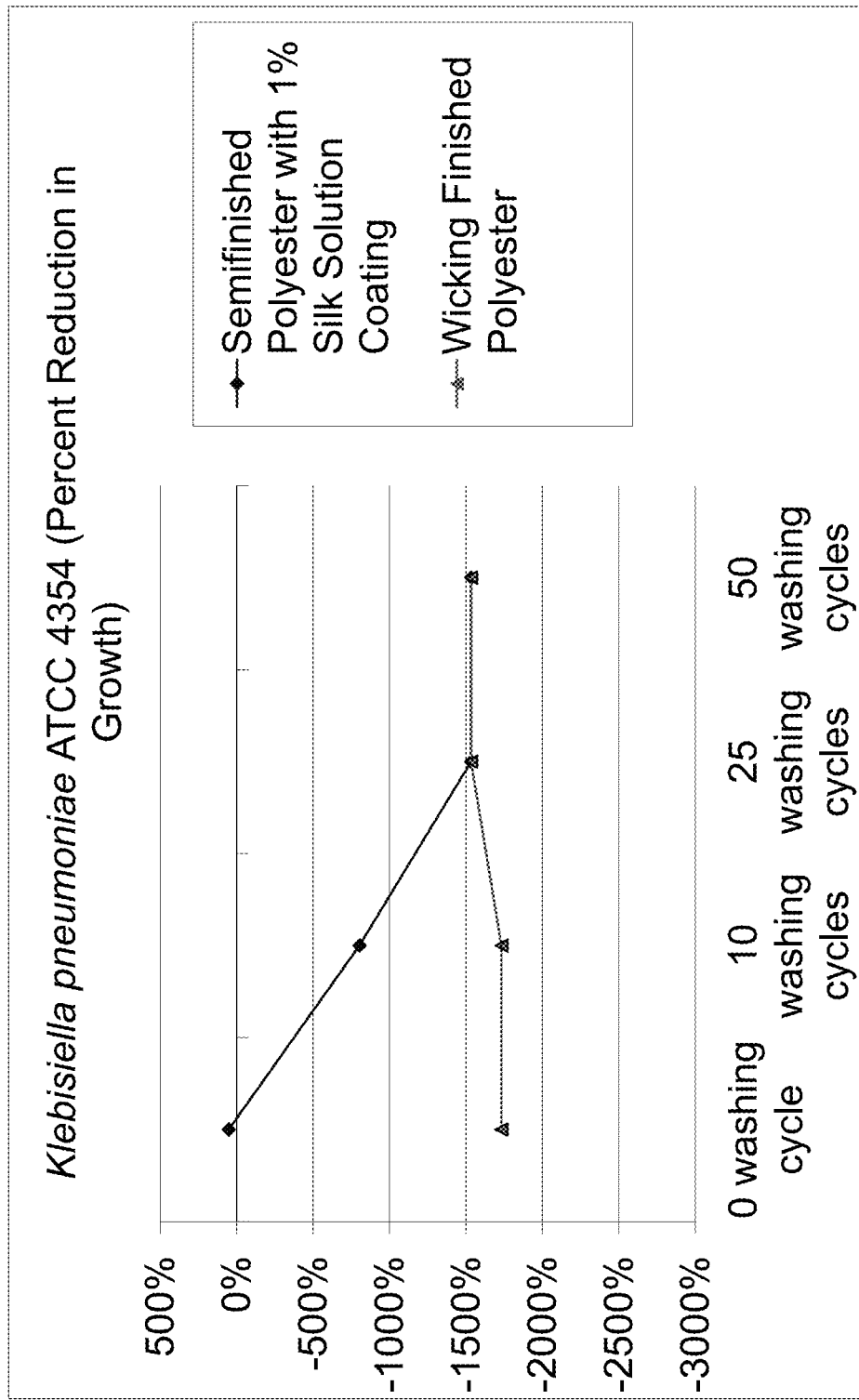

FIG. 104 illustrates percent reduction in growth of Klebisiella pneumoniae ATCC 4354 versus fabric washing cycles.

Figure 105:
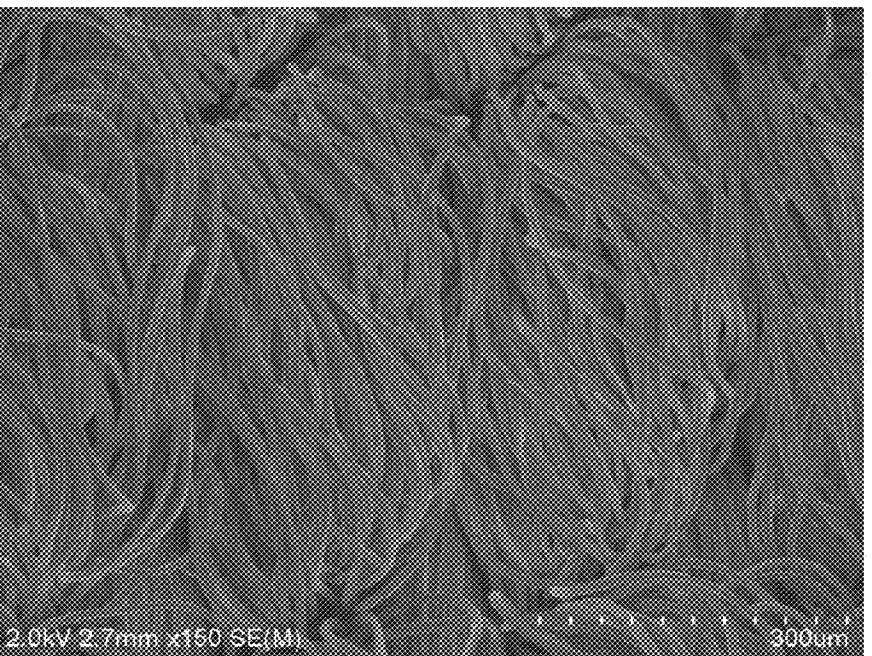

FIG. 105 illustrates a scanning electron microscopy image of fabric sample FAB-01-BATH-B (first view).

Figure 106:
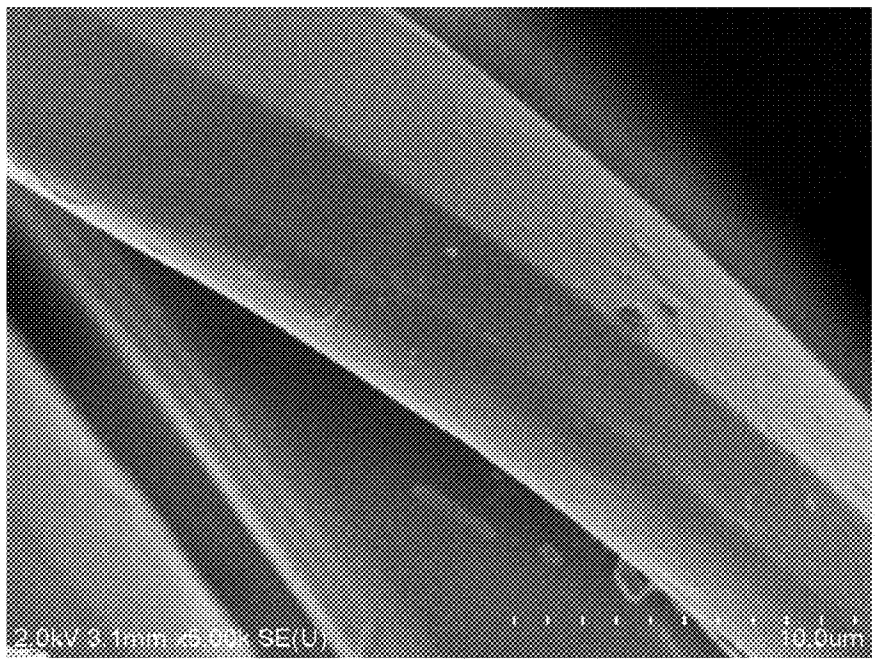

FIG. 106 illustrates a scanning electron microscopy image of fabric sample FAB-01-BATH-B (second view).

Figure 107:
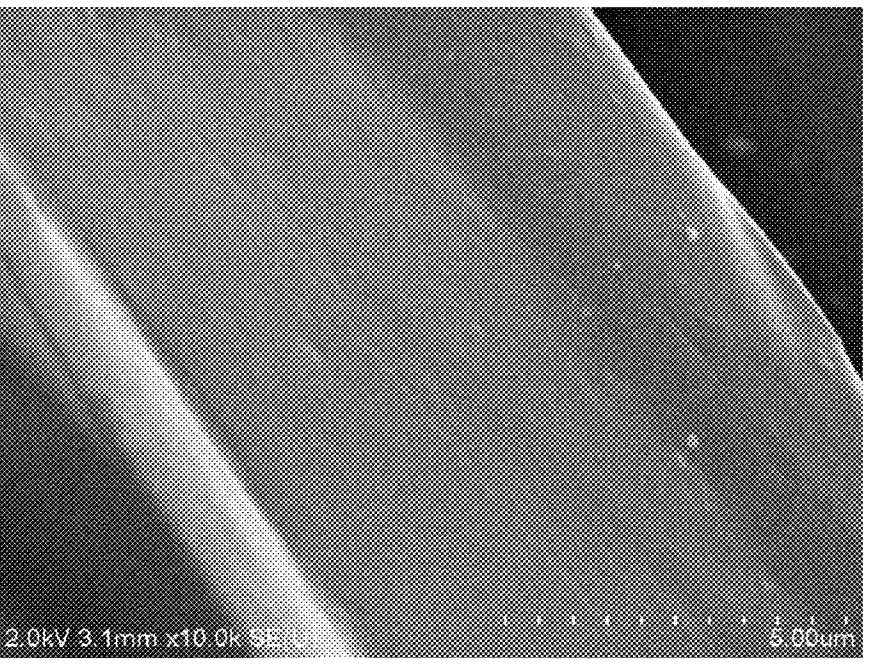

FIG. 107 illustrates a scanning electron microscopy image of fabric sample FAB-01-BATH-B (third view).

Figure 108:

FIG. 108 illustrates a scanning electron microscopy image of fabric sample FAB-01-BATH-B (fourth view).

Figure 109:

FIG. 109 illustrates a scanning electron microscopy image of fabric sample FAB-01-SPRAY-B (first view).

Figure 110:
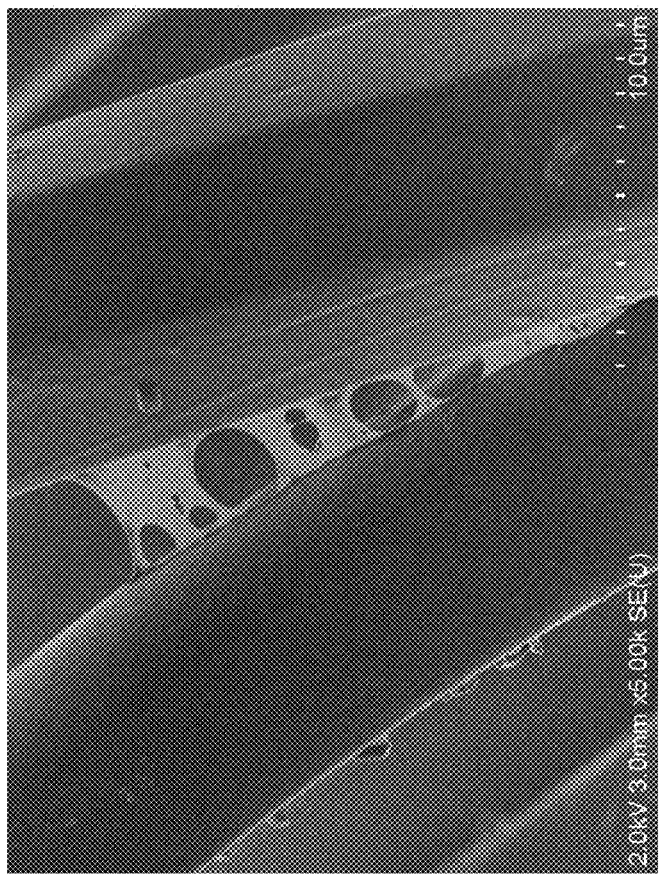

FIG. 110 illustrates a scanning electron microscopy image of fabric sample FAB-01-SPRAY-B (second view).

Figure 111:
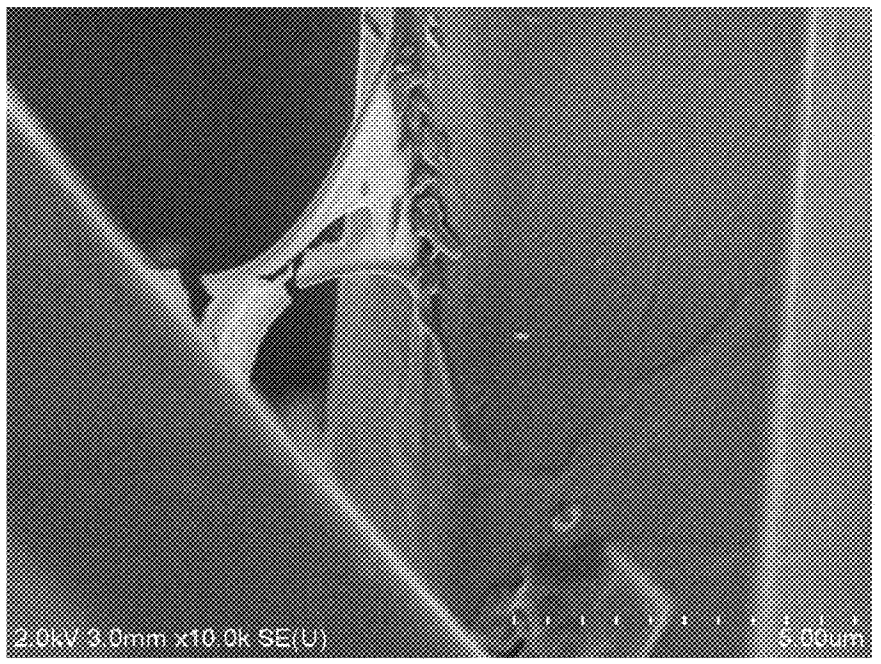

FIG. 111 illustrates a scanning electron microscopy image of fabric sample FAB-01-SPRAY-B (third view).

Figure 112:

FIG. 112 illustrates a scanning electron microscopy image of fabric sample FAB-01-SPRAY-B (fourth view).

Figure 113:

FIG. 113 illustrates a scanning electron microscopy image of fabric sample FAB-01-SPRAY-B (fifth view).

Figure 114:
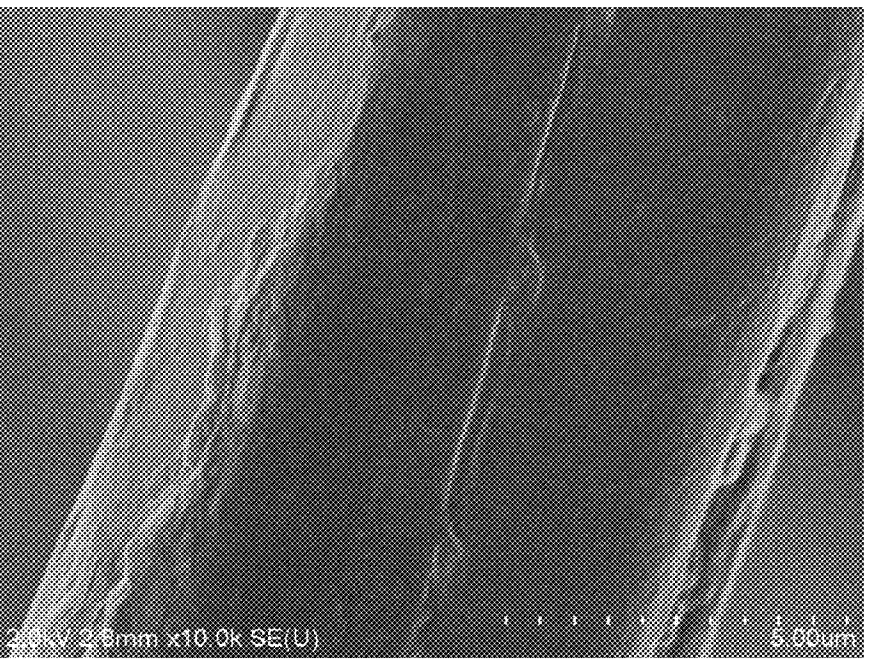

FIG. 114 illustrates a scanning electron microscopy image of fabric sample FAB-01-SPRAY-B (sixth view).

Figure 115:

FIG. 115 illustrates a scanning electron microscopy image of fabric sample FAB-01-SPRAY-B (seventh view).

Figure 116:

FIG. 116 illustrates a scanning electron microscopy image of fabric sample FAB-01-SPRAY-C (first view).

Figure 117:

FIG. 117 illustrates a scanning electron microscopy image of fabric sample FAB-01-SPRAY-C (second view).

Figure 118:

FIG. 118 illustrates a scanning electron microscopy image of fabric sample FAB-01-SPRAY-C (third view).

Figure 119:

FIG. 119 illustrates a scanning electron microscopy image of fabric sample FAB-01-SPRAY-C (fourth view).

Figure 120:

FIG. 120 illustrates a scanning electron microscopy image of fabric sample FAB-01-SPRAY-C (fifth view).

Figure 121:

FIG. 121 illustrates a scanning electron microscopy image of fabric sample FAB-01-STEN-C (first view).

Figure 122:

FIG. 122 illustrates a scanning electron microscopy image of fabric sample FAB-01-STEN-C (second view).

Figure 123:

FIG. 123 illustrates a scanning electron microscopy image of fabric sample FAB-01-STEN-C (third view).

Figure 124:
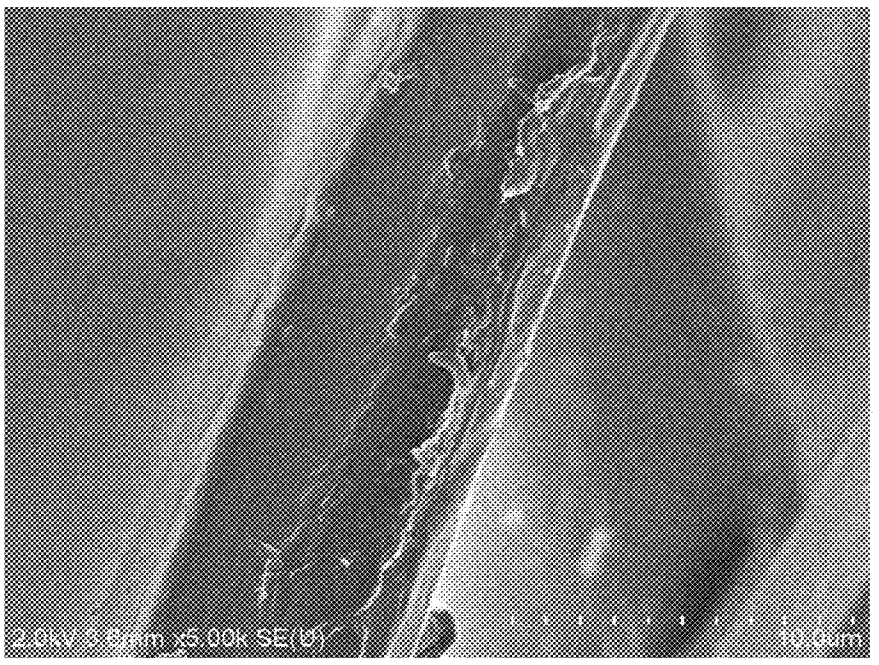

FIG. 124 illustrates a scanning electron microscopy image of fabric sample FAB-01-STEN-C (fourth view).

Figure 125:
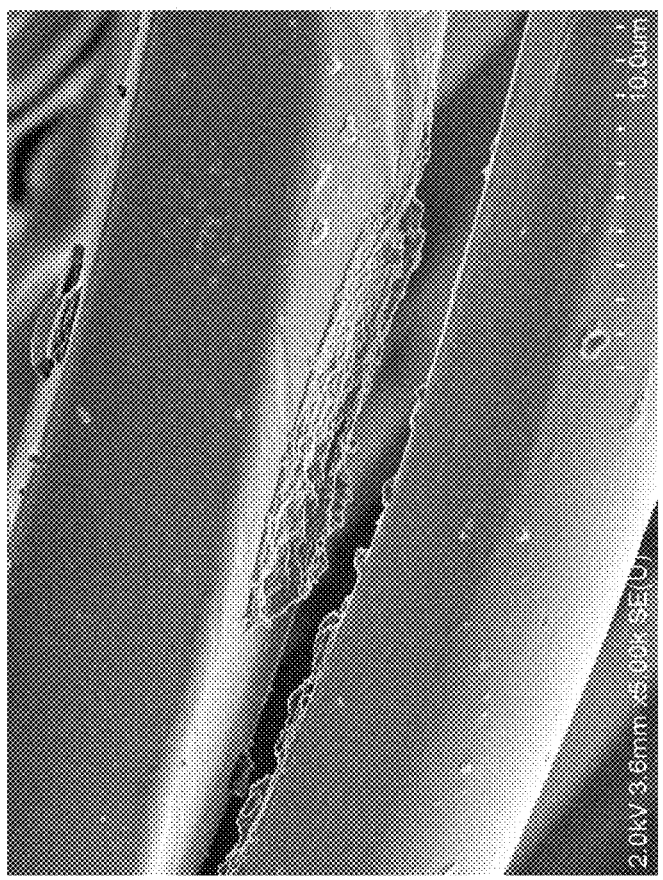

FIG. 125 illustrates a scanning electron microscopy image of fabric sample FAB-01-STEN-C (fifth view).

Figure 126:
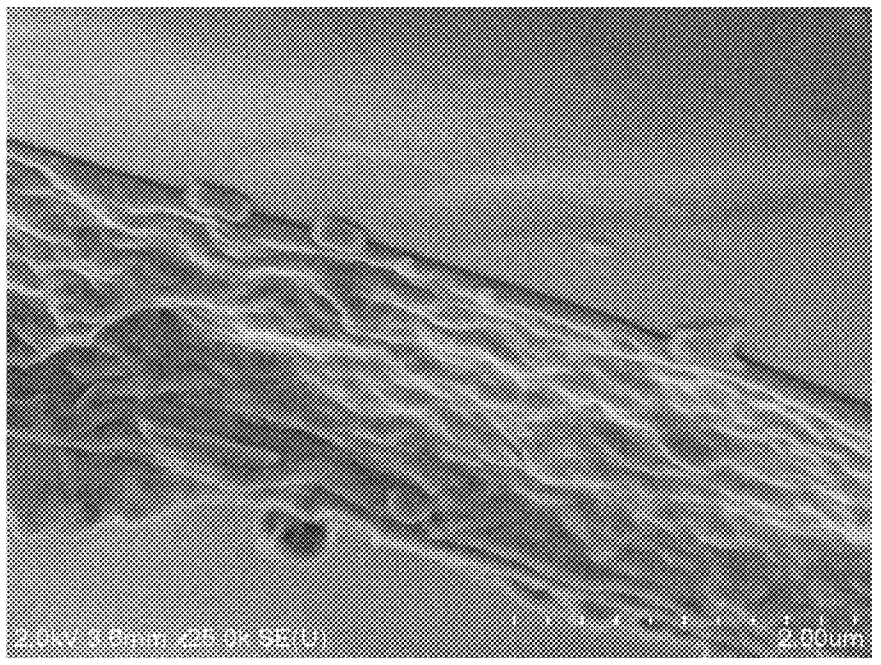

FIG. 126 illustrates a scanning electron microscopy image of fabric sample FAB-01-STEN-C (sixth view).

Figure 127:

FIG. 127 illustrates a scanning electron microscopy image of fabric sample FAB-01-STEN-C (seventh view).

Figure 128:

FIG. 128 illustrates a scanning electron microscopy image of fabric sample FAB-01-STEN-C (eighth view).

Figure 129:
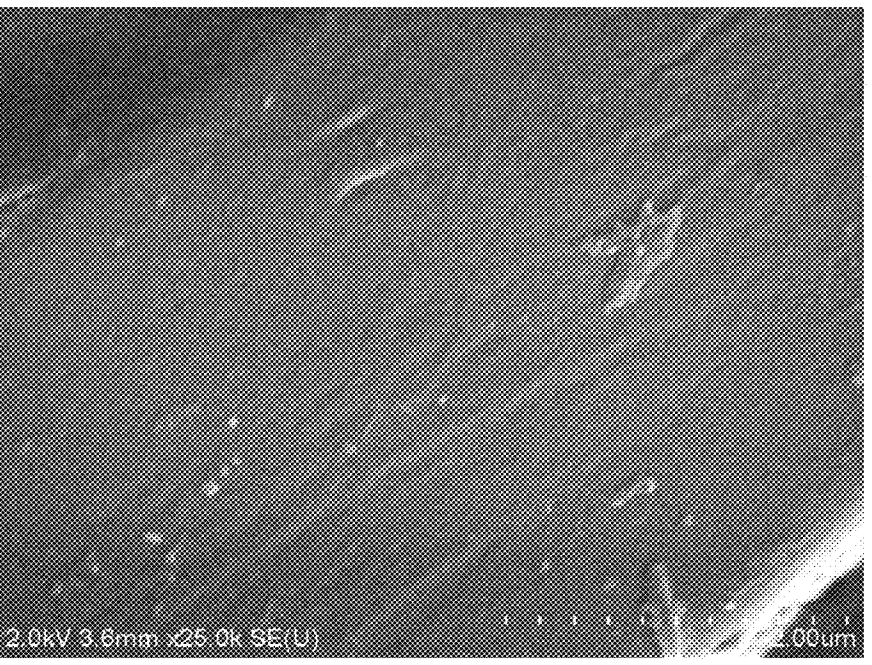

FIG. 129 illustrates a scanning electron microscopy image of fabric sample FAB-01-STEN-C (ninth view).

Figure 130:

FIG. 130 illustrates a scanning electron microscopy image of fabric sample FAB-10-BATH-B (first view).

Figure 131:
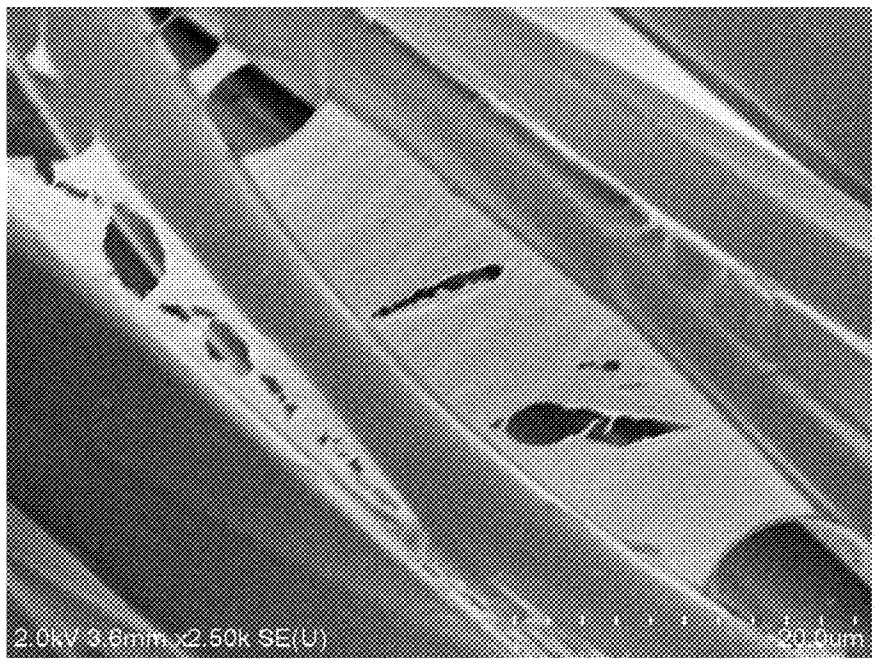

FIG. 131 illustrates a scanning electron microscopy image of fabric sample FAB-10-BATH-B (second view).

Figure 132:
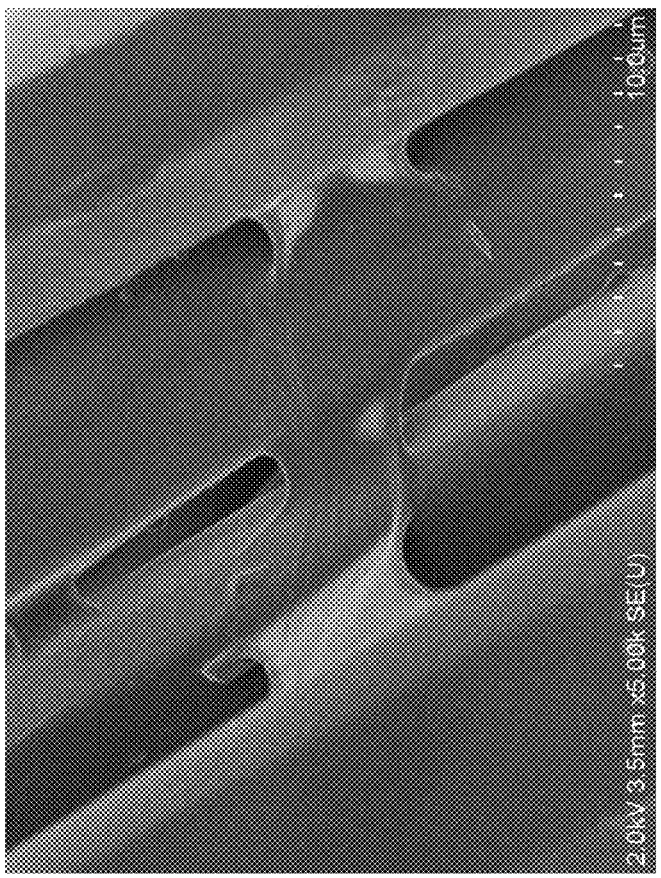

FIG. 132 illustrates a scanning electron microscopy image of fabric sample FAB-10-BATH-B (third view).

Figure 133:
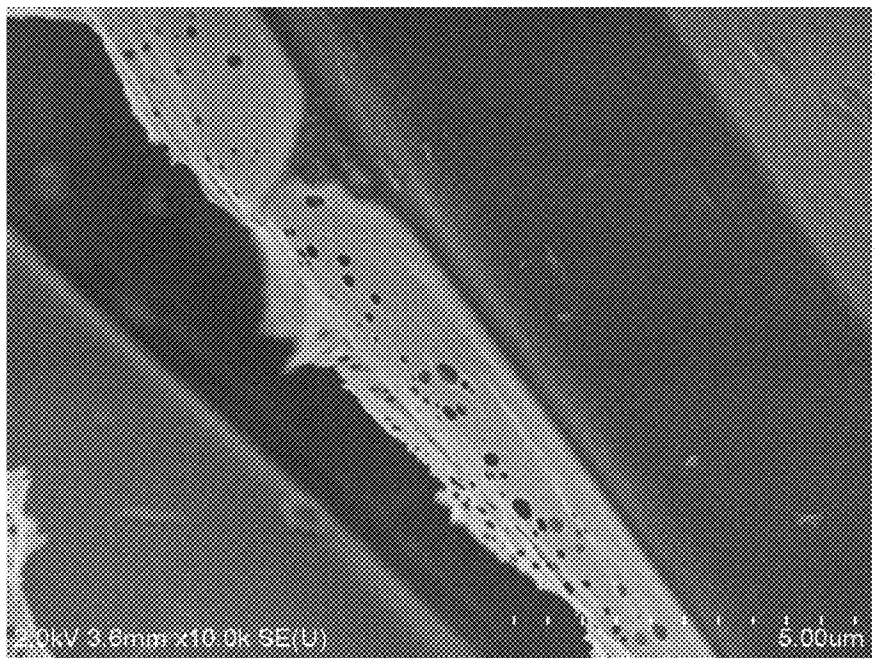

FIG. 133 illustrates a scanning electron microscopy image of fabric sample FAB-10-BATH-B (fourth view).

Figure 134:
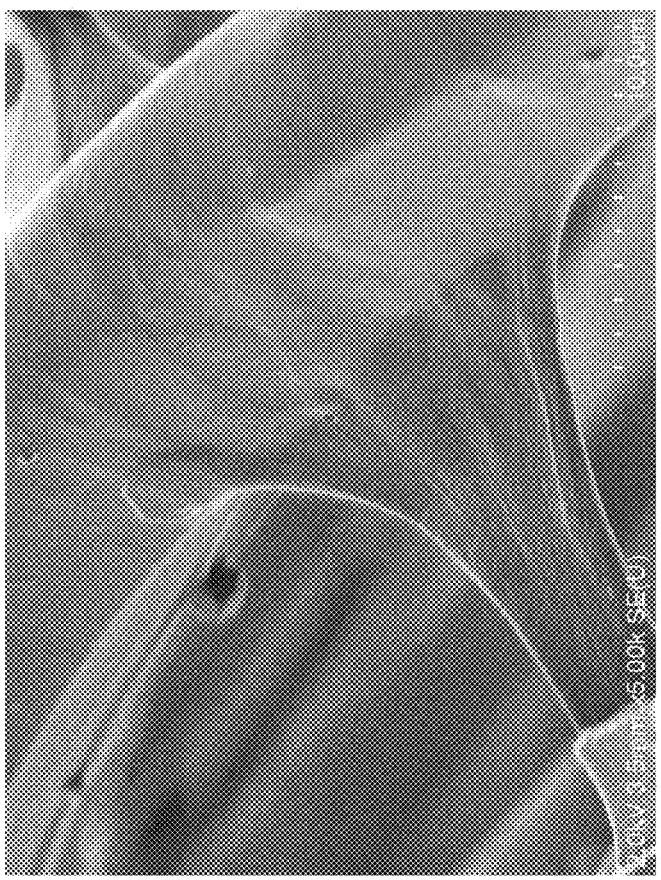

FIG. 134 illustrates a scanning electron microscopy image of fabric sample FAB-10-BATH-B (fifth view).

Figure 135:
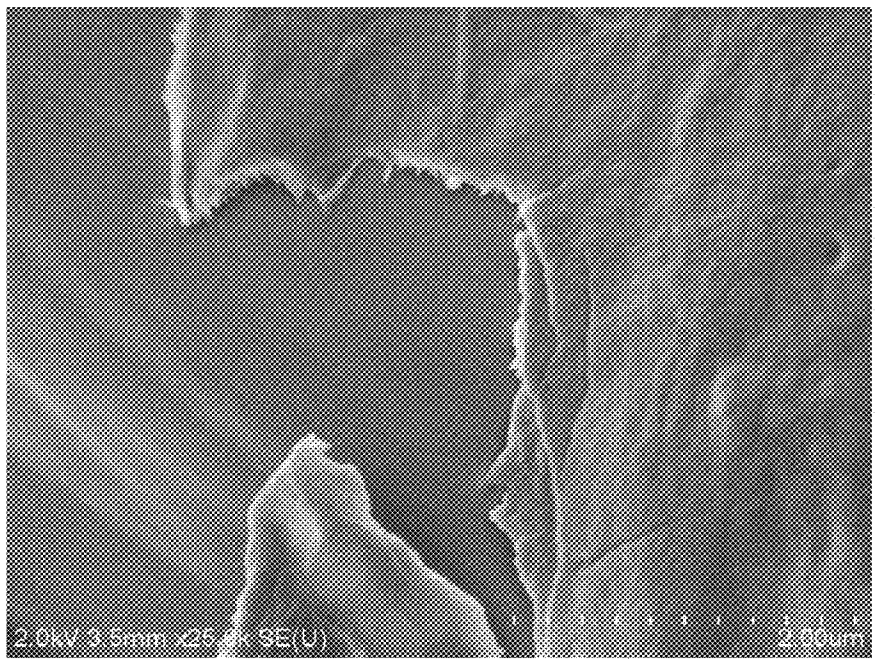

FIG. 135 illustrates a scanning electron microscopy image of fabric sample FAB-10-BATH-B (sixth view).

Figure 136:

FIG. 136 illustrates a scanning electron microscopy image of fabric sample FAB-10-BATH-B (seventh view).

Figure 137:
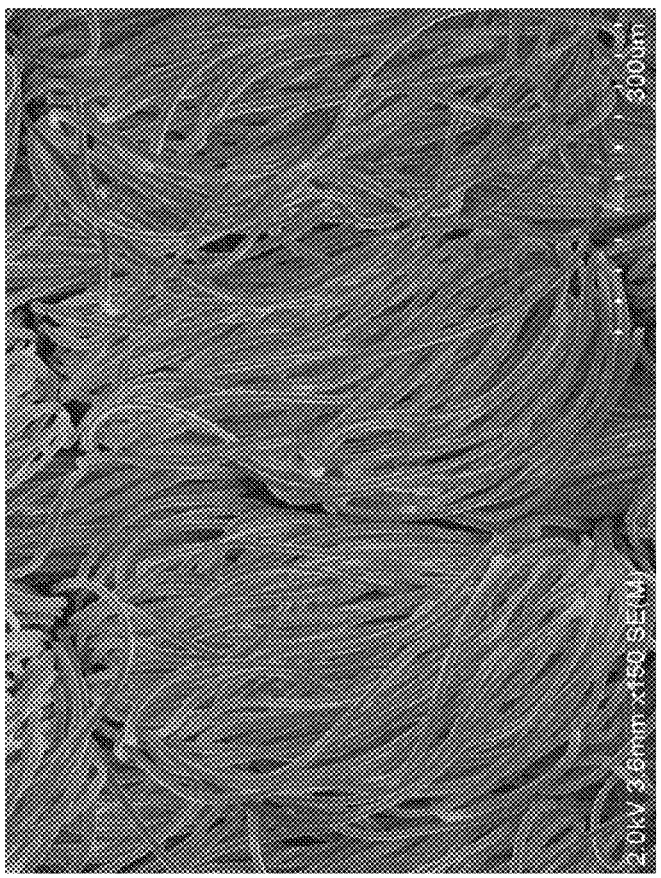

FIG. 137 illustrates a scanning electron microscopy image of fabric sample FAB-10-BATH-C (first view).

Figure 138:

FIG. 138 illustrates a scanning electron microscopy image of fabric sample FAB-10-BATH-C (second view).

Figure 139:
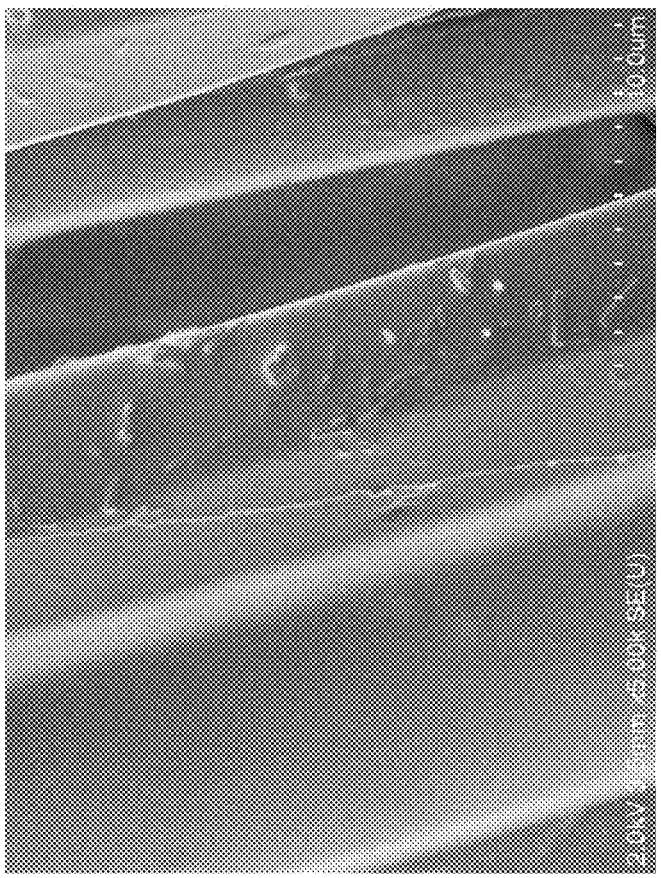

FIG. 139 illustrates a scanning electron microscopy image of fabric sample FAB-10-BATH-C (third view).

Figure 140:
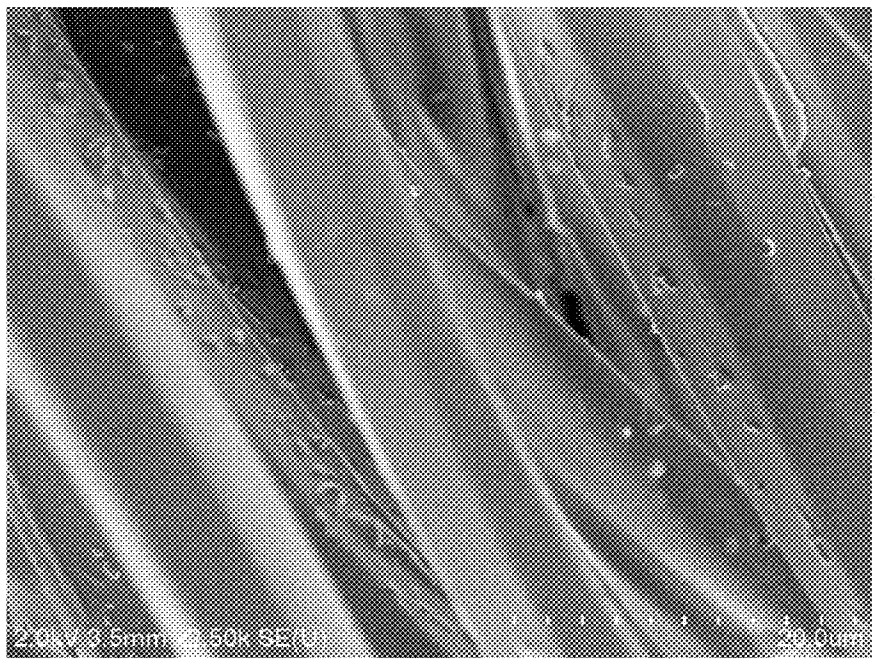

FIG. 140 illustrates a scanning electron microscopy image of fabric sample FAB-10-BATH-C (fourth view).

Figure 141:
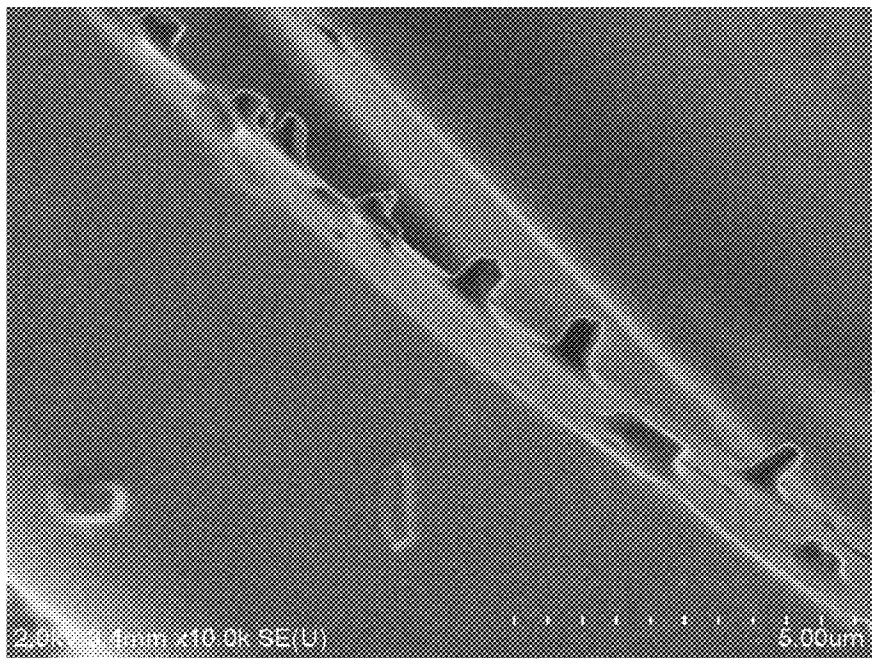

FIG. 141 illustrates a scanning electron microscopy image of fabric sample FAB-10-BATH-C (fifth view).

Figure 142:
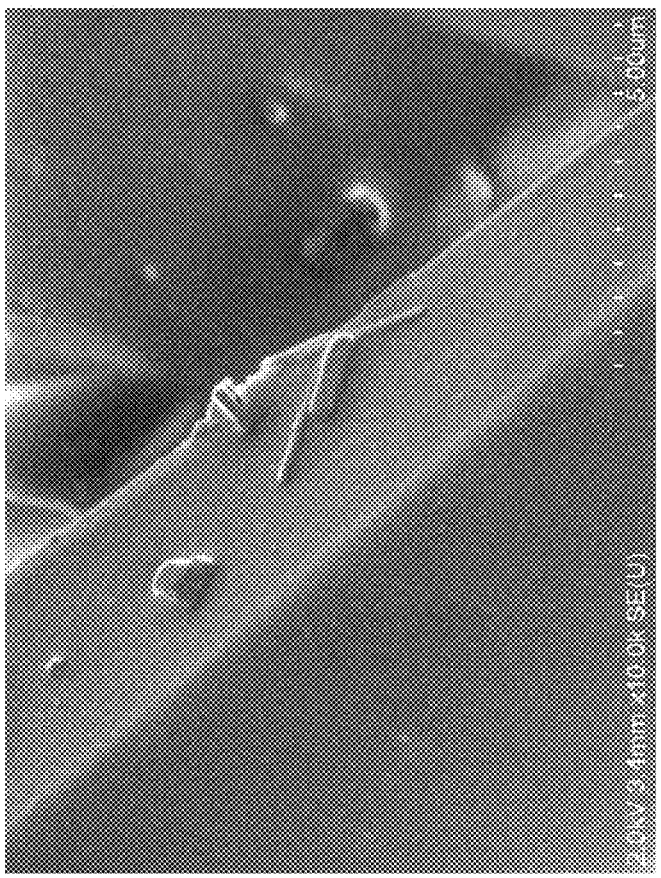

FIG. 142 illustrates a scanning electron microscopy image of fabric sample FAB-10-BATH-C (sixth view).

Figure 143:
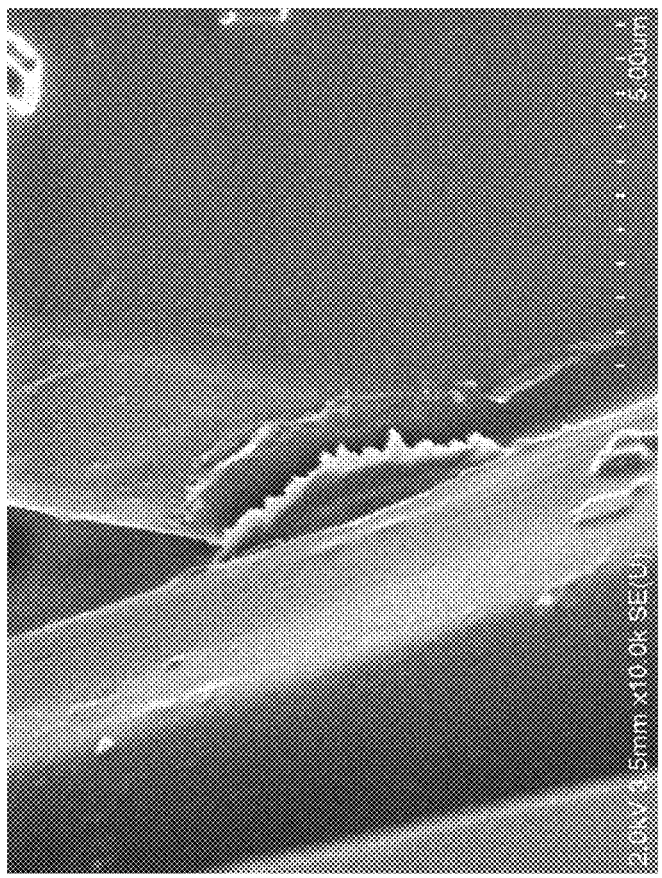

FIG. 143 illustrates a scanning electron microscopy image of fabric sample FAB-10-BATH-C (seventh view).

Figure 144:
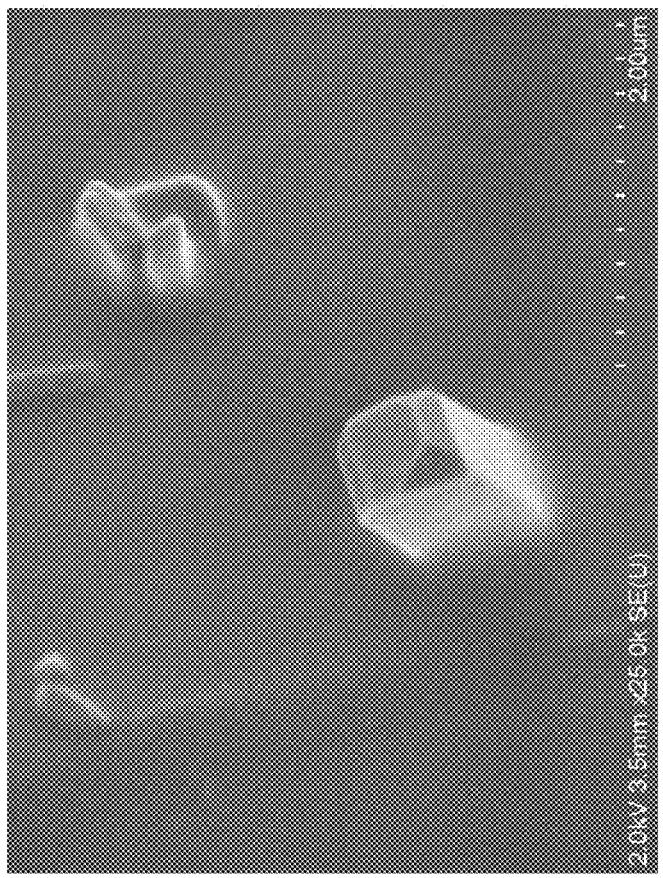

FIG. 144 illustrates a scanning electron microscopy image of fabric sample FAB-10-BATH-C (eighth view).

Figure 145:
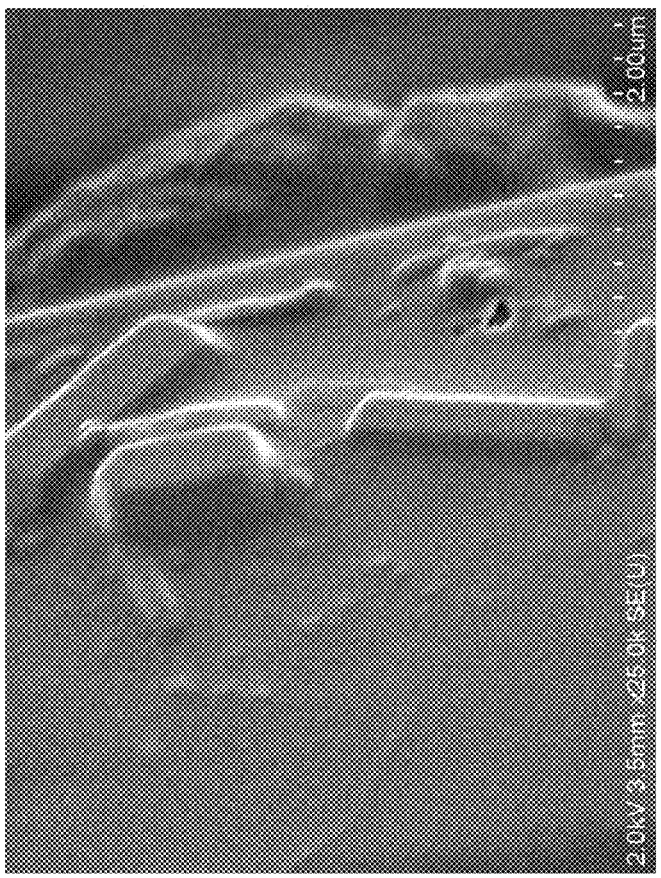

FIG. 145 illustrates a scanning electron microscopy image of fabric sample FAB-10-BATH-C (ninth view).

Figure 146:

FIG. 146 illustrates a scanning electron microscopy image of fabric sample FAB-10-SPRAY-B (first view).

Figure 147:
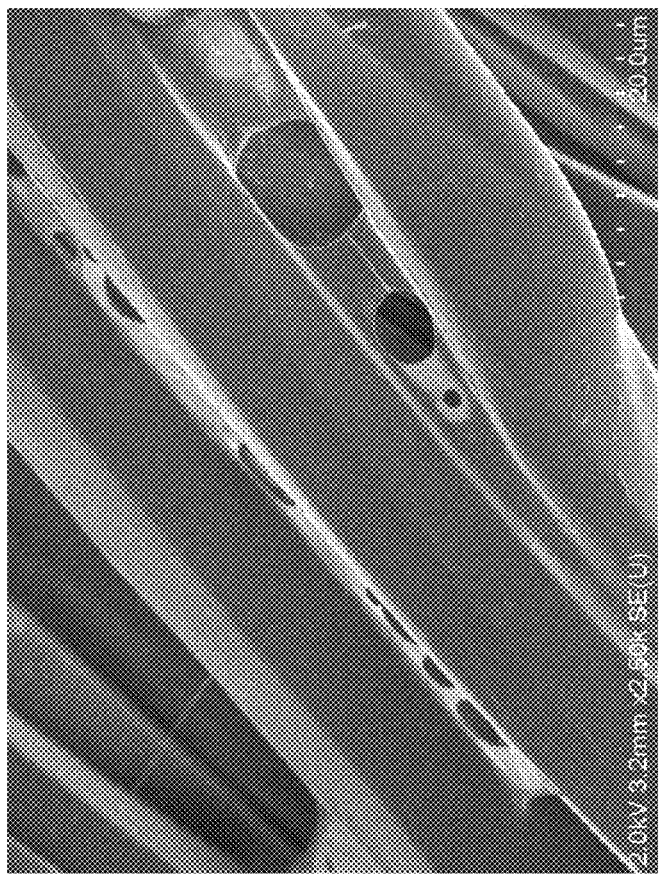

FIG. 147 illustrates a scanning electron microscopy image of fabric sample FAB-10-SPRAY-B (second view).

Figure 148:
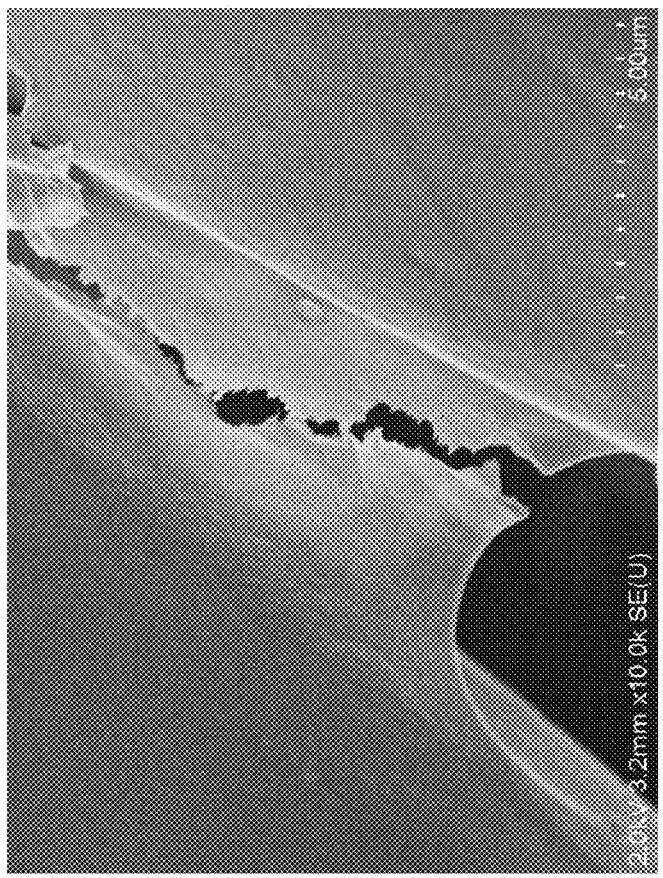

FIG. 148 illustrates a scanning electron microscopy image of fabric sample FAB-10-SPRAY-B (third view).

Figure 149:
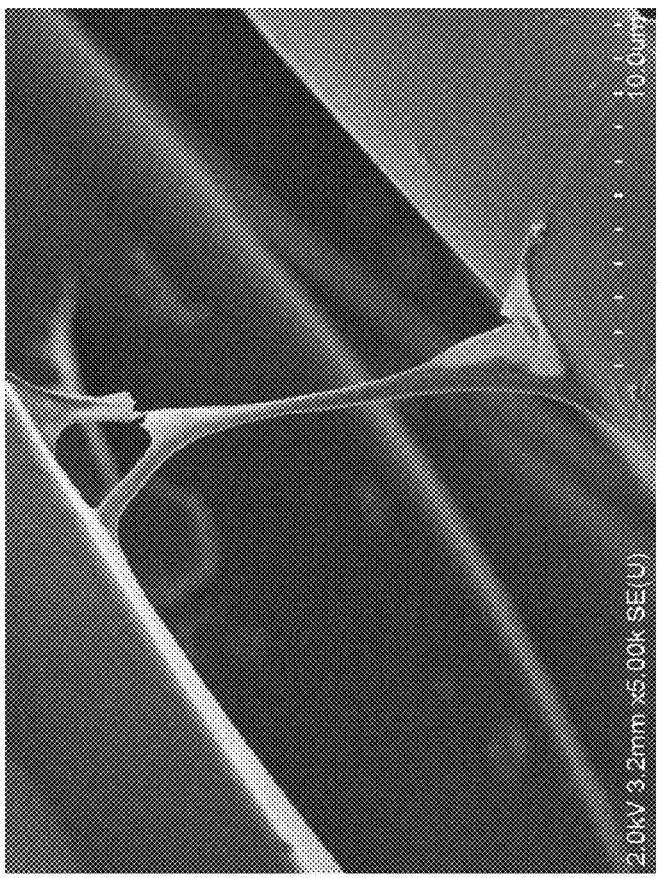

FIG. 149 illustrates a scanning electron microscopy image of fabric sample FAB-10-SPRAY-B (fourth view).

Figure 150:
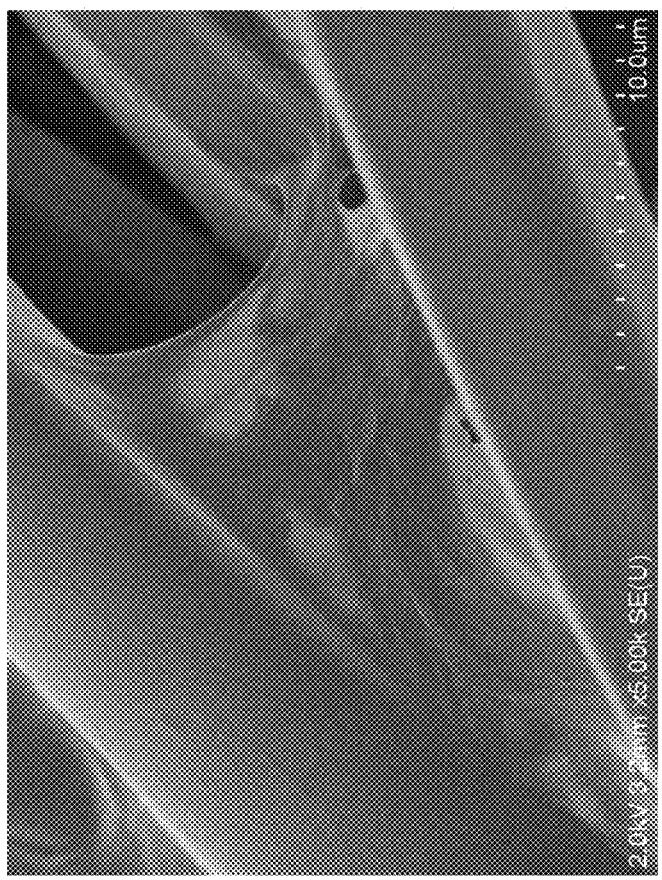

FIG. 150 illustrates a scanning electron microscopy image of fabric sample FAB-10-SPRAY-B (fifth view).

Figure 151:
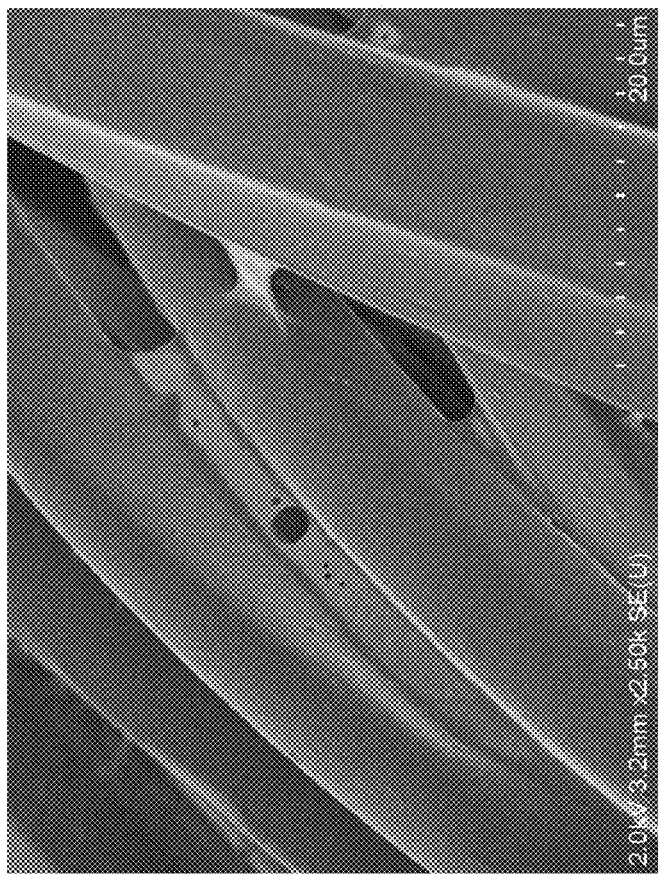

FIG. 151 illustrates a scanning electron microscopy image of fabric sample FAB-10-SPRAY-B (sixth view).

Figure 152:

FIG. 152 illustrates a scanning electron microscopy image of fabric sample FAB-10-SPRAY-B (seventh view).

Figure 153:
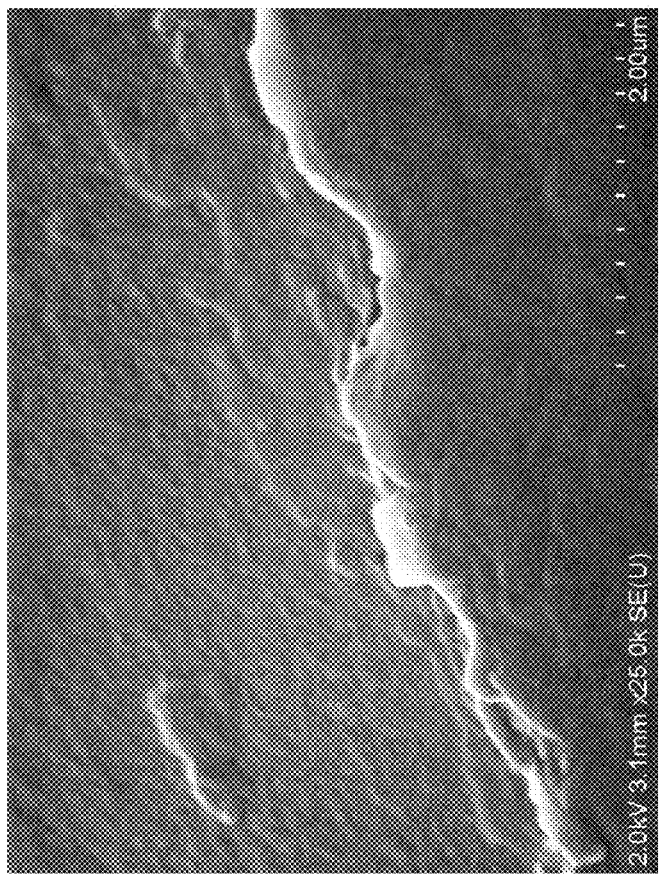

FIG. 153 illustrates a scanning electron microscopy image of fabric sample FAB-10-SPRAY-B (eighth view).

Figure 154:
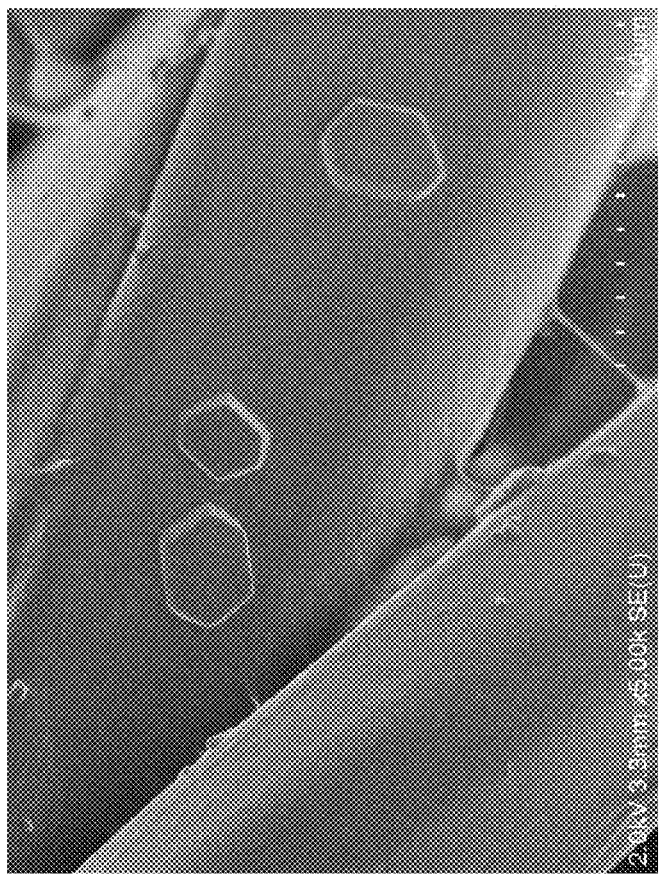

FIG. 154 illustrates a scanning electron microscopy image of fabric sample FAB-10-SPRAY-B (ninth view).

Figure 155:
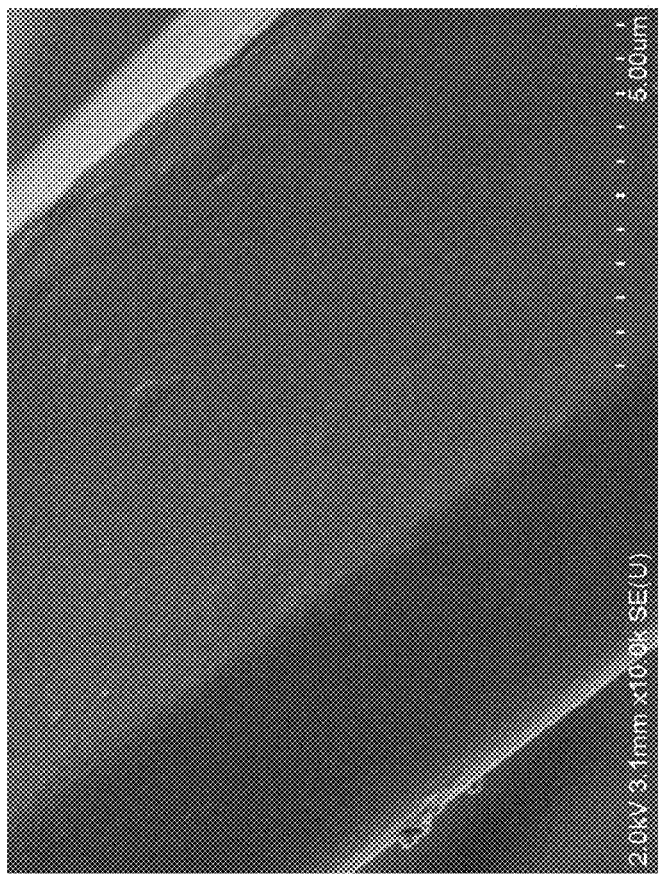

FIG. 155 illustrates a scanning electron microscopy image of fabric sample FAB-10-SPRAY-C.

Figure 156:

FIG. 156 illustrates a scanning electron microscopy image of fabric sample FAB-10-STEN-B (first view).

Figure 157:
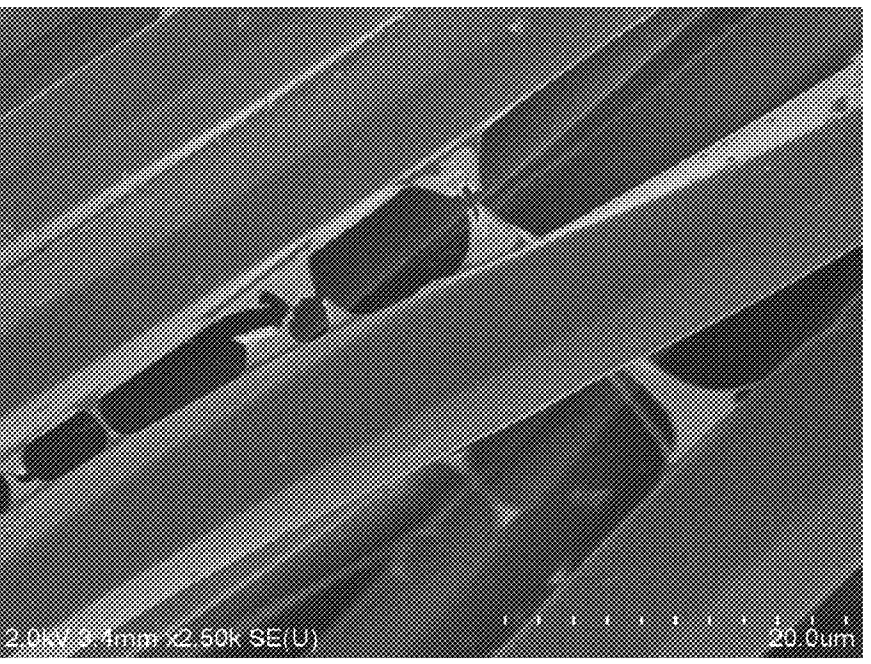

FIG. 157 illustrates a scanning electron microscopy image of fabric sample FAB-10-STEN-B (second view).

Figure 158:
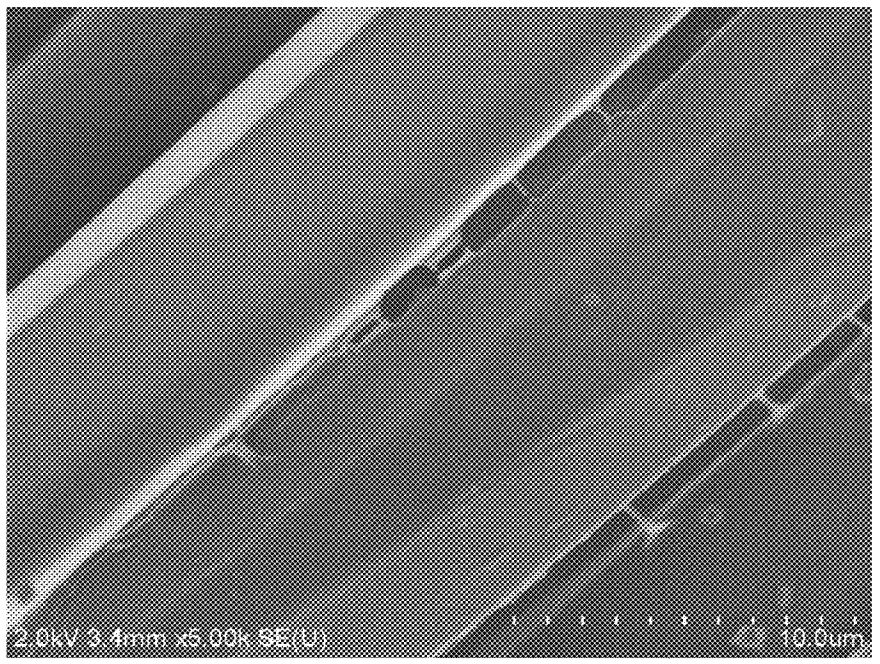

FIG. 158 illustrates a scanning electron microscopy image of fabric sample FAB-10-STEN-B (third view).

Figure 159:
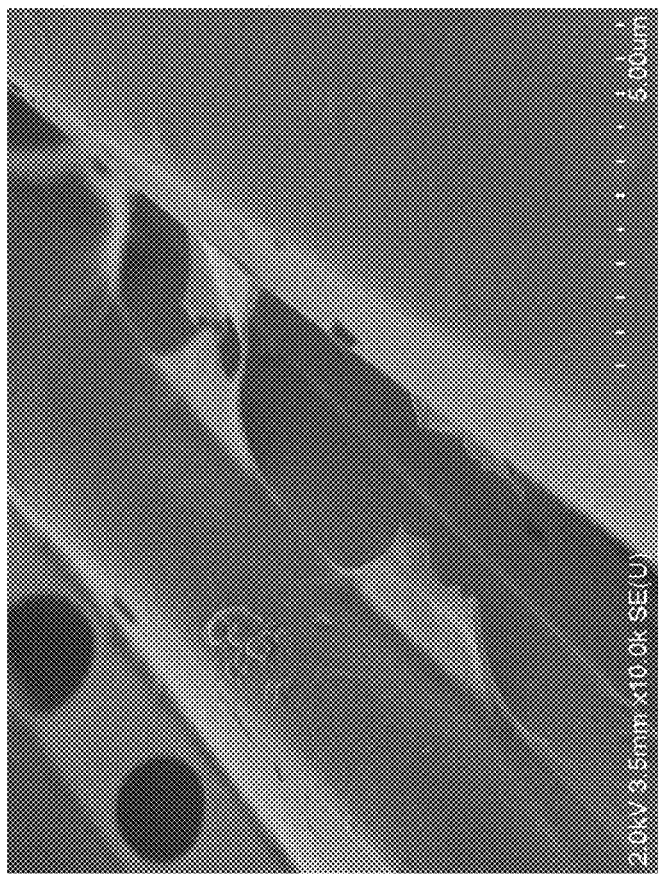

FIG. 159 illustrates a scanning electron microscopy image of fabric sample FAB-10-STEN-B (fourth view).

Figure 160:
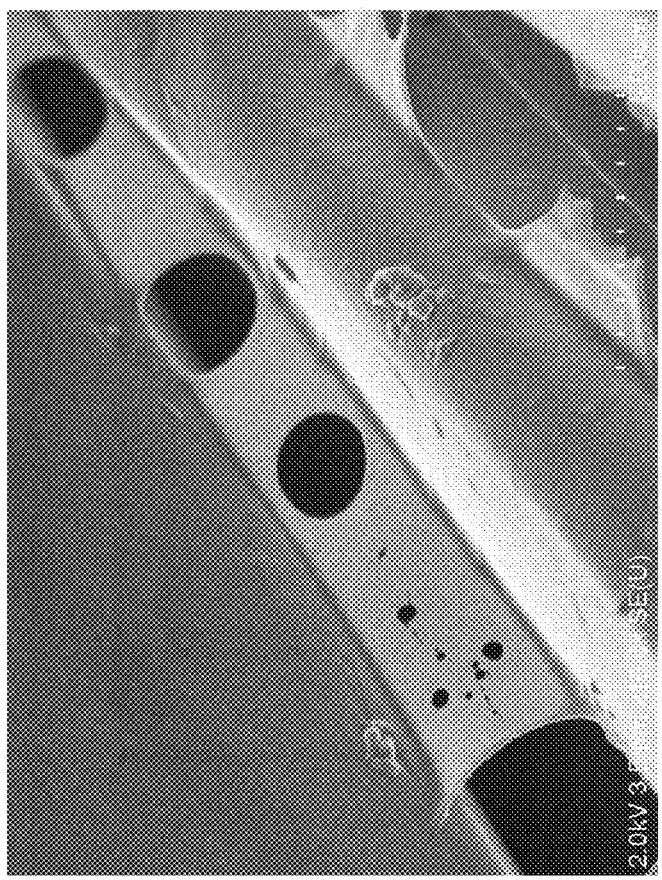

FIG. 160 illustrates a scanning electron microscopy image of fabric sample FAB-10-STEN-B (fifth view).

Figure 161:

FIG. 161 illustrates a scanning electron microscopy image of fabric sample FAB-10-STEN-B (sixth view).

Figure 162:
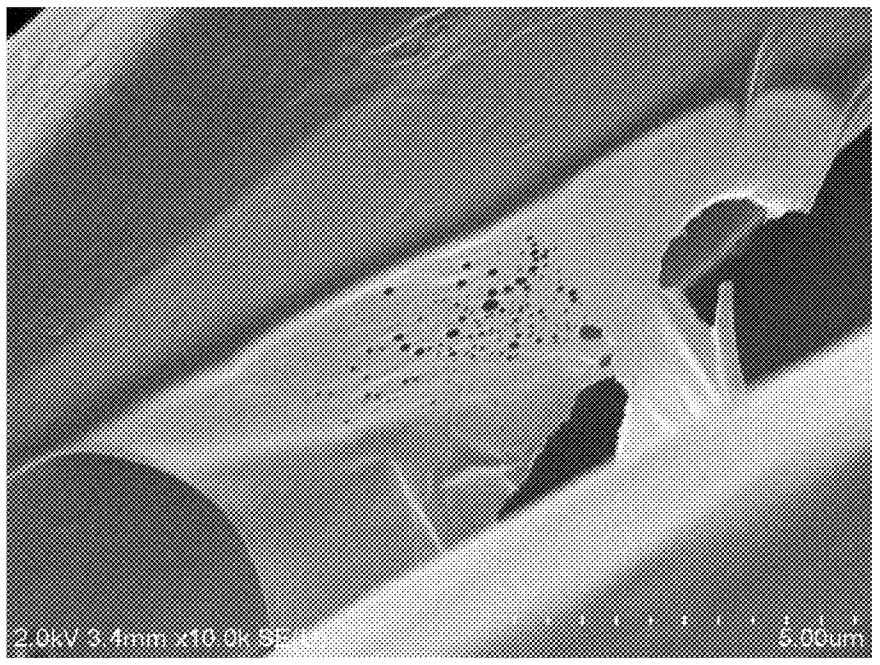

FIG. 162 illustrates a scanning electron microscopy image of fabric sample FAB-10-STEN-B (seventh view).

Figure 163:
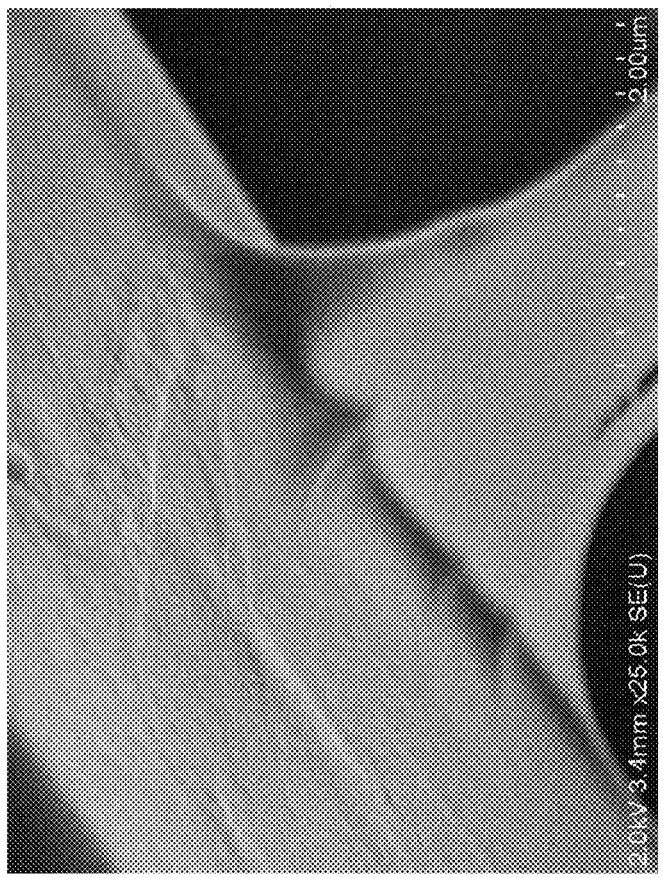

FIG. 163 illustrates a scanning electron microscopy image of fabric sample FAB-10-STEN-B (eighth view).

Figure 164:
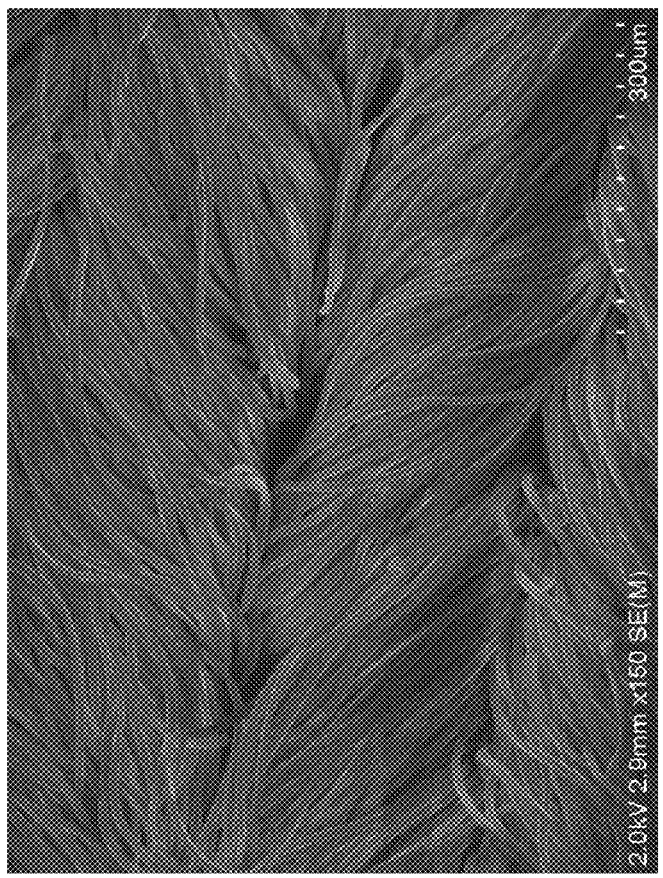

FIG. 164 illustrates a scanning electron microscopy image of a fabric control sample (first view).

Figure 165:
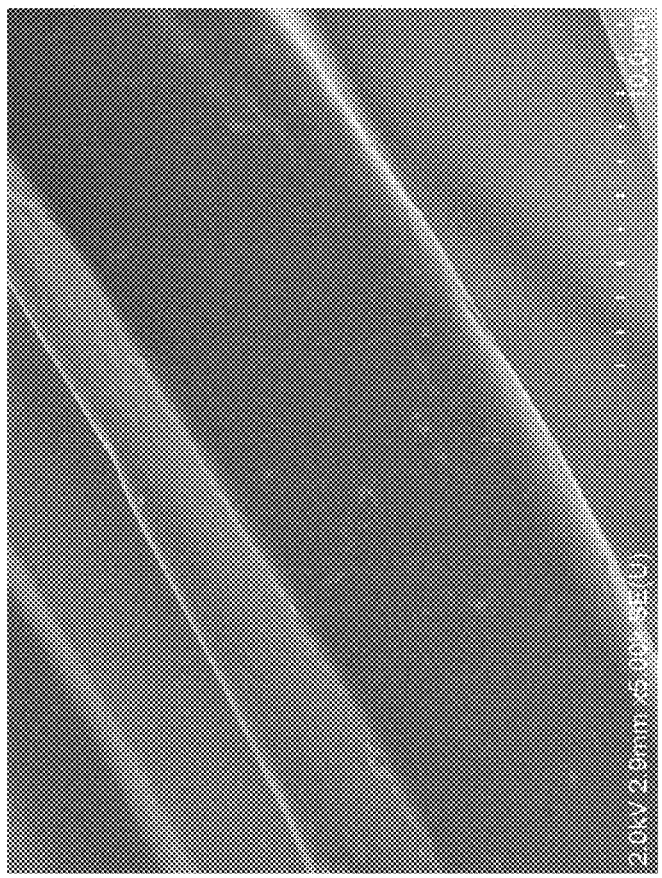

FIG. 165 illustrates a scanning electron microscopy image of a fabric control sample (second view).

Figure 166:
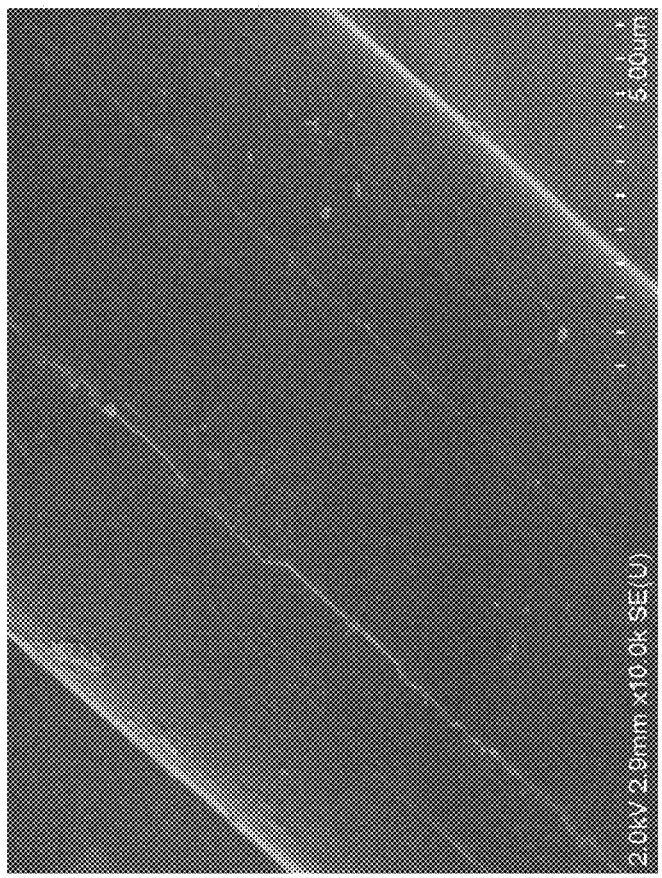

FIG. 166 illustrates a scanning electron microscopy image of a fabric control sample (third view).

Figure 167:
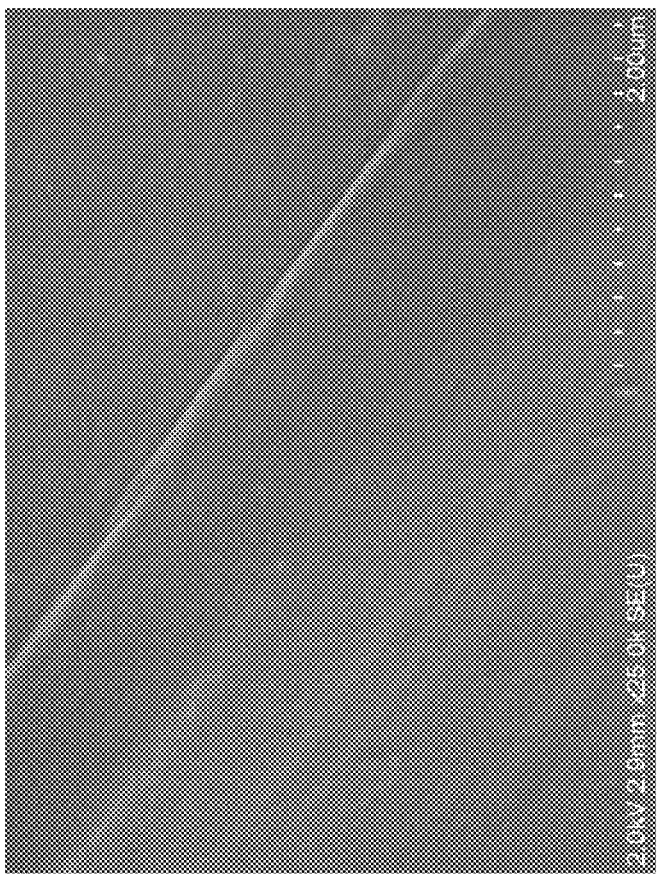

FIG. 167 illustrates a scanning electron microscopy image of a fabric control sample (fourth view).

Figure 168:
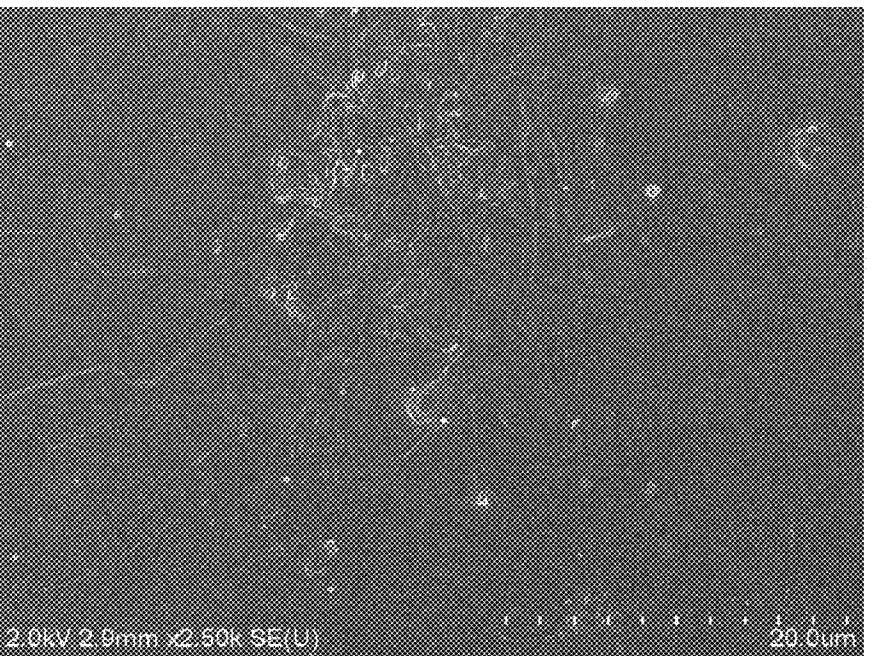

FIG. 168 illustrates a scanning electron microscopy image of film sample FIL-01-BATH-B-01MYL (first view).

Figure 169:
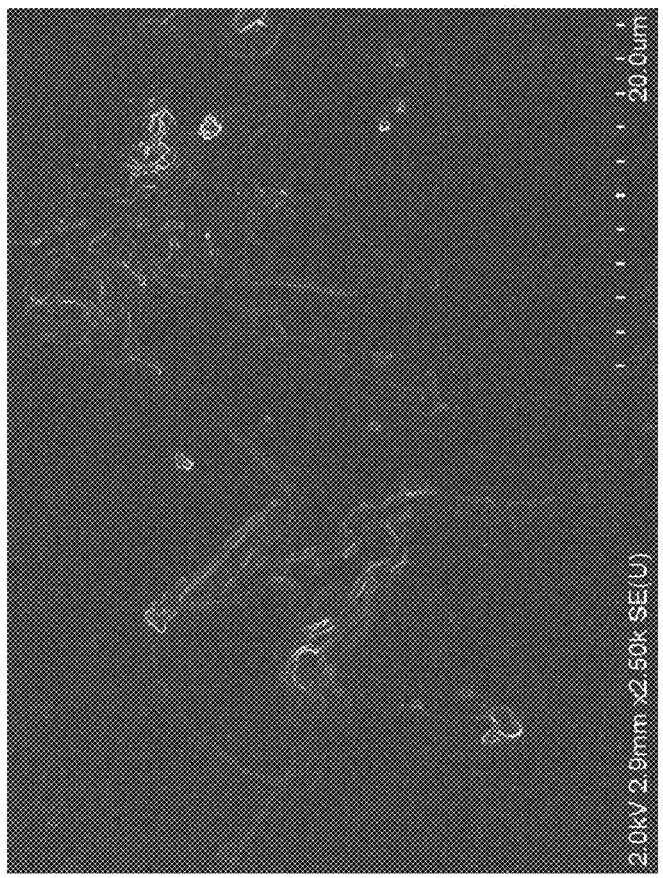

FIG. 169 illustrates a scanning electron microscopy image of film sample FIL-01-BATH-B-01MYL (second view).

Figure 170:
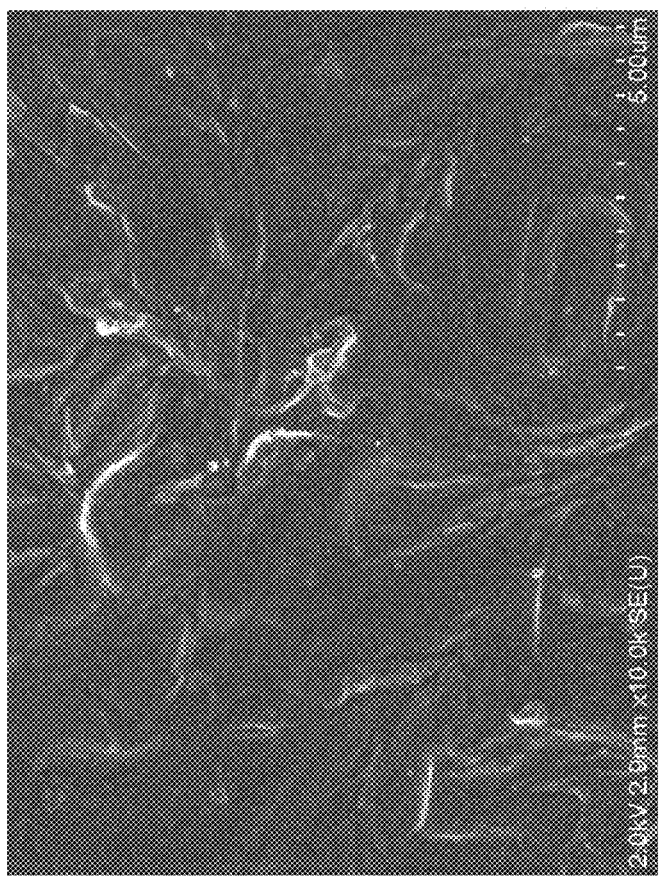

FIG. 170 illustrates a scanning electron microscopy image of film sample FIL-01-BATH-B-01MYL (third view).

Figure 171:
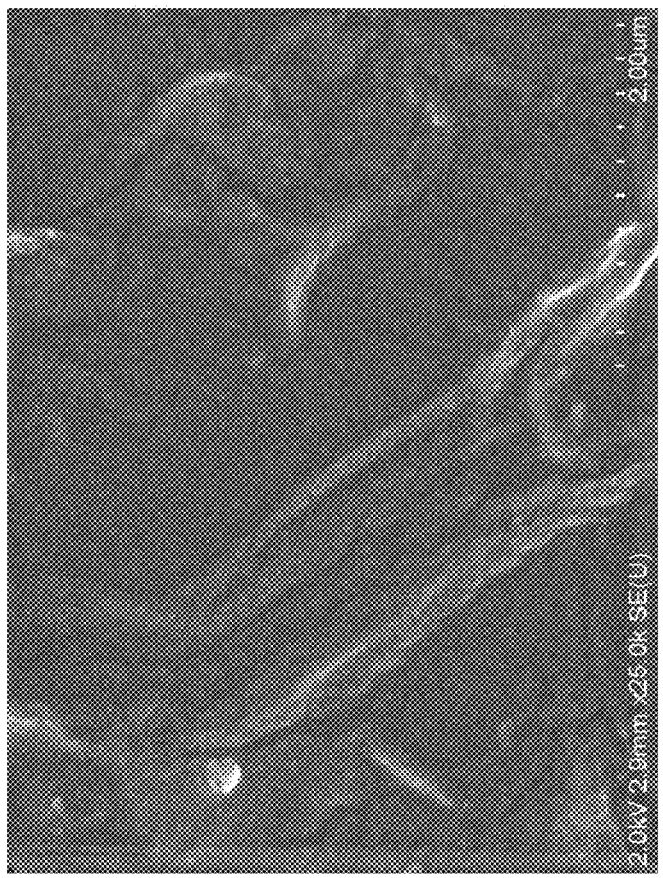

FIG. 171 illustrates a scanning electron microscopy image of film sample FIL-01-BATH-B-01MYL (fourth view).

Figure 172:
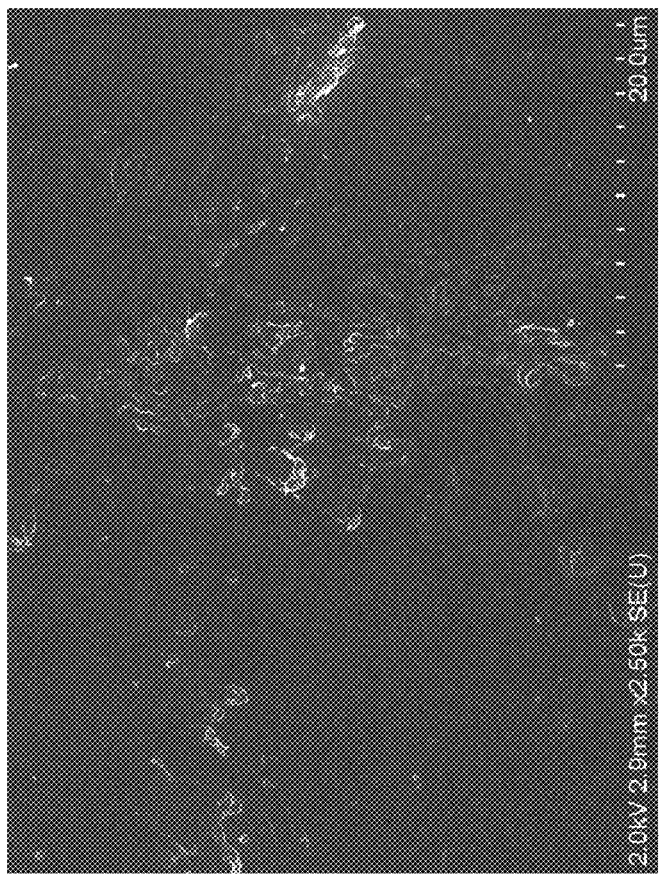

FIG. 172 illustrates a scanning electron microscopy image of film sample FIL-01-BATH-B-01MYL (fifth view).

Figure 173:
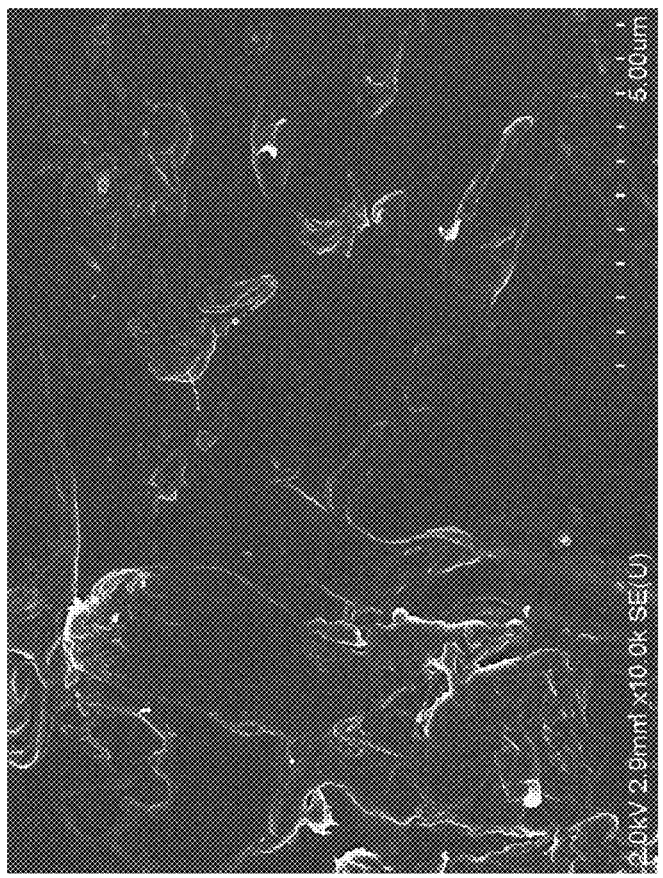

FIG. 173 illustrates a scanning electron microscopy image of film sample FIL-01-BATH-B-01MYL (sixth view).

Figure 174:

FIG. 174 illustrates a scanning electron microscopy image of film sample FIL-01-BATH-B-01MYL (seventh view).

Figure 175:
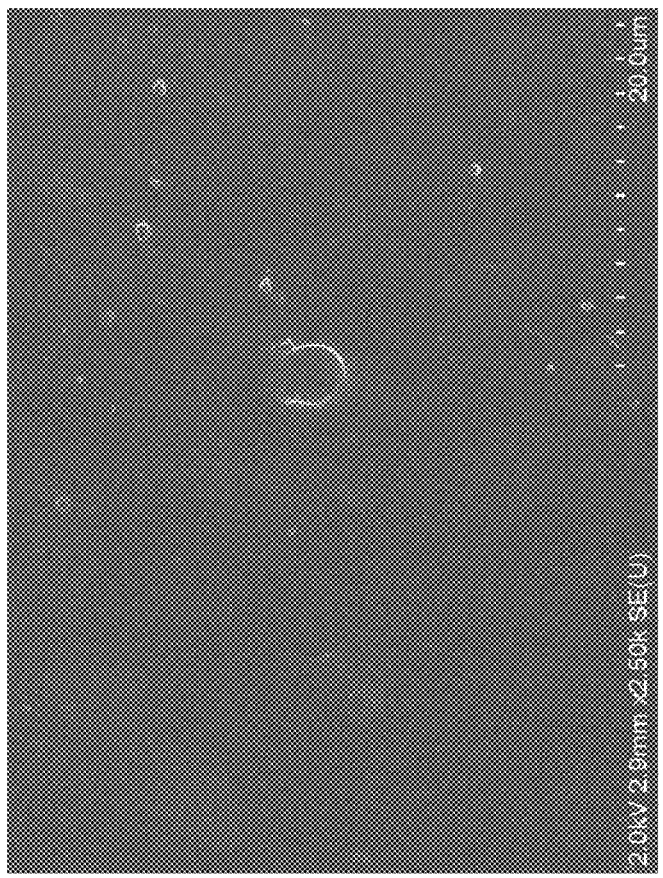

FIG. 175 illustrates a scanning electron microscopy image of film sample FIL-01-SPRAY-B-01MYL (first view).

Figure 176:

FIG. 176 illustrates a scanning electron microscopy image of film sample FIL-01-SPRAY-B-01MYL (second view).

Figure 177:
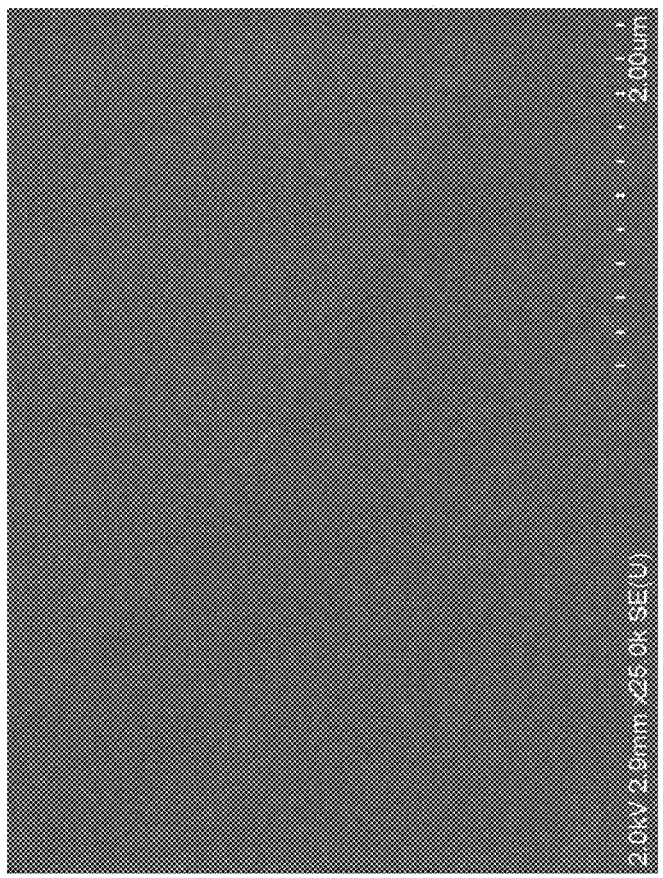

FIG. 177 illustrates a scanning electron microscopy image of film sample FIL-01-SPRAY-B-01MYL (third view).

Figure 178:

FIG. 178 illustrates a scanning electron microscopy image of film sample FIL-01-SPRAY-B-01MYL (fourth view).

Figure 179:

FIG. 179 illustrates a scanning electron microscopy image of film sample FIL-01-SPRAY-B-01MYL (fifth view).

Figure 180:
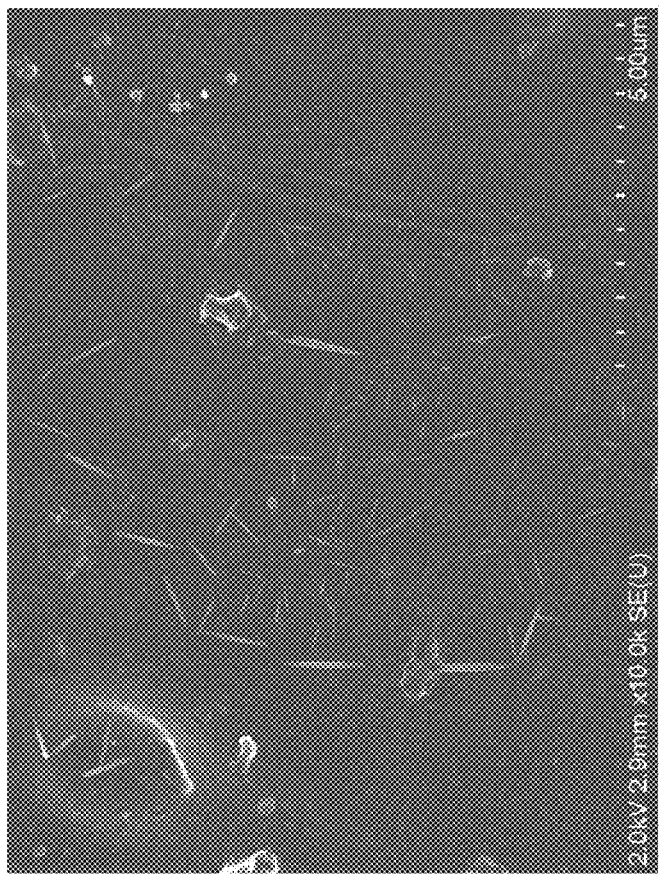

FIG. 180 illustrates a scanning electron microscopy image of film sample FIL-01-SPRAY-B-01MYL (sixth view).

Figure 181:

FIG. 181 illustrates a scanning electron microscopy image of film sample FIL-01-SPRAY-B-01MYL (seventh view).

Figure 182:
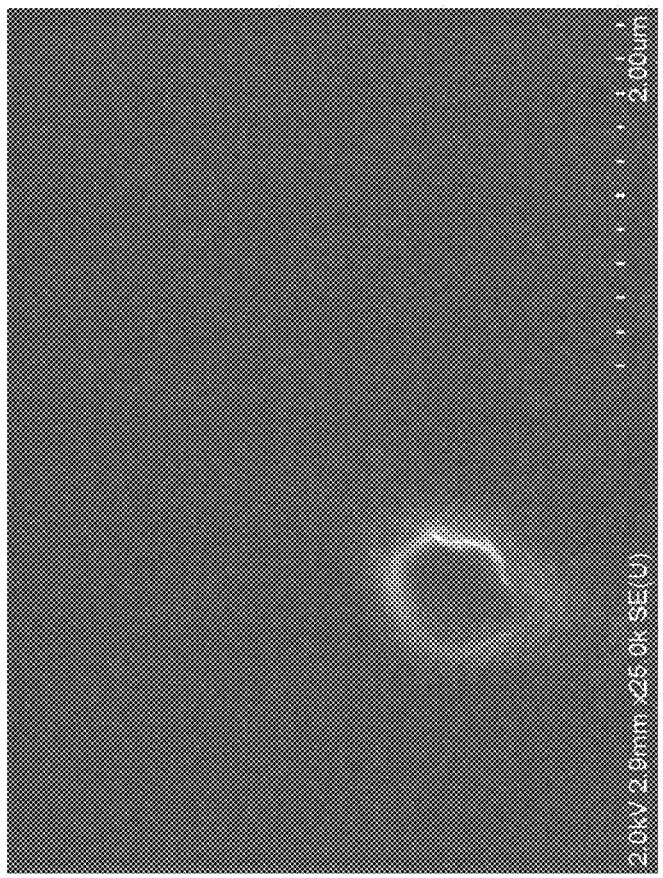

FIG. 182 illustrates a scanning electron microscopy image of film sample FIL-01-SPRAY-B-01MYL (eighth view).

Figure 183:

FIG. 183 illustrates a scanning electron microscopy image of film sample FIL-01-SPRAY-B-007MYL (first view).

Figure 184:
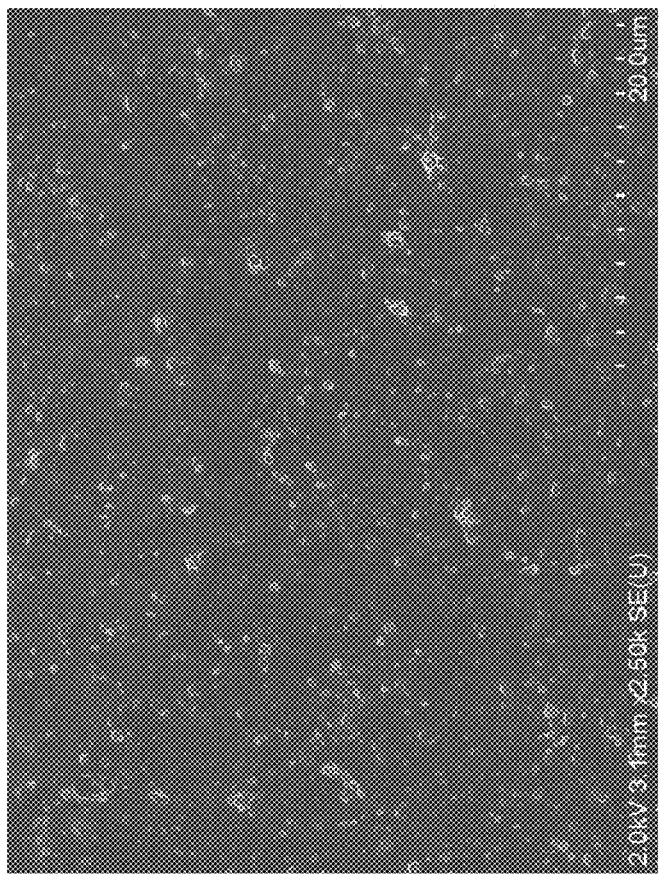

FIG. 184 illustrates a scanning electron microscopy image of film sample FIL-01-SPRAY-B-007MYL (second view).

Figure 185:
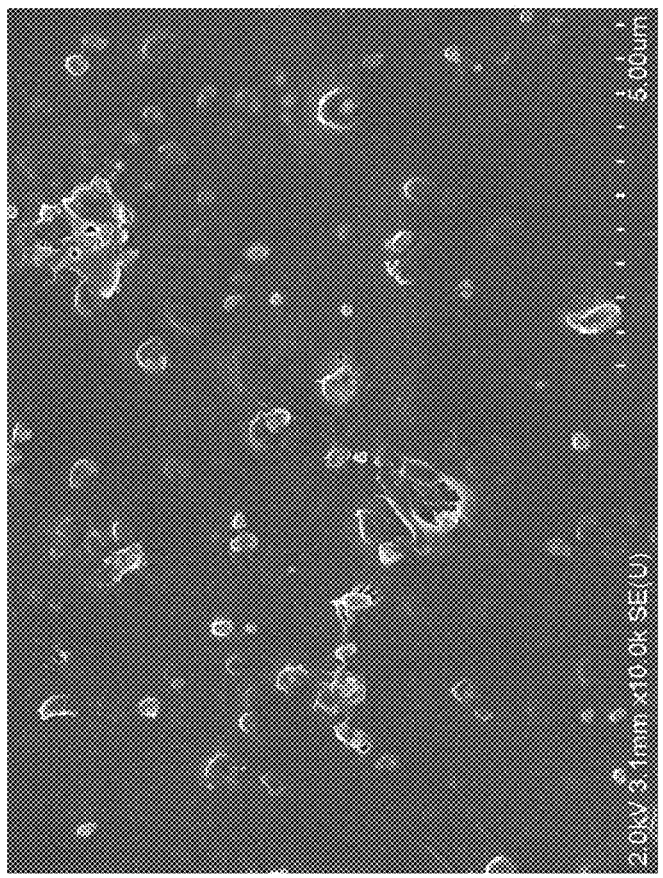

FIG. 185 illustrates a scanning electron microscopy image of film sample FIL-01-SPRAY-B-007MYL (third view).

Figure 186:

FIG. 186 illustrates a scanning electron microscopy image of film sample FIL-01-SPRAY-B-007MYL (fourth view).

Figure 187:
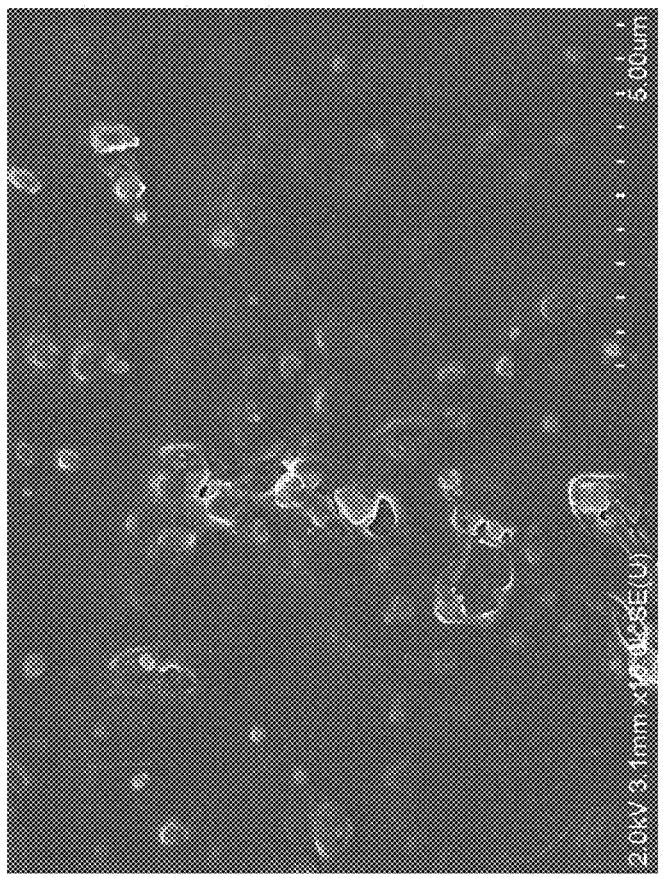

FIG. 187 illustrates a scanning electron microscopy image of film sample FIL-01-SPRAY-B-007MYL (fifth view).

Figure 188:
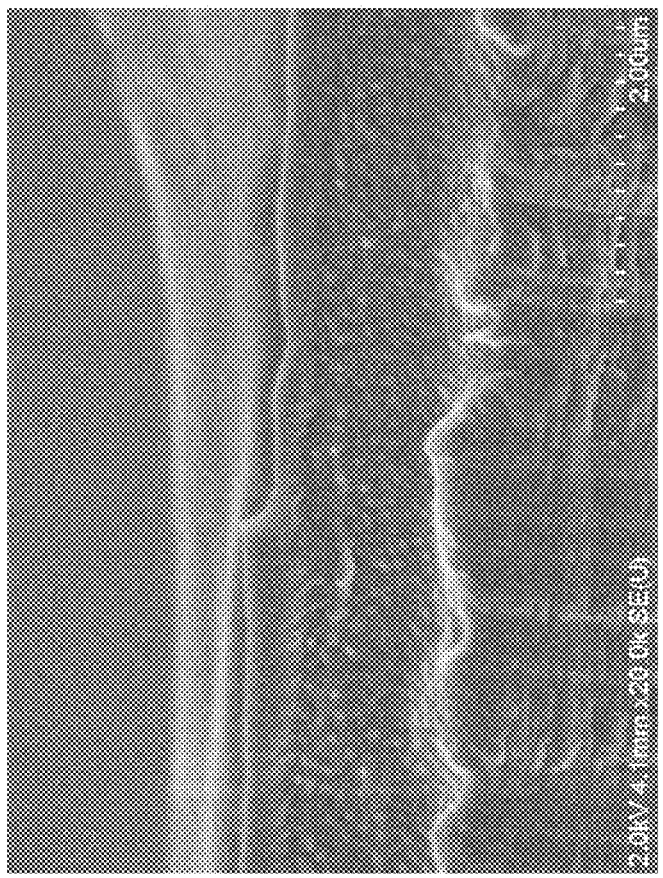

FIG. 188 illustrates a scanning electron microscopy image of film sample FIL-01-SPRAY-B-O1MYL_cross-section (first view).

Figure 189:
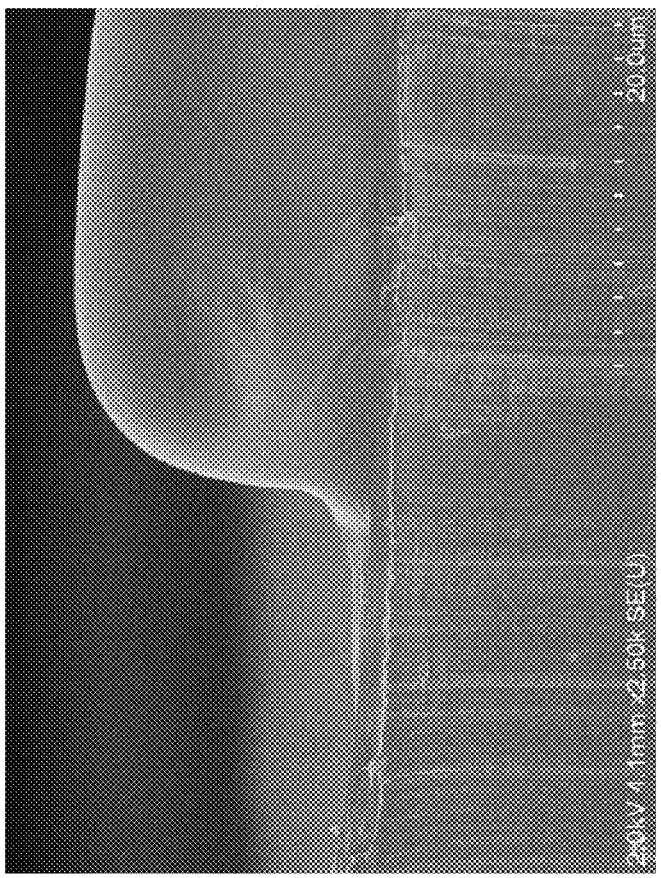

FIG. 189 illustrates a scanning electron microscopy image of film sample FIL-01-SPRAY-B-O1MYL_cross-section (second view).

Figure 190:
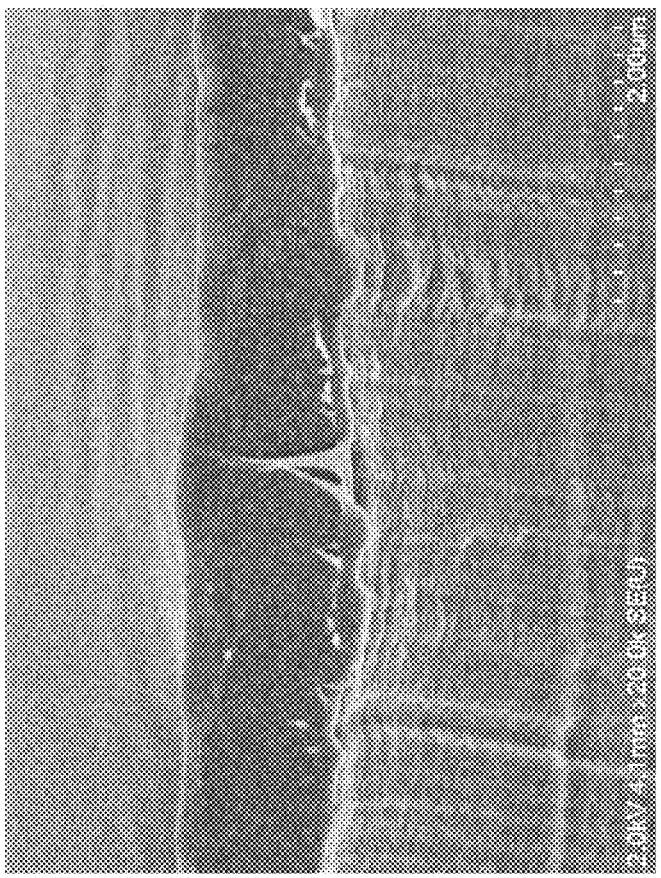

FIG. 190 illustrates a scanning electron microscopy image of film sample FIL-01-SPRAY-B-O1MYL_cross-section (third view).

Figure 191:
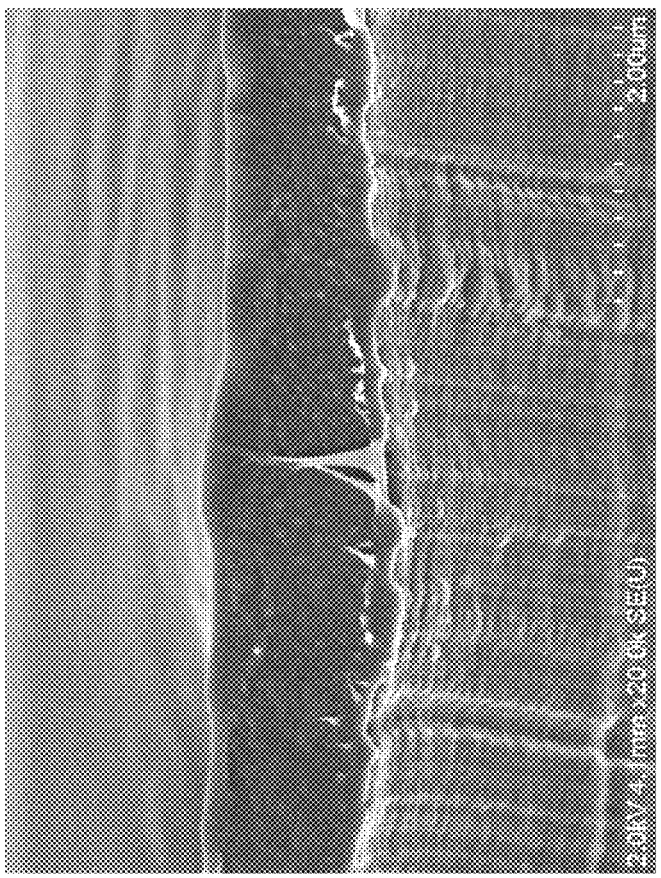

FIG. 191 illustrates a scanning electron microscopy image of film sample FIL-01-SPRAY-B-O1MYL_cross-section (fourth view).

Figure 192:
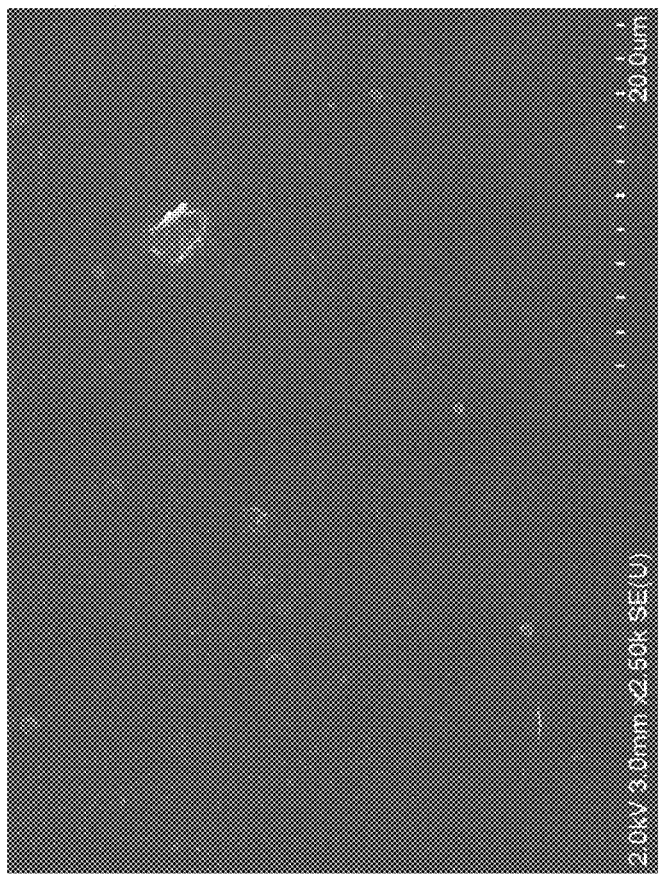

FIG. 192 illustrates a scanning electron microscopy image of film sample FIL-01-SPRAY-C-01MYL (first view).

Figure 193:

FIG. 193 illustrates a scanning electron microscopy image of film sample FIL-01-SPRAY-C-01MYL (second view).

Figure 194:

FIG. 194 illustrates a scanning electron microscopy image of film sample FIL-01-SPRAY-C-01MYL (third view).

Figure 195:

FIG. 195 illustrates a scanning electron microscopy image of film sample FIL-01-SPRAY-C-01MYL (fourth view).

Figure 196:

FIG. 196 illustrates a scanning electron microscopy image of film sample FIL-01-SPRAY-C-01MYL (fifth view).

Figure 197:
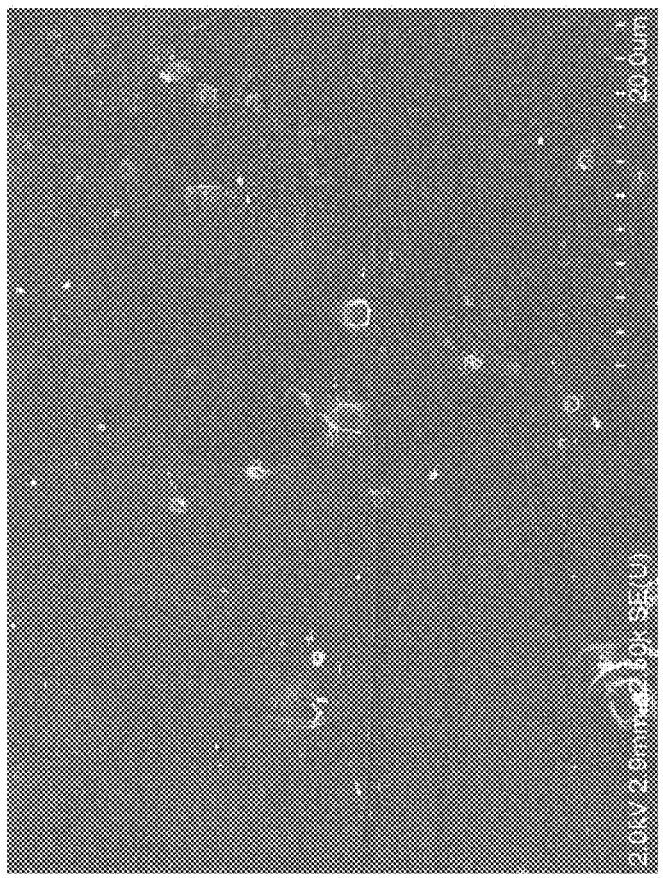

FIG. 197 illustrates a scanning electron microscopy image of film sample FIL-01-STEN-B-01-MYL (first view).

Figure 198:

FIG. 198 illustrates a scanning electron microscopy image of film sample FIL-01-STEN-B-01-MYL (second view).

Figure 199:
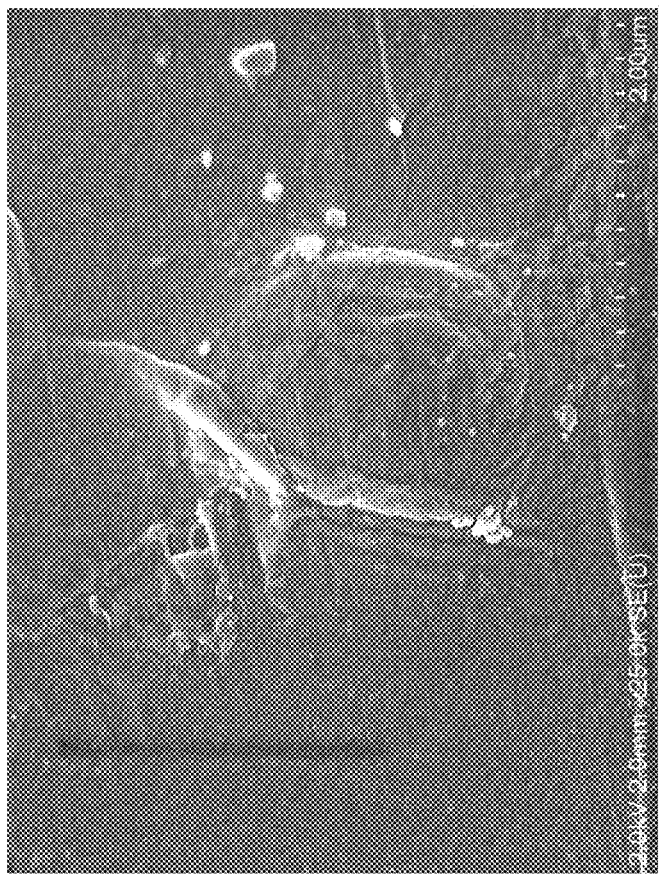

FIG. 199 illustrates a scanning electron microscopy image of film sample FIL-01-STEN-B-01-MYL (third view).

Figure 200:
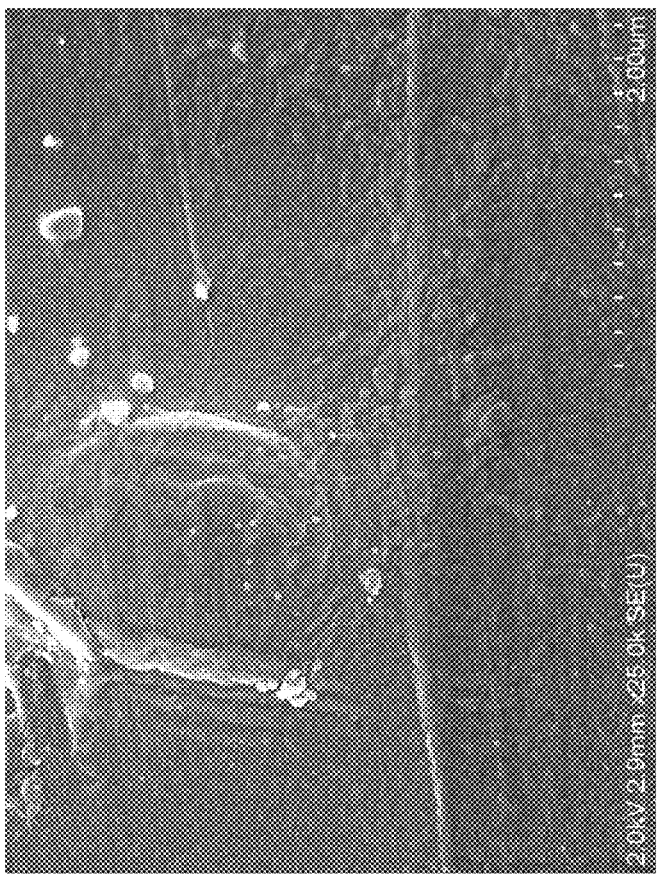

FIG. 200 illustrates a scanning electron microscopy image of film sample FIL-01-STEN-B-01-MYL (fourth view).

Figure 201:
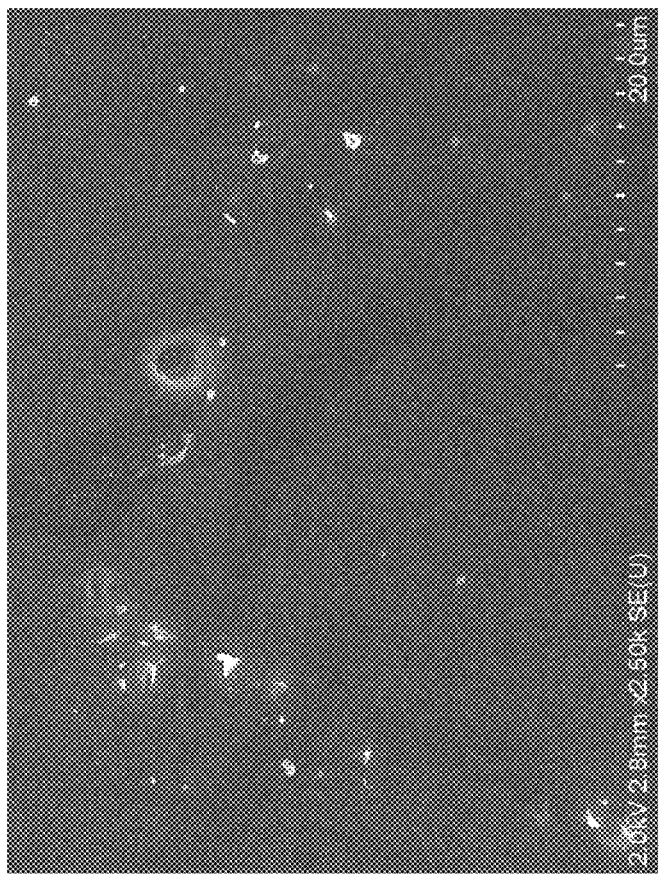

FIG. 201 illustrates a scanning electron microscopy image of film sample FIL-01-STEN-C-01-MYL (first view).

Figure 202:
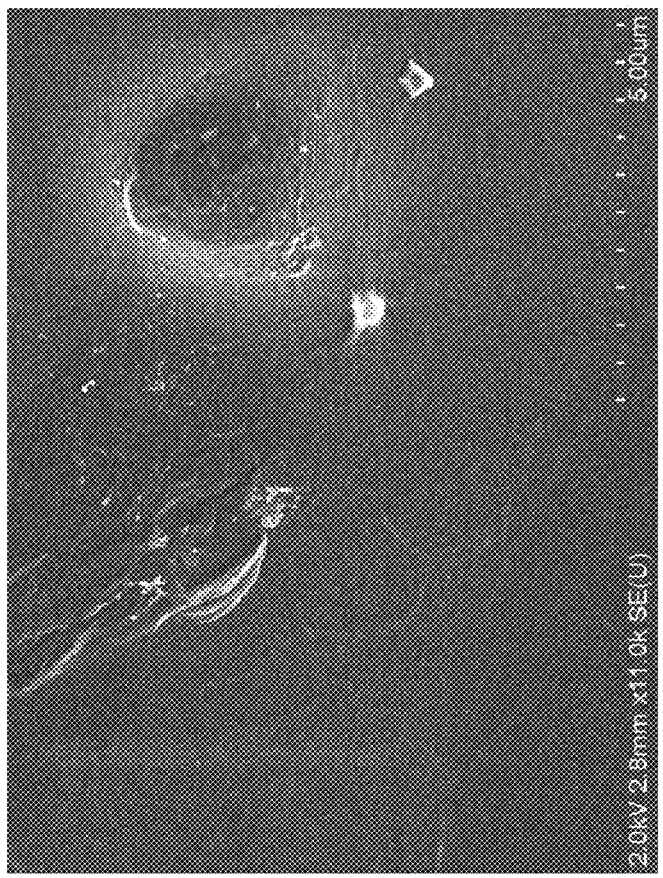

FIG. 202 illustrates a scanning electron microscopy image of film sample FIL-01-STEN-C-01-MYL (second view).

Figure 203:
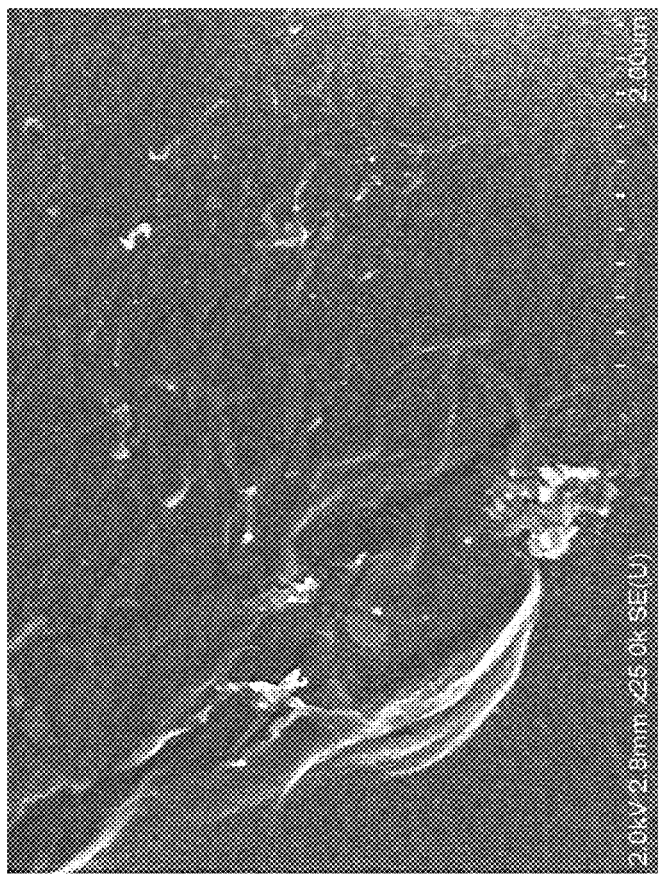

FIG. 203 illustrates a scanning electron microscopy image of film sample FIL-01-STEN-C-01-MYL (third view).

Figure 204:
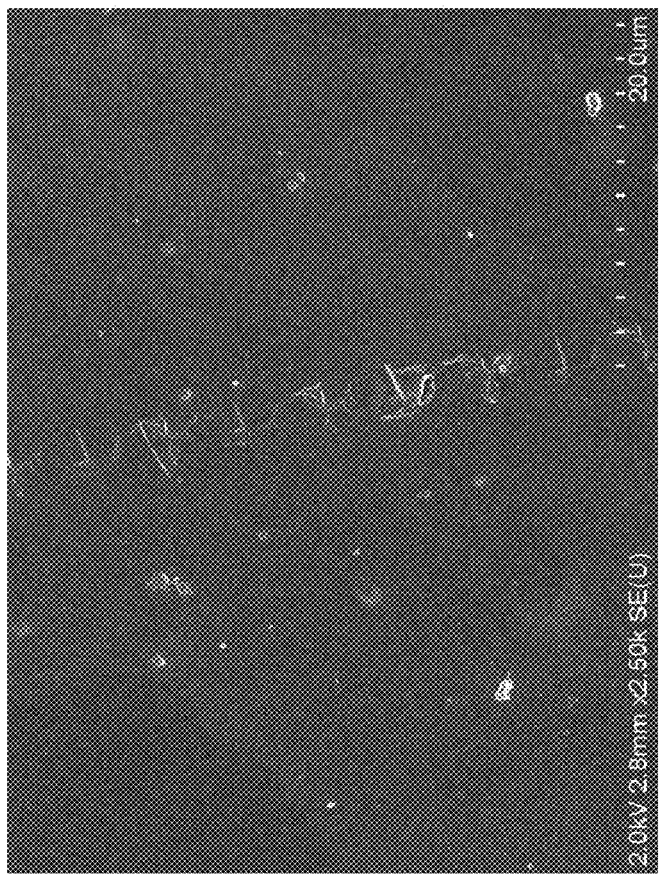

FIG. 204 illustrates a scanning electron microscopy image of film sample FIL-01-STEN-C-01-MYL (fourth view).

Figure 205:
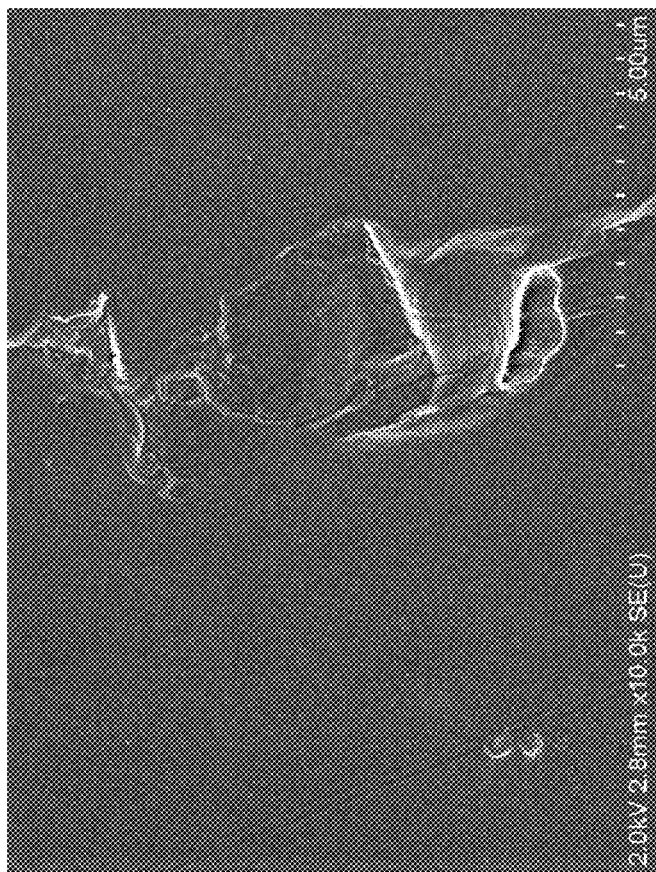

FIG. 205 illustrates a scanning electron microscopy image of film sample FIL-01-STEN-C-01-MYL (fifth view).

Figure 206:
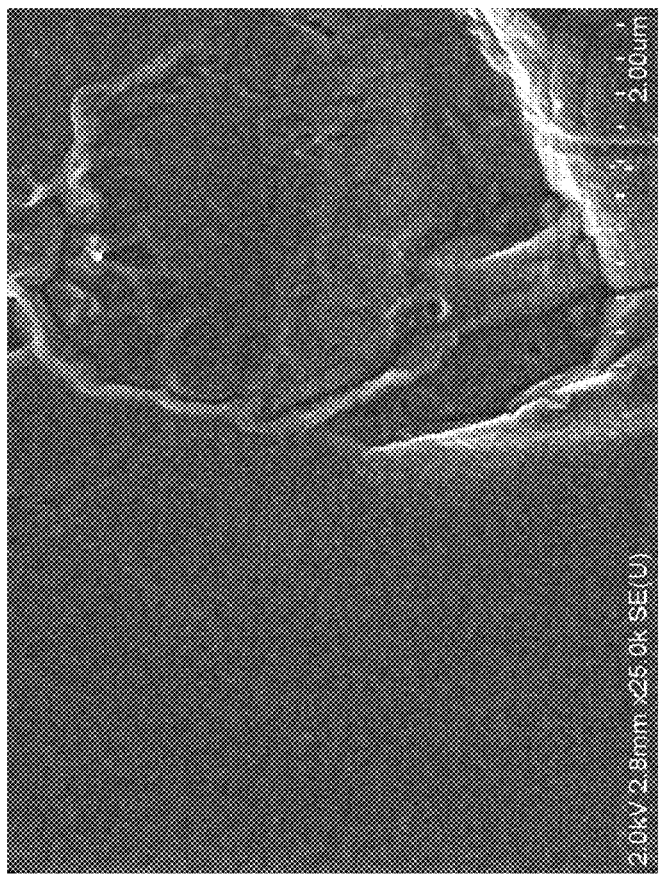

FIG. 206 illustrates a scanning electron microscopy image of film sample FIL-01-STEN-C-01-MYL (sixth view).

Figure 207:
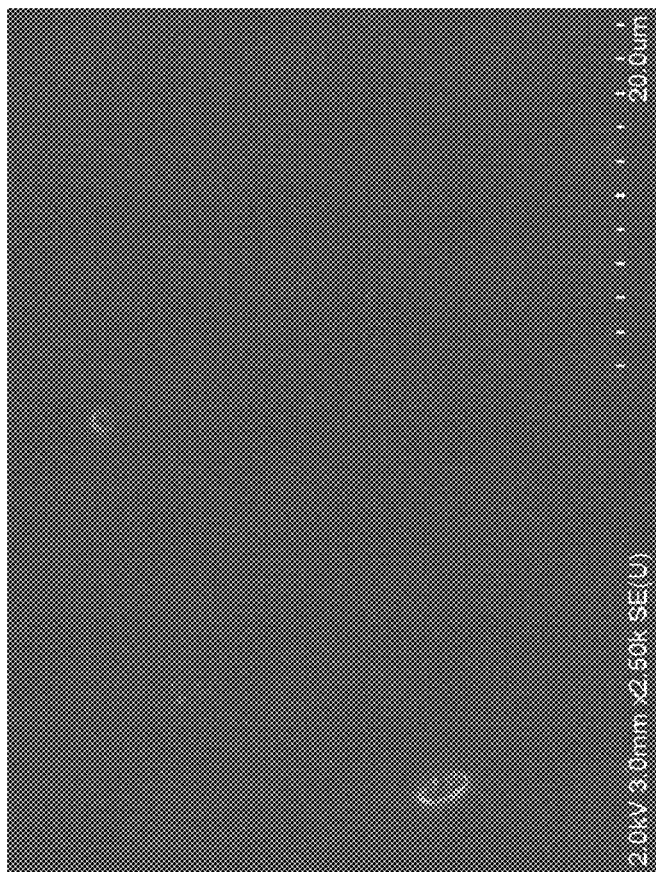

FIG. 207 illustrates a scanning electron microscopy image of film sample FIL-10-BATH-B-01MYL (first view).

Figure 208:

FIG. 208 illustrates a scanning electron microscopy image of film sample FIL-10-BATH-B-01MYL (second view).

Figure 209:

FIG. 209 illustrates a scanning electron microscopy image of film sample FIL-10-BATH-B-01MYL (third view).

Figure 210:
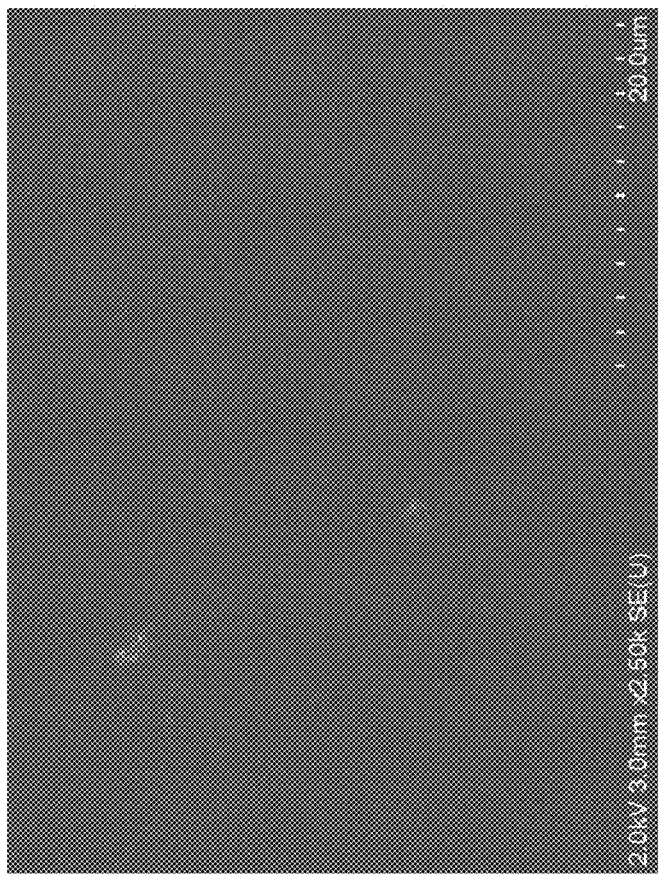

FIG. 210 illustrates a scanning electron microscopy image of film sample FIL-10-BATH-B-01MYL (fourth view).

Figure 211:
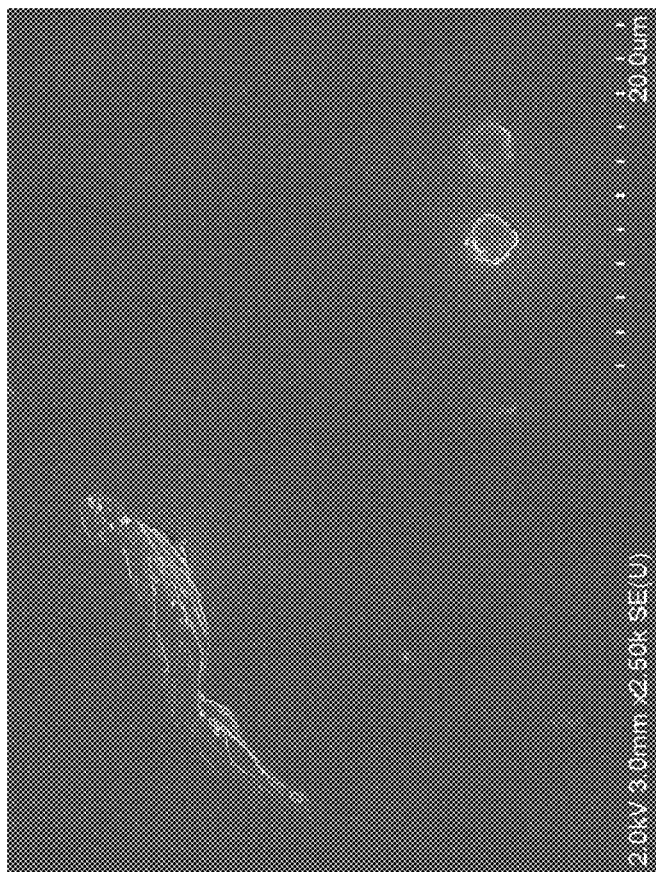

FIG. 211 illustrates a scanning electron microscopy image of film sample FIL-10-BATH-B-01MYL (fifth view).

Figure 212:

FIG. 212 illustrates a scanning electron microscopy image of film sample FIL-10-BATH-B-01MYL (sixth view).

Figure 213:

FIG. 213 illustrates a scanning electron microscopy image of film sample FIL-10-BATH-B-01MYL (seventh view).

Figure 214:
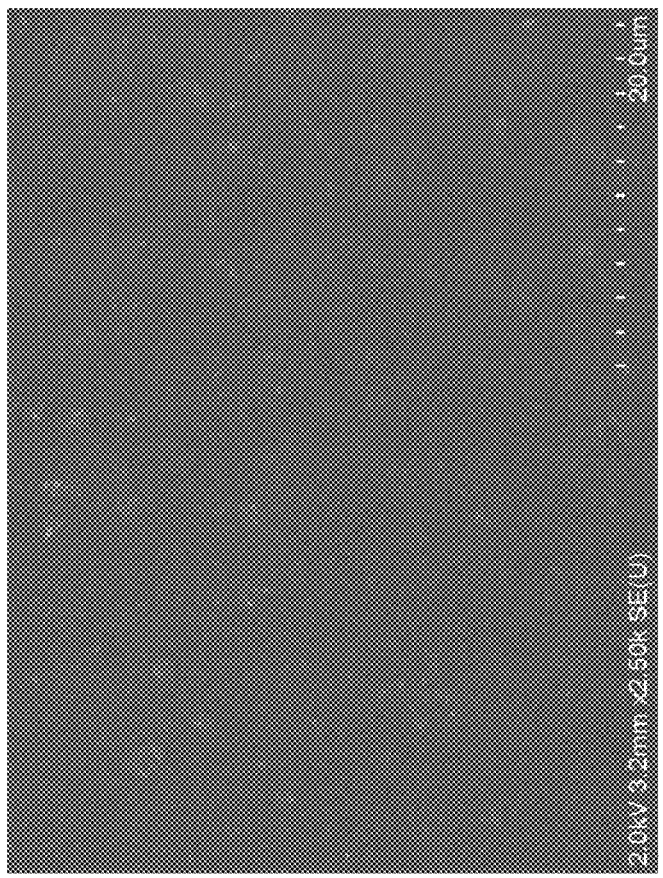

FIG. 214 illustrates a scanning electron microscopy image of film sample FIL-10-BATH-B-007MEL (first view).

Figure 215:

FIG. 215 illustrates a scanning electron microscopy image of film sample FIL-10-BATH-B-007MEL (second view).

Figure 216:

FIG. 216 illustrates a scanning electron microscopy image of film sample FIL-10-BATH-B-007MEL (third view).

Figure 217:

FIG. 217 illustrates a scanning electron microscopy image of film sample FIL-10-BATH-B-007MEL (fourth view).

Figure 218:

FIG. 218 illustrates a scanning electron microscopy image of film sample FIL-10-BATH-B-007MEL (fifth view).

Figure 219:

FIG. 219 illustrates a scanning electron microscopy image of film sample FIL-10-BATH-C-01MYL cross-section (first view).

Figure 220:

FIG. 220 illustrates a scanning electron microscopy image of film sample FIL-10-SPRAY-B-01MYL (first view).

Figure 221:

FIG. 221 illustrates a scanning electron microscopy image of film sample FIL-10-SPRAY-B-01MYL (second view).

Figure 222:

FIG. 222 illustrates a scanning electron microscopy image of film sample FIL-10-SPRAY-B-01MYL (third view).

Figure 223:

FIG. 223 illustrates a scanning electron microscopy image of film sample FIL-10-SPRAY-B-01MYL (fourth view).

Figure 224:
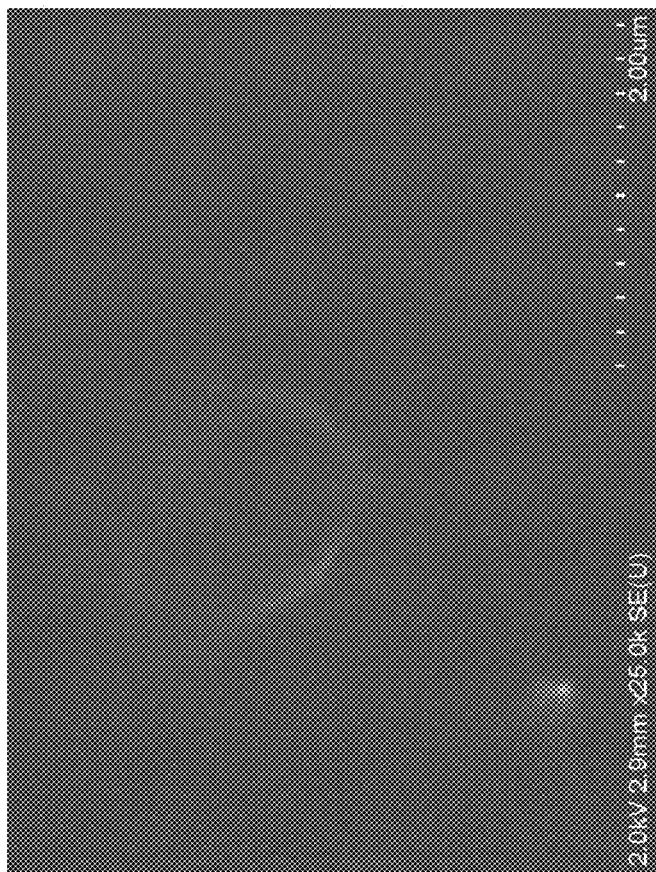

FIG. 224 illustrates a scanning electron microscopy image of film sample FIL-10-SPRAY-B-01MYL (fifth view).

Figure 225:
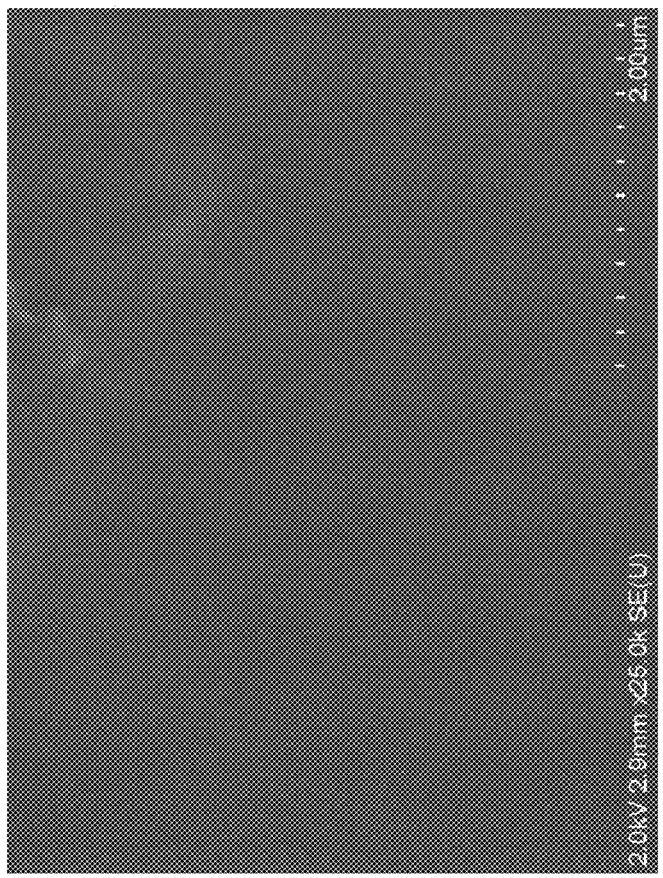

FIG. 225 illustrates a scanning electron microscopy image of film sample FIL-10-SPRAY-B-01MYL (sixth view).

Figure 226:
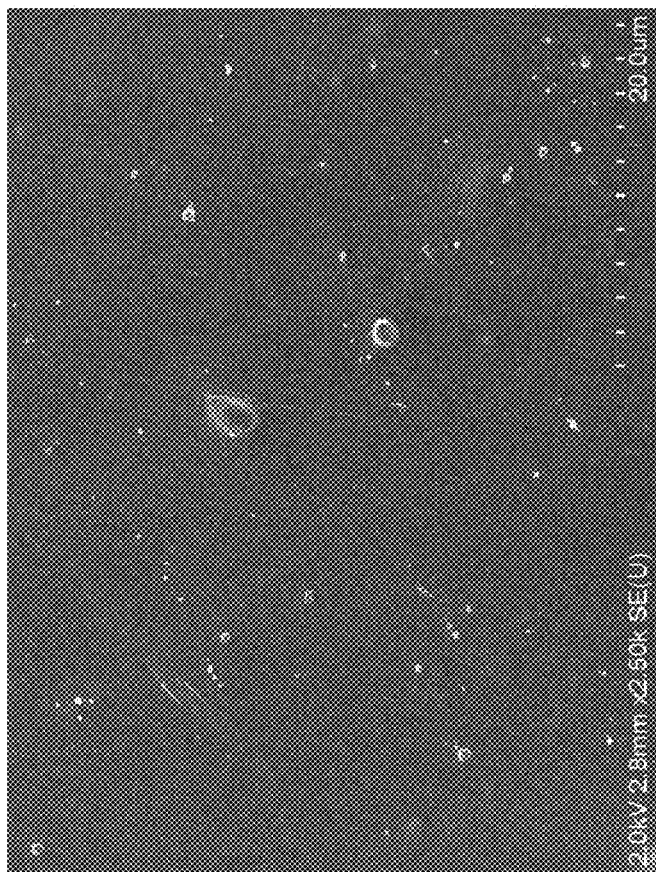

FIG. 226 illustrates a scanning electron microscopy image of film sample FIL-BATH-C-01-MYL (first view).

Figure 227:

FIG. 227 illustrates a scanning electron microscopy image of film sample FIL-BATH-C-01-MYL (second view).

Figure 228:

FIG. 228 illustrates a scanning electron microscopy image of film sample FIL-BATH-C-01-MYL (third view).

Figure 229:
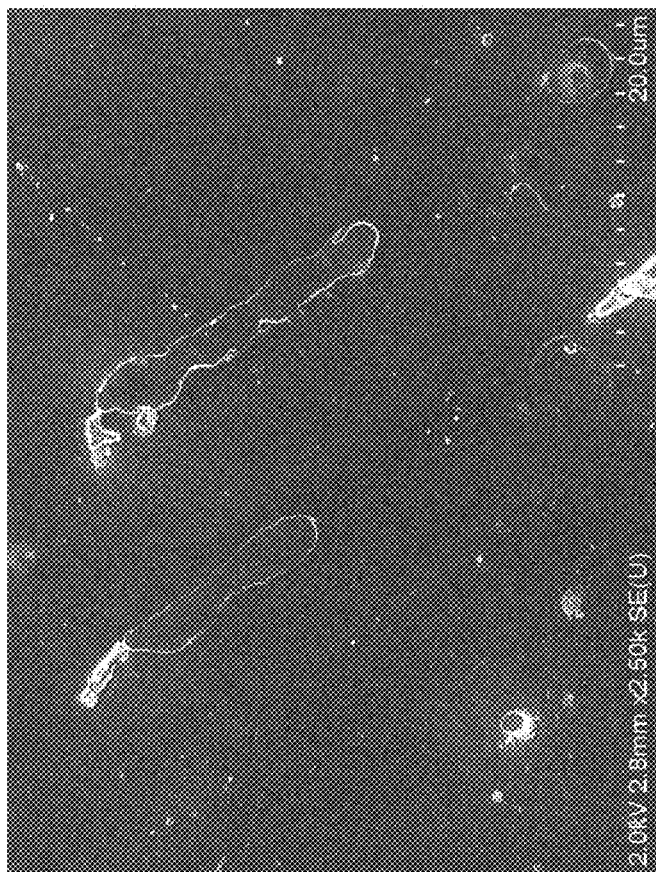

FIG. 229 illustrates a scanning electron microscopy image of film sample FIL-BATH-C-01-MYL (fourth view).

Figure 230:

FIG. 230 illustrates a scanning electron microscopy image of film sample FIL-BATH-C-01-MYL (fifth view).

Figure 231:
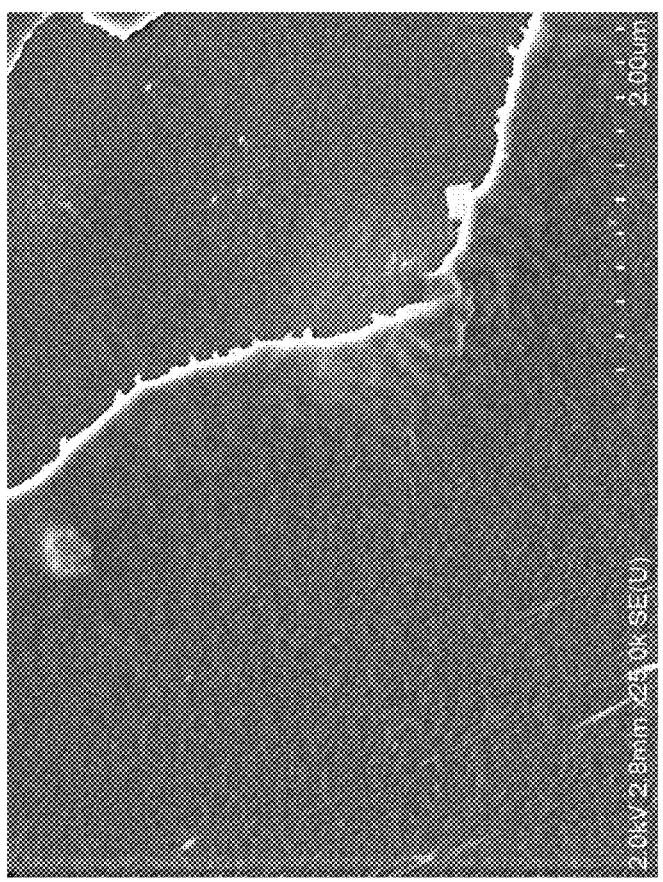

FIG. 231 illustrates a scanning electron microscopy image of film sample FIL-BATH-C-01-MYL (sixth view).

Figure 232:
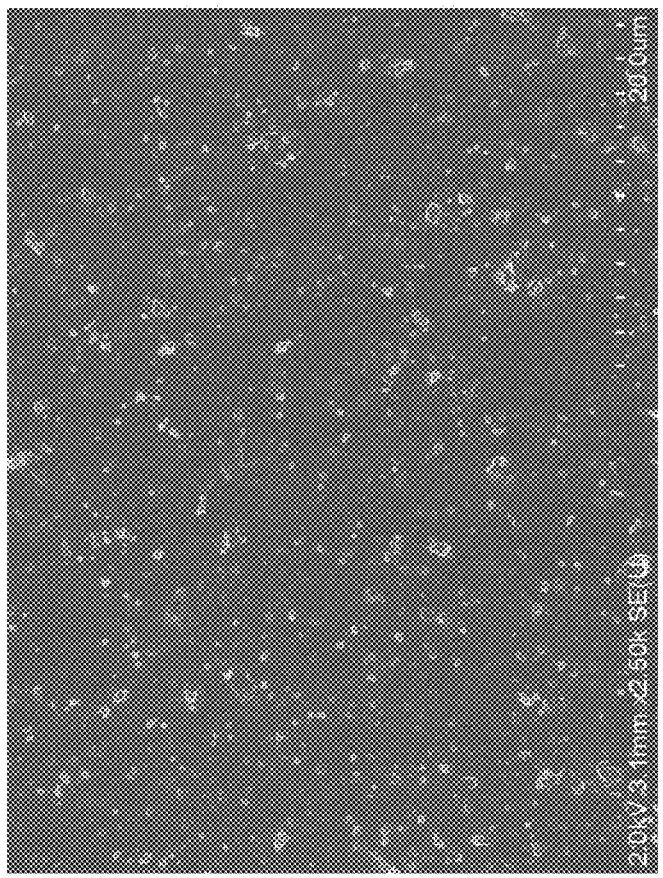

FIG. 232 illustrates a scanning electron microscopy image of film sample Melinex Control (first view).

Figure 233:
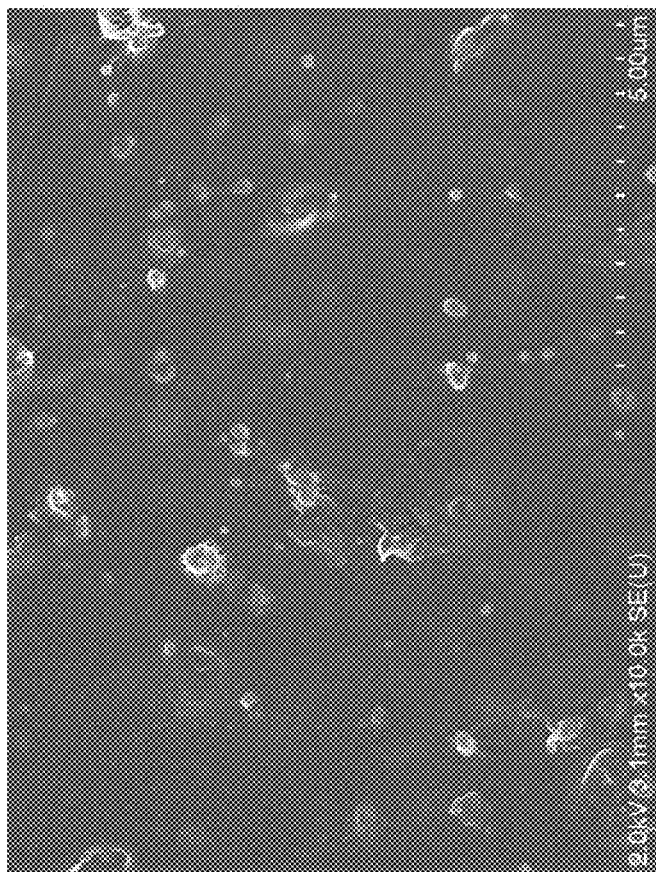

FIG. 233 illustrates a scanning electron microscopy image of film sample Melinex Control (second view).

Figure 234:
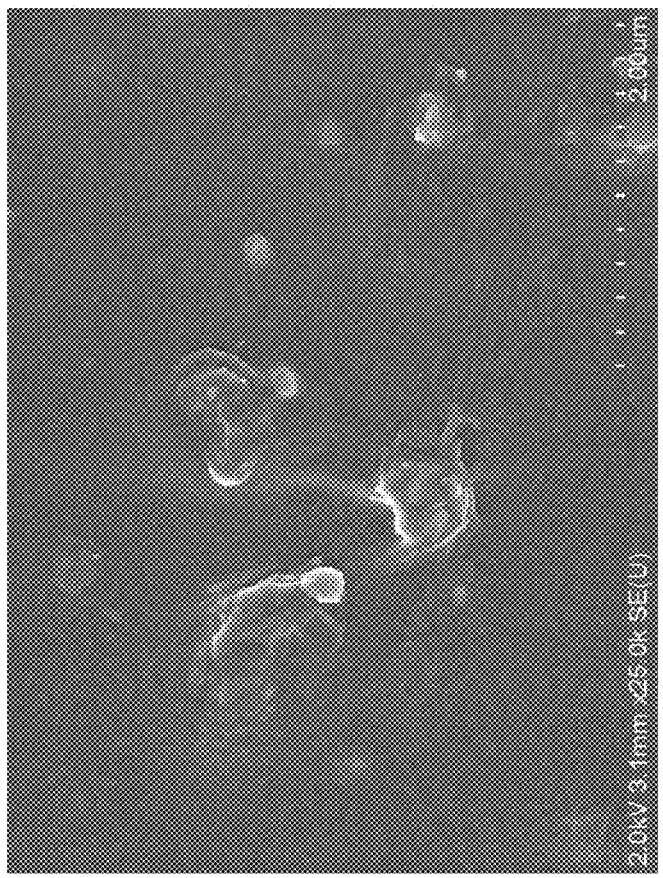

FIG. 234 illustrates a scanning electron microscopy image of film sample Melinex Control (third view).

Figure 235:
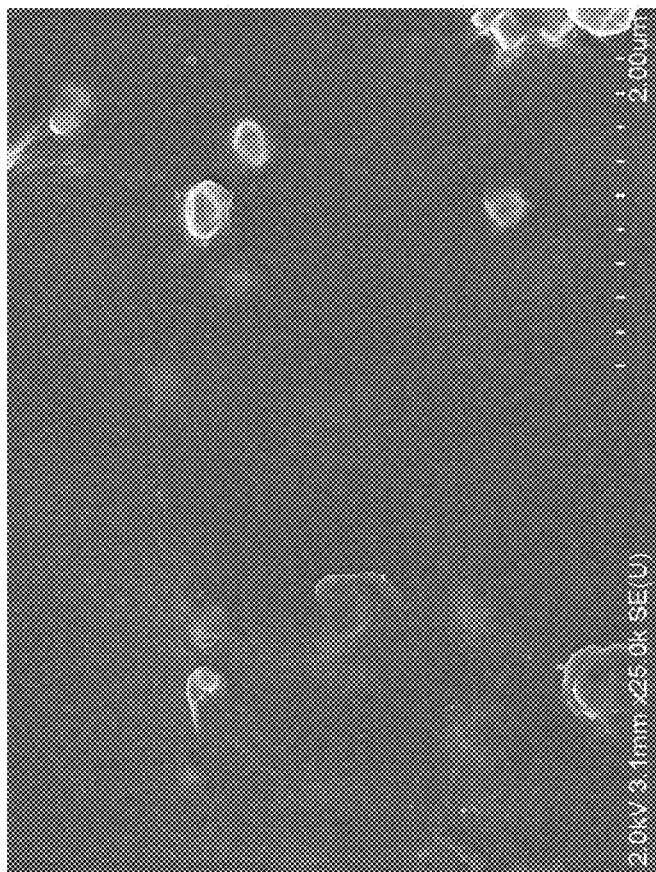

FIG. 235 illustrates a scanning electron microscopy image of film sample Melinex Control (fourth view).

Figure 236:

FIG. 236 illustrates a scanning electron microscopy image of film sample Mylar Control (first view).

Figure 237:
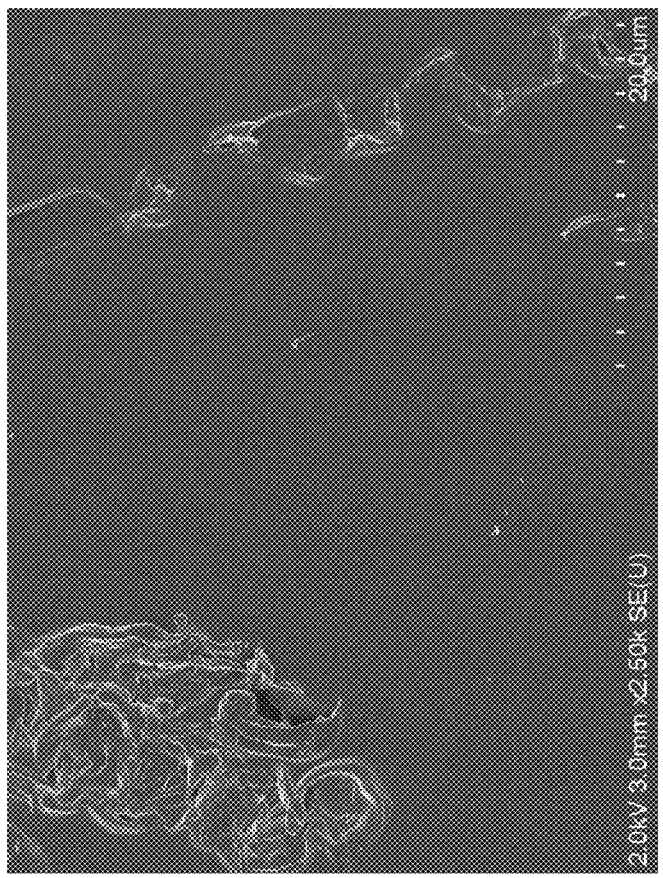

FIG. 237 illustrates a scanning electron microscopy image of film sample Mylar Control (second view).

Figure 238:

FIG. 238 illustrates a scanning electron microscopy image of film sample Mylar Control (third view).

Figure 239:
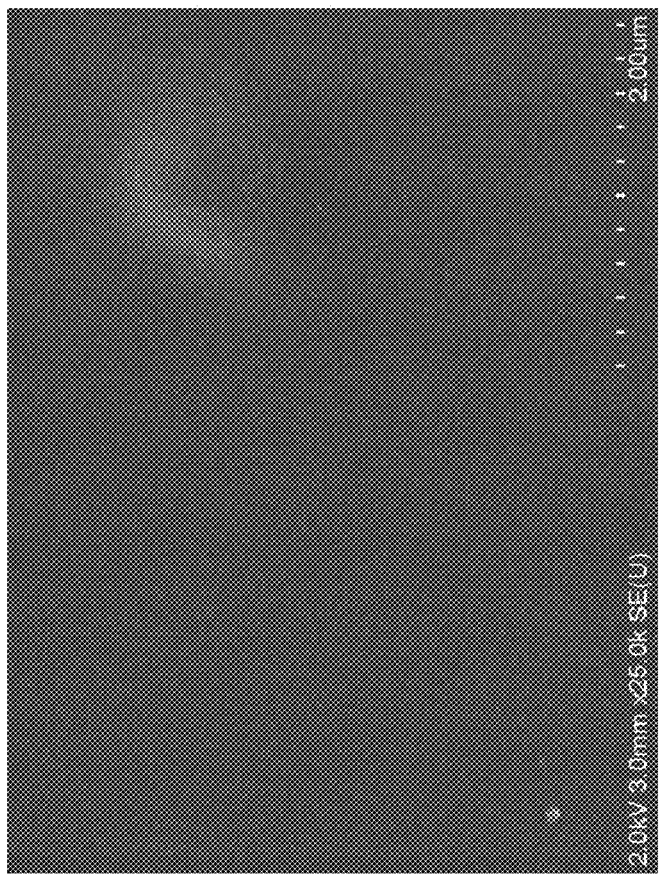

FIG. 239 illustrates a scanning electron microscopy image of film sample Mylar Control (fourth view).

Figure 240:
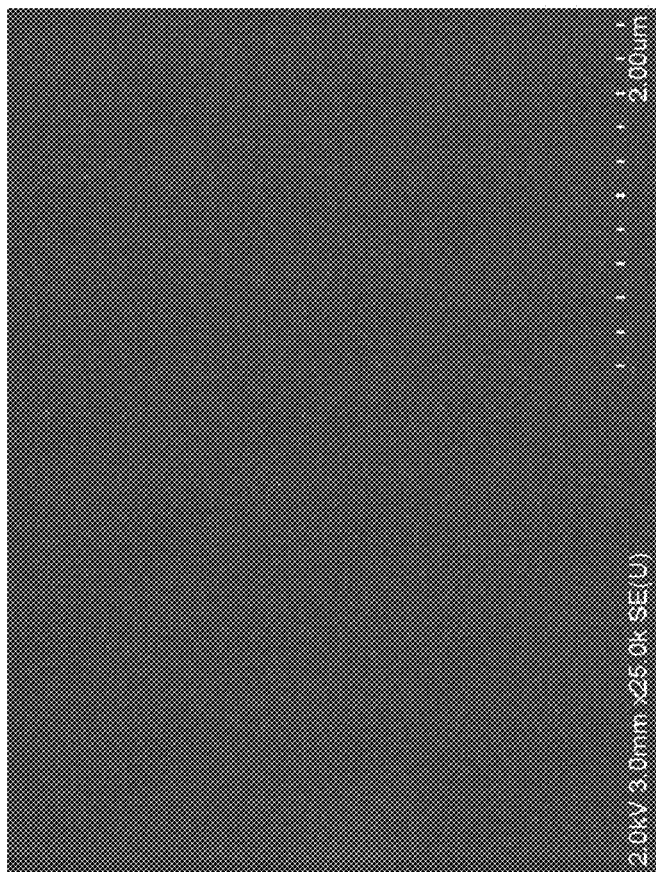

FIG. 240 illustrates a scanning electron microscopy image of film sample Mylar Control (fifth view).

Figure 241:
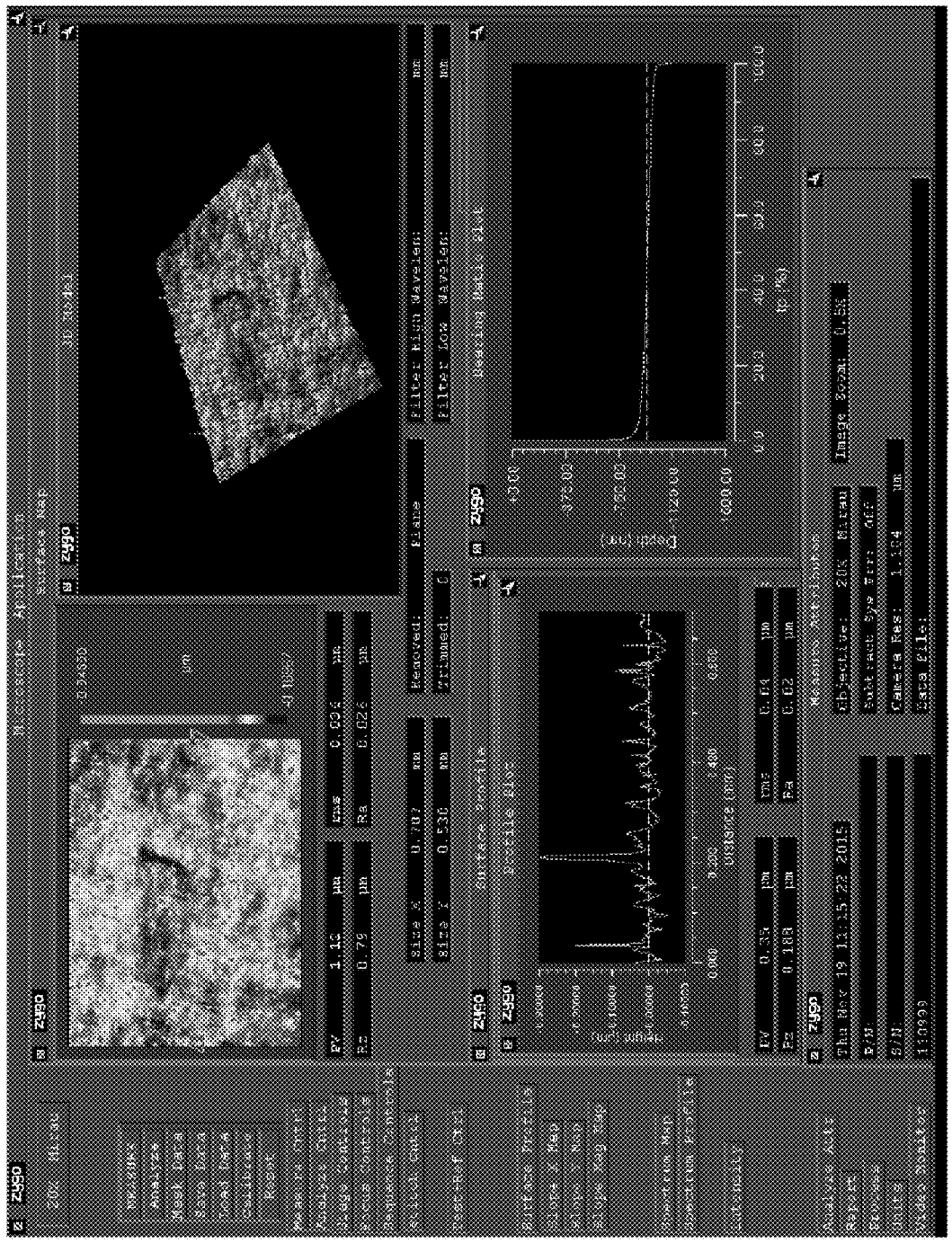

FIG. 241 shows results from optical profiling measurements on the Mylar Control sample taken at the top, location 1 (shiny side).

Figure 242:
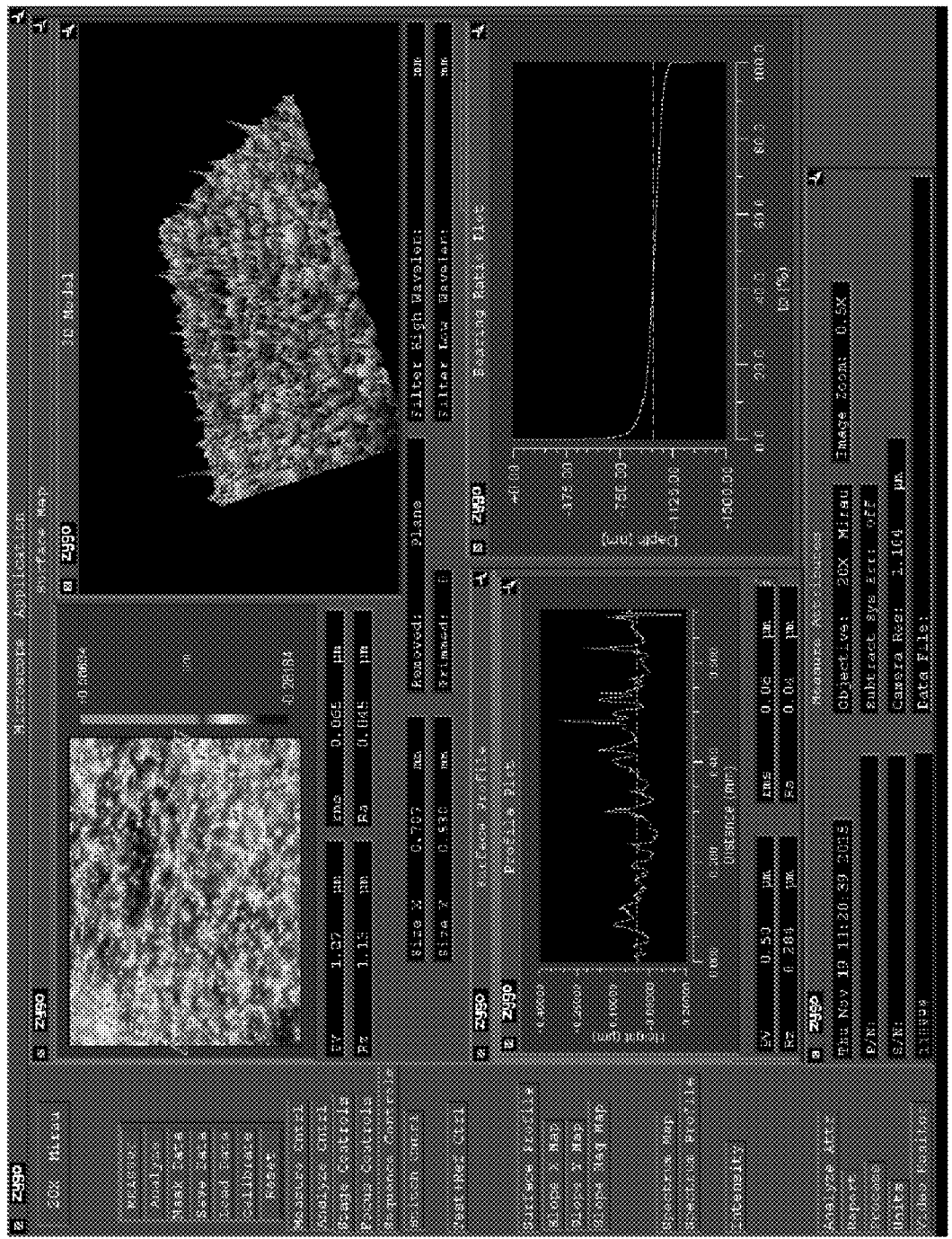

FIG. 242 shows results from optical profiling measurements on the Mylar Control sample taken at the bottom, location 2 (more matte side).

Figure 243:
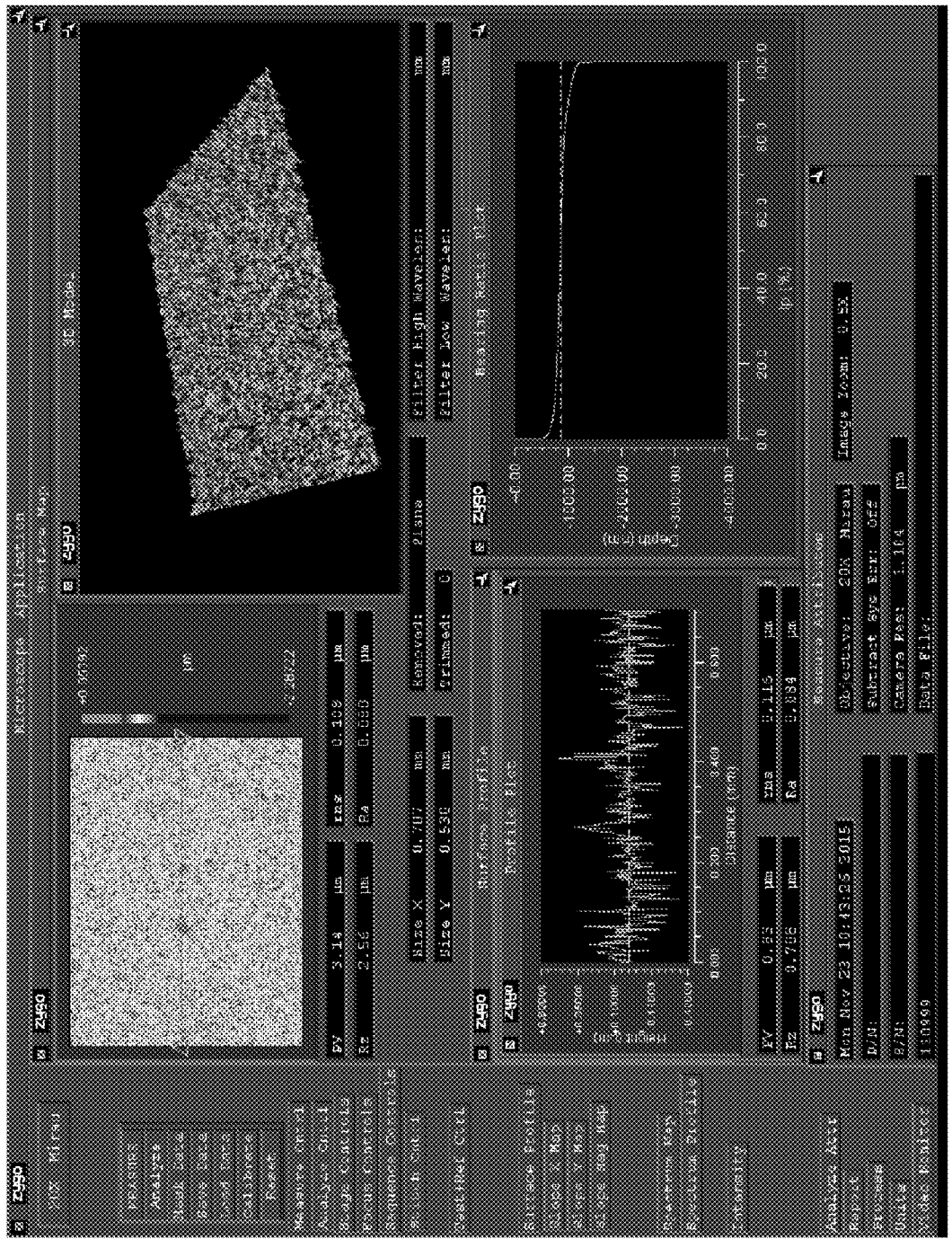

FIG. 243 shows results from optical profiling measurements on the Melinex Control sample taken at the top, location 1.

Figure 244:
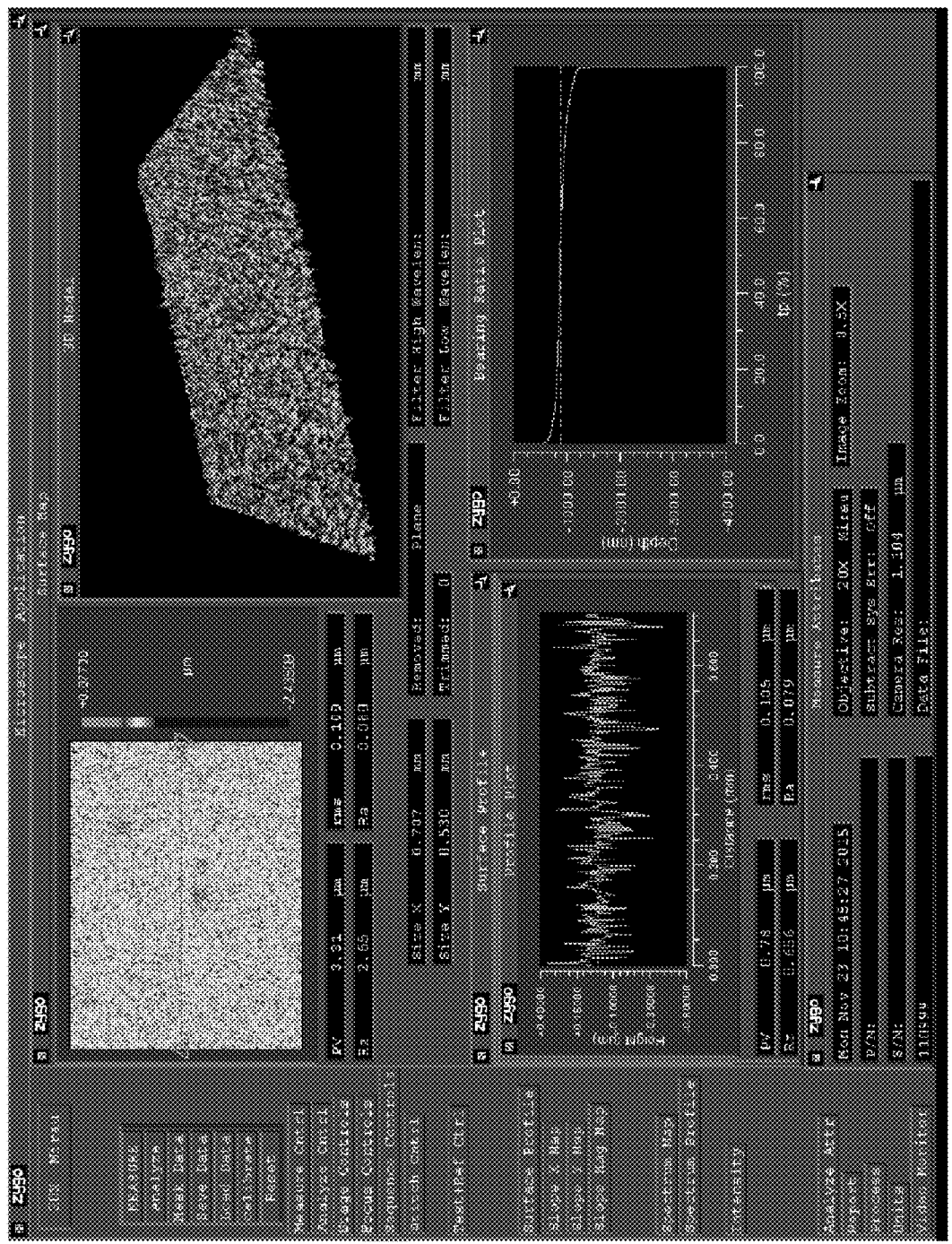

FIG. 244 shows results from optical profiling measurements on the Melinex Control sample taken at the bottom, location 2.

Figure 245:
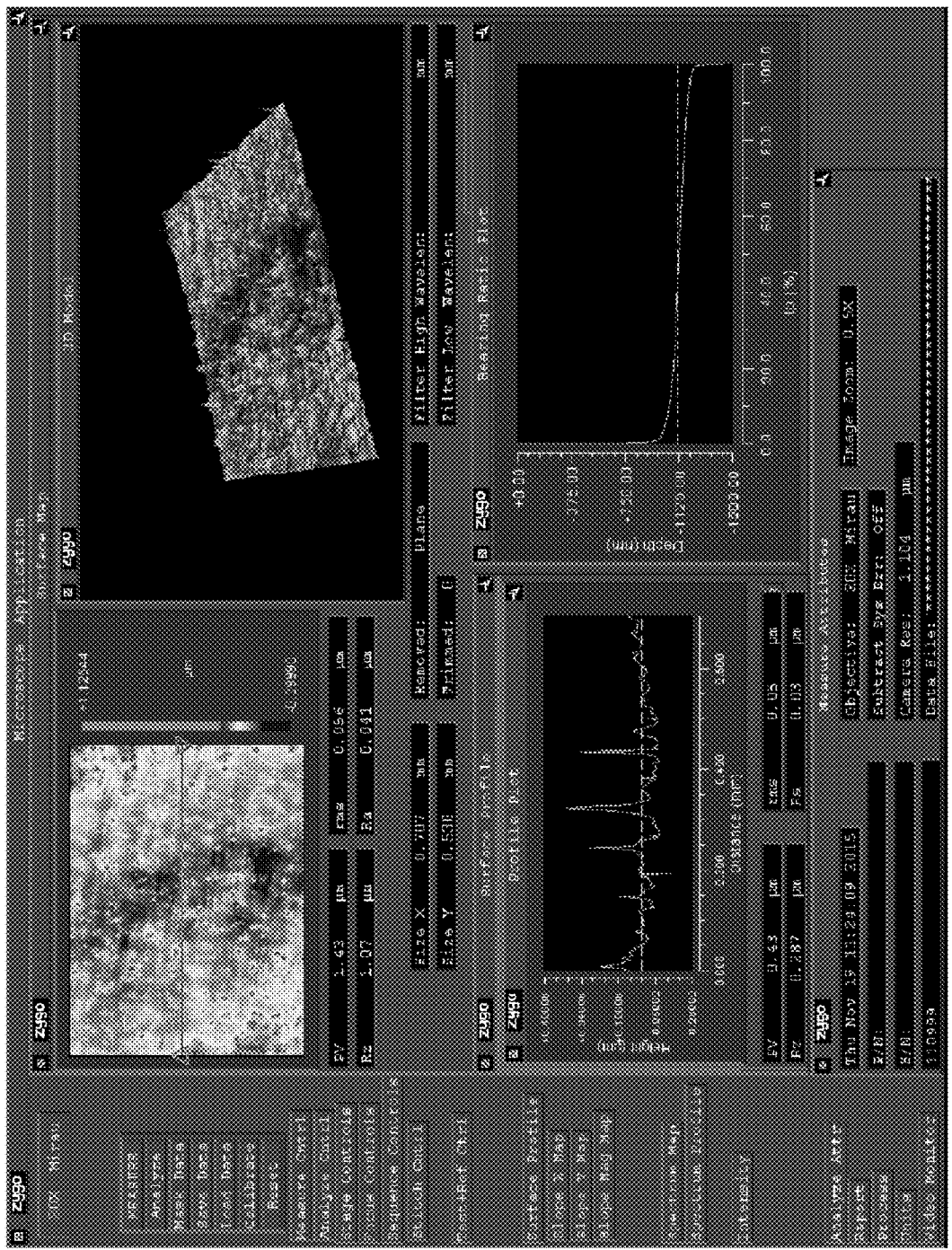

FIG. 245 shows results from optical profiling measurements on sample FIL-10-SPRAY-B-01MYL taken at the top, location 1.

Figure 246:
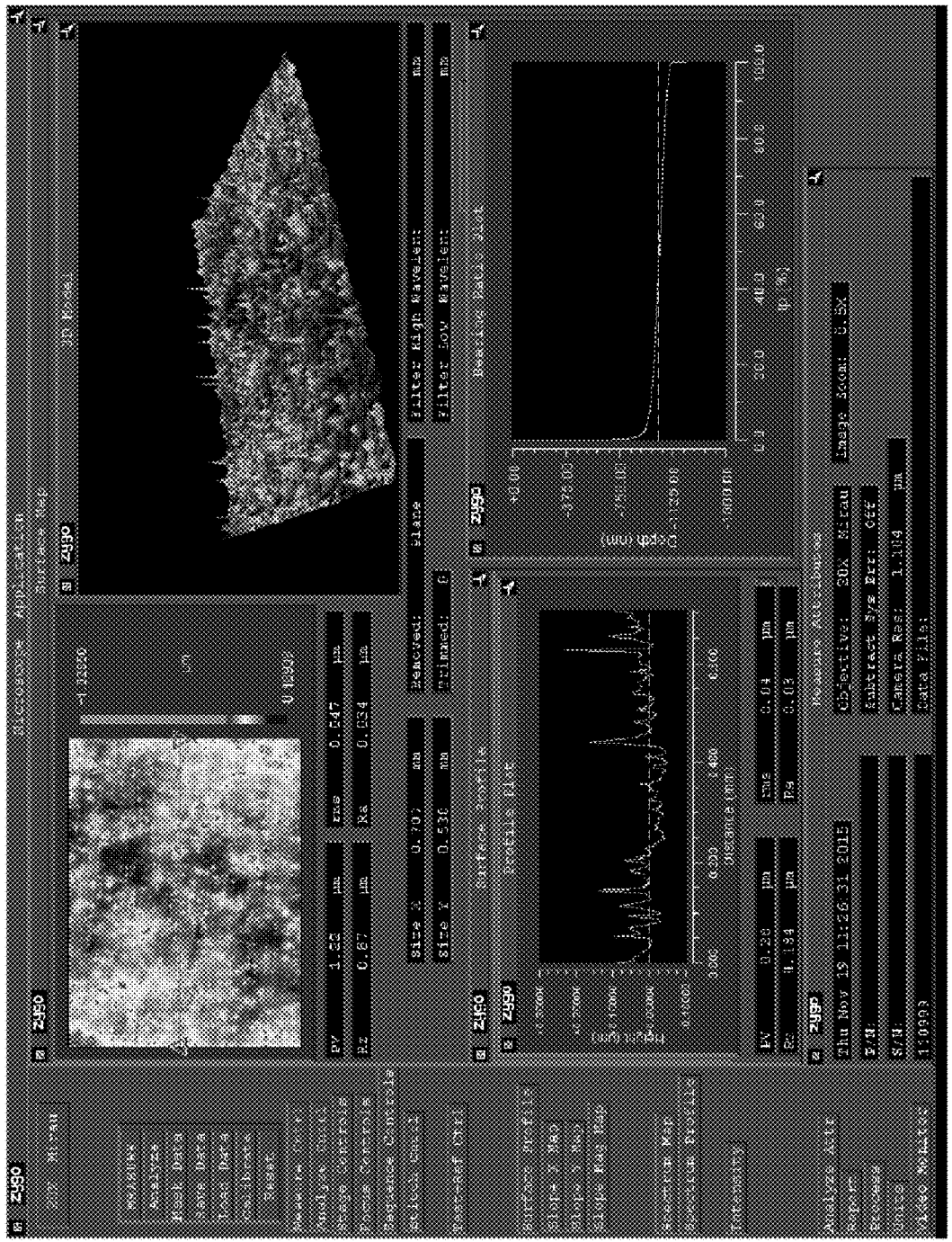

FIG. 246 shows results from optical profiling measurements on sample FIL-10-SPRAY-B-01MYL taken at the bottom, location 2.

Figure 247:
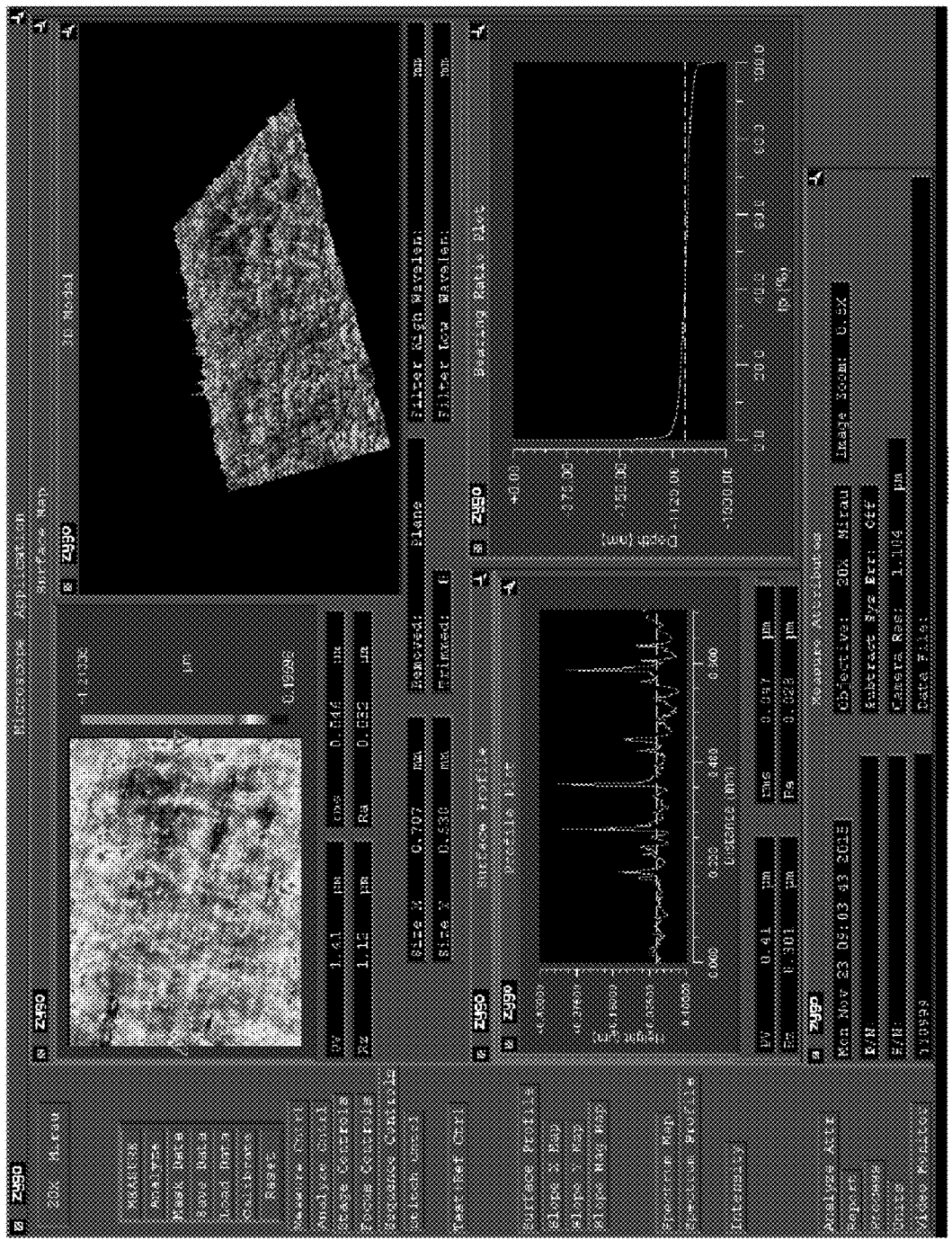

FIG. 247 shows results from optical profiling measurements on sample FIL-01-SPRAY-B-01MYL taken at the top, location 1.

Figure 248:
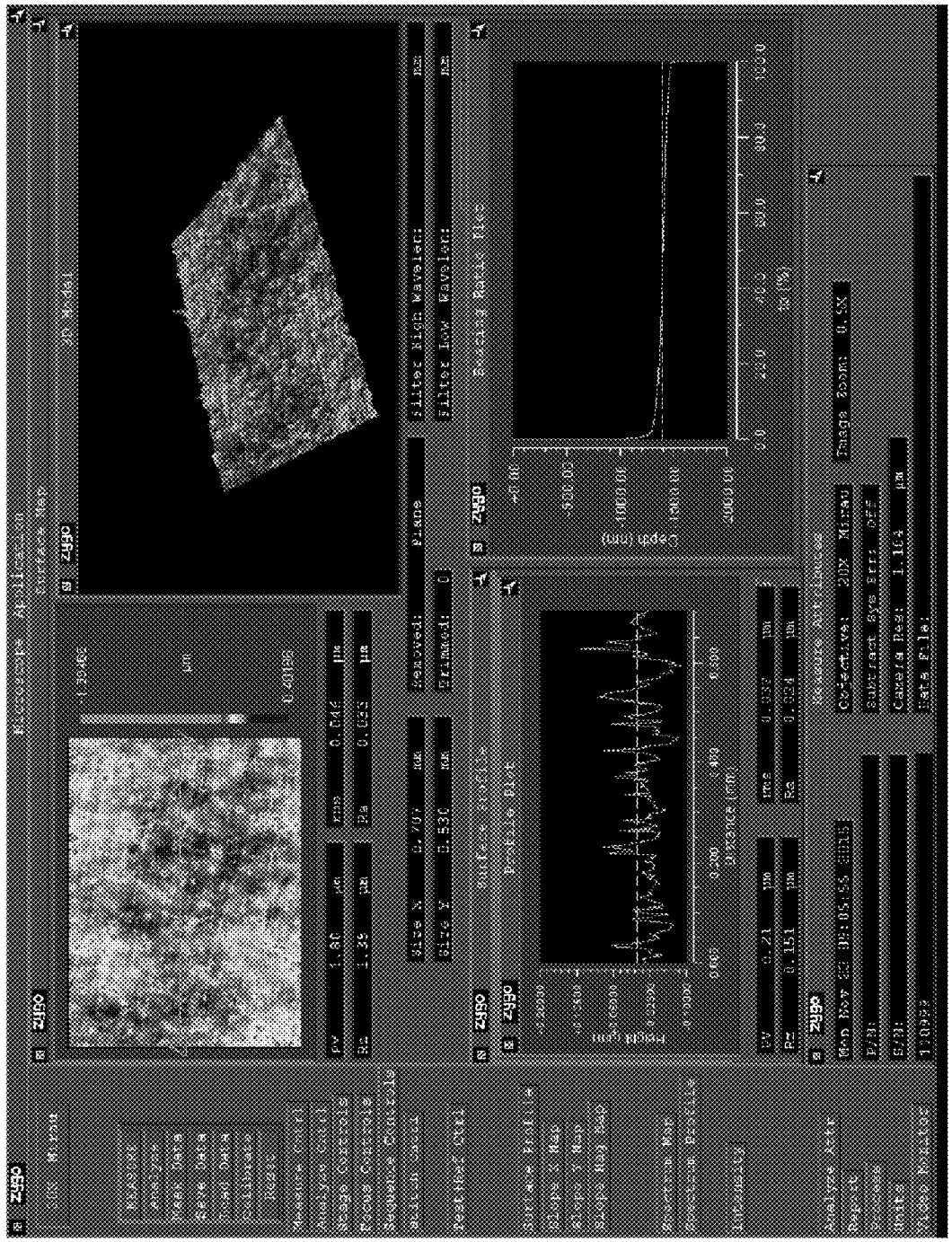

FIG. 248 shows results from optical profiling measurements on sample FIL-01-SPRAY-B-01MYL taken at the bottom, location 2.

Figure 249:
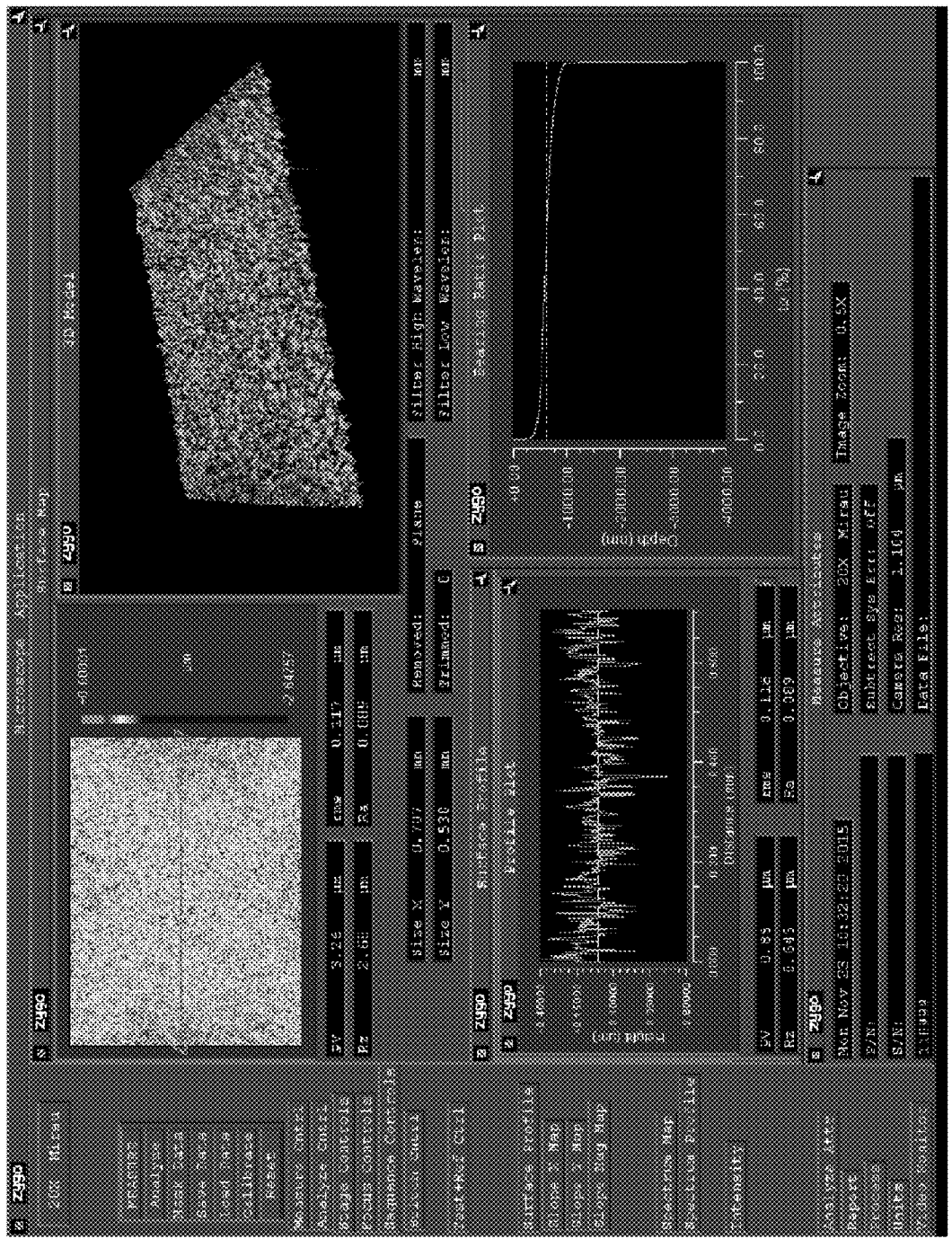

FIG. 249 shows results from optical profiling measurements on sample FIL-01-SPRAY-B-007MEL taken the top, location 1.

Figure 250:
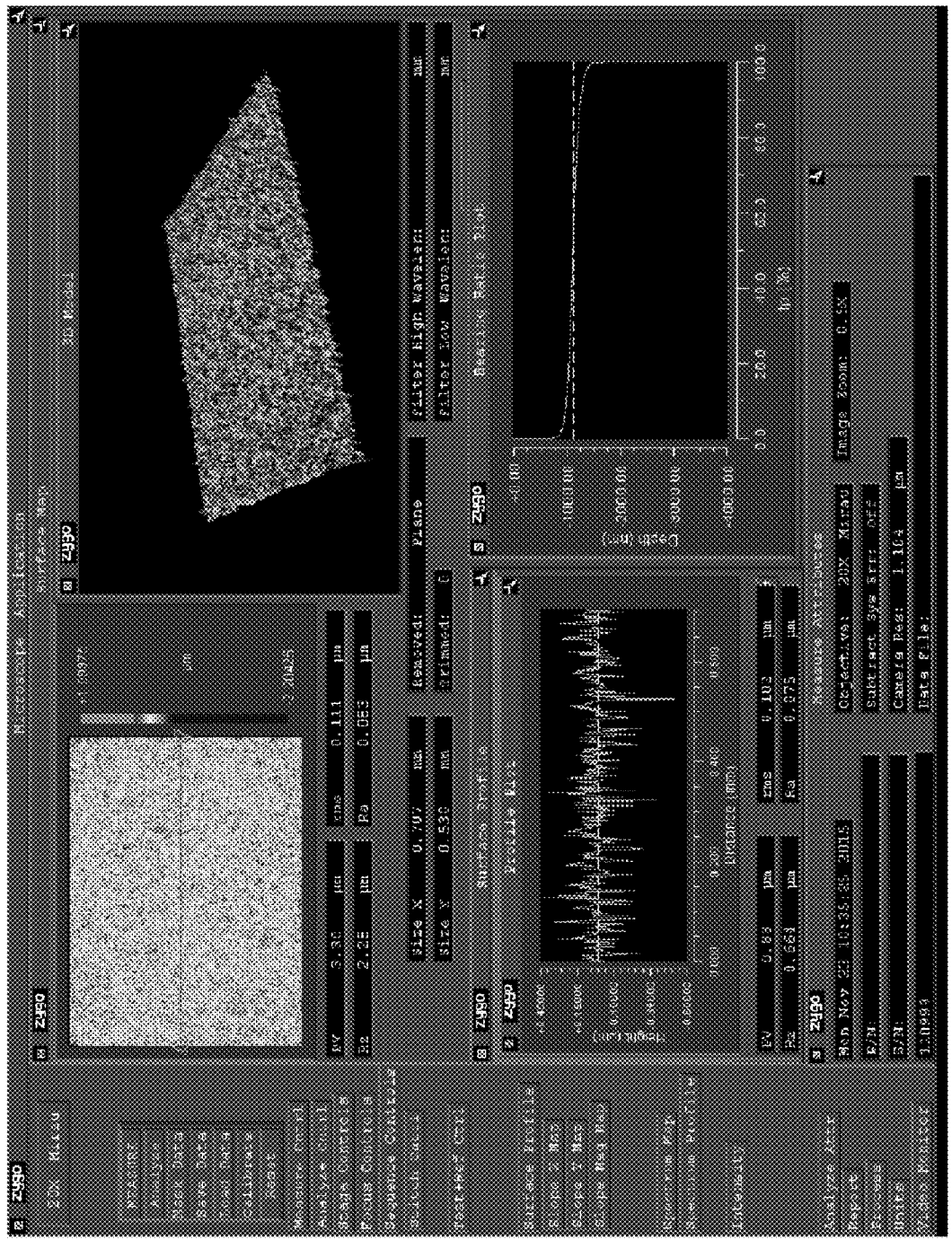

FIG. 250 shows results from optical profiling measurements on sample FIL-01-SPRAY-B-007MEL taken at the bottom, location 2.

Figure 251:
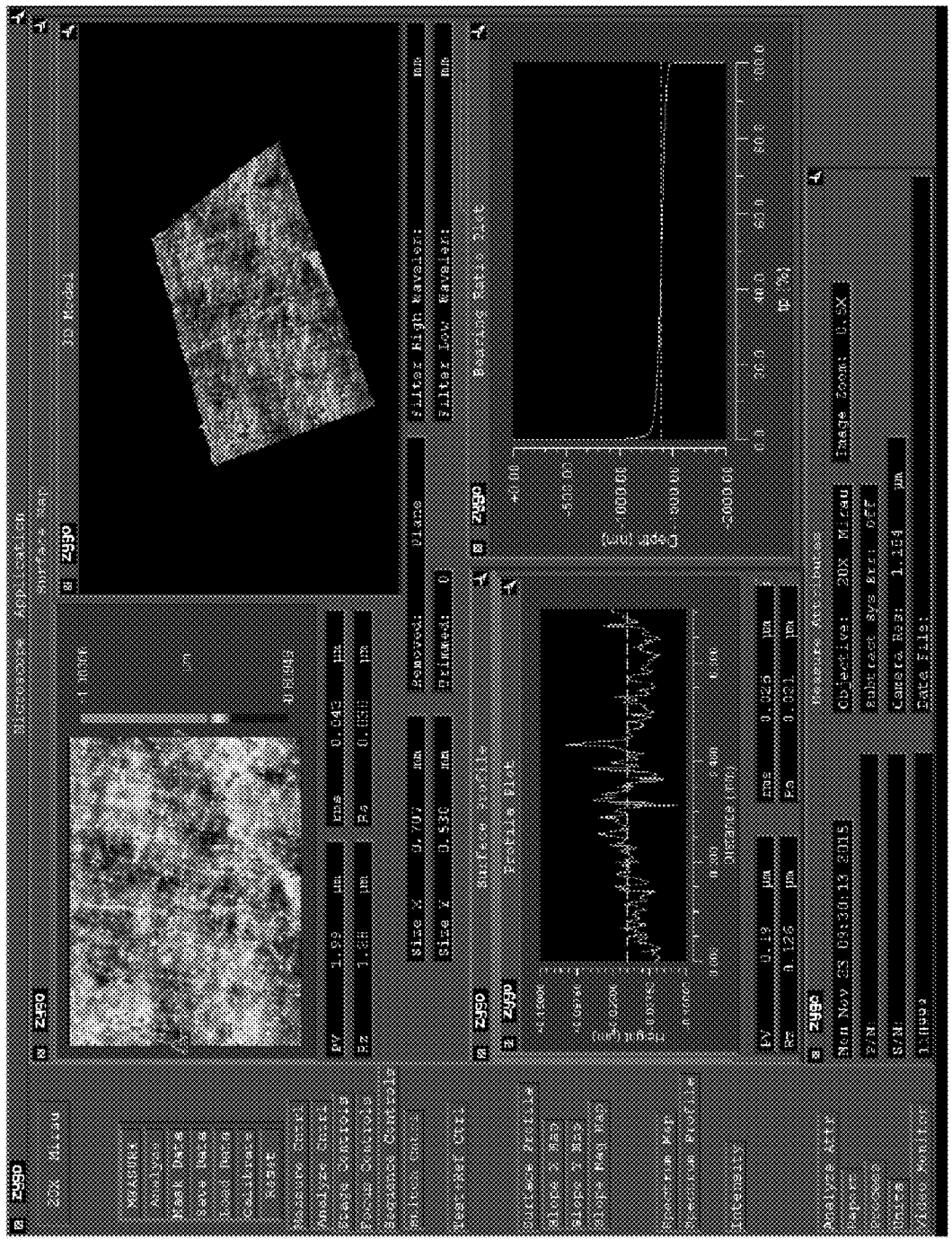

FIG. 251 shows results from optical profiling measurements on sample FIL-01-SPRAY-C-01MYL taken at the top, location 1.

Figure 252:
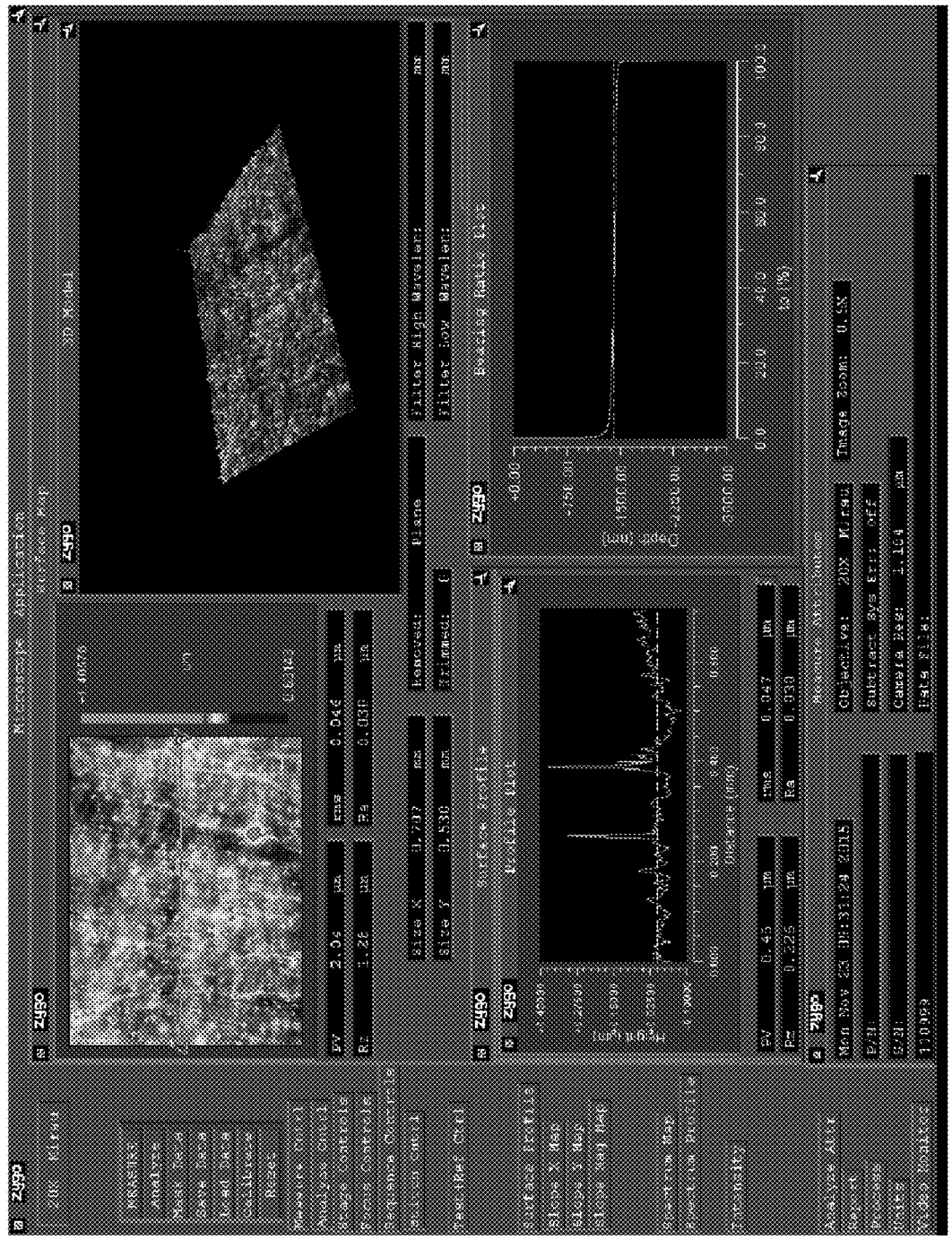

FIG. 252 shows results from optical profiling measurements on sample FIL-01-SPRAY-C-01MYL taken at bottom, location 2

Figure 253:
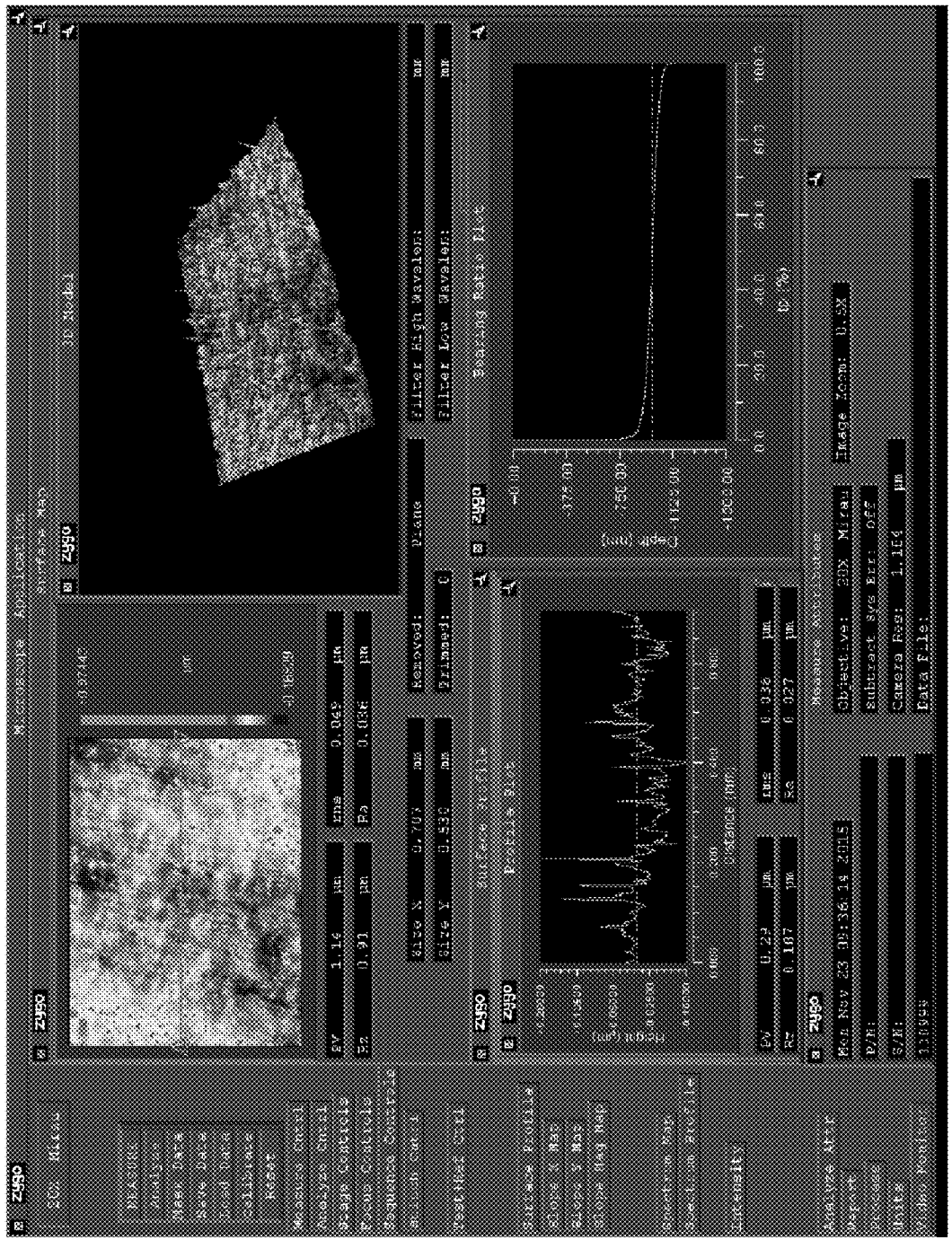

FIG. 253 shows results from optical profiling measurements on sample FIL-01-STEN-B-01MYL taken at the top, location 1.

Figure 254:
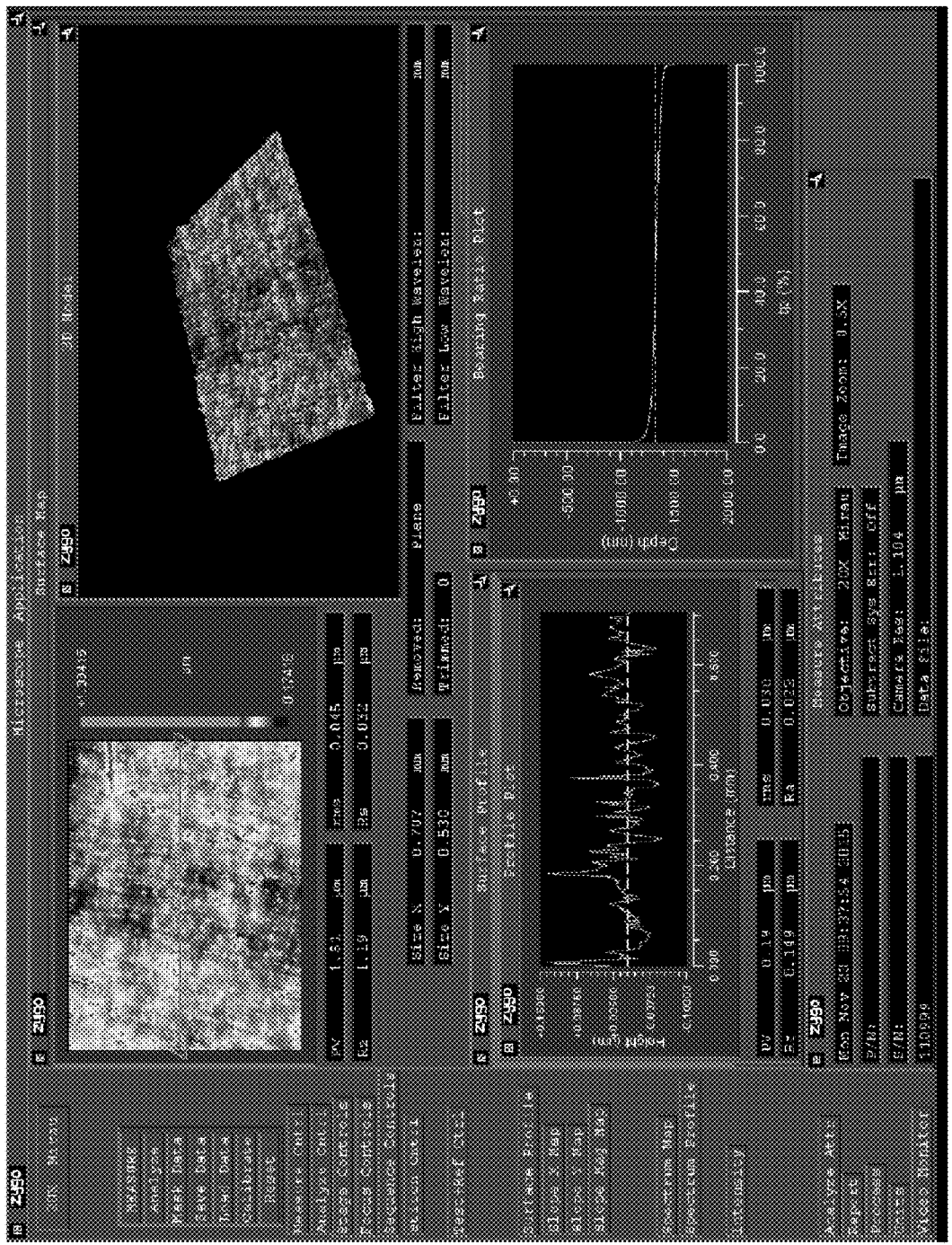

FIG. 254 shows results from optical profiling measurements on sample FIL-01-STEN-B-01MYL taken at the bottom, location 2.

Figure 255:
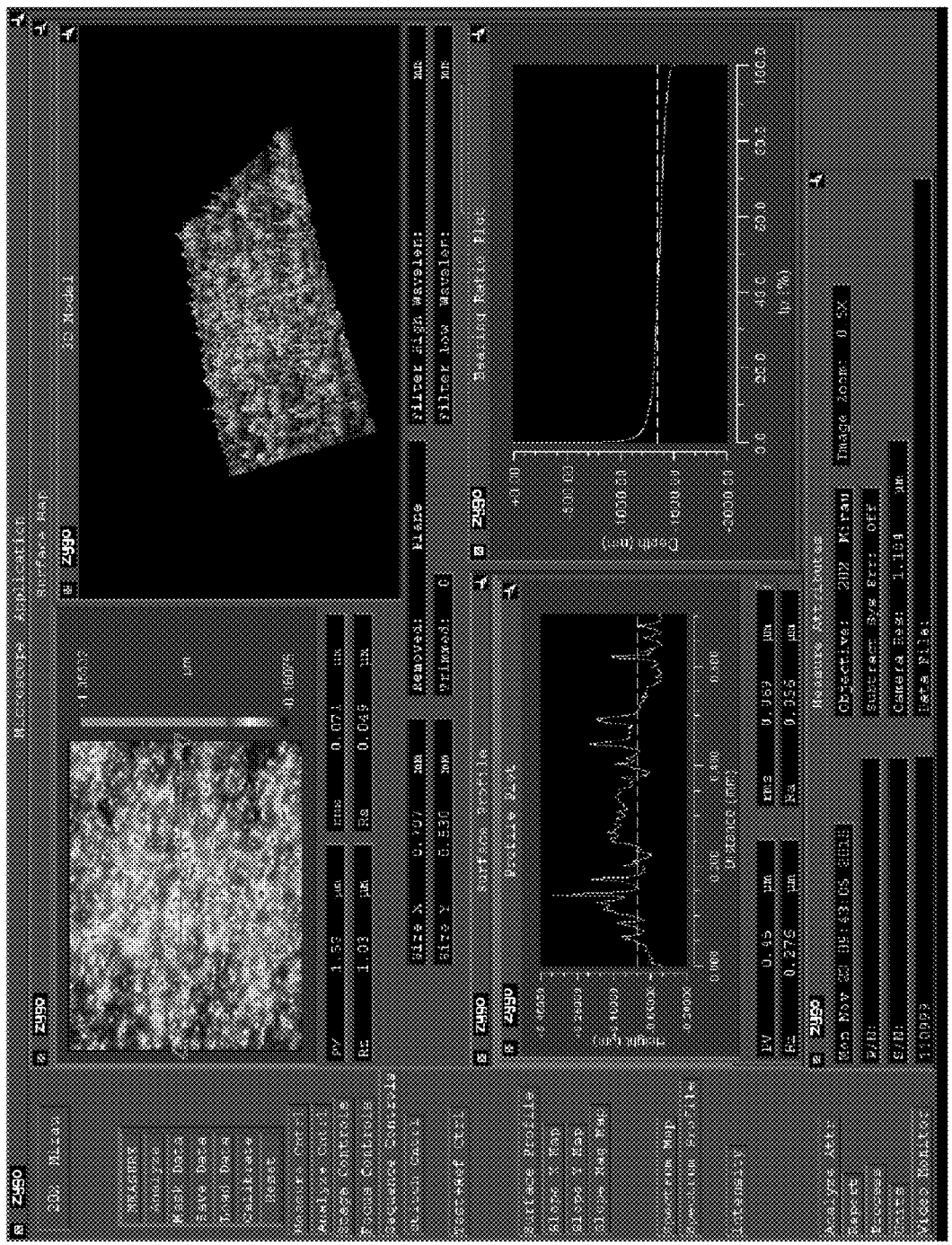

FIG. 255 shows results from optical profiling measurements on sample FIL-01-STEN-C-01MYL taken at the top, location 1.

Figure 256:
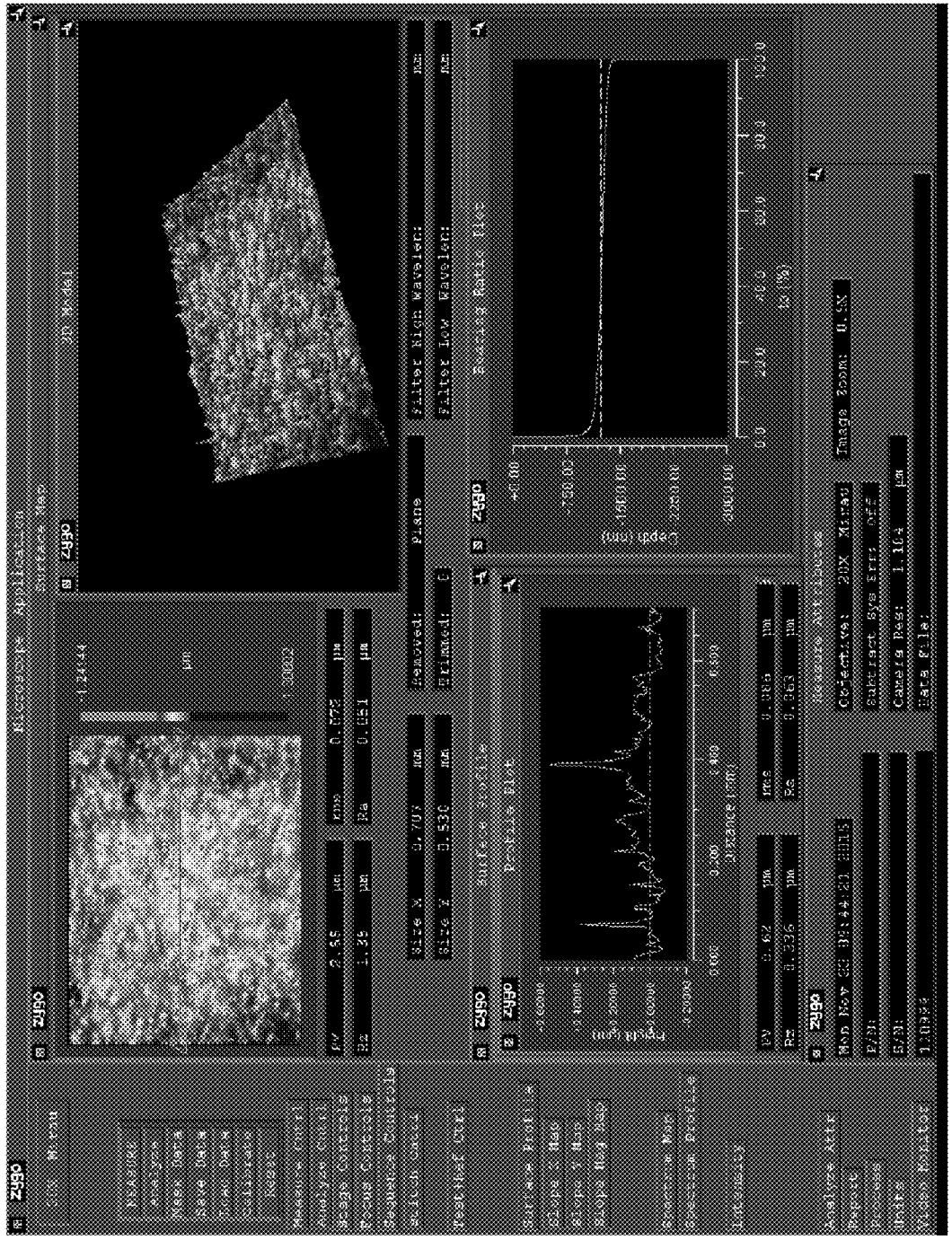

FIG. 256 shows results from optical profiling measurements on sample FIL-01-STEN-C-01MYL taken at the bottom, location 2.

Figure 257:
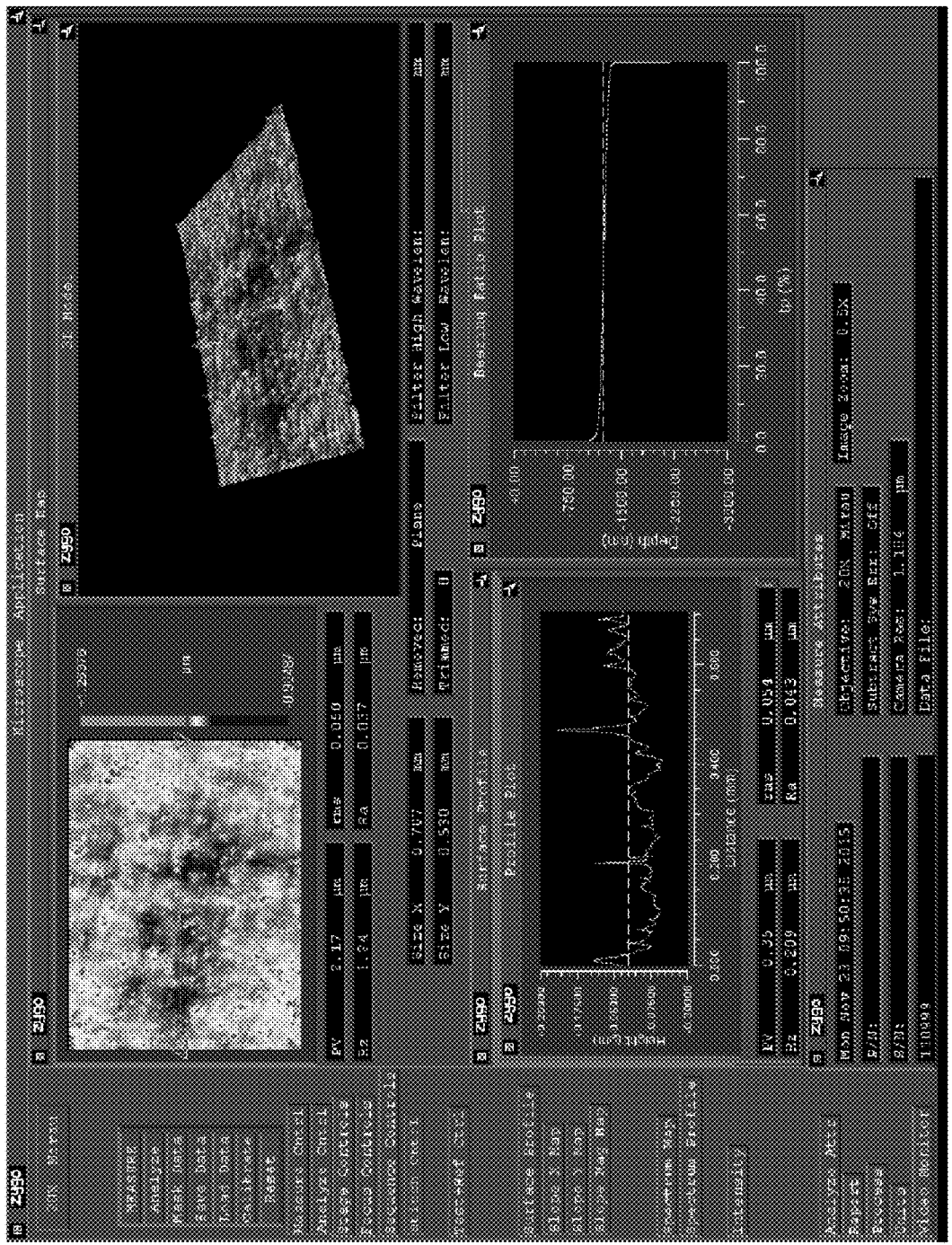

FIG. 257 shows results from optical profiling measurements on sample FIL-10-BATH-B-01MYL taken at the top, location 1.

Figure 258:
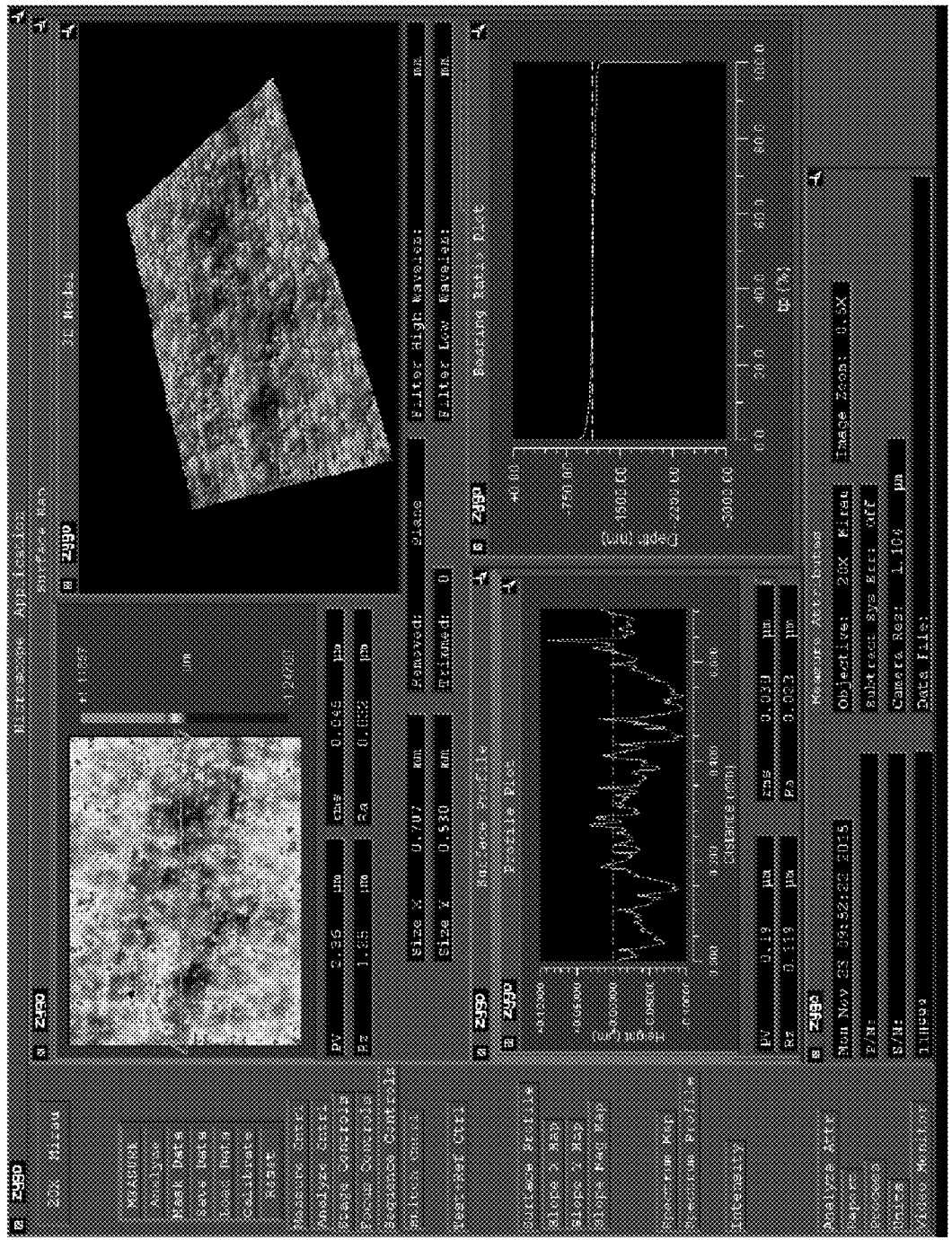

FIG. 258 shows results from optical profiling measurements on sample FIL-10-BATH-B-01MYL taken at the bottom, Location 2.

Figure 259:
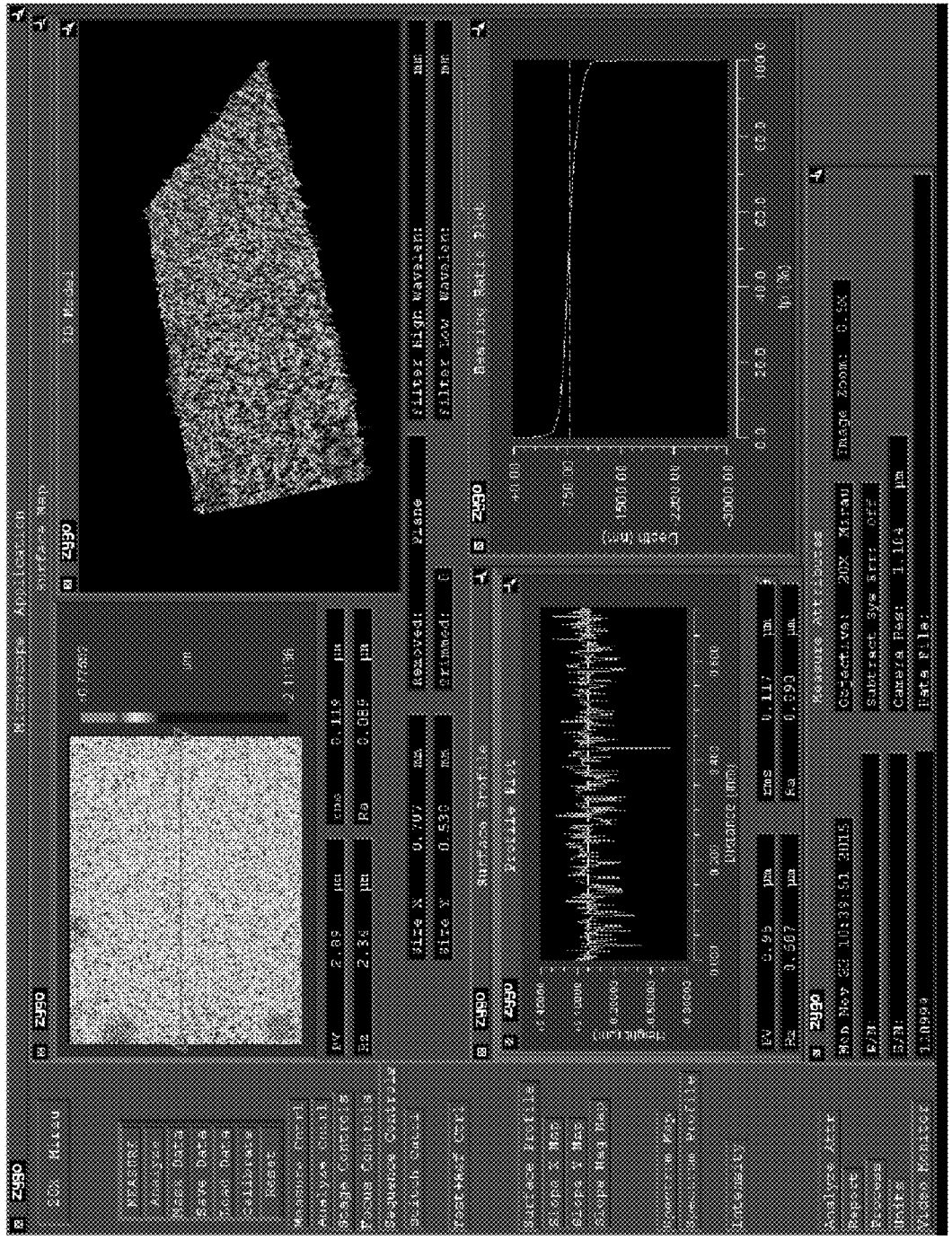

FIG. 259 shows results from optical profiling measurements on sample FIL-10-BATH-B-007MEL taken at the top, location 1.

Figure 260:
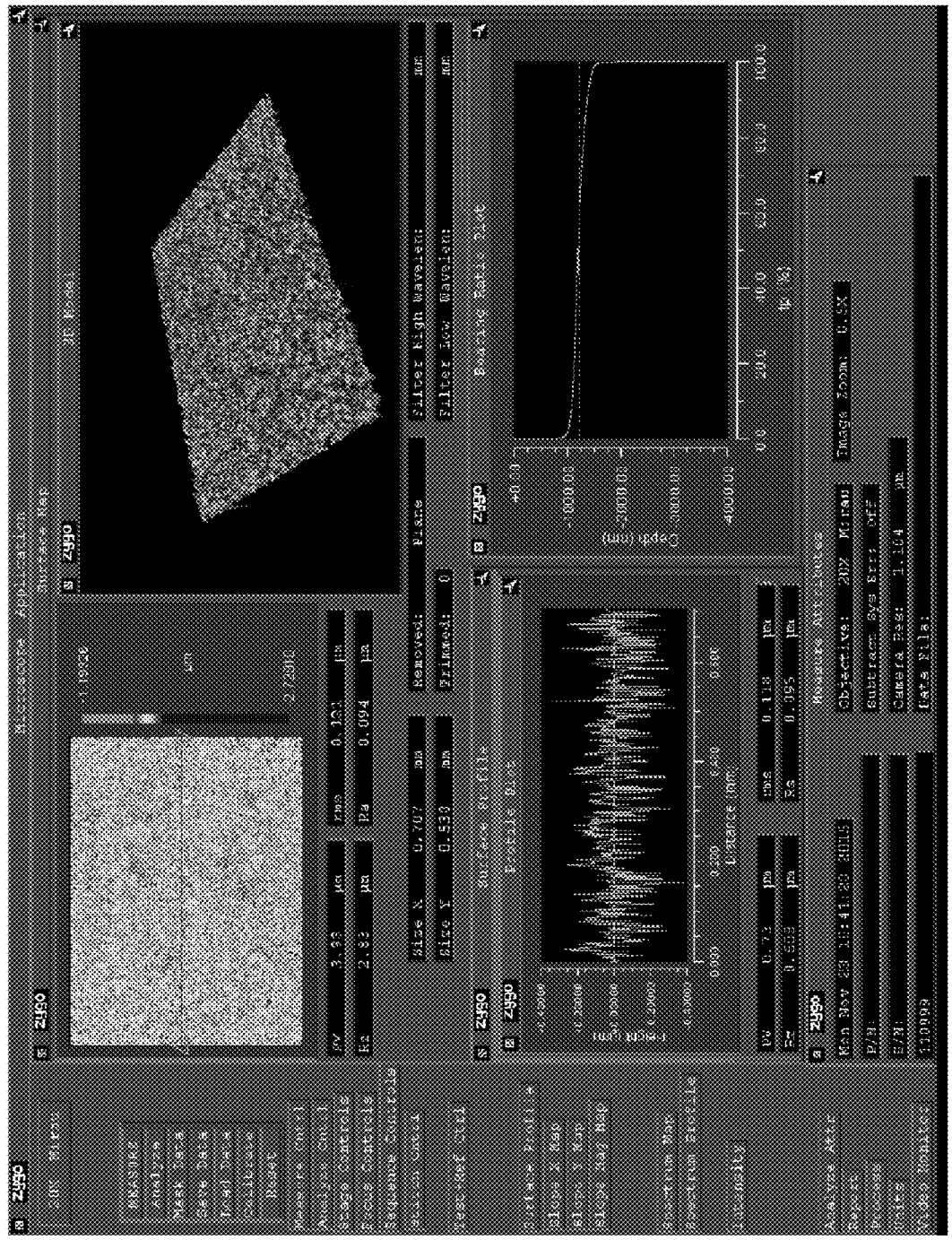

FIG. 260 shows results from optical profiling measurements on sample FIL-10-BATH-B-007MEL taken at the bottom, location 2.

Figure 261:
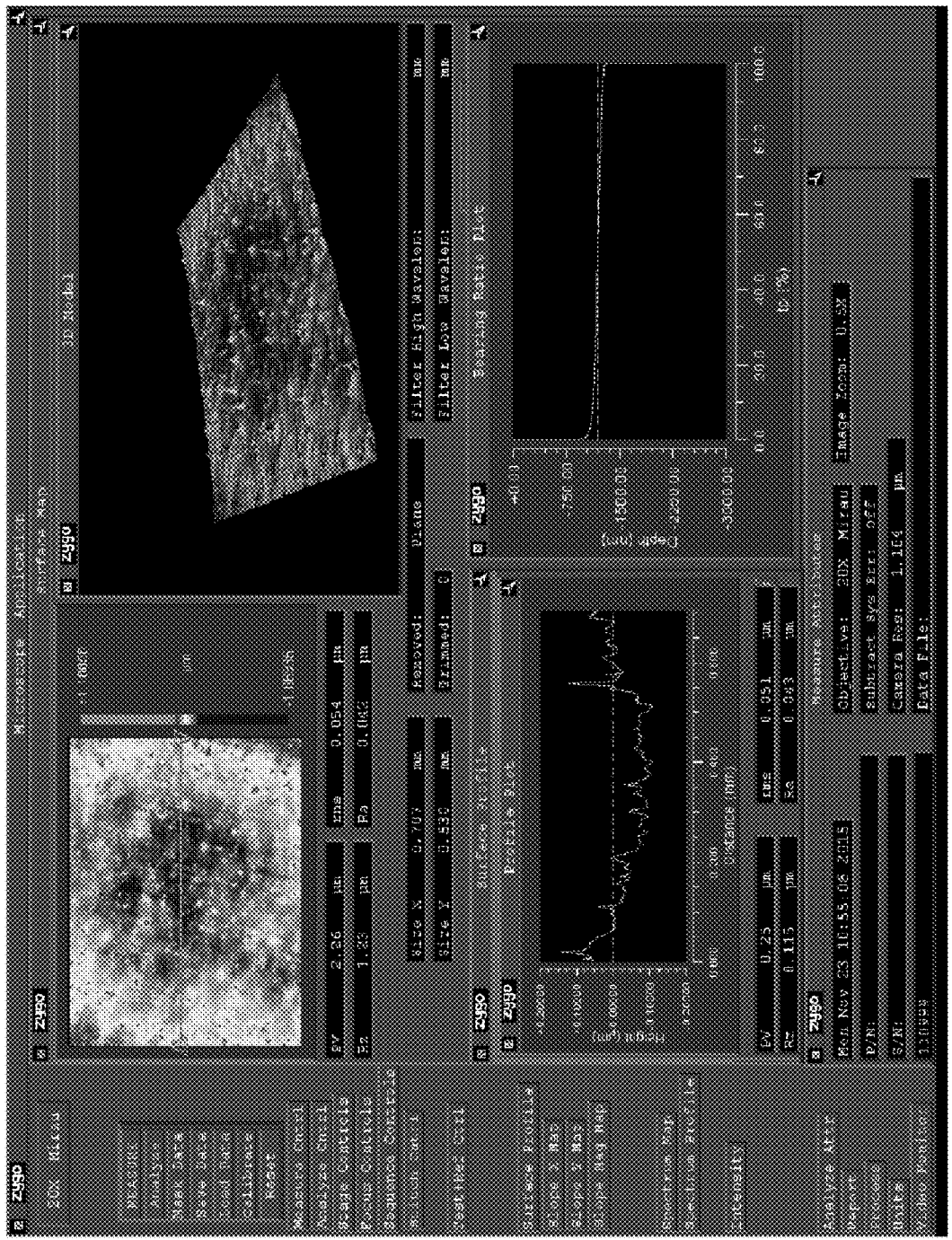

FIG. 261 shows results from optical profiling measurements on sample FIL-10-BATH-C-01MYL taken at top, location 1.

Figure 262:
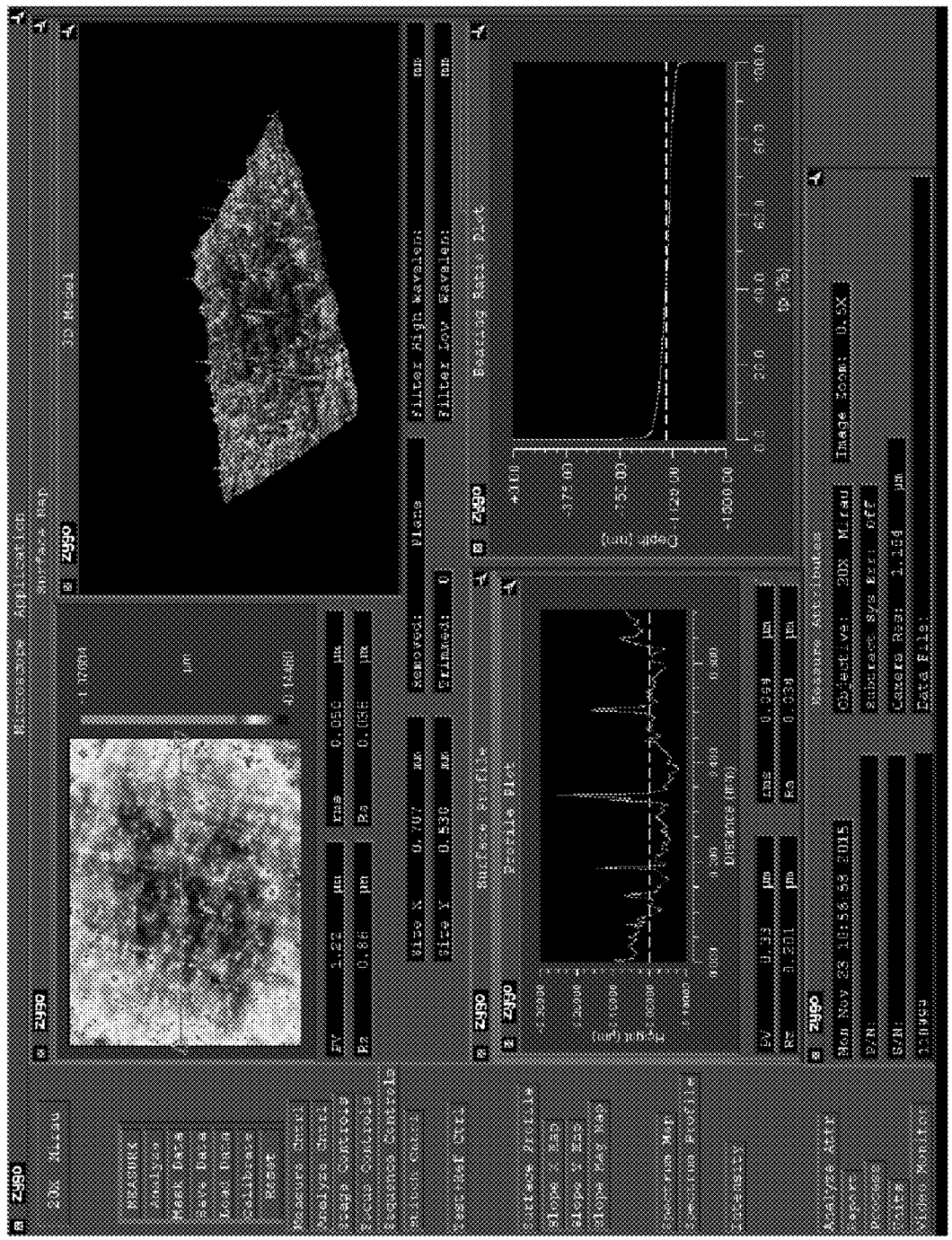

FIG. 262 shows results from optical profiling measurements on sample FIL-10-BATH-C-01MYL taken at the bottom, location 2.

Figure 263:
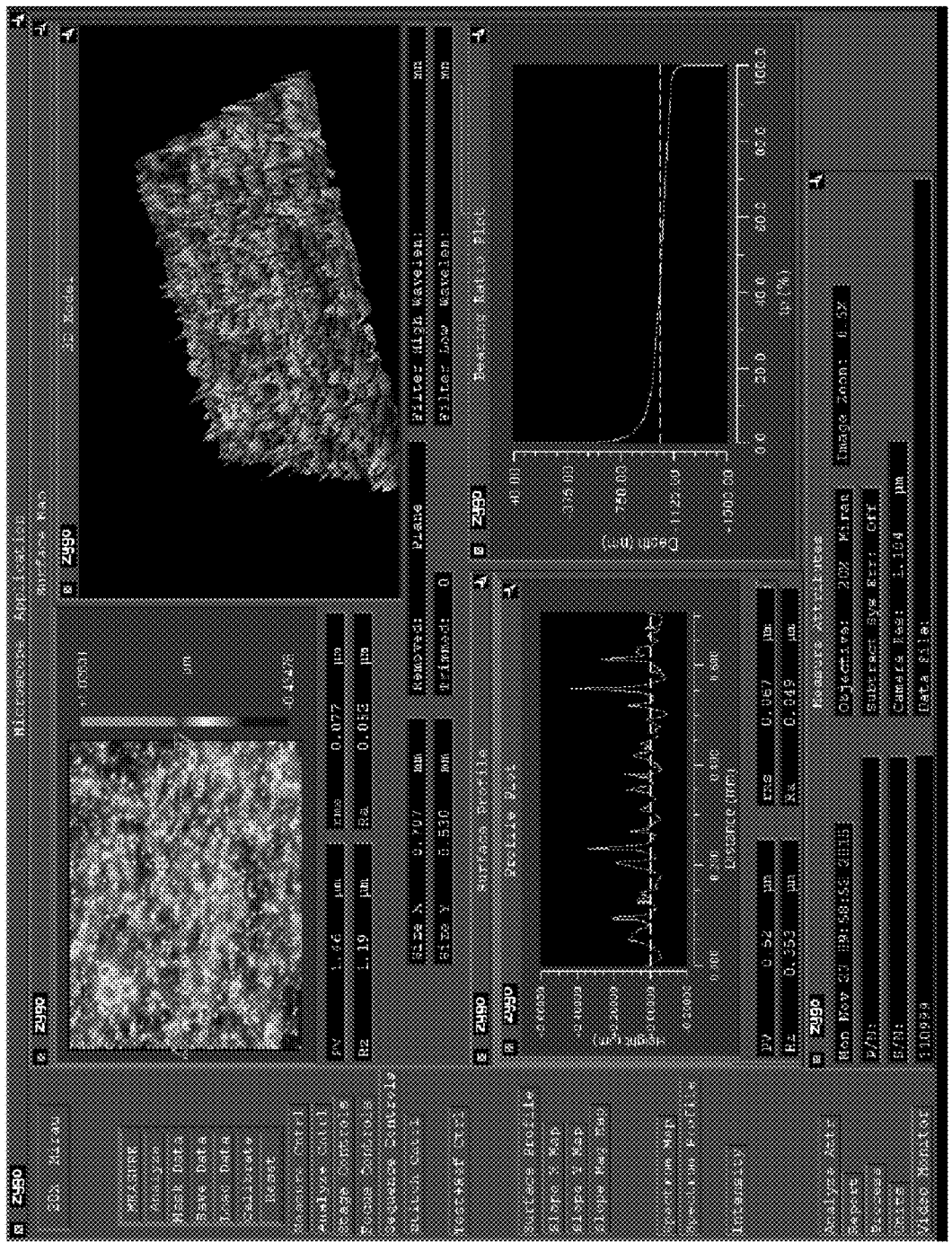

FIG. 263 shows results from optical profiling measurements on sample FIL-01-BATH-B-01MYL taken at the top, location 1.

Figure 264:
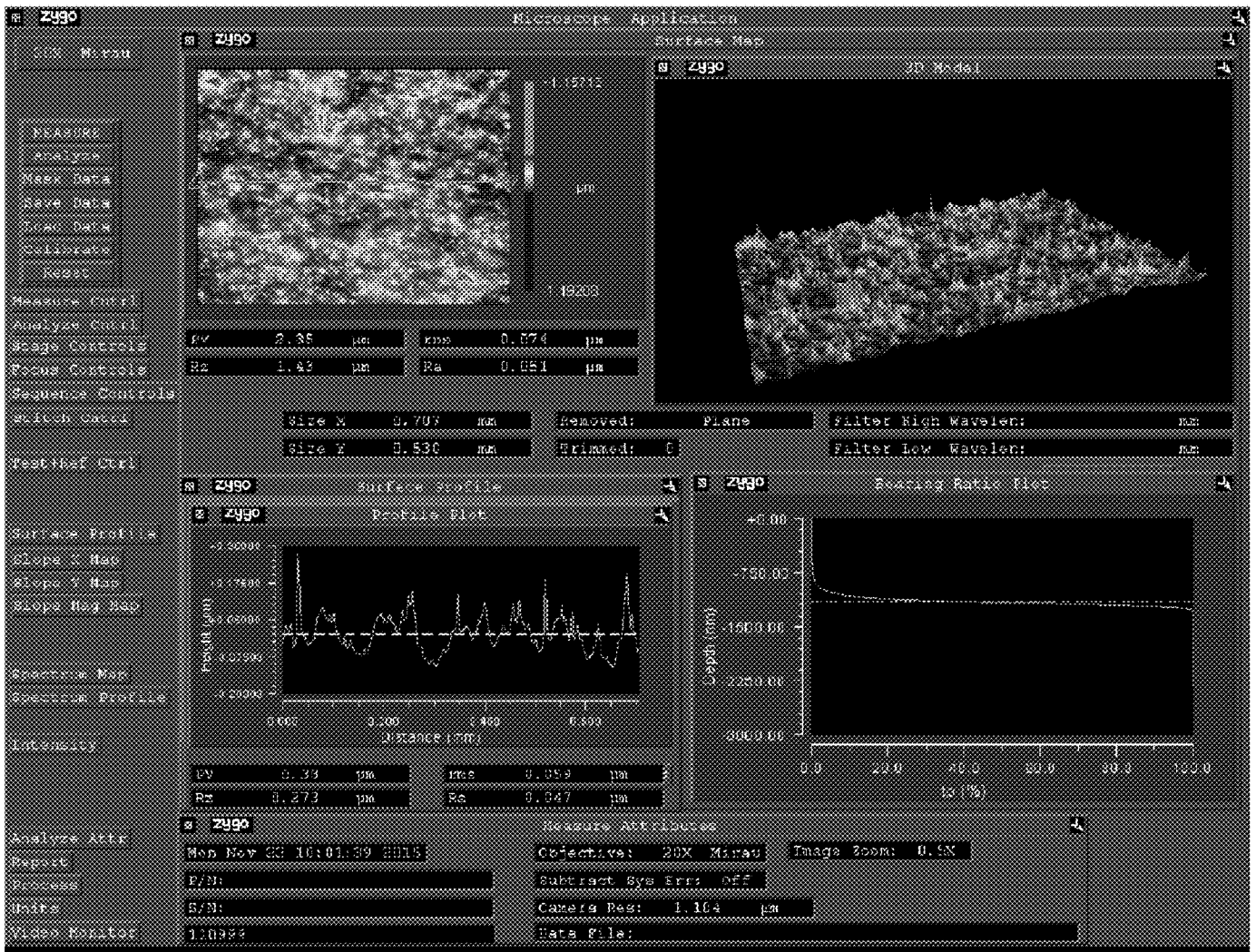

FIG. 264 shows results from optical profiling measurements on sample FIL-01-BATH-B-01MYL taken at the bottom, location 2.

Figure 265:
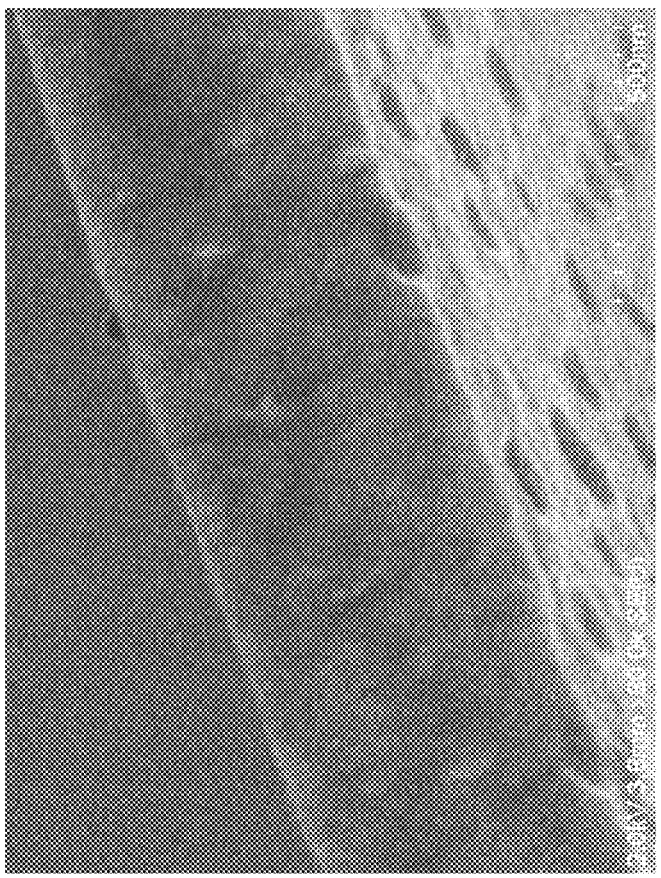

FIG. 265 illustrates a scanning electron microscopy image of film sample FIL-01-SPRAY-B-01MYL_cross-section.

Figure 266:
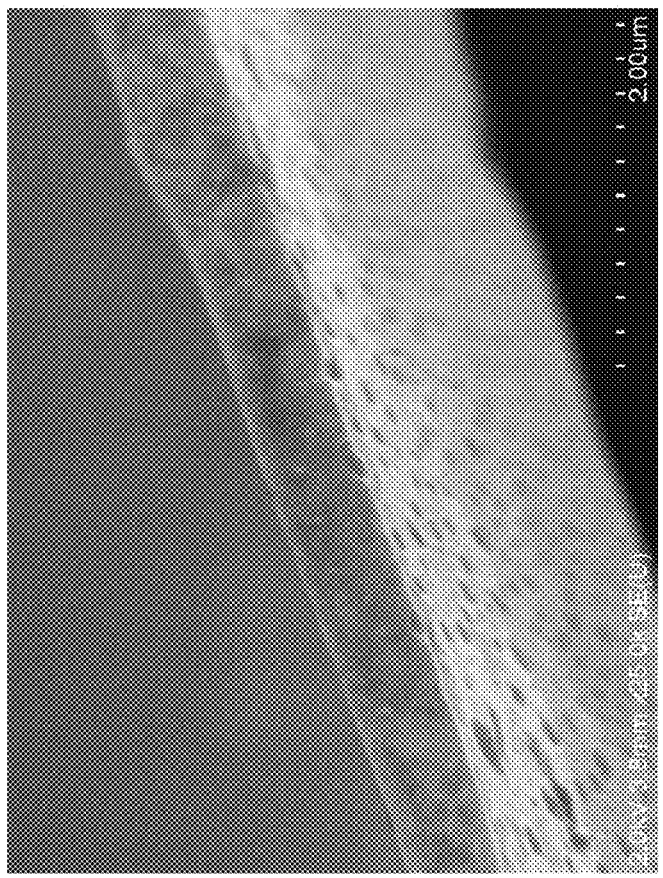

FIG. 266 illustrates a scanning electron microscopy image of film sample FIL-01-SPRAY-B-01MYL_cross-section.

Figure 267:
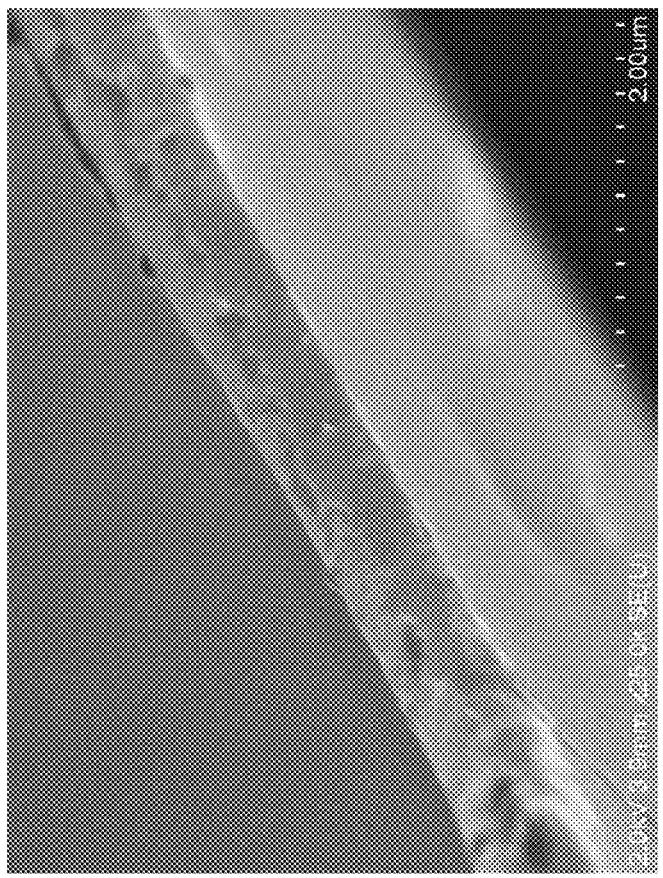

FIG. 267 illustrates a scanning electron microscopy image of film sample FIL-01-SPRAY-B-01MYL_cross-section.

Figure 268:
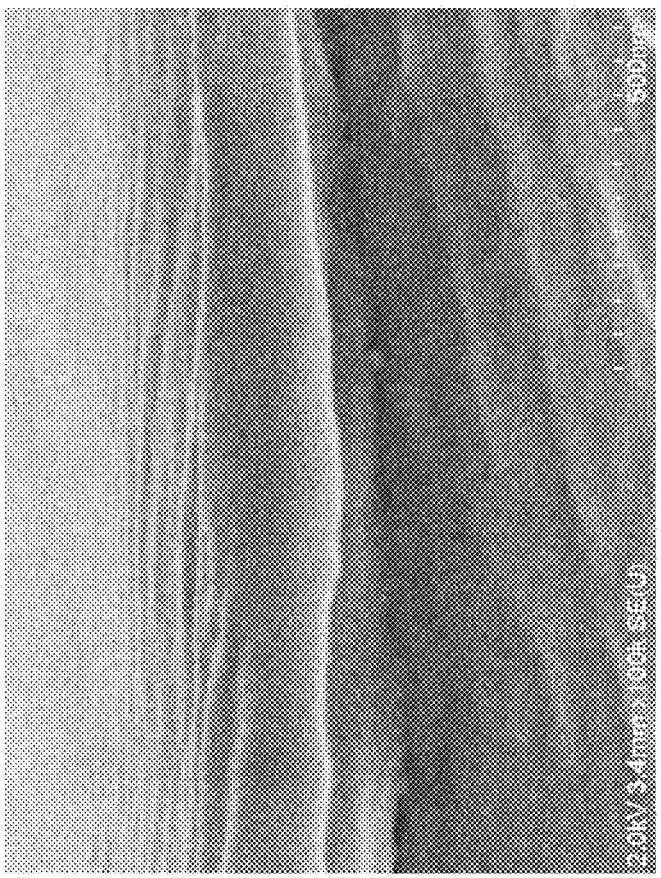

FIG. 268 illustrates a scanning electron microscopy image of film sample FIL-10-BATH-C-01MYL_cross-section.

Figure 269:
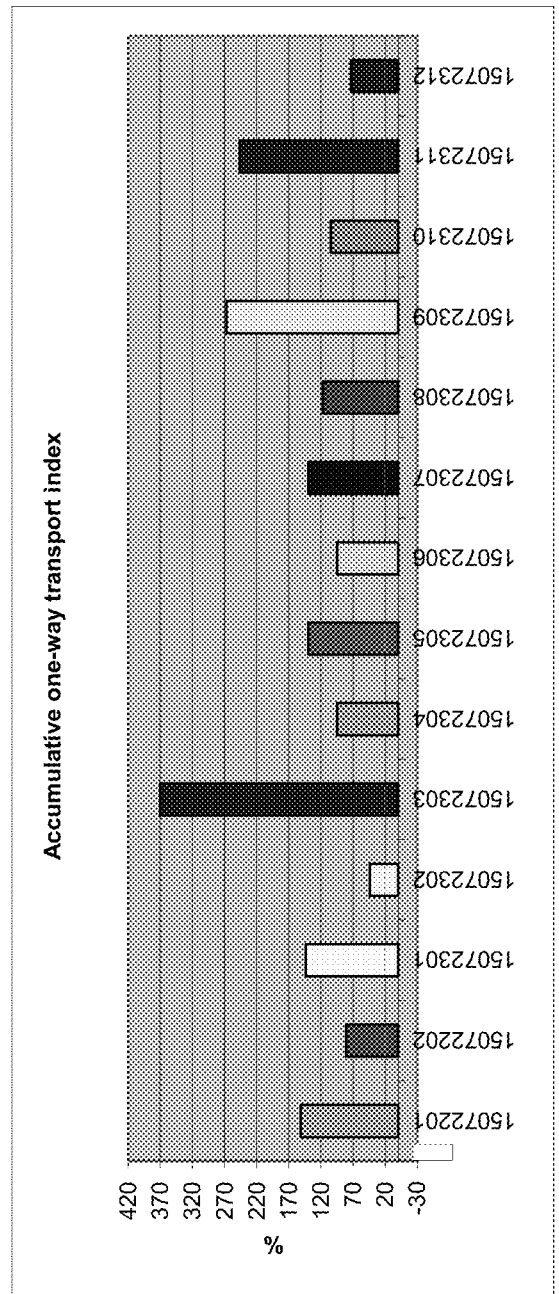

FIG. 269 illustrates accumulative one-way transport index results for natural fibers.

Figure 270:
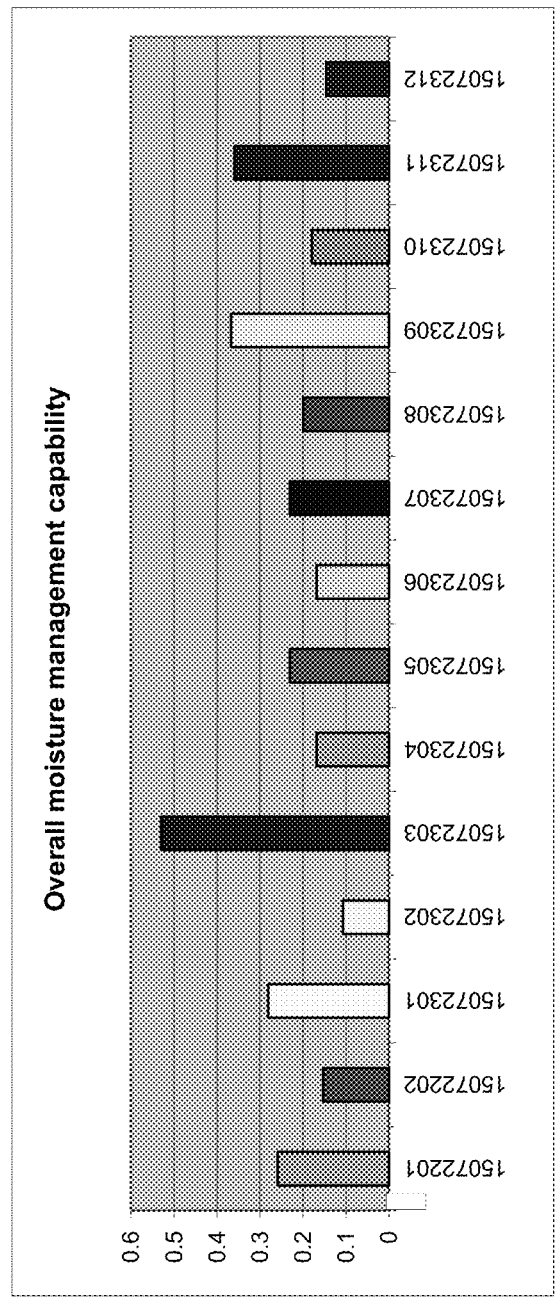

FIG. 270 illustrates overall moisture management capability for natural fibers.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

Provided herein are methods for producing pure and highly scalable silk protein fragment (SPF) mixture solutions that may be used to coat at least a portion of textiles or may be formed into usable fibers for weaving into yarn. The solutions are generated from raw pure intact silk protein material and processed in order to remove any sericin and achieve the desired weight average molecular weight (MW) and polydispersity of the fragment mixture. Select method parameters may be altered to achieve distinct final silk protein fragment characteristics depending upon the intended use. The resulting final fragment solution is pure silk protein fragments and water with PPM to non-detectable levels of process contaminants. The concentration, size and polydispersity of silk protein fragments in the solution may further be altered depending upon the desired use and performance requirements. In an embodiment, the pure silk fibroin-based protein fragments in the solution are substantially devoid of sericin, have an average weight average molecular weight ranging from about 6 kDa to about 16 kDa, and have a polydispersity ranging from about 1.5 and about 3.0. In an embodiment, the pure silk fibroin-based protein fragments in the solution are substantially devoid of sericin, have an average weight average molecular weight ranging from about 17 kDa to about 38 kDa, and have a polydispersity ranging from about 1.5 and about 3.0. In an embodiment, the pure silk fibroin-based protein fragments in the solution are substantially devoid of sericin, have an average weight average molecular weight ranging from about 39 kDa to about 80 kDa, and have a polydispersity ranging from about 1.5 and about 3.0. In an embodiment, the solutions may be used to generate articles, such as silk gels of varying gel and liquid consistencies by varying water content/concentration, or sold as a raw ingredient into the consumer market.

As used herein, the terms "substantially sericin free" or "substantially devoid of sericin" refer to silk fibers in which a majority of the sericin protein has been removed. In an embodiment, silk fibroin that is substantially devoid of sericin refers to silk fibroin having between about 0.01% (w/w) and about 10.0% (w/w) sericin. In an embodiment, silk fibroin that is substantially devoid of sericin refers to silk fibroin having between about 0.01% (w/w) and about 9.0% (w/w) sericin. In an embodiment, silk fibroin that is substantially devoid of sericin refers to silk fibroin having between about 0.01% (w/w) and about 8.0% (w/w) sericin. In an embodiment, silk fibroin that is substantially devoid of sericin refers to silk fibroin having between about 0.01% (w/w) and about 7.0% (w/w) sericin. In an embodiment, silk fibroin that is substantially devoid of sericin refers to silk fibroin having between about 0.01% (w/w) and about 6.0% (w/w) sericin. In an embodiment, silk fibroin that is substantially devoid of sericin refers to silk fibroin having between about 0.01% (w/w) and about 5.0% (w/w) sericin. In an embodiment, silk fibroin that is substantially devoid of sericin refers to silk fibroin having between about 0% (w/w) and about 4.0% (w/w) sericin. In an embodiment, silk fibroin that is substantially devoid of sericin refers to silk fibroin having between about 0.05% (w/w) and about 4.0% (w/w) sericin. In an embodiment, silk fibroin that is substantially devoid of sericin refers to silk fibroin having between about 0.1% (w/w) and about 4.0% (w/w) sericin. In an embodiment, silk fibroin that is substantially devoid of sericin refers to silk fibroin having between about 0.5% (w/w) and about 4.0% (w/w) sericin. In an embodiment, silk fibroin that is substantially devoid of sericin refers to silk fibroin having between about 1.0% (w/w) and about 4.0% (w/w) sericin. In an embodiment, silk fibroin that is substantially devoid of sericin refers to silk fibroin having between about 1.5% (w/w) and about 4.0% (w/w) sericin. In an embodiment, silk fibroin that is substantially devoid of sericin refers to silk fibroin having between about 2.0% (w/w) and about 4.0% (w/w) sericin. In an embodiment, silk fibroin that is substantially devoid of sericin refers to silk fibroin having between about 2.5% (w/w) and about 4.0% (w/w) sericin. In an embodiment, silk fibroin that is substantially devoid of sericin refers to silk fibroin having a sericin content between about 0.01% (w/w) and about 0.1% (w/w). In an embodiment, silk fibroin that is substantially devoid of sericin refers to silk fibroin having a sericin content below about 0.1% (w/w). In an embodiment, silk fibroin that is substantially devoid of sericin refers to silk fibroin having a sericin content below about 0.05% (w/w). In an embodiment, when a silk source is added to a boiling (100° C.) aqueous solution of sodium carbonate for a treatment time of between about 30 minutes to about 60 minutes, a degumming loss of about 26 wt. % to about 31 wt. % is obtained.

As used herein, the term "substantially homogeneous" may refer to pure silk fibroin-based protein fragments that are distributed in a normal distribution about an identified molecular weight. As used herein, the term "substantially homogeneous" may refer to an even distribution of additive, for example vitamin C, throughout a composition of the present disclosure.

As used herein, the term "substantially free of inorganic residuals" means that the composition exhibits residuals of 0.1% (w/w) or less. In an embodiment, substantially free of inorganic residuals refers to a composition that exhibits residuals of 0.05% (w/w) or less. In an embodiment, substantially free of inorganic residuals refers to a composition that exhibits residuals of 0.01% (w/w) or less. In an embodiment, the amount of inorganic residuals is between 0 ppm ("non-detectable" or "ND") and 1000 ppm. In an embodiment, the amount of inorganic residuals is ND to about 500 ppm. In an embodiment, the amount of inorganic residuals is ND to about 400 ppm. In an embodiment, the amount of inorganic residuals is ND to about 300 ppm. In an embodiment, the amount of inorganic residuals is ND to about 200 ppm. In an embodiment, the amount of inorganic residuals is ND to about 100 ppm. In an embodiment, the amount of inorganic residuals is between 10 ppm and 1000 ppm.

As used herein, the term "substantially free of organic residuals" means that the composition exhibits residuals of 0.1% (w/w) or less. In an embodiment, substantially free of organic residuals refers to a composition that exhibits residuals of 0.05% (w/w) or less. In an embodiment, substantially free of organic residuals refers to a composition that exhibits residuals of 0.01% (w/w) or less. In an embodiment, the amount of organic residuals is between 0 ppm ("non-detectable" or "ND") and 1000 ppm. In an embodiment, the amount of organic residuals is ND to about 500 ppm. In an embodiment, the amount of organic residuals is ND to about 400 ppm. In an embodiment, the amount of organic residuals is ND to about 300 ppm. In an embodiment, the amount of organic residuals is ND to about 200 ppm. In an embodiment, the amount of organic residuals is ND to about 100 ppm. In an embodiment, the amount of organic residuals is between 10 ppm and 1000 ppm.

Compositions of the present disclosure exhibit "biocompatibility" meaning that the compositions are compatible with living tissue or a living system by not being toxic, injurious, or physiologically reactive and not causing immunological rejection. Such biocompatibility can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely.

Compositions of the present disclosure are "hypoallergenic" meaning that they are relatively unlikely to cause an allergic reaction. Such hypoallergenicity can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely.

As used herein, the term "washable" and "exhibiting washability" means that a silk coated fabric of the present disclosure is capable of being washed without shrinking, fading, or the like.

As used herein, the term "textile" refers to a flexible woven material consisting of a network of natural or artificial fibers often referred to as thread or yarn. In an embodiment, textiles can be used to fabricate clothing, shoes and bags. In an embodiment, textiles can be used to fabricate carpeting, upholstered furnishings, window shades, towels, and coverings for tables, beds, and other flat surfaces. In an embodiment, textiles can be used to fabricate flags, backpacks, tents, nets, handkerchiefs, balloons, kites, sails, and parachutes.

As used herein, the term "hand" refers to the feel of a fabric, which may be further described as the feeling of softness, crispness, dryness, silkiness, and combinations thereof. Fabric hand is also referred to as "drape." A fabric with a hard hand is coarse, rough, and generally less comfortable for the wearer. A fabric with a soft hand is fluid and smooth, such as fine silk or wool, and generally more comfortable for the wearer. Fabric hand can be determined by comparison to collections of fabric samples, or by use of methods such as the Kawabata Evaluation System (KES) or the Fabric Assurance by Simple Testing (FAST) methods. Behera and Hari, *Ind. J. Fibre & Textile Res.*, 1994, 19, 168-71.

As used herein, the term "yarn" refers to a single or multi-fiber construct.

As used herein, the term "bath coating" encompasses coating a fabric in a batch, immersing a fabric in a bath, and submerging a fabric in a bath.

In an embodiment, the silk coating is applied using a bath process, a screen (or stencil) process, a spray process, a silk-foam based process, and a roller based process.

In an embodiment, a fiber or a yarn comprises a synthetic fiber or yarn, including polyester, Mylar, cotton, nylon, polyester-polyurethane copolymer, rayon, acetate, aramid (aromatic polyamide), acrylic, ingeo (polylactide), lurex (polyamide-polyester), olefin (polyethylene-polypropylene), and combinations thereof.

In an embodiment, a fiber or a yarn comprises a natural fiber or yarn, including alpaca fiber, alpaca fleece, alpaca wool, lama fiber, lama fleece, lama wool, cotton, cashmere and sheep fiber, sheep fleece, and sheep wool.

In an embodiment, a water-soluble silk coating may be used as an adhesive or binder for binding particles to fabrics or for binding fabrics. In an embodiment, an article comprises a fabric bound to another fabric using a silk coating. In an embodiment, an article comprises a fabric with particles bound to the fabric using a silk adhesive.

In an embodiment, the coating is applied to an article including a fabric at the yarn level. In an embodiment, the coating is applied at the fabric level. In an embodiment, the coating has a thickness selected from the group consisting of about 5 nm, about 10 nm, about 15 nm, about 20 nm, about 25 nm, about 50 nm, about 100 nm, about 200 nm, about 500 nm, about 1 µm, about 5 µm, about 10 µm, and about 20 µm. In an embodiment, the coating has a thickness range selected from the group consisting of about 5 nm to about 100 nm, about 100 nm to about 200 nm, about 200 nm to about 500 nm, about 1 µm to about 2 µm, about 2 µm to about 5 µm, about 5 µm to about 10 µm, and about 10 µm to about 20 µm.

In an embodiment, a fiber or a yarn is treated with a polymer, such as polyglycolide (PGA), polyethylene glycols, copolymers of glycolide, glycolide/L-lactide copolymers (PGA/PLLA), glycolide/trimethylene carbonate copolymers (PGA/TMC), polylactides (PLA), stereocopolymers of PLA, poly-L-lactide (PLLA), poly-DL-lactide (PDLLA), L-lactide/DL-lactide copolymers, co-polymers of PLA, lactide/tetramethylglycolide copolymers, lactide/trimethylene carbonate copolymers, lactide/δ-valerolactone copolymers, lactide/ε-caprolactone copolymers, polydepsipeptides, PLA/polyethylene oxide copolymers, unsymmetrically 3,6-substituted poly-1,4-dioxane-2,5-diones, poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerol actone, poly-ε-caprolactone, methylmethacrylate-N-vinyl pyrrolidine copolymers, polyesteramides, polyesters of oxalic acid, polydihydropyrans, polyalkyl-2-cyanoacrylates, polyurethanes (PU), polyvinylalcohols (PVA), polypeptides, poly-β-malic acid (PMLA), poly-β-alkanoic acids, polyvinyl alcohol (PVA), polyethyleneoxide (PEO), chitine polymers, polyethylene, polypropylene, polyasetal, polyamides, polyesters, polysulphone, polyether ether ketone, polyethylene terephthalate, polycarbonate, polyaryl ether ketone, and polyether ketone ketone.

In an embodiment, the silk coating surface can be modified silk crystals that range in size from nm to µm.

The criterion for "visibility" is satisfied by any one of the following: a change in the surface character of the textile; the silk coating fills the interstices where the yarns intersect; or the silk coating blurs or obscures the weave.

In an embodiment, a silk based protein or fragment solution may be utilized to coat at least a portion of a fabric which can be used to create a textile. In an embodiment, a silk based protein or fragment solution may be weaved into yarn that can be used as a fabric in a textile. In an embodiment, a silk based protein or fragment solution may be used to coat a fiber. In an embodiment, the invention provides an article comprising a silk based protein or fragment solution coating at least a portion of a fabric or a textile. In an embodiment, the invention provides an article comprising a silk based protein or fragment solution coating a yarn. In an embodiment, the invention provides an article comprising a silk based protein or fragment solution coating a fiber.

In an embodiment, a solution of the present disclosure is contacted with an additive, such as a therapeutic agent and/or a molecule. In an embodiment, molecules include, but are not limited to, antioxidants and enzymes. In an embodiment, molecules include, but are not limited to, ceramics, ceramic particles, metals, metal particles, polymer particles, inorganic particles, organic particles, selenium, ubiquinone derivatives, thiol-based antioxidants, saccharide-containing antioxidants, polyphenols, botanical extracts, caffeic acid, apigenin, pycnogenol, resveratrol, folic acid, vitamin B12, vitamin B6, vitamin B3, vitamin E, vitamin C and derivatives thereof, vitamin D, vitamin A, astaxathin, Lutein, lycopene, essential fatty acids (omegas 3 and 6), iron, zinc, magnesium, flavonoids (soy, Curcumin, Silymarin, Pycnongeol), growth factors, aloe, hyaluronic acid, extracellular matrix proteins, cells, nucleic acids, biomarkers, biological reagents, zinc oxide, benzyol peroxide, retnoids, titanium, allergens in a known dose (for sensitization treatment), essential oils including, but not limited to, lemongrass or rosemary oil, and fragrances. Therapeutic agents include, but are not limited to, small molecules, drugs, proteins, peptides and nucleic acids. In an embodiment, a solution of the present disclosure is contacted with an allergen of known quantity prior to forming the article. Allergens include but are not limited to milk, eggs, peanuts, tree nuts, fish, shellfish, soy and wheat. Known doses of allergen loaded within a silk article can be released at a known rate for controlled exposure allergy study, tests and sensitization treatment.

In an embodiment, a solution of the present disclosure is used to create an article with microneedles by standard methods known to one in the art for controlled delivery of molecules or therapeutic agents to or through the skin.

As used herein, the term "fibroin" includes silkworm fibroin and insect or spider silk protein. In an embodiment, fibroin is obtained from *Bombyx mori*. In an embodiment, the spider silk protein is selected from the group consisting of swathing silk (Achniform gland silk), egg sac silk (Cylindriform gland silk), egg case silk (Tubuliform silk), non-sticky dragline silk (Ampullate gland silk), attaching thread silk (Pyriform gland silk), sticky silk core fibers (Flagelliform gland silk), and sticky silk outer fibers (Aggregate gland silk).

Figure 1:
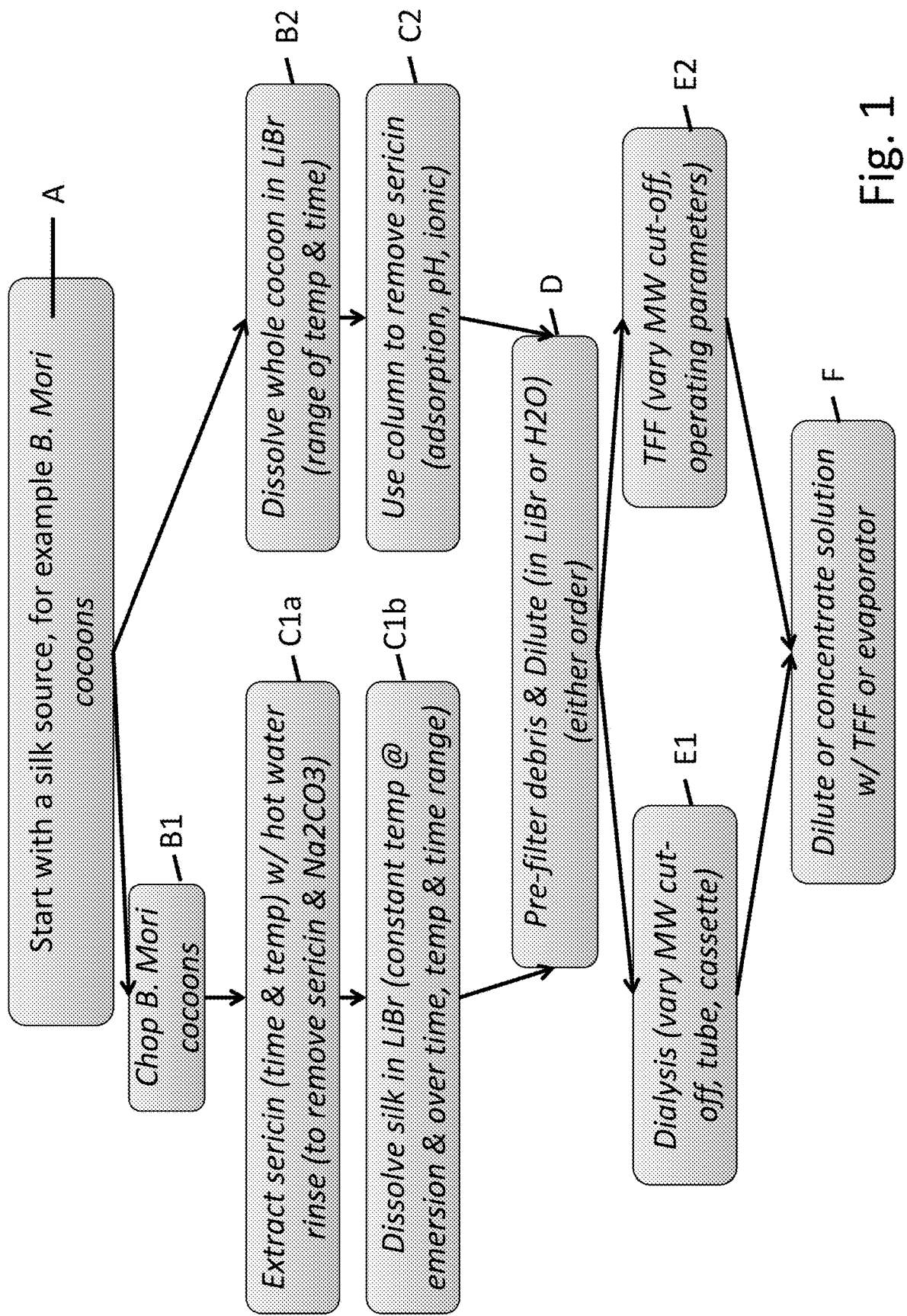
FIG. 1 is a flow chart showing various embodiments for producing pure silk fibroin-based protein fragments (SPFs) of the present disclosure.
Figure 38A:
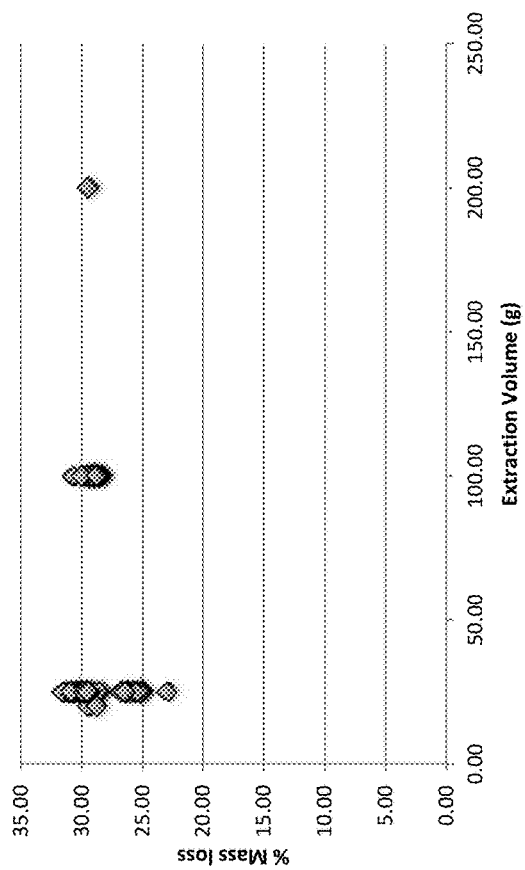
FIGS. 38A and 38B are graphs representing the effect of extraction volume on % mass loss.
Figure 38B:
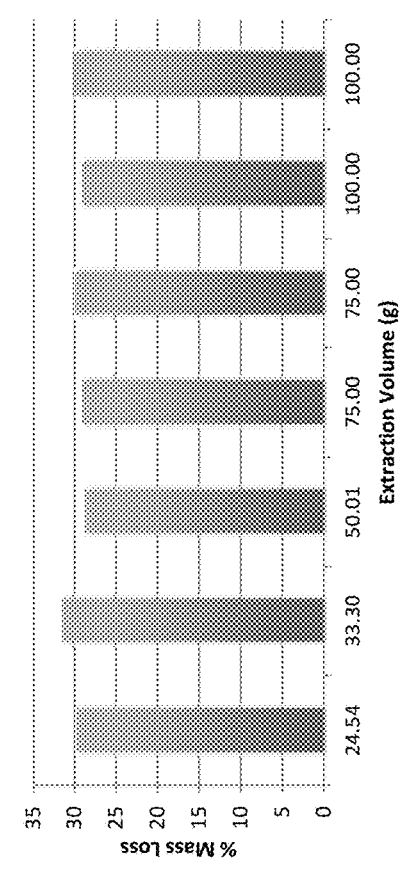
Figure 40:
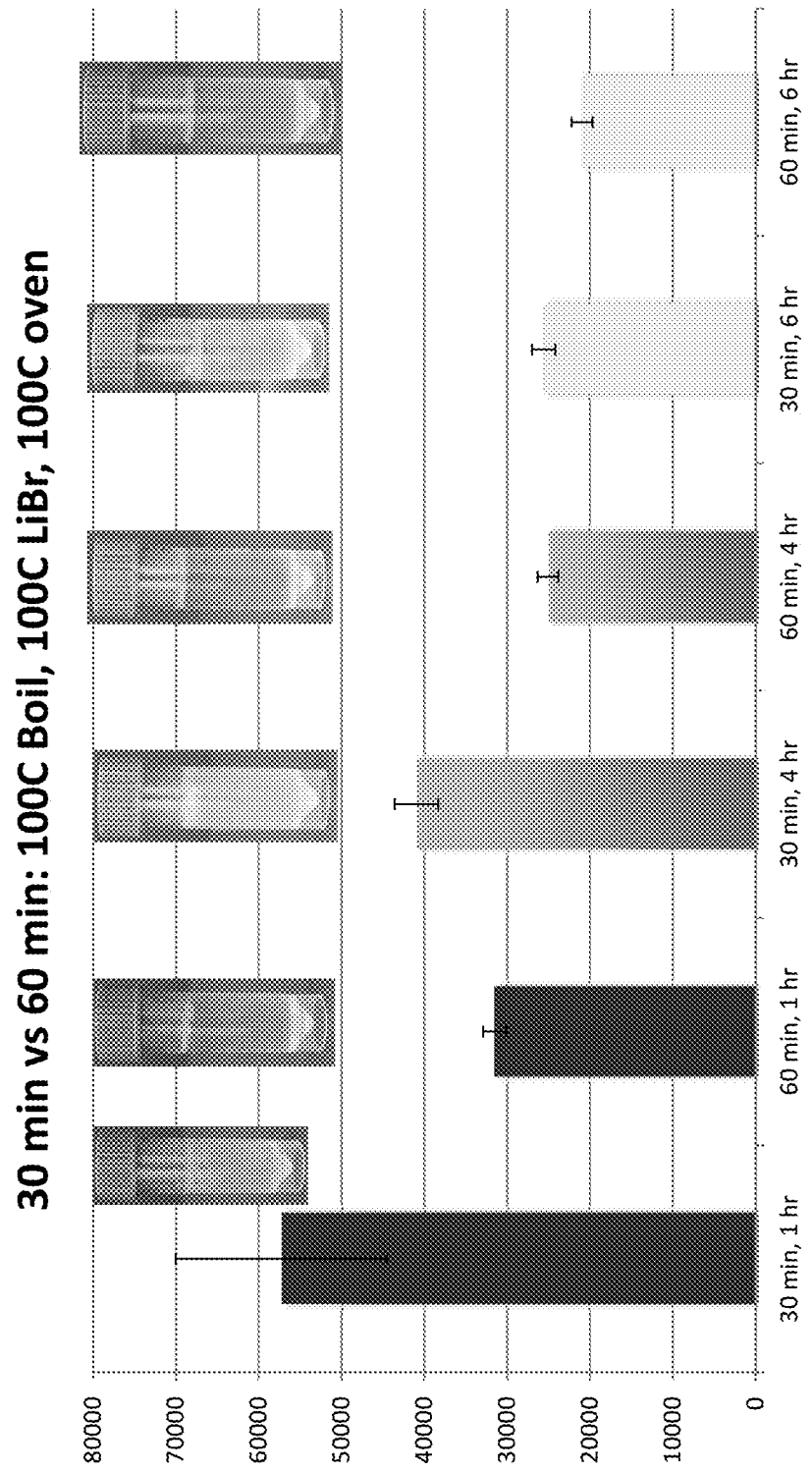
FIG. 40 is a graph summarizing the effect of Extraction Time on Molecular Weight of silk processed under the conditions of 100° C. Extraction Temperature, 100° C. LiBr and 100° C. Oven Dissolution (Oven/Dissolution Time was varied).
Figure 41:
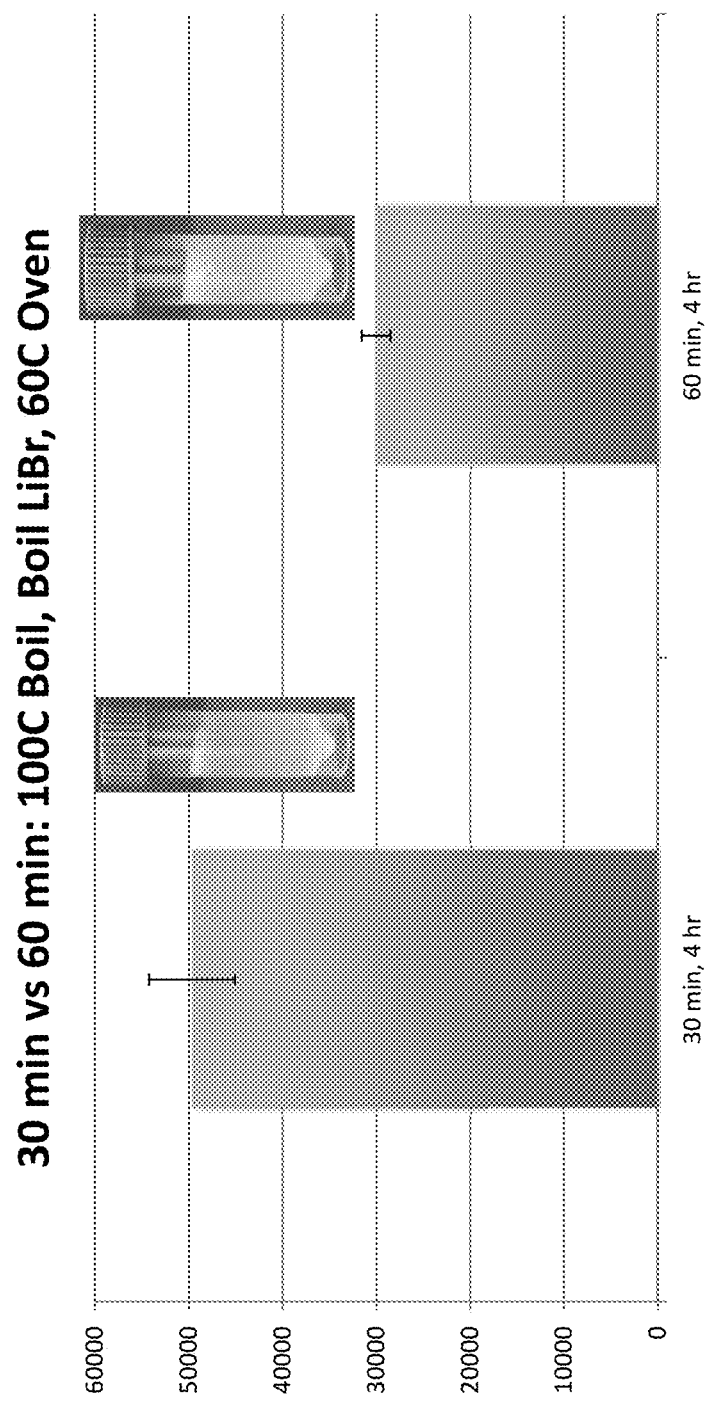
FIG. 41 is a graph summarizing the effect of Extraction Time on Molecular Weight of silk processed under the conditions of 100° C. Extraction Temperature, boiling LiBr and 60° C. Oven Dissolution (Oven/Dissolution Time was varied).
Figure 42:
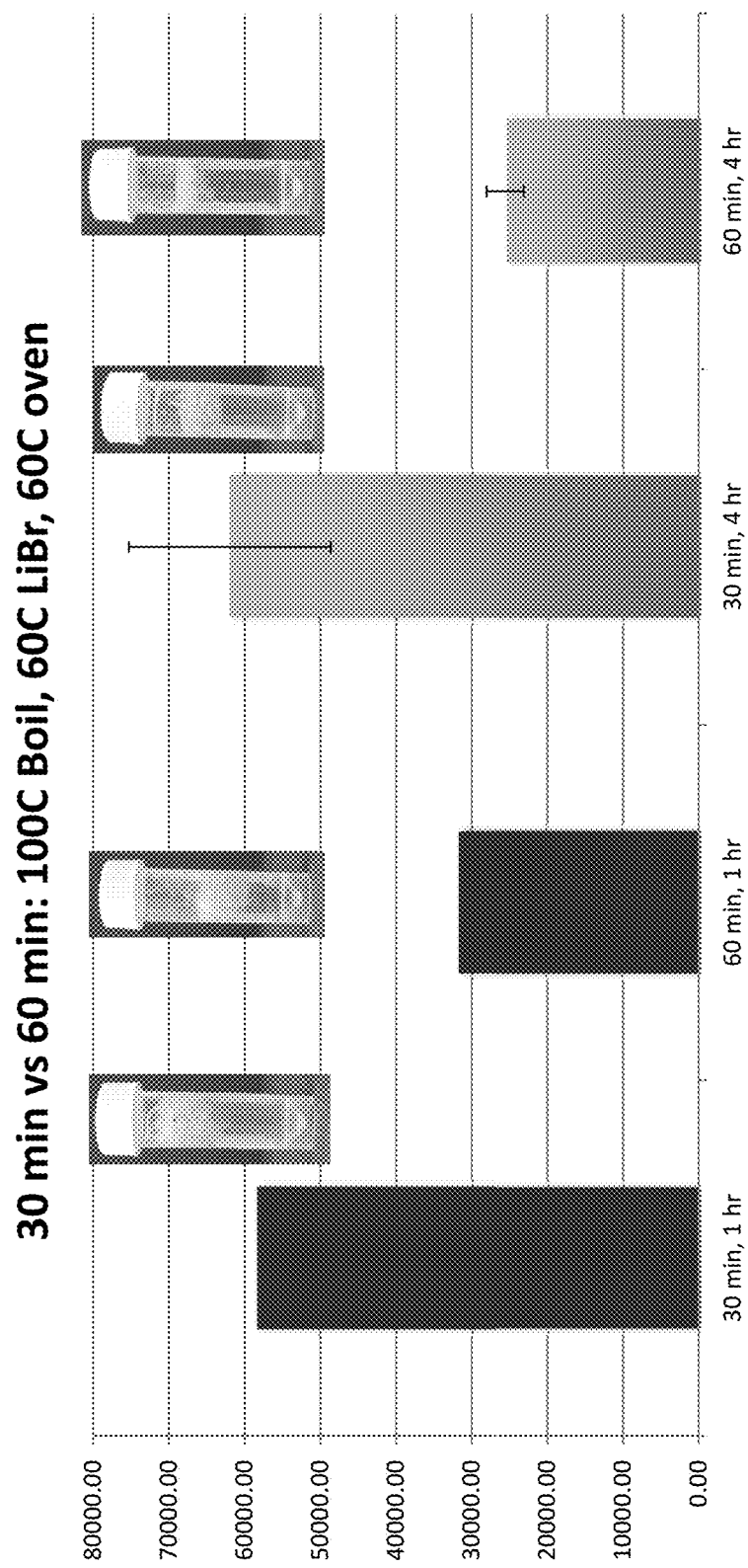
FIG. 42 is a graph summarizing the effect of Extraction Time on Molecular Weight of silk processed under the conditions of 100° C. Extraction Temperature, 60° C. LiBr and 60° C. Oven Dissolution (Oven/Dissolution Time was varied).
Figure 43:
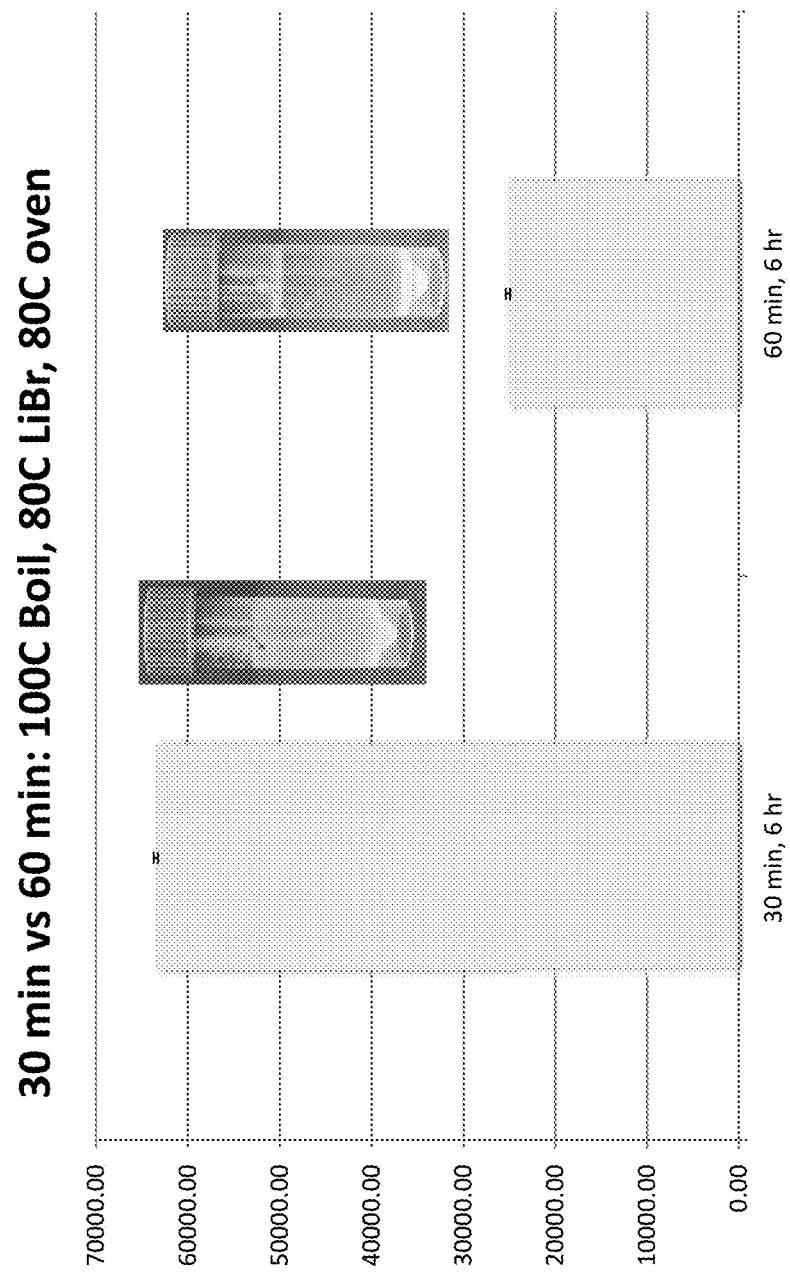
FIG. 43 is a graph summarizing the effect of Extraction Time on Molecular Weight of silk processed under the conditions of 100° C. Extraction Temperature, 80° C. LiBr and 80° C. Oven Dissolution (Oven/Dissolution Time was varied).
Figure 44:
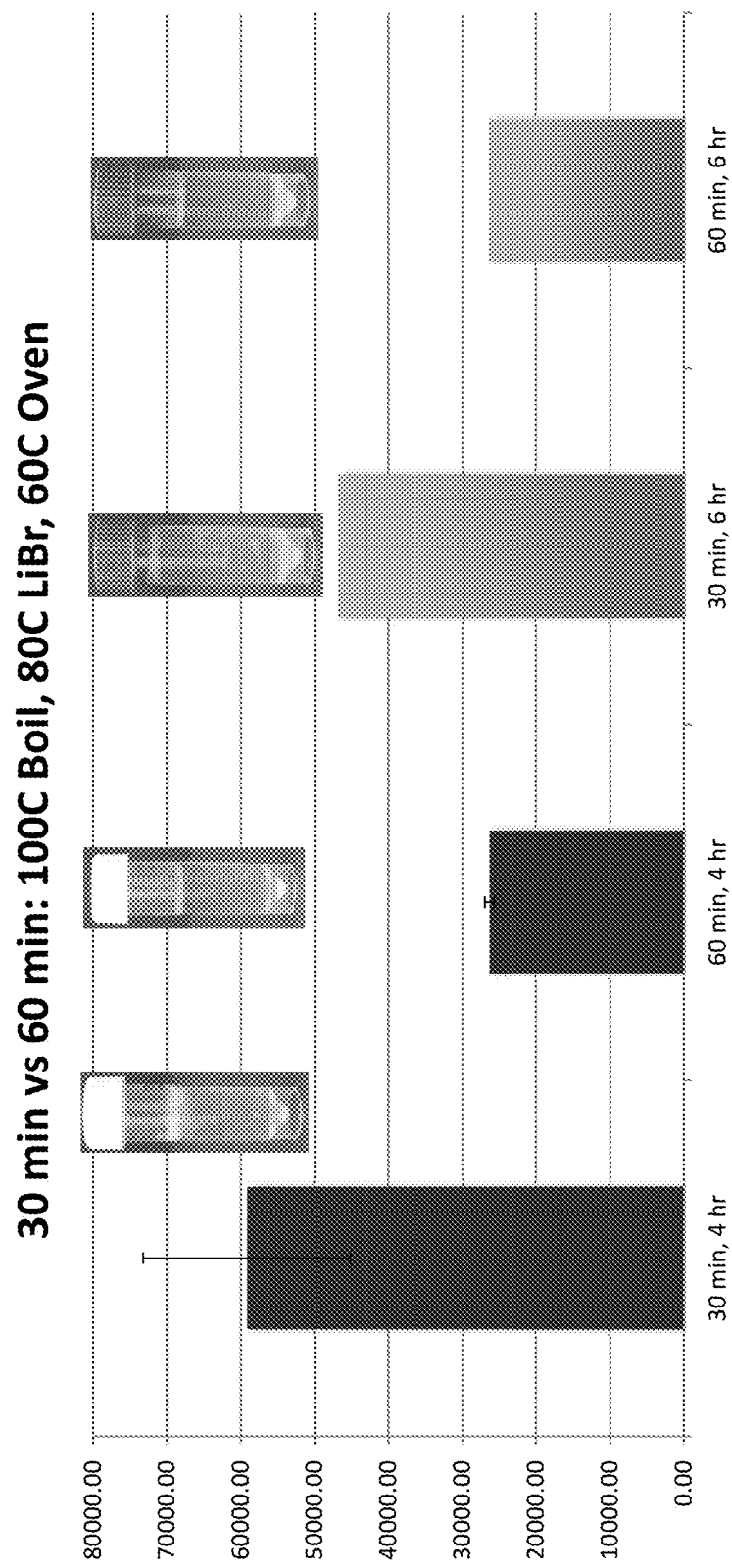
FIG. 44 is a graph summarizing the effect of Extraction Time on Molecular Weight of silk processed under the conditions of 100° C. Extraction Temperature, 80° C. LiBr and 60° C. Oven Dissolution (Oven/Dissolution Time was varied).
Figure 45:
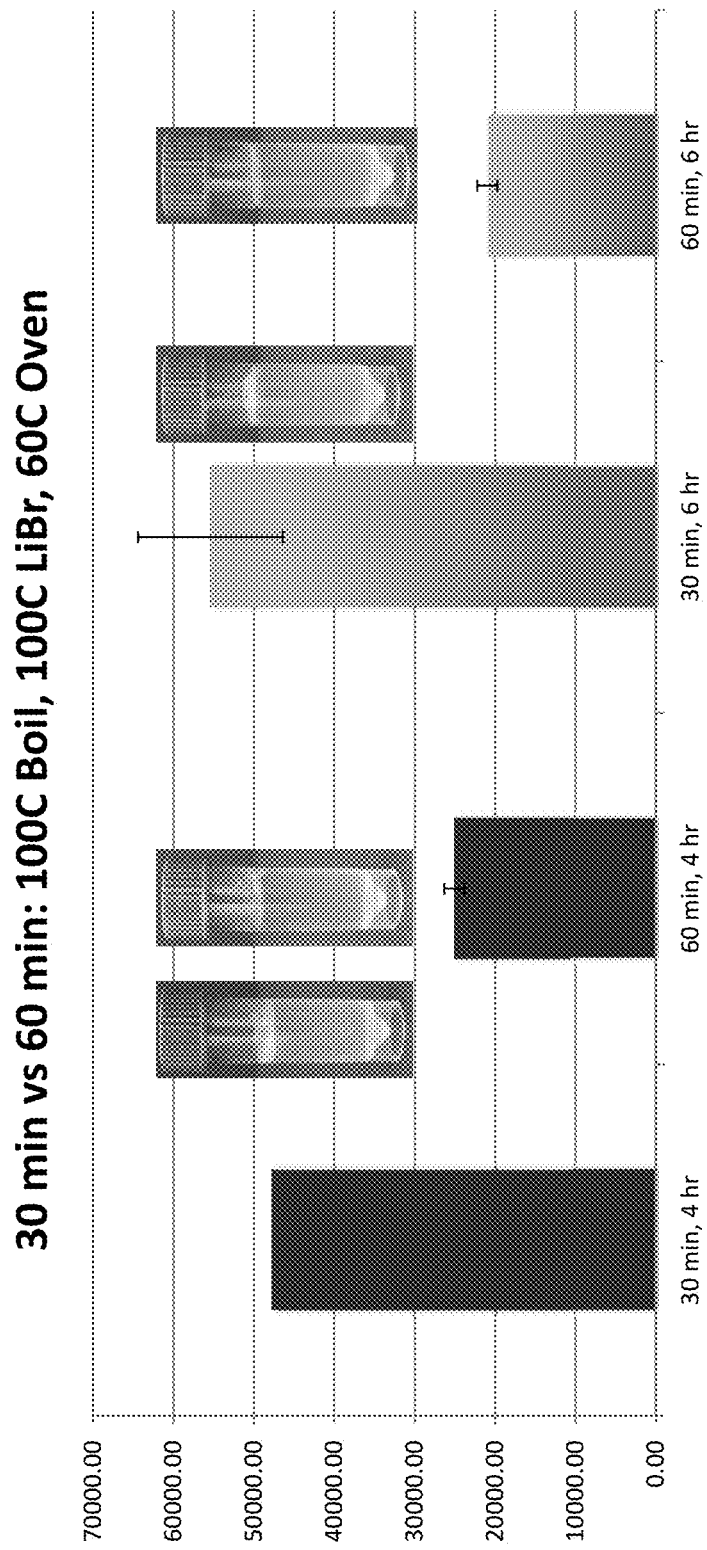
FIG. 45 is a graph summarizing the effect of Extraction Time on Molecular Weight of silk processed under the conditions of 100° C. Extraction Temperature, 100° C. LiBr and 60° C. Oven Dissolution (Oven/Dissolution Time was varied).
Figure 46:
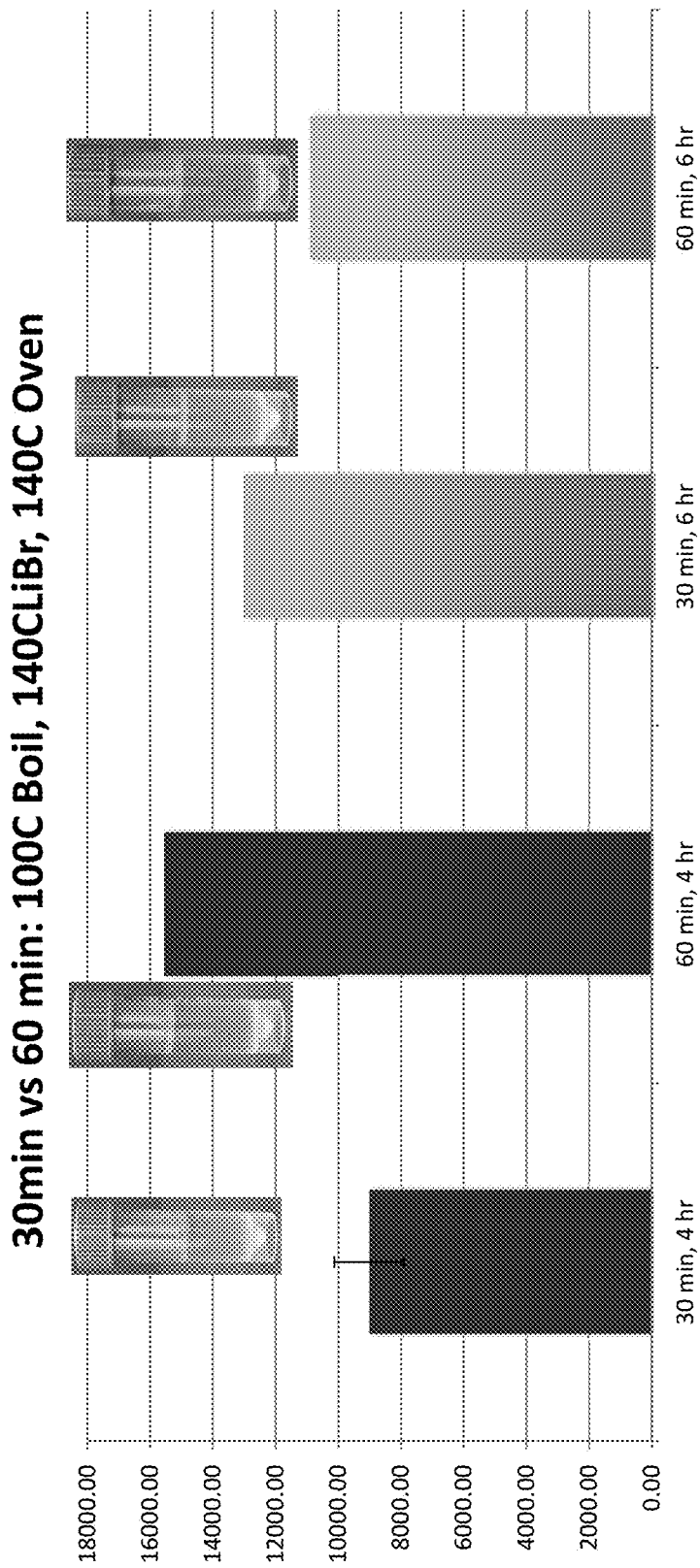
FIG. 46 is a graph summarizing the effect of Extraction Time on Molecular Weight of silk processed under the conditions of 100° C. Extraction Temperature, 140° C. LiBr and 140° C. Oven Dissolution (Oven/Dissolution Time was varied).

FIG. 1 is a flow chart showing various embodiments for producing pure silk fibroin-based protein fragments (SPFs) of the present disclosure. It should be understood that not all of the steps illustrated are necessarily required to fabricate all silk solutions of the present disclosure. As illustrated in FIG. 1, step A, cocoons (heat-treated or non-heat-treated), silk fibers, silk powder or spider silk can be used as the silk source. If starting from raw silk cocoons from *Bombyx mori*, the cocoons can be cut into small pieces, for example pieces of approximately equal size, step B1. The raw silk is then extracted and rinsed to remove any sericin, step C1*a*. This results in substantially sericin free raw silk. In an embodiment, water is heated to a temperature between 84° C. and 100° C. (ideally boiling) and then $Na_2CO_3$ (sodium carbonate) is added to the boiling water until the $Na_2CO_3$ is completely dissolved. The raw silk is added to the boiling water/$Na_2CO_3$ (100° C.) and submerged for approximately 15-90 minutes, where boiling for a longer time results in smaller silk protein fragments. In an embodiment, the water volume equals about 0.4×raw silk weight and the $Na_2CO_3$ volume equals about 0.848×raw silk weight. In an embodiment, the water volume equals 0.1×raw silk weight and the $Na_2CO_3$ volume is maintained at 2.12 g/L. This is demonstrated in FIG. 38A and FIG. 38B silk mass (x-axis) was varied in the same volume of extraction solution (i.e., the same volume of water and concentration of $Na_2CO_3$) achieving sericin removal (substantially sericin free) as demonstrated by an overall silk mass loss of 26 to 31 percent (y-axis). Subsequently, the water dissolved $Na_2CO_3$ solution is drained and excess water/$Na_2CO_3$ is removed from the silk fibroin fibers (e.g., ring out the fibroin extract by hand, spin cycle using a machine, etc.). The resulting silk fibroin extract is rinsed with warm to hot water to remove any remaining adsorbed sericin or contaminate, typically at a temperature range of about 40° C. to about 80° C., changing the volume of water at least once (repeated for as many times as required). The resulting silk fibroin extract is a substantially sericin-depleted silk fibroin. In an embodiment, the resulting silk fibroin extract is rinsed with water at a temperature of about 60° C. In an embodiment, the volume of rinse water for each cycle equals 0.1 L to 0.2 L×raw silk weight. It may be advantageous to agitate, turn or circulate the rinse water to maximize the rinse effect. After rinsing, excess water is removed from the extracted silk fibroin fibers (e.g., ring out fibroin extract by hand or using a machine). Alternatively, methods known to one skilled in the art such as pressure, temperature, or other reagents or combinations thereof may be used for the purpose of sericin extraction. Alternatively, the silk gland (100% sericin free silk protein) can be removed directly from a worm. This would result in liquid silk protein, without any alteration of the protein structure, free of sericin.

Figure 3:
FIG. 3 is a photograph showing dry extracted silk fibroin.

The extracted fibroin fibers are then allowed to dry completely. FIG. 3 is a photograph showing dry extracted silk fibroin. Once dry, the extracted silk fibroin is dissolved using a solvent added to the silk fibroin at a temperature between ambient and boiling, step C1*b*. In an embodiment, the solvent is a solution of Lithium bromide (LiBr) (boiling for LiBr is 140° C.). Alternatively, the extracted fibroin fibers are not dried but wet and placed in the solvent; solvent concentration can then be varied to achieve similar concentrations as to when adding dried silk to the solvent. The final concentration of LiBr solvent can range from 0.1M to 9.3M. FIG. 39 is a table summarizing the Molecular Weights of silk dissolved from different concentrations of Lithium Bromide (LiBr) and from different extraction and dissolution sizes. Complete dissolution of the extracted fibroin fibers can be achieved by varying the treatment time and temperature along with the concentration of dissolving solvent. Other solvents may be used including, but not limited to, phosphate phosphoric acid, calcium nitrate, calcium chloride solution or other concentrated aqueous solutions of inorganic salts. To ensure complete dissolution, the silk fibers should be fully immersed within the already heated solvent solution and then maintained at a temperature ranging from about 60° C. to about 140° C. for 1-168 hrs. In an embodiment, the silk fibers should be fully immersed within the solvent solution and then placed into a dry oven at a temperature of about 100° C. for about 1 hour.

The temperature at which the silk fibroin extract is added to the LiBr solution (or vice versa) has an effect on the time required to completely dissolve the fibroin and on the resulting molecular weight and polydispersity of the final SPF mixture solution. In an embodiment, silk solvent solution concentration is less than or equal to 20% w/v. In addition, agitation during introduction or dissolution may be used to facilitate dissolution at varying temperatures and concentrations. The temperature of the LiBr solution will provide control over the silk protein fragment mixture molecular weight and polydispersity created. In an embodiment, a higher temperature will more quickly dissolve the silk offering enhanced process scalability and mass production of silk solution. In an embodiment, using a LiBr solution heated to a temperature between 80° C.-140° C. reduces the time required in an oven in order to achieve full dissolution. Varying time and temperature at or above 60° C. of the dissolution solvent will alter and control the MW and polydispersity of the SPF mixture solutions formed from the original molecular weight of the native silk fibroin protein.

Alternatively, whole cocoons may be placed directly into a solvent, such as LiBr, bypassing extraction, step B2. This requires subsequent filtration of silk worm particles from the silk and solvent solution and sericin removal using methods know in the art for separating hydrophobic and hydrophilic proteins such as a column separation and/or chromatography, ion exchange, chemical precipitation with salt and/or pH, and or enzymatic digestion and filtration or extraction, all methods are common examples and without limitation for standard protein separation methods, step C2. Non-heat treated cocoons with the silkworm removed, may alternatively be placed into a solvent such as LiBr, bypassing extraction. The methods described above may be used for sericin separation, with the advantage that non-heat treated cocoons will contain significantly less worm debris.

Dialysis may be used to remove the dissolution solvent from the resulting dissolved fibroin protein fragment solution by dialyzing the solution against a volume of water, step E1. Pre-filtration prior to dialysis is helpful to remove any debris (i.e., silk worm remnants) from the silk and LiBr solution, step D. In one example, a 3 μm or 5 μm filter is used with a flow-rate of 200-300 mL/min to filter a 0.1% to 1.0% silk-LiBr solution prior to dialysis and potential concentration if desired. A method disclosed herein, as described above, is to use time and/or temperature to decrease the concentration from 9.3M LiBr to a range from 0.1M to 9.3M to facilitate filtration and downstream dialysis, particularly when considering creating a scalable process method. Alternatively, without the use of additional time or temperate, a 9.3M LiBr-silk protein fragment solution may be diluted with water to facilitate debris filtration and dialysis. The result of dissolution at the desired time and temperate filtration is a translucent particle-free room temperature shelf-stable silk protein fragment-LiBr solution of a known MW and polydispersity. It is advantageous to change the dialysis water regularly until the solvent has been removed (e.g., change water after 1 hour, 4 hours, and then every 12 hours for a total of 6 water changes). The total number of water volume changes may be varied based on the resulting concentration of solvent used for silk protein dissolution and fragmentation. After dialysis, the final silk solution maybe further filtered to remove any remaining debris (i.e., silk worm remnants).

Alternatively, Tangential Flow Filtration (TFF), which is a rapid and efficient method for the separation and purification of biomolecules, may be used to remove the solvent from the resulting dissolved fibroin solution, step E2. TFF offers a highly pure aqueous silk protein fragment solution and enables scalability of the process in order to produce large volumes of the solution in a controlled and repeatable manner. The silk and LiBr solution may be diluted prior to TFF (20% down to 0.1% silk in either water or LiBr). Pre-filtration as described above prior to TFF processing may maintain filter efficiency and potentially avoids the creation of silk gel boundary layers on the filter's surface as the result of the presence of debris particles. Pre-filtration prior to TFF is also helpful to remove any remaining debris (i.e., silk worm remnants) from the silk and LiBr solution that may cause spontaneous or long-term gelation of the resulting water only solution, step D. TFF, recirculating or single pass, may be used for the creation of water-silk protein fragment solutions ranging from 0.1% silk to 30.0% silk (more preferably, 0.1%-6.0% silk). Different cutoff size TFF membranes may be required based upon the desired concentration, molecular weight and polydispersity of the silk protein fragment mixture in solution. Membranes ranging from 1-100 kDa may be necessary for varying molecular weight silk solutions created for example by varying the length of extraction boil time or the time and temperate in dissolution solvent (e.g., LiBr). In an embodiment, a TFF 5 or 10 kDa membrane is used to purify the silk protein fragment mixture solution and to create the final desired silk-to-water ratio. As well, TFF single pass, TFF, and other methods known in the art, such as a falling film evaporator, may be used to concentrate the solution following removal of the dissolution solvent (e.g., LiBr) (with resulting desired concentration ranging from 0.1% to 30% silk). This can be used as an alternative to standard HFIP concentration methods known in the art to create a water-based solution. A larger pore membrane could also be utilized to filter out small silk protein fragments and to create a solution of higher molecular weight silk with and/or without tighter polydispersity values. FIG. 37 is a table summarizing Molecular Weights for some embodiments of silk protein solutions of the present disclosure. Silk protein solution processing conditions were as follows: 100° C. extraction for 20 min, room temperature rinse, LiBr in 60° C. oven for 4-6 hours. FIGS. 40-49 further demonstrate manipulation of extraction time, LiBr dissolution conditions, and TFF processing and resultant example molecular weights and polydispersities. These examples are not intended to be limiting, but rather to demonstrate the potential of specifying parameters for specific molecular weight silk fragment solutions.

An assay for LiBr and $Na_2CO_3$ detection was performed using an HPLC system equipped with evaporative light scattering detector (ELSD). The calculation was performed by linear regression of the resulting peak areas for the analyte plotted against concentration. More than one sample of a number of formulations of the present disclosure was used for sample preparation and analysis. Generally, four samples of different formulations were weighed directly in a 10 mL volumetric flask.

The analytical method developed for the quantitation of $Na_2CO_3$ and LiBr in silk protein formulations was found to be linear in the range 10-165 μg/mL, with RSD for injection precision as 2% and 1% for area and 0.38% and 0.19% for retention time for sodium carbonate and lithium bromide respectively. The analytical method can be applied for the quantitative determination of sodium carbonate and lithium bromide in silk protein formulations.

Figure 4:
FIG. 4 is a photograph showing an embodiment of a SPF in the form of a solution of the present disclosure.
Figures 6A, 6B, 6C, 6D:
FIGS. 6A-6D are photographs showing dissolved silk in room temperature LiBr solutions dissolved in a 60° C. oven for 6 hours (sericin extraction temperature and time were varied).
Figures 7A, 7B, 7C, 7D:
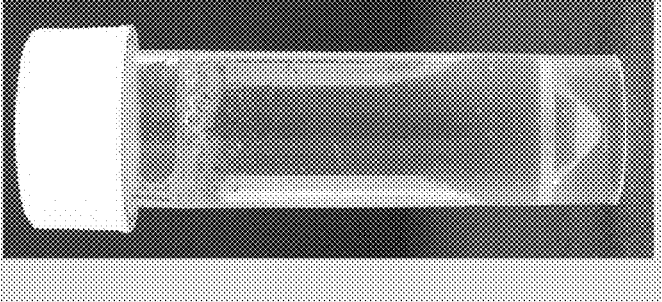
FIGS. 7A-7D are photographs showing dissolved silk in room temperature LiBr solutions dissolved in a 60° C. oven for 8 hours (sericin extraction temperature and time were varied).
Figures 8A, 8B, 8C, 8D:
FIGS. 8A-8D are photographs showing dissolved silk in room temperature LiBr solutions dissolved in a 60° C. oven for 12 hours (sericin extraction temperature and time were varied).
Figure 9A:
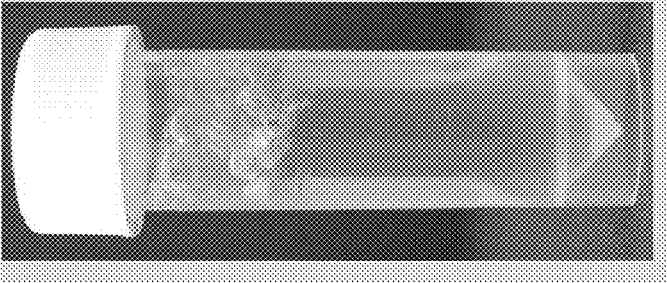
FIGS. 9A-9D are photographs showing dissolved silk in room temperature LiBr solutions dissolved in a 60° C. oven for 24 hours (sericin extraction temperature and time were varied).
Figure 9B:
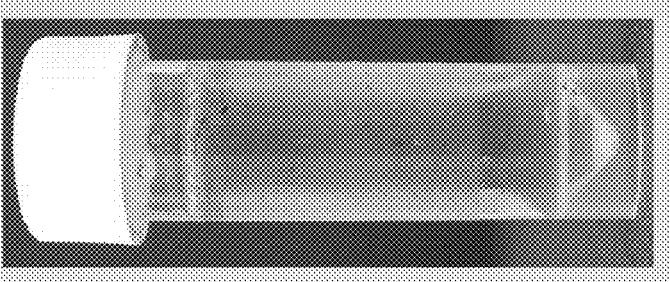
Figure 9C:
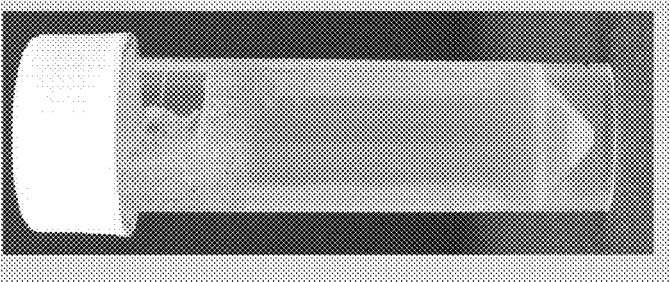
Figure 9D:
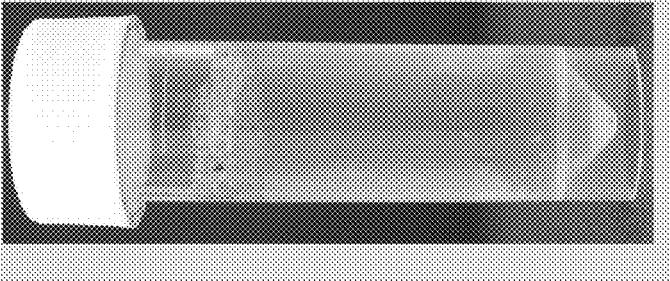
Figures 10A, 10B, 10C, 10D:
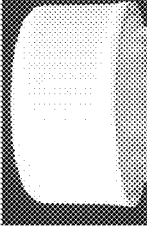
FIGS. 10A-10D are photographs showing dissolved silk in room temperature LiBr solutions dissolved in a 60° C. oven for 168/192 hours (sericin extraction temperature and time were varied).
Figures 11A, 11B, 11C:
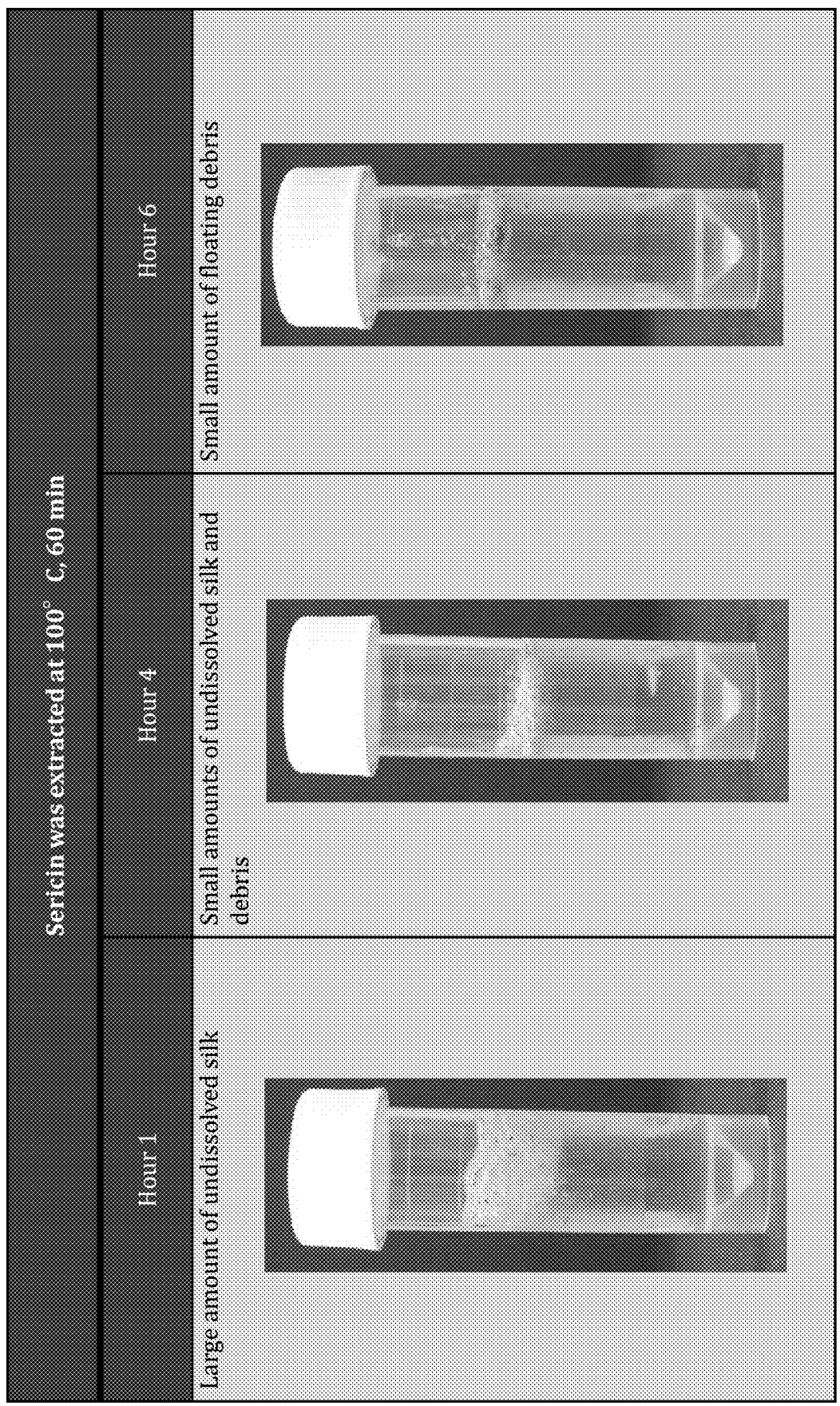
FIGS. 11A-11C are photographs showing dissolved silk in room temperature LiBr solutions dissolved in 60° C. oven for 1, 4, and 6 hours, where sericin extraction was completed at 100° C. for 60 min.
Figures 14A, 14B, 14C, 14D:
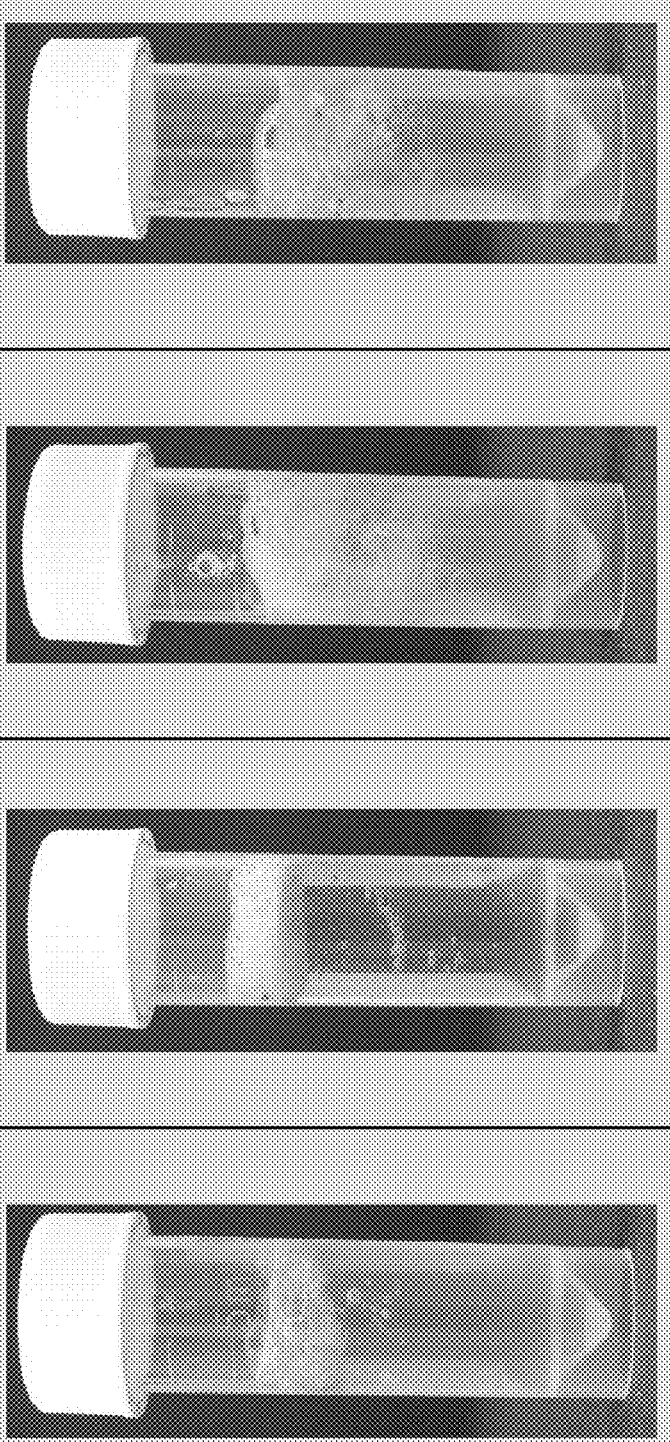
FIGS. 14A-14D are photographs showing dissolved silk in 60° C. LiBr solutions dissolved in a 60° C. oven for 6 hours (sericin extraction temperature and time were varied).
Figure 15A:
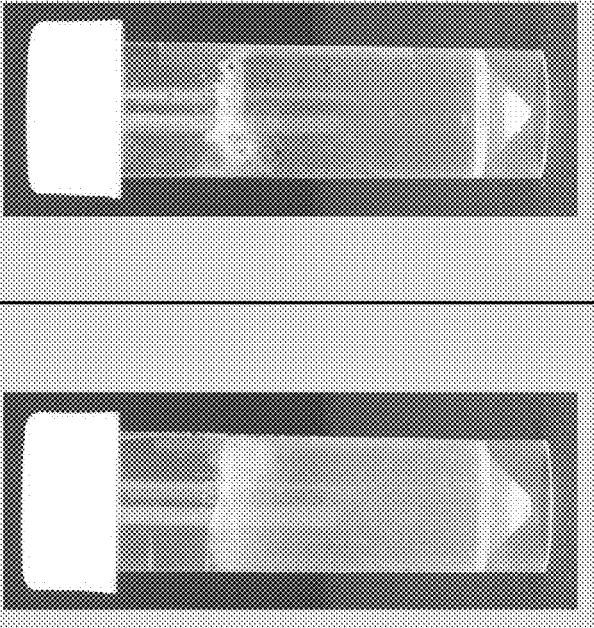
FIGS. 15A-15D are photographs showing dissolved silk in 80° C. LiBr solutions dissolved in a 60° C. oven for 1 hour (sericin extraction temperature and time were varied).
Figure 15B:
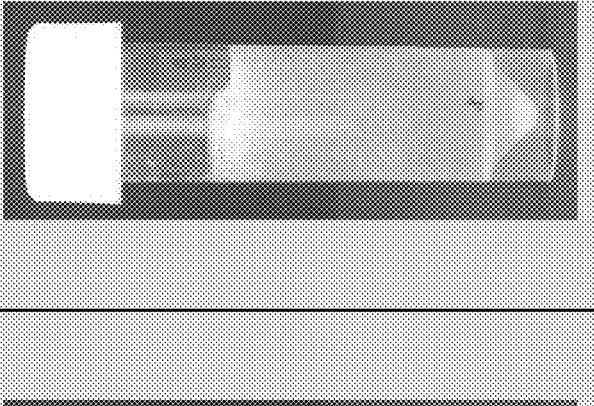
Figure 15C:
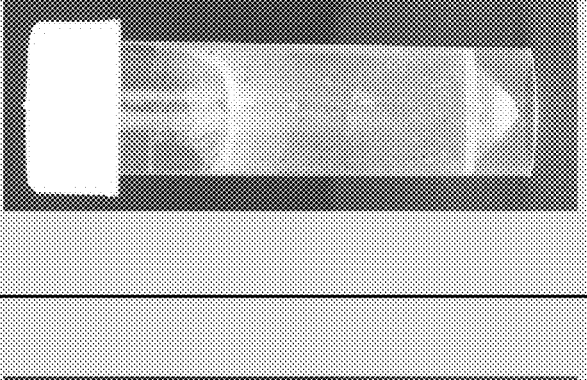
Figure 15D:
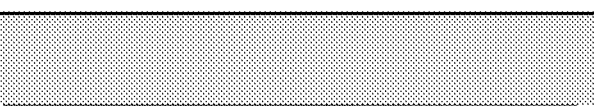
Figures 16A, 16B, 16C, 16D:
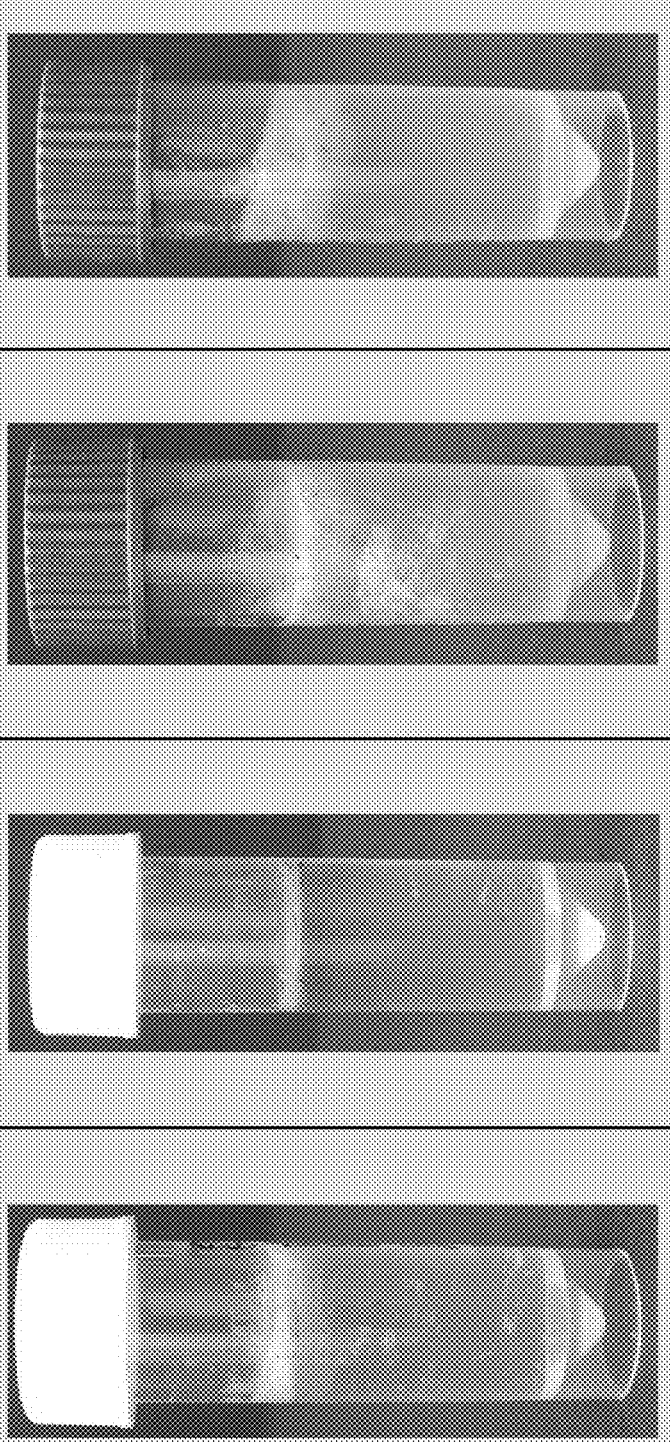
FIGS. 16A-16D are photographs showing dissolved silk in 80° C. LiBr solutions dissolved in a 60° C. oven for 4 hours (sericin extraction temperature and time were varied).
Figures 17A, 17B, 17C, 17D:
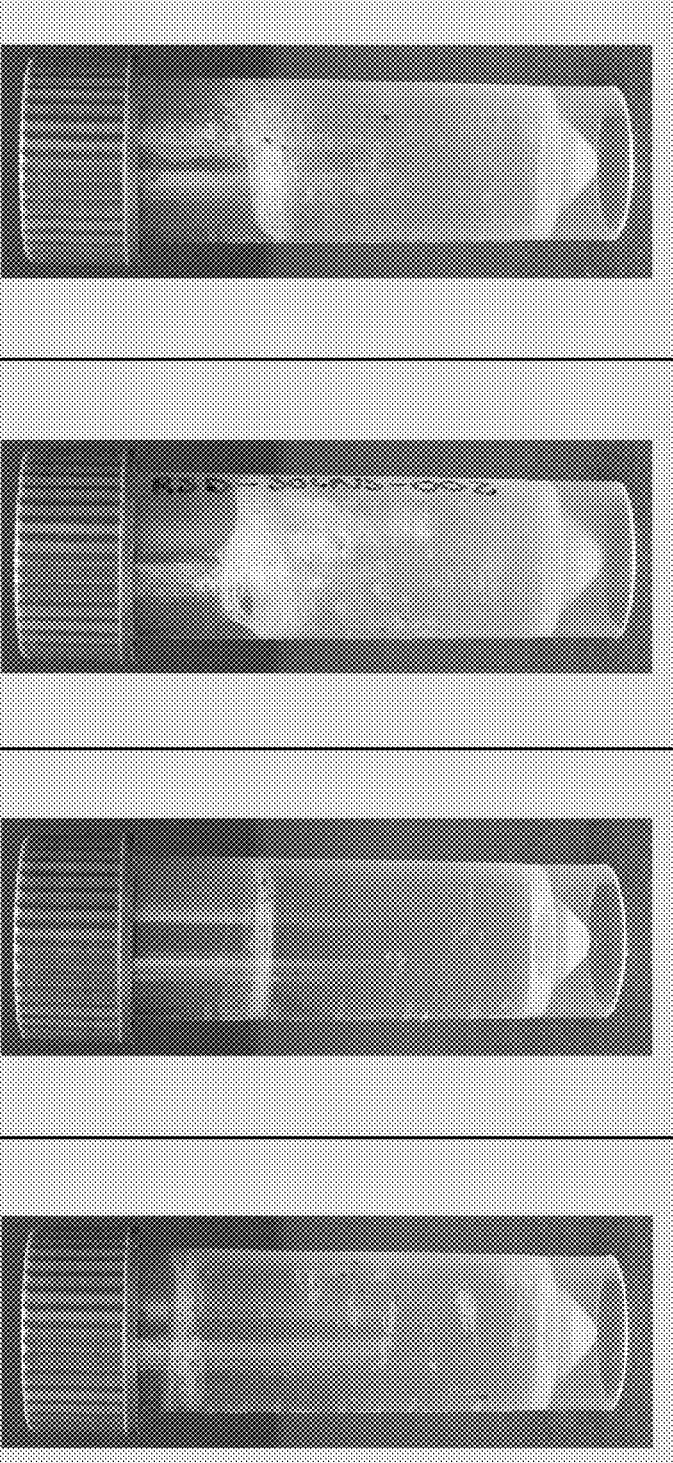
FIGS. 17A-17D are photographs showing dissolved silk in 80° C. LiBr solutions dissolved in a 60° C. oven for 4 hours (sericin extraction temperature and time were varied).
Figure 18A:
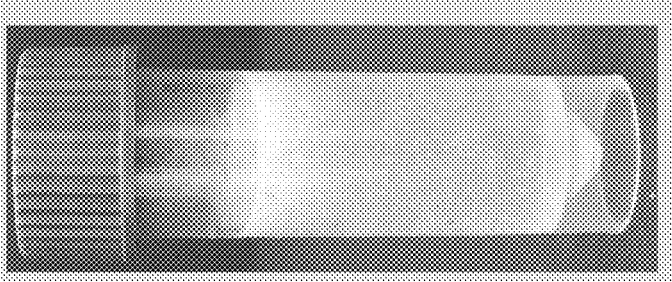
FIGS. 18A-18D are photographs showing dissolved silk in 100° C. LiBr solutions dissolved in a 60° C. oven for 1 hour (sericin extraction temperature and time were varied).
Figure 18B:
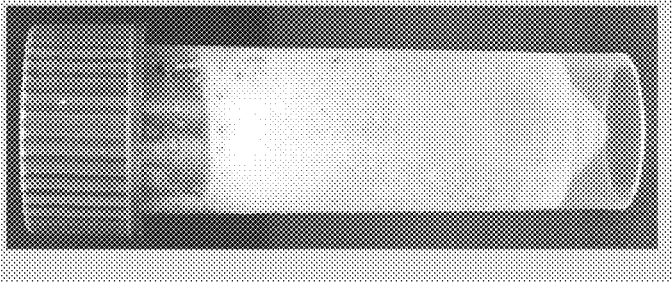
Figure 18C:
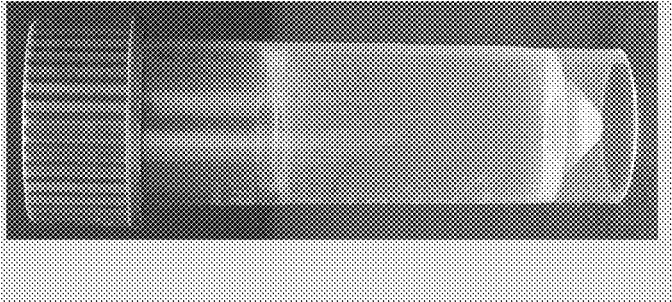
Figure 18D:
Figure 21A:
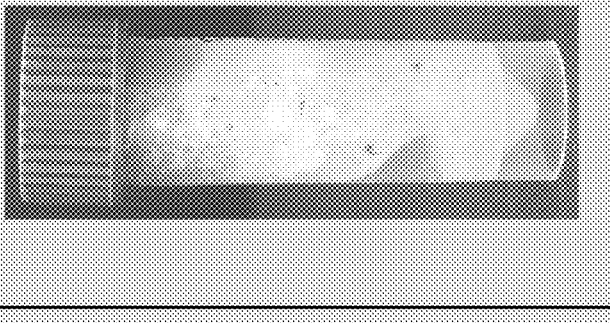
FIGS. 21A-21D are photographs showing dissolved silk in 140° C. (boiling point for LiBr) LiBr solutions dissolved in a 60° C. oven for 1 hour (sericin extraction temperature and time were varied time).
Figure 21B:
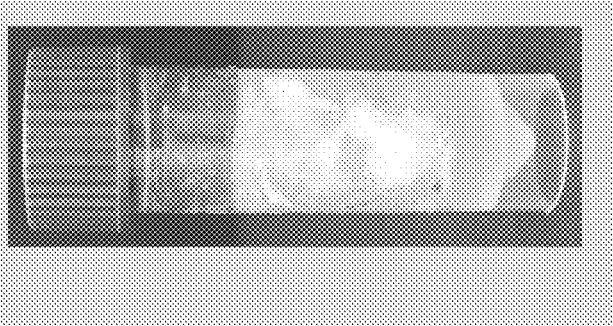
Figure 21C:
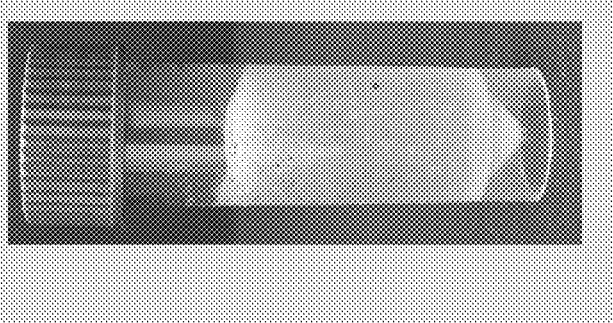
Figure 21D:
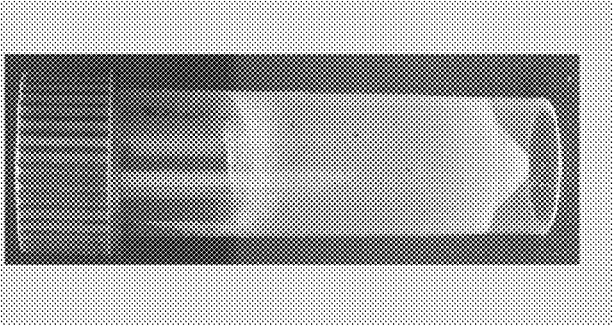
Figure 22A:
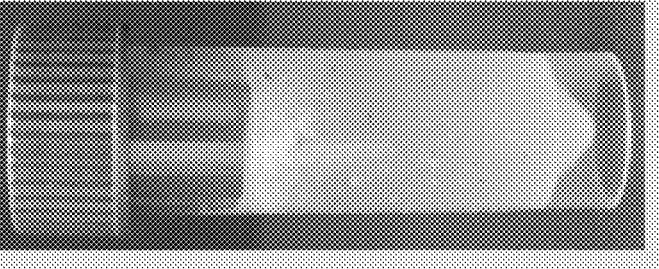
FIGS. 22A-22D are photographs showing dissolved silk in 140° C. (boiling point for LiBr) LiBr solutions dissolved in a 60° C. oven for 4 hours (sericin extraction temperature and time were varied).
Figure 22B:
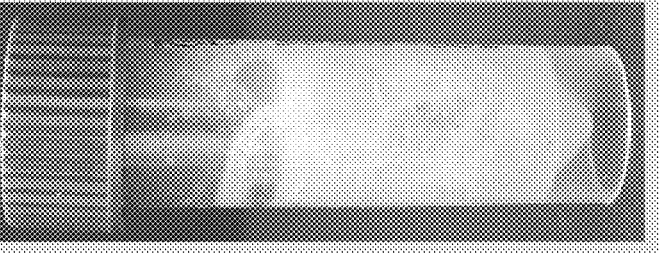
Figure 22C:
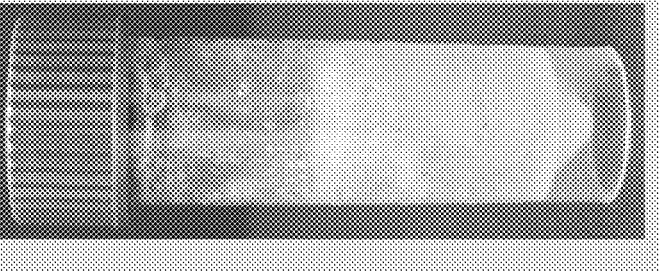
Figure 22D:
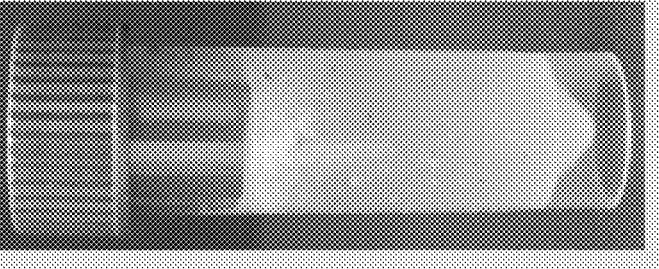
Figure 23A:
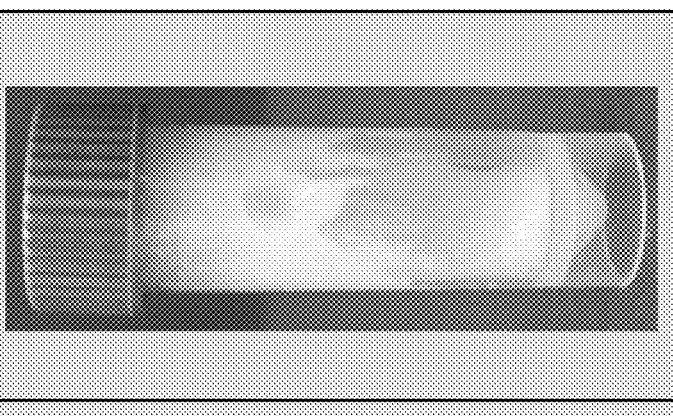
FIGS. 23A-23D are photographs showing dissolved silk in 140° C. (boiling point for LiBr) LiBr solutions dissolved in a 60° C. oven for 6 hours (sericin extraction temperature and time were varied).
Figure 23B:
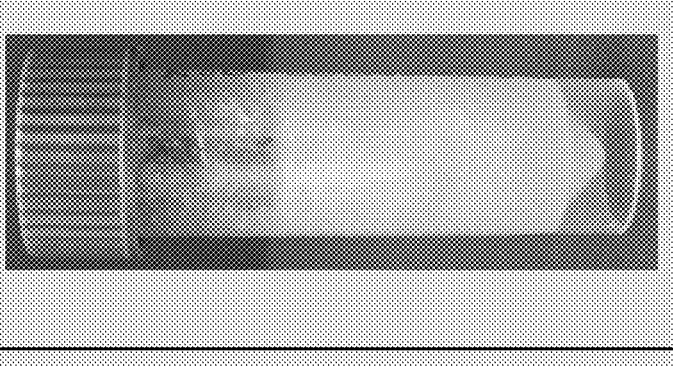
Figure 23C:
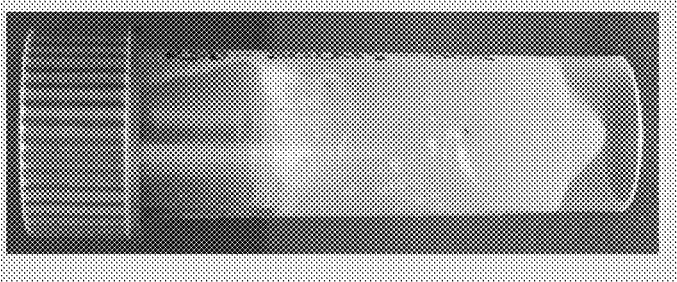
Figure 23D:
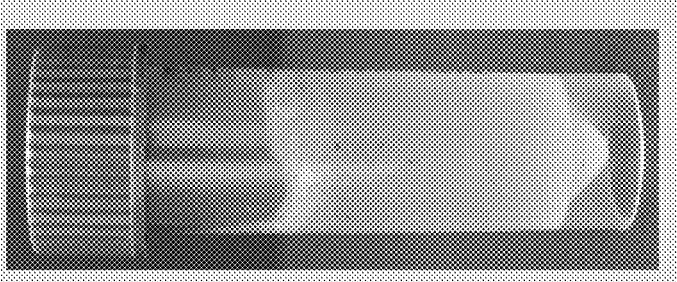
Figures 24A, 24B, 24C, 24D:
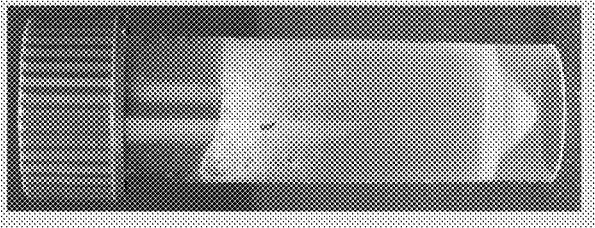
FIGS. 24A-24D are photographs showing dissolved silk in 80° C. LiBr solutions dissolved in a 80° C. oven for 1 hour (sericin extraction temperature and time were varied).
Figures 28A, 28B, 28C, 28D:
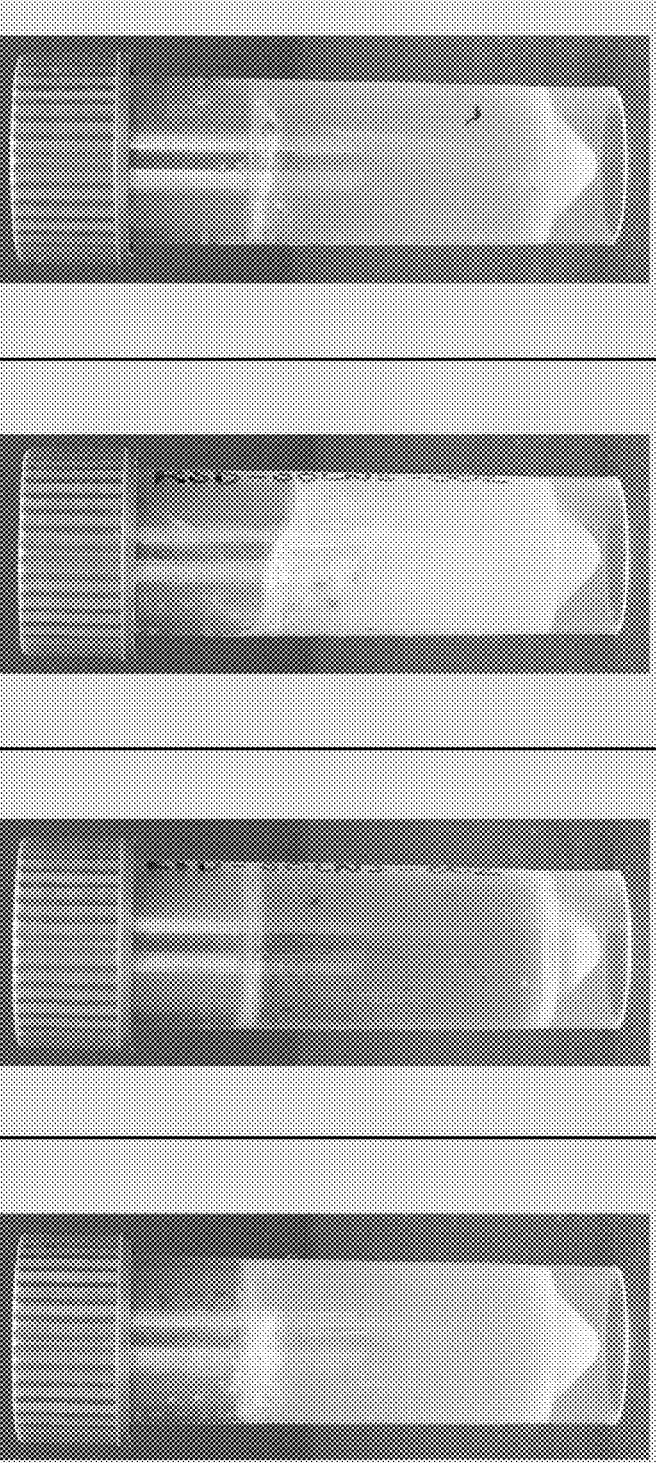
FIGS. 28A-28D are photographs showing dissolved silk in 100° C. LiBr solutions dissolved in a 100° C. oven for 4 hours (sericin extraction temperature and time were varied).
Figures 29A, 29B, 29C, 29D:
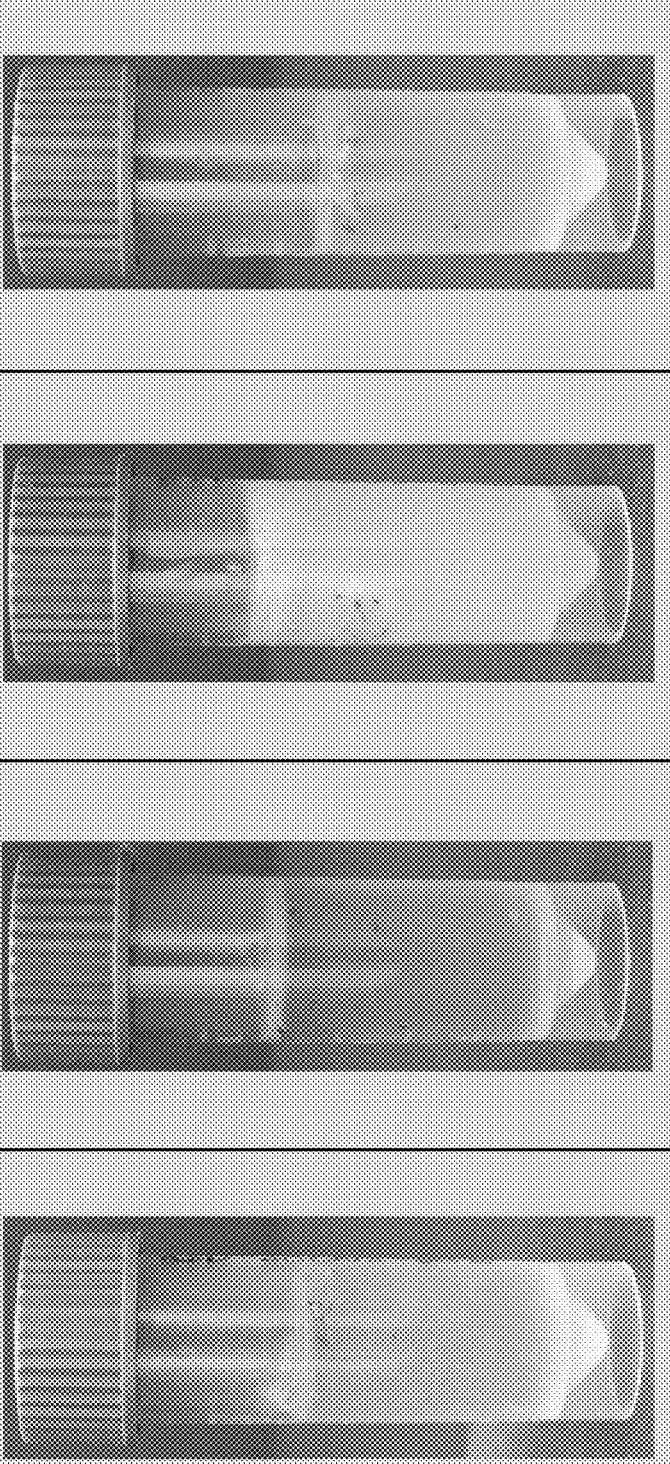
FIGS. 29A-29D are photographs showing dissolved silk in 100° C. LiBr solutions dissolved in a 100° C. oven for 6 hours (sericin extraction temperature and time were varied).
Figures 30A, 30B, 30C, 30D:
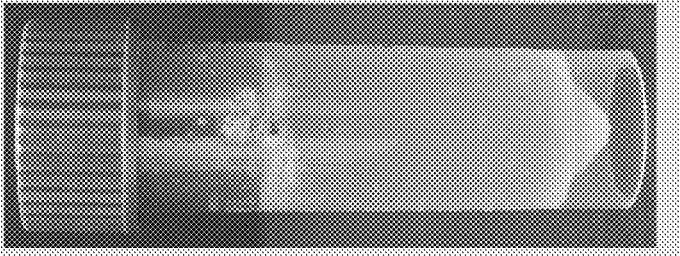
FIGS. 30A-30D are photographs showing dissolved silk in 140° C. (boiling point for LiBr) LiBr solutions dissolved in a 120° C. oven for 1 hour (sericin extraction temperature and time were varied).
Figures 32A, 32B, 32C, 32D:
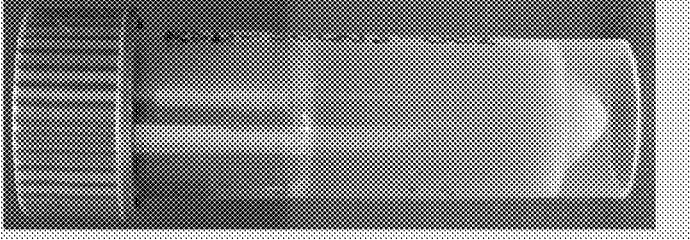
FIG. 32A-32D are photographs showing dissolved silk in 140° C. (boiling point for LiBr) LiBr solutions dissolved in a 120° C. oven for 6 hours (sericin extraction temperature and time were varied).

The final silk protein fragment solution, as shown in FIG. 4, is pure silk protein fragments and water with PPM to undetectable levels of particulate debris and/or process contaminants, including LiBr and $Na_2CO_3$. FIG. 34 and FIG. 35 are tables summarizing LiBr and $Na_2CO_3$ concentrations in solutions of the present disclosure. In FIG. 34, the processing conditions included 100° C. extraction for 60 min, 60° C. rinse, 100° C. LiBr in 100° C. oven for 60 min. TFF conditions including pressure differential and number of dia-filtration volumes were varied. In FIG. 35, the processing conditions included 100° C. boil for 60 min, 60° C. rinse, LiBr in 60° C. oven for 4-6 hours. In an embodiment, a SPF composition of the present disclosure is not soluble in an aqueous solution due to the crystallinity of the protein. In an embodiment, a SPF composition of the present disclosure is soluble in an aqueous solution. In an embodiment, the SPFs of a composition of the present disclosure include a crystalline portion of about two-thirds and an amorphous region of about one-third. In an embodiment, the SPFs of a composition of the present disclosure include a crystalline portion of about one-half and an amorphous region of about one-half. In an embodiment, the SPFs of a composition of the present disclosure include a 99% crystalline portion and a 1% amorphous region. In an embodiment, the SPFs of a composition of the present disclosure include a 95% crystalline portion and a 5% amorphous region. In an embodiment, the SPFs of a composition of the present disclosure include a 90% crystalline portion and a 10% amorphous region. In an embodiment, the SPFs of a composition of the present disclosure include a 85% crystalline portion and a 15% amorphous region. In an embodiment, the SPFs of a composition of the present disclosure include a 80% crystalline portion and a 20% amorphous region. In an embodiment, the SPFs of a composition of the present disclosure include a 75% crystalline portion and a 25% amorphous region. In an embodiment, the SPFs of a composition of the present disclosure include a 70% crystalline portion and a 30% amorphous region. In an embodiment, the SPFs of a composition of the present disclosure include a 65% crystalline portion and a 35% amorphous region. In an embodiment, the SPFs of a composition of the present disclosure include a 60% crystalline portion and a 40% amorphous region. In an embodiment, the SPFs of a composition of the present disclosure include a 50% crystalline portion and a 50% amorphous region. In an embodiment, the SPFs of a composition of the present disclosure include a 40% crystalline portion and a 60% amorphous region. In an embodiment, the SPFs of a composition of the present disclosure include a 35% crystalline portion and a 65% amorphous region. In an embodiment, the SPFs of a composition of the present disclosure include a 30% crystalline portion and a 70% amorphous region. In an embodiment, the SPFs of a composition of the present disclosure include a 25% crystalline portion and a 75% amorphous region. In an embodiment, the SPFs of a composition of the present disclosure include a 20% crystalline portion and a 80% amorphous region. In an embodiment, the SPFs of a composition of the present disclosure include a 15% crystalline portion and a 85% amorphous region. In an embodiment, the SPFs of a composition of the present disclosure include a 10% crystalline portion and a 90% amorphous region. In an embodiment, the SPFs of a composition of the present disclosure include a 5% crystalline portion and a 90% amorphous region. In an embodiment, the SPFs of a composition of the present disclosure include a 1% crystalline portion and a 99% amorphous region.

A unique feature of the SPF compositions of the present disclosure are shelf stability (they will not slowly or spontaneously gel when stored in an aqueous solution and there is no aggregation of fragments and therefore no increase in molecular weight over time), from 10 days to 3 years depending on storage conditions, percent silk, and number of shipments and shipment conditions. Additionally pH may be altered to extend shelf-life and/or support shipping conditions by preventing premature folding and aggregation of the silk. In an embodiment, a SPF solution composition of the present disclosure has a shelf stability for up to 2 weeks at room temperature (RT). In an embodiment, a SPF solution composition of the present disclosure has a shelf stability for up to 4 weeks at RT. In an embodiment, a SPF solution composition of the present disclosure has a shelf stability for up to 6 weeks at RT. In an embodiment, a SPF solution composition of the present disclosure has a shelf stability for up to 8 weeks at RT. In an embodiment, a SPF solution composition of the present disclosure has a shelf stability for up to 10 weeks at RT. In an embodiment, a SPF solution composition of the present disclosure has a shelf stability for up to 12 weeks at RT. In an embodiment, a SPF solution composition of the present disclosure has a shelf stability ranging from about 4 weeks to about 52 weeks at RT. Table 1 below shows shelf stability test results for embodiments of SPF compositions of the present disclosure.

TABLE 1

Shelf Stability of SPF Compositions of the Present Disclosure

| % Silk | Temperature | Time to Gelation |
| --- | --- | --- |
| 2 | RT | 4 weeks |
| 2 | 4 C. | >9 weeks |

TABLE 1-continued

Shelf Stability of SPF Compositions of the Present Disclosure

| % Silk | Temperature | Time to Gelation |
| --- | --- | --- |
| 4 | RT | 4 weeks |
| 4 | 4 C. | >9 weeks |
| 6 | RT | 2 weeks |
| 6 | 4 C. | >9 weeks |

A silk fragment-water solution of the present disclosure can be sterilized following standard methods in the art not limited to filtration, heat, radiation or e-beam. It is anticipated that the silk protein fragment mixture, because of its shorter protein polymer length, will withstand sterilization better than intact silk protein solutions described in the art. Additionally, silk articles created from the SPF mixtures described herein may be sterilized as appropriate to application.

Figure 2:
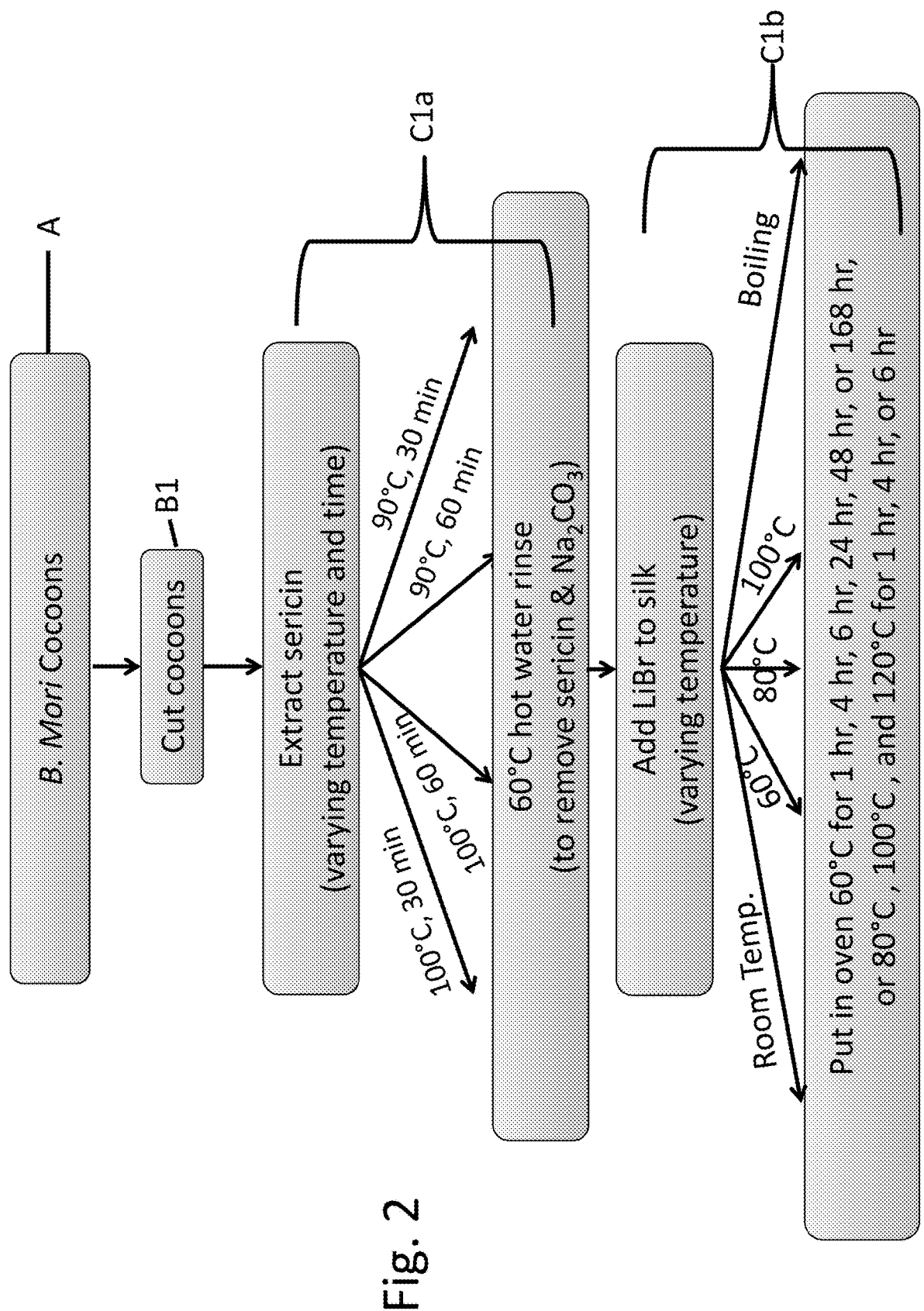
FIG. 2 is a flow chart showing various parameters that can be modified during the process of producing SPFs of the present disclosure during the extraction and the dissolution steps.

FIG. 2 is a flow chart showing various parameters that can be modified during the process of producing a silk protein fragment solution of the present disclosure during the extraction and the dissolution steps. Select method parameters may be altered to achieve distinct final solution characteristics depending upon the intended use, e.g., molecular weight and polydispersity. It should be understood that not all of the steps illustrated are necessarily required to fabricate all silk solutions of the present disclosure.

In an embodiment, a process for producing a silk protein fragment solution of the present disclosure includes forming pieces of silk cocoons from the *Bombyx mori* silk worm; extracting the pieces at about 100° C. in a solution of water and $Na_2CO_3$ for about 60 minutes, wherein a volume of the water equals about 0.4×raw silk weight and the amount of $Na_2CO_3$ is about 0.848×the weight of the pieces to form a silk fibroin extract; triple rinsing the silk fibroin extract at about 60° C. for about 20 minutes per rinse in a volume of rinse water, wherein the rinse water for each cycle equals about 0.2 L×the weight of the pieces; removing excess water from the silk fibroin extract; drying the silk fibroin extract; dissolving the dry silk fibroin extract in a LiBr solution, wherein the LiBr solution is first heated to about 100° C. to create a silk and LiBr solution and maintained; placing the silk and LiBr solution in a dry oven at about 100° C. for about 60 minutes to achieve complete dissolution and further fragmentation of the native silk protein structure into mixture with desired molecular weight and polydispersity; filtering the solution to remove any remaining debris from the silkworm; diluting the solution with water to result in a 1% silk solution; and removing solvent from the solution using Tangential Flow Filtration (TFF). In an embodiment, a 10 kDa membrane is utilized to purify the silk solution and create the final desired silk-to-water ratio. TFF can then be used to further concentrate the pure silk solution to a concentration of 2% silk to water.

Each process step from raw cocoons to dialysis is scalable to increase efficiency in manufacturing. Whole cocoons are currently purchased as the raw material, but pre-cleaned cocoons or non-heat treated cocoons, where worm removal leaves minimal debris, have also been used. Cutting and cleaning the cocoons is a manual process, however for scalability this process could be made less labor intensive by, for example, using an automated machine in combination with compressed air to remove the worm and any particulates, or using a cutting mill to cut the cocoons into smaller pieces. The extraction step, currently performed in small batches, could be completed in a larger vessel, for example an industrial washing machine where temperatures at or in between 60° C. to 100° C. can be maintained. The rinsing step could also be completed in the industrial washing machine, eliminating the manual rinse cycles. Dissolution of the silk in LiBr solution could occur in a vessel other than a convection oven, for example a stirred tank reactor. Dialyzing the silk through a series of water changes is a manual and time intensive process, which could be accelerated by changing certain parameters, for example diluting the silk solution prior to dialysis. The dialysis process could be scaled for manufacturing by using semi-automated equipment, for example a tangential flow filtration system.

Varying extraction (i.e., time and temperature), LiBr (i.e., temperature of LiBr solution when added to silk fibroin extract or vice versa) and dissolution (i.e., time and temperature) parameters results in solvent and silk solutions with different viscosities, homogeneities, and colors (see FIGS. 5-32). Increasing the temperature for extraction, lengthening the extraction time, using a higher temperature LiBr solution at emersion and over time when dissolving the silk and increasing the time at temperature (e.g., in an oven as shown here, or an alternative heat source) all resulted in less viscous and more homogeneous solvent and silk solutions. While almost all parameters resulted in a viable silk solution, methods that allow complete dissolution to be achieved in fewer than 4 to 6 hours are preferred for process scalability.

FIGS. 5-10 show photographs of four different silk extraction combinations tested: 90° C. 30 min, 90° C. 60 min, 100° C. 30 min, and 100° C. 60 min. Briefly, 9.3 M LiBr was prepared and allowed to sit at room temperature for at least 30 minutes. 5 mL of LiBr solution was added to 1.25 g of silk and placed in the 60° C. oven. Samples from each set were removed at 4, 6, 8, 12, 24, 168 and 192 hours. The remaining sample was photographed.

FIGS. 11-23 show photographs of four different silk extraction combinations tested: 90° C. 30 min, 90° C. 60 min, 100° C. 30 min, and 100° C. 60 min. Briefly, 9.3 M LiBr solution was heated to one of four temperatures: 60° C., 80° C., 100° C. or boiling. 5 mL of hot LiBr solution was added to 1.25 g of silk and placed in the 60° C. oven. Samples from each set were removed at 1, 4 and 6 hours. The remaining sample was photographed.

FIGS. 24-32 show photographs of four different silk extraction combinations tested: Four different silk extraction combinations were used: 90° C. 30 min, 90° C. 60 min, 100° C. 30 min, and 100° C. 60 min. Briefly, 9.3 M LiBr solution was heated to one of four temperatures: 60° C., 80° C., 100° C. or boiling. 5 mL of hot LiBr solution was added to 1.25 g of silk and placed in the oven at the same temperature of the LiBr. Samples from each set were removed at 1, 4 and 6 hours. 1 mL of each sample was added to 7.5 mL of 9.3 M LiBr and refrigerated for viscosity testing. The remaining sample was photographed.

Molecular weight of the silk protein fragments may be controlled based upon the specific parameters utilized during the extraction step, including extraction time and temperature; specific parameters utilized during the dissolution step, including the LiBr temperature at the time of submersion of the silk in to the lithium bromide and time that the solution is maintained at specific temperatures; and specific parameters utilized during the filtration step. By controlling process parameters using the disclosed methods, it is possible to create SPF mixture solutions with polydispersity equal to or lower than 2.5 at a variety of different molecular weight ranging from 5 kDa to 200 kDa, more preferably between 10 kDa and 80 kDA. By altering process parameters to achieve silk solutions with different molecular weights, a range of fragment mixture end products, with desired polydispersity of equal to or less than 2.5 may be targeted based upon the desired performance requirements. Additionally, SPF mixture solutions with a polydispersity of greater than 2.5 can be achieved. Further, two solutions with different average molecular weights and polydispersities can be mixed to create combination solutions. Alternatively, a liquid silk gland (100% sericin free silk protein) that has been removed directly from a worm could be used in combination with any of the SPF mixture solutions of the present disclosure. Molecular weight of the pure silk fibroin-based protein fragment composition was determined using High Pressure Liquid Chromatography (HPLC) with a Refractive Index Detector (RID). Polydispersity was calculated using Cirrus GPC Online GPC/SEC Software Version 3.3 (Agilent).

Parameters were varied during the processing of raw silk cocoons into silk solution. Varying these parameters affected the MW of the resulting silk solution. Parameters manipulated included (i) time and temperature of extraction, (ii) temperature of LiBr, (iii) temperature of dissolution oven, and (iv) dissolution time. Molecular weight was determined with mass spec as shown in FIGS. 40-54.

Experiments were carried out to determine the effect of varying the extraction time. FIGS. 40-46 are graphs showing these results, and Tables 2-8 summarize the results. Below is a summary:

- A sericin extraction time of 30 minutes resulted in larger MW than a sericin extraction time of 60 minutes
- MW decreases with time in the oven
- 140° C. LiBr and oven resulted in the low end of the confidence interval to be below a MW of 9500 Da
- 30 min extraction at the 1 hour and 4 hour time points have undigested silk
- 30 min extraction at the 1 hour time point resulted in a significantly high molecular weight with the low end of the confidence interval being 35,000 Da
- The range of MW reached for the high end of the confidence interval was 18000 to 216000 Da (important for offering solutions with specified upper limit)

TABLE 2

The effect of extraction time (30 min vs 60 min) on molecular weight of silk processed under the conditions of 100° C. Extraction Temperature, 100° C. Lithium Bromide (LiBr) and 100° C. Oven Dissolution (Oven/Dissolution Time was varied).

| Boil Time | Oven Time | Average Mw | Std dev | Confidence Interval | | PD |
|---|---|---|---|---|---|---|
| 30 | 1 | 57247 | 12780 | 35093 | 93387 | 1.63 |
| 60 | 1 | 31520 | 1387 | 11633 | 85407 | 2.71 |
| 30 | 4 | 40973 | 2632 | 14268 | 117658 | 2.87 |
| 60 | 4 | 25082 | 1248 | 10520 | 59803 | 2.38 |
| 30 | 6 | 25604 | 1405 | 10252 | 63943 | 2.50 |
| 60 | 6 | 20980 | 1262 | 10073 | 43695 | 2.08 |

TABLE 3

The effect of extraction time (30 min vs 60 min) on molecular weight of silk processed under the conditions of 100° C. Extraction Temperature, boiling Lithium Bromide (LiBr) and 60° C. Oven Dissolution for 4 hr.

| Sample | Boil Time | Average Mw | Std dev | Confidence Interval | | PD |
|---|---|---|---|---|---|---|
| 30 min, 4 hr | 30 | 49656 | 4580 | 17306 | 142478 | 2.87 |
| 60 min, 4 hr | 60 | 30042 | 1536 | 11183 | 80705 | 2.69 |

TABLE 4

The effect of extraction time (30 min vs 60 min) on molecular weight of silk processed under the conditions of 100° C. Extraction Temperature, 60° C. Lithium Bromide (LiBr) and 60° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 1 hr | 30 | 1 | 58436 | | 22201 | 153809 | 2.63 |
| 60 min, 1 hr | 60 | 1 | 31700 | | 11931 | 84224 | 2.66 |
| 30 min, 4 hr | 30 | 4 | 61956.5 | 13337 | 21463 | 178847 | 2.89 |
| 60 min, 4 hr | 60 | 4 | 25578.5 | 2446 | 9979 | 65564 | 2.56 |

TABLE 5

The effect of extraction time (30 min vs 60 min) on molecular weight of silk processed under the conditions of 100° C. Extraction Temperature, 80° C. Lithium Bromide (LiBr) and 80° C. Oven Dissolution for 6 hr.

| Sample | Boil Time | Average Mw | Std dev | Confidence Interval | | PD |
|---|---|---|---|---|---|---|
| 30 min, 6 hr | 30 | 63510 | | 18693 | 215775 | 3.40 |
| 60 min, 6 hr | 60 | 25164 | 238 | 9637 | 65706 | 2.61 |

TABLE 6

The effect of extraction time (30 min vs 60 min) on molecular weight of silk processed under the conditions of 100° C. Extraction Temperature, 80° C. Lithium Bromide (LiBr) and 60° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 4 hr | 30 | 4 | 59202 | 14028 | 19073 | 183760 | 3.10 |
| 60 min, 4 hr | 60 | 4 | 26312.5 | 637 | 10266 | 67442 | 2.56 |
| 30 min, 6 hr | 30 | 6 | 46824 | | 18076 | 121293 | 2.59 |
| 60 min, 6 hr | 60 | 6 | 26353 | | 10168 | 68302 | 2.59 |

TABLE 7

The effect of extraction time (30 min vs 60 min) on molecular weight of silk processed under the conditions of 100° C. Extraction Temperature, 100° C. Lithium Bromide (LiBr) and 60° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 4 hr | 30 | 4 | 47853 | | 19758 | 115900 | 2.42 |
| 60 min, 4 hr | 60 | 4 | 25082 | 1248 | 10520 | 59804 | 2.38 |
| 30 min, 6 hr | 30 | 6 | 55421 | 8992 | 19153 | 160366 | 2.89 |
| 60 min, 6 hr | 60 | 6 | 20980 | 1262 | 10073 | 43694 | 2.08 |

TABLE 8

The effect of extraction time (30 min vs 60 min) on molecular weight of silk processed under the conditions of 100° C. Extraction Temperature, 140° C. Lithium Bromide (LiBr) and 140° C. Oven Dissolution (Oven/Dissolution Time was varied).

| Sample | Boil Time | Oven Time | Average Mw | Std dev | Confidence Interval | | PD |
|---|---|---|---|---|---|---|---|
| 30 min, 4 hr | 30 | 4 | 9024.5 | 1102 | 4493 | 18127 | 2.00865 |
| 60 min, 4 hr | 60 | 4 | 15548 | | 6954 | 34762 | 2.2358 |
| 30 min, 6 hr | 30 | 6 | 13021 | | 5987 | 28319 | 2.1749 |
| 60 min, 6 hr | 60 | 6 | 10888 | | 5364 | 22100 | 2.0298 |

Figure 47:
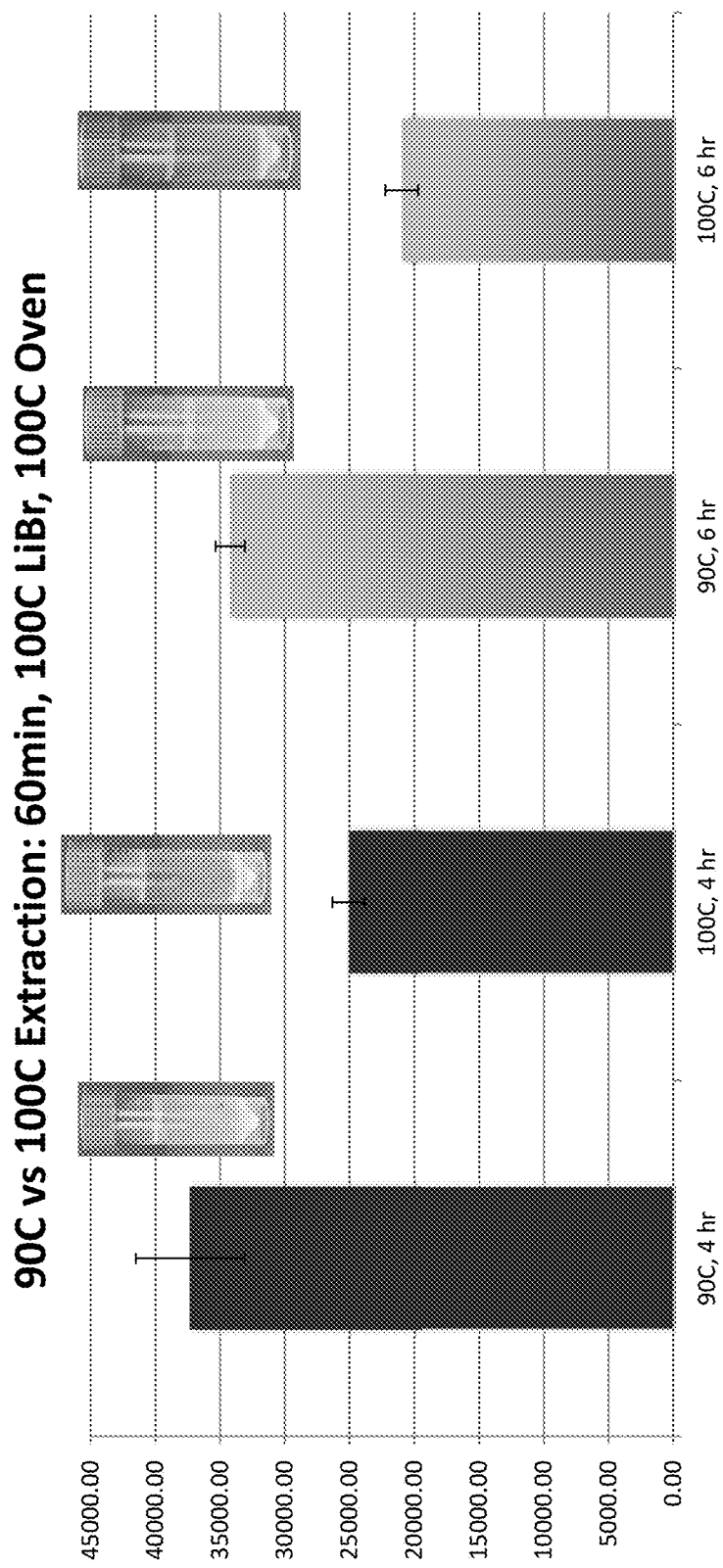
FIG. 47 is a graph summarizing the effect of Extraction Temperature on Molecular Weight of silk processed under the conditions of 60 minute Extraction Time, 100° C. LiBr and 100° C. Oven Dissolution (Oven/Dissolution Time was varied).

Experiments were carried out to determine the effect of varying the extraction temperature. FIG. 47 is a graph showing these results, and Table 9 summarizes the results. Below is a summary:

Sericin extraction at 90° C. resulted in higher MW than sericin extraction at 100° C. extraction Both 90° C. and 100° C. show decreasing MW over time in the oven

TABLE 9

The effect of extraction temperature (90° C. vs. 100° C.) on molecular weight of silk processed under the conditions of 60 min. Extraction Temperature, 100° C. Lithium Bromide (LiBr) and 100° C. Oven Dissolution (Oven/Dissolution Time was varied).

| Sample | Boil Time | Oven Time | Average Mw | Std dev | Confidence Interval | | PD |
|---|---|---|---|---|---|---|---|
| 90 C., 4 hr | 60 | 4 | 37308 | 4204 | 13368 | 104119 | 2.79 |
| 100 C., 4 hr | 60 | 4 | 25082 | 1248 | 10520 | 59804 | 2.38 |
| 90 C., 6 hr | 60 | 6 | 34224 | 1135 | 12717 | 92100 | 2.69 |
| 100 C., 6 hr | 60 | 6 | 20980 | 1262 | 10073 | 43694 | 2.08 |

Figure 48:
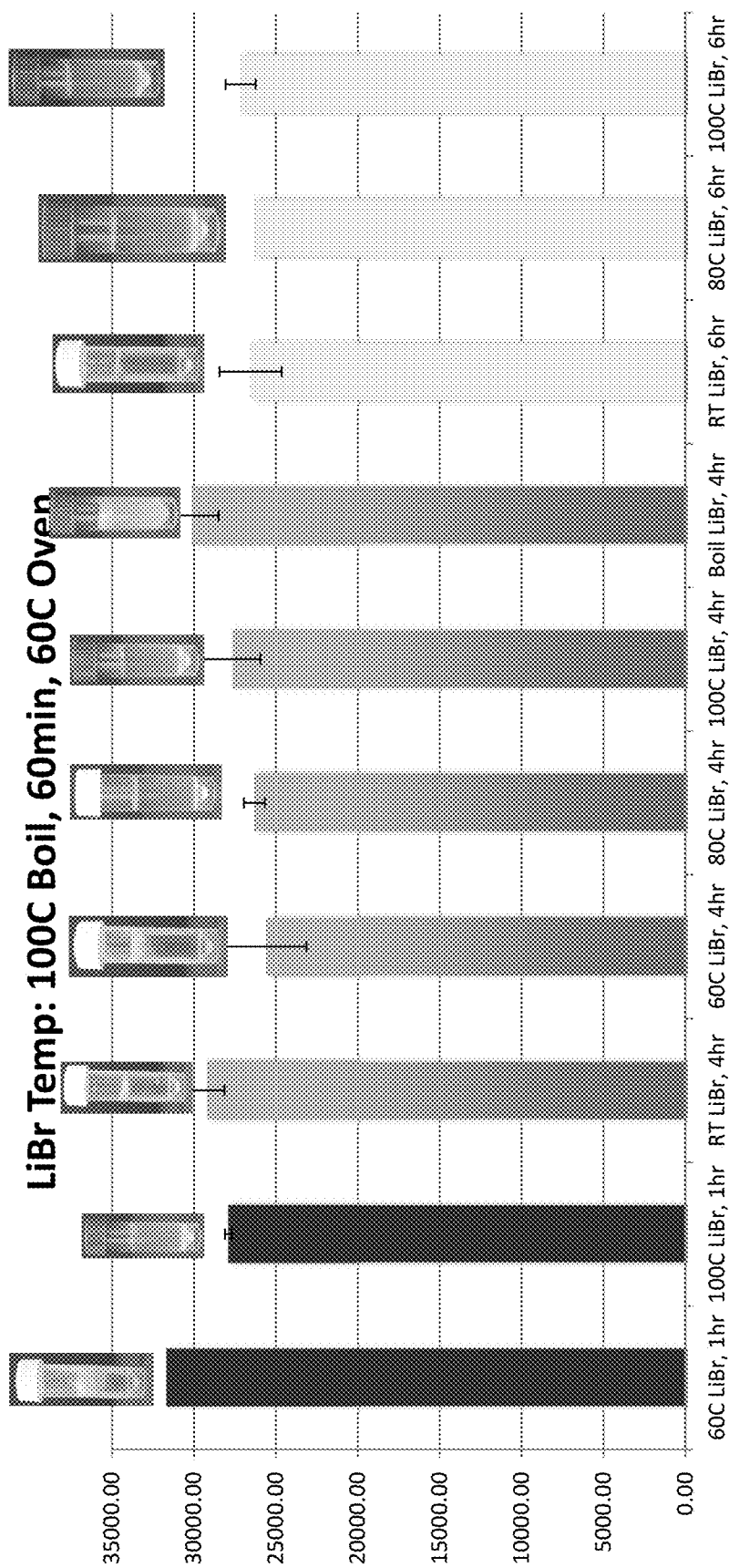
FIG. 48 is a graph summarizing the effect of LiBr Temperature on Molecular Weight of silk processed under the conditions of 60 minute Extraction Time, 100° C. Extraction Temperature and 60° C. Oven Dissolution (Oven/Dissolution Time was varied).
Figure 49:
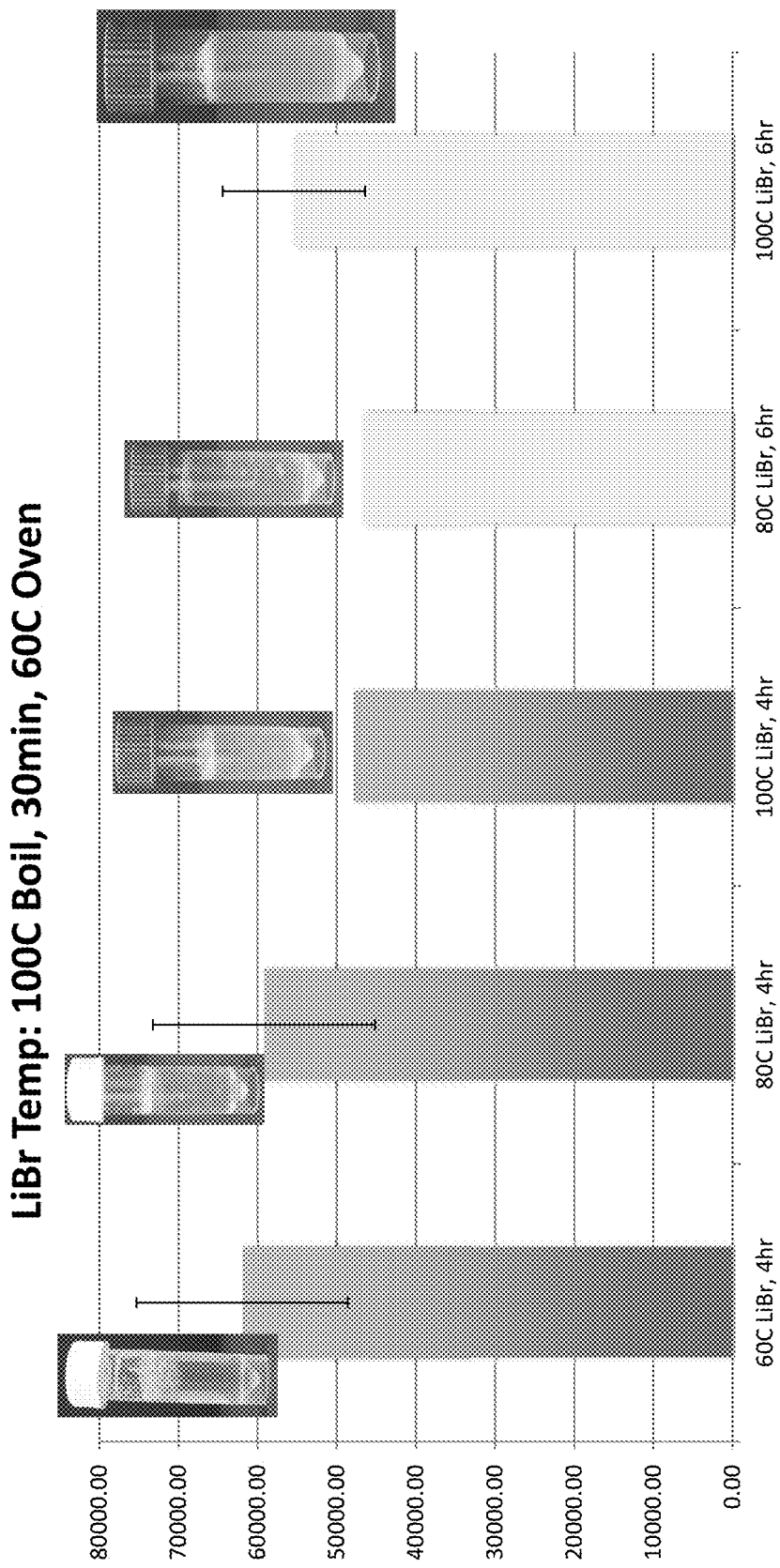
FIG. 49 is a graph summarizing the effect of LiBr Temperature on Molecular Weight of silk processed under the conditions of 30 minute Extraction Time, 100° C. Extraction Temperature and 60° C. Oven Dissolution (Oven/Dissolution Time was varied).
Figure 50:
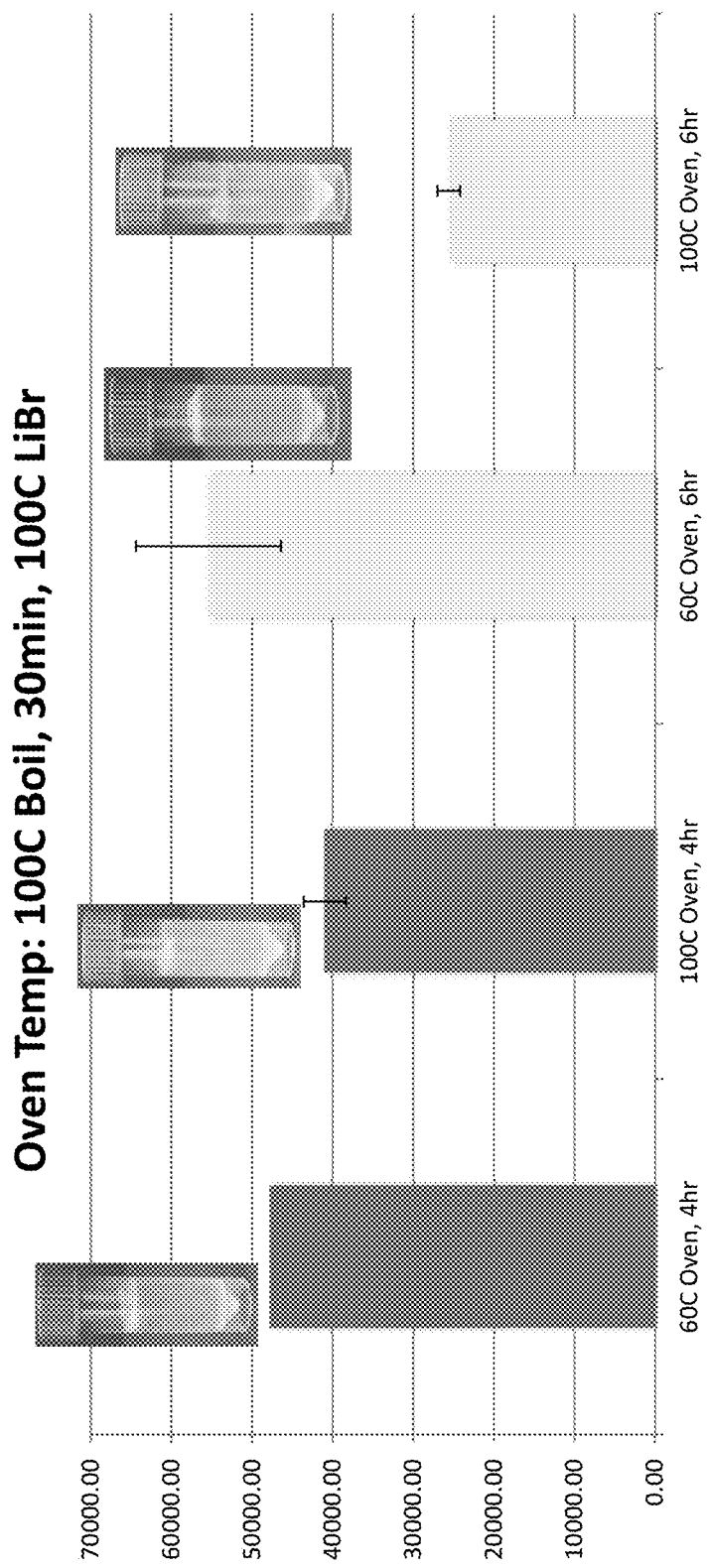
FIG. 50 is a graph summarizing the effect of Oven/Dissolution Temperature on Molecular Weight of silk processed under the conditions of 100° C. Extraction Temperature, 30 minute Extraction Time, and 100° C. Lithium Bromide (Oven/Dissolution Time was varied).
Figure 51:
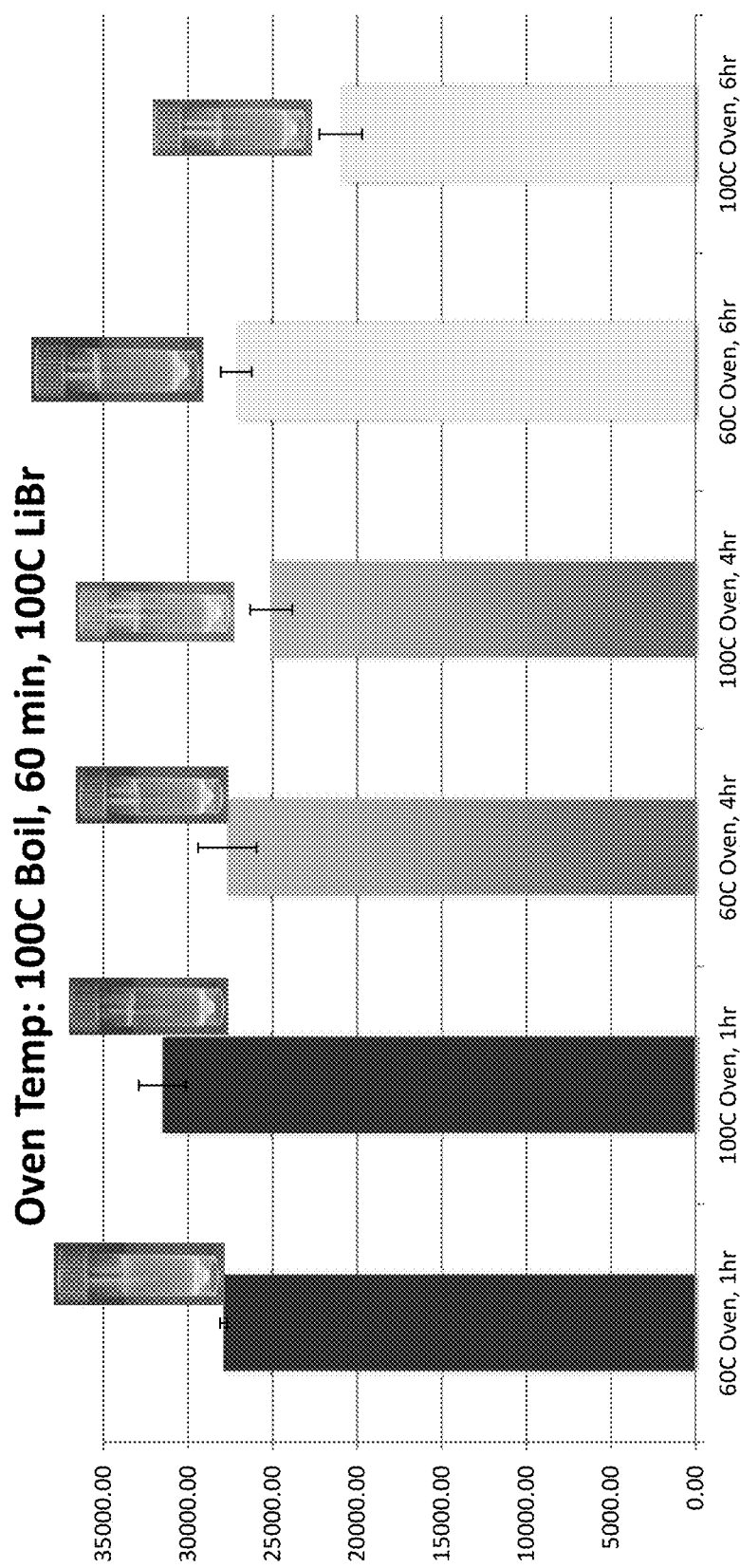
FIG. 51 is a graph summarizing the effect of Oven/Dissolution Temperature on Molecular Weight of silk processed under the conditions of 100° C. Extraction Temperature, 60 minute Extraction Time, and 100° C. Lithium Bromide. (Oven/Dissolution Time was varied).
Figure 52:
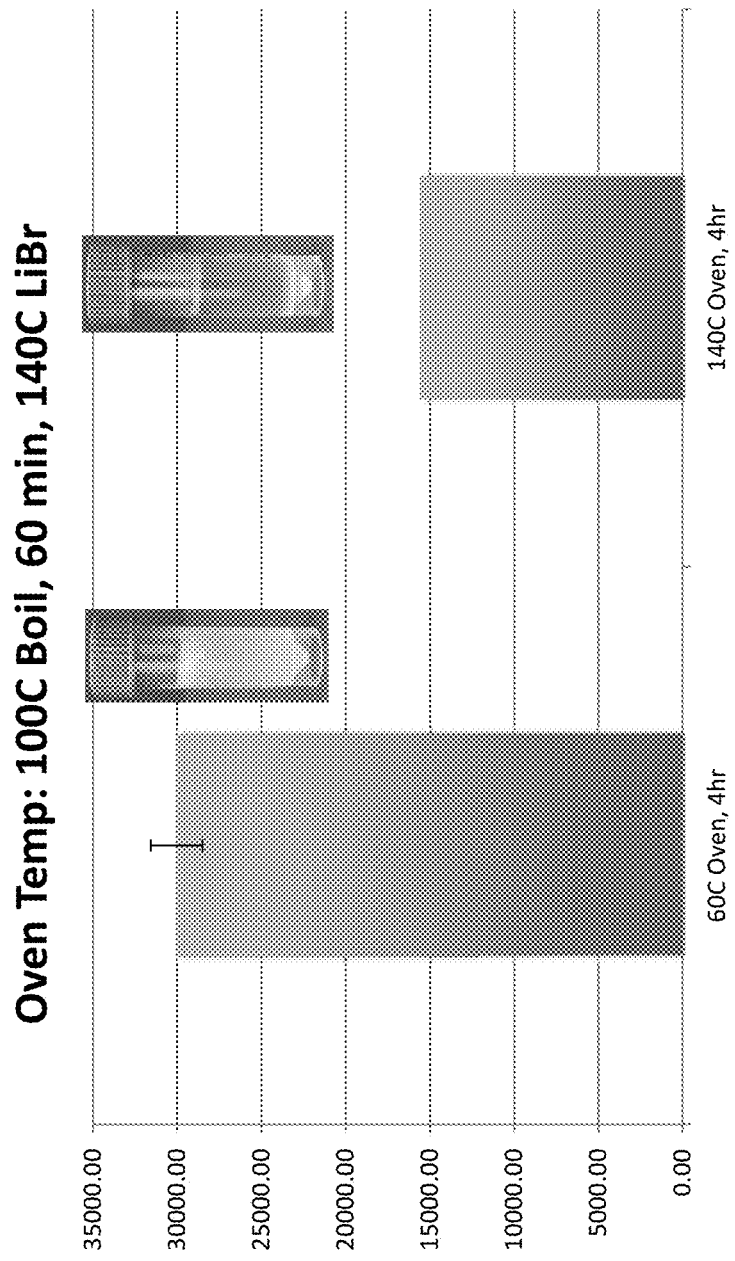
FIG. 52 is a graph summarizing the effect of Oven/Dissolution Temperature on Molecular Weight of silk processed under the conditions of 100° C. Extraction Temperature, 60 minute Extraction Time, and 140° C. Lithium Bromide (Oven/Dissolution Time was varied).
Figure 53:
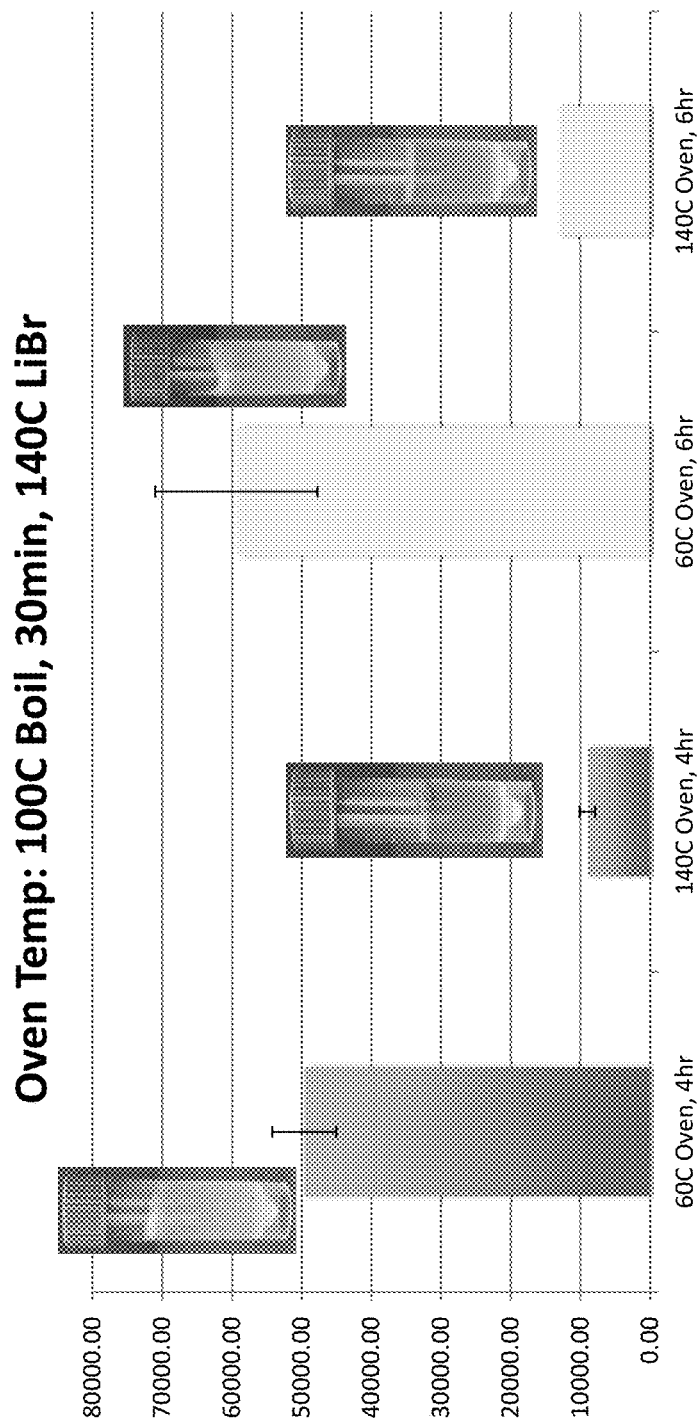
FIG. 53 is a graph summarizing the effect of Oven/Dissolution Temperature on Molecular Weight of silk processed under the conditions of 100° C. Extraction Temperature, 30 minute Extraction Time, and 140° C. Lithium Bromide (Oven/Dissolution Time was varied).
Figure 54:
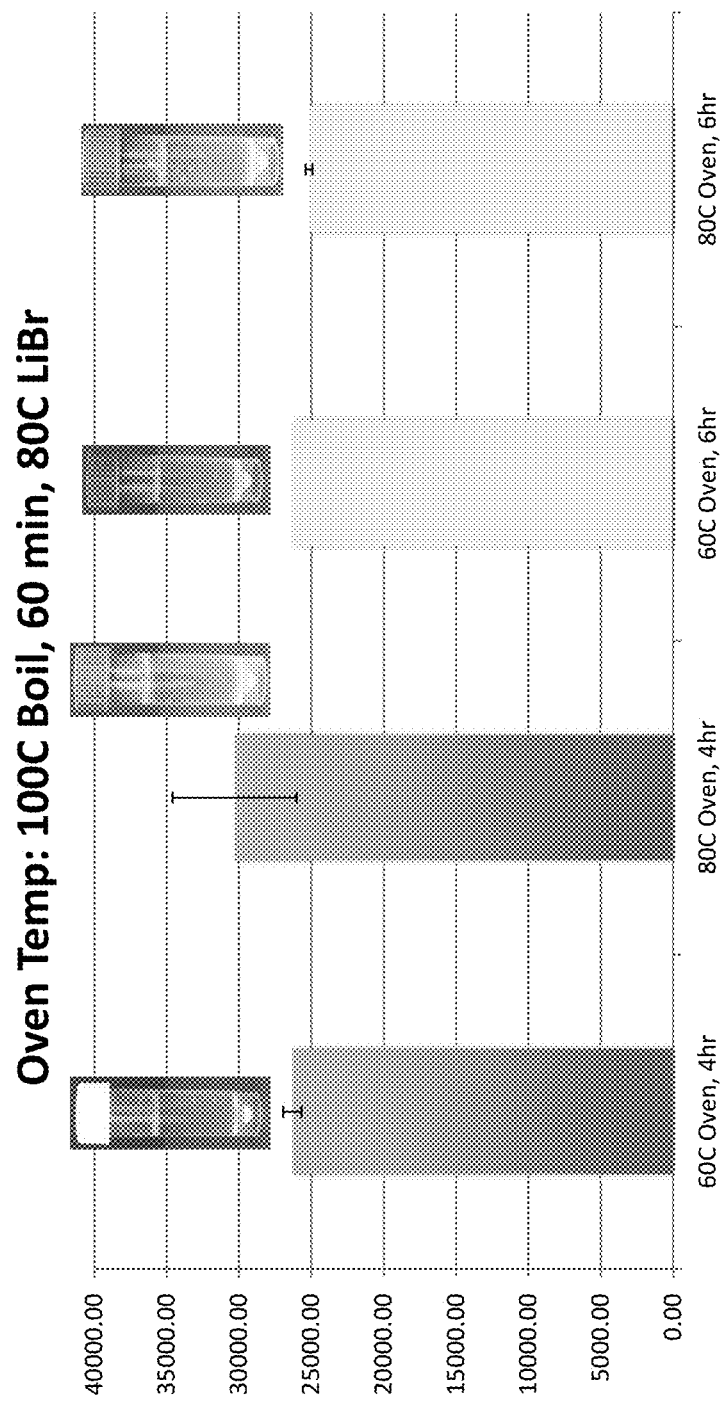
FIG. 54 is a graph summarizing the effect of Oven/Dissolution Temperature on Molecular Weight of silk processed under the conditions of 100° C. Extraction Temperature, 60 minute Extraction Time, and 80° C. Lithium Bromide (Oven/Dissolution Time was varied).
Figure 55:
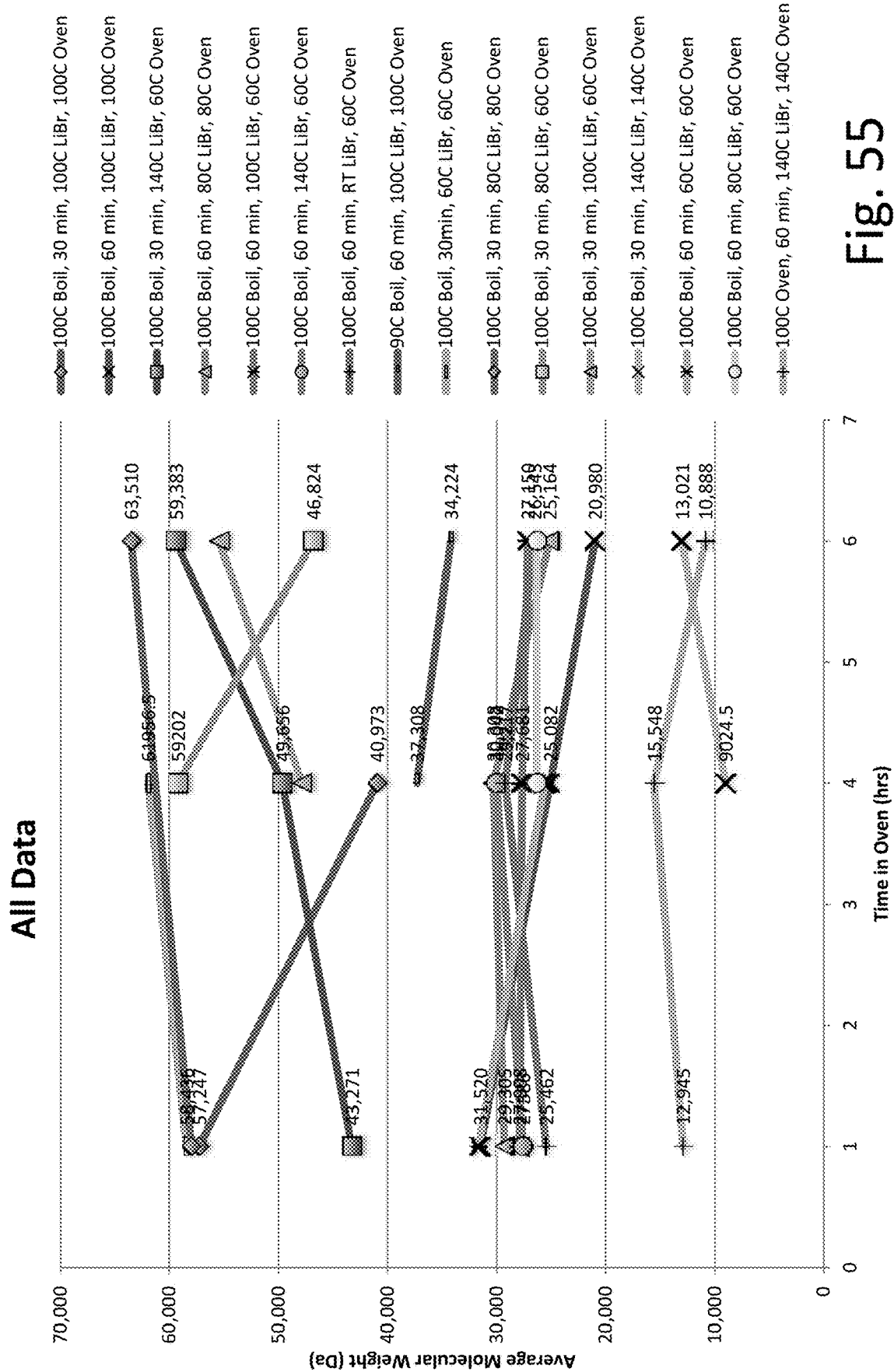
FIG. 55 is a graph summarizing the Molecular Weights of silk processed under varying conditions including Extraction Time, Extraction Temperature, Lithium Bromide (LiBr) Temperature, Oven Temperature for Dissolution, Oven Time for Dissolution.
Figure 56:
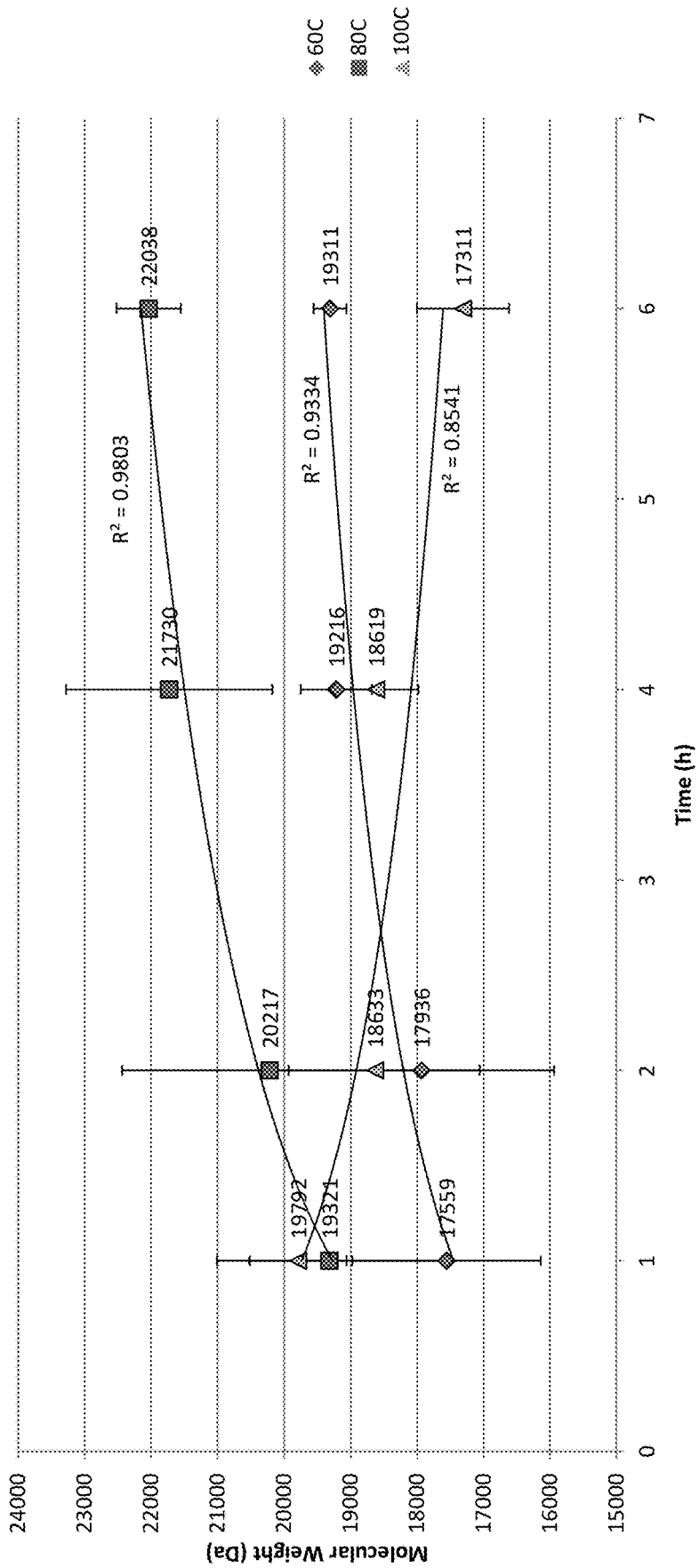
FIG. 56 is a graph summarizing the Molecular Weights of silk processed under conditions in which Oven/Dissolution Temperature is equal to LiBr Temperature.
Figure 57A:
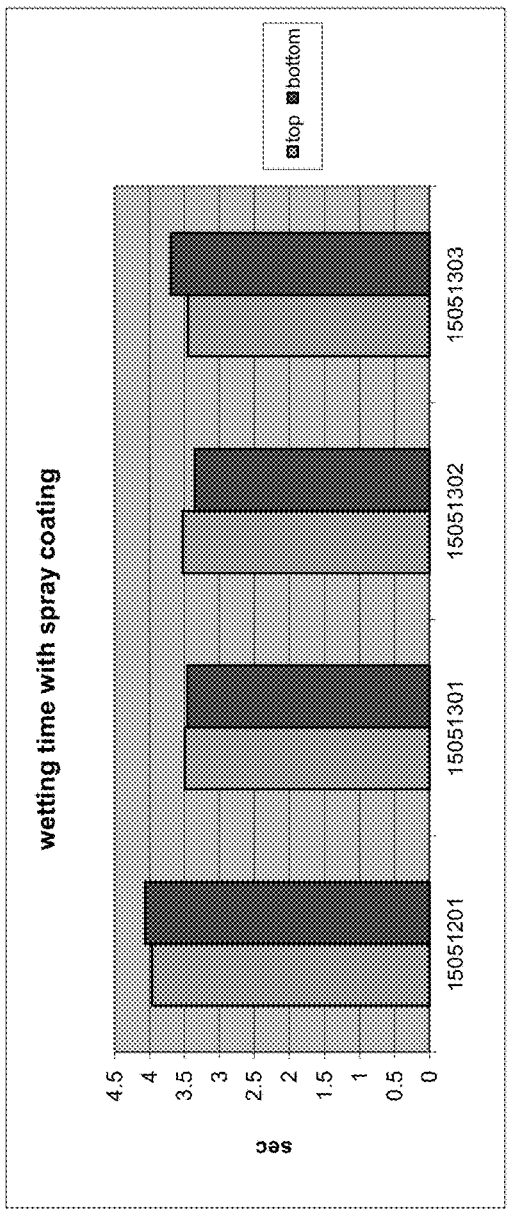
FIG. 57A is a graph illustrating wetting time with spray coating.
Figure 57B:
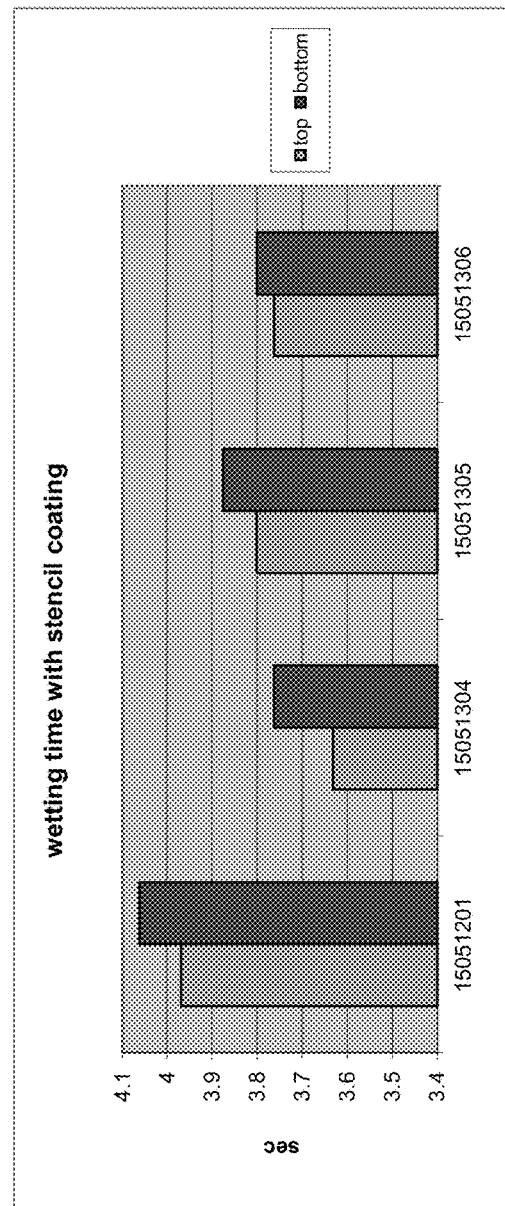
FIG. 57B is a graph illustrating wetting time with stencil coating.
Figure 57C:
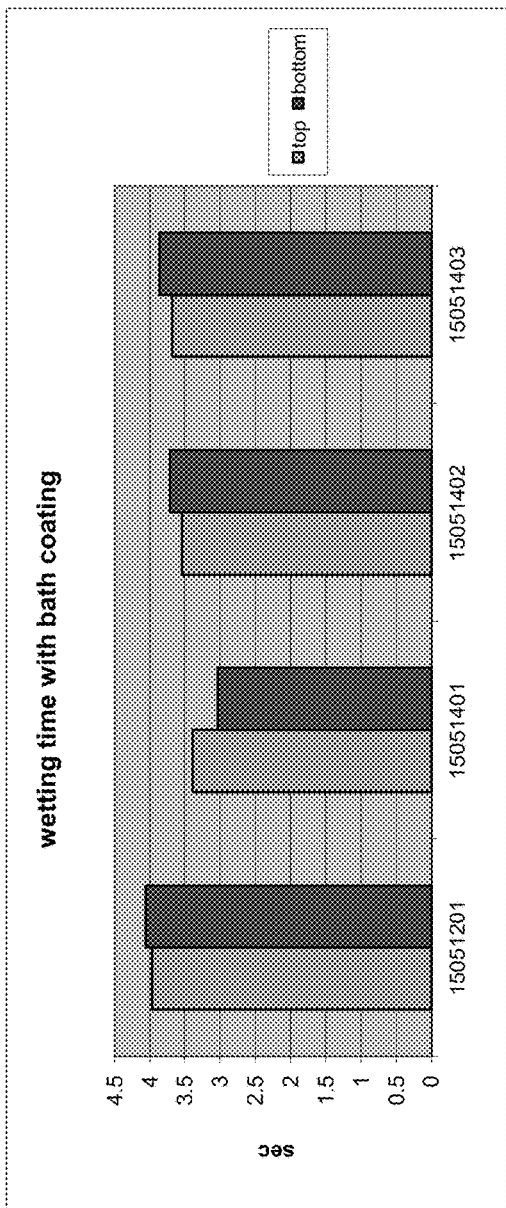
FIG. 57C is a graph illustrating wetting time with bath coating.
Figure 57D:
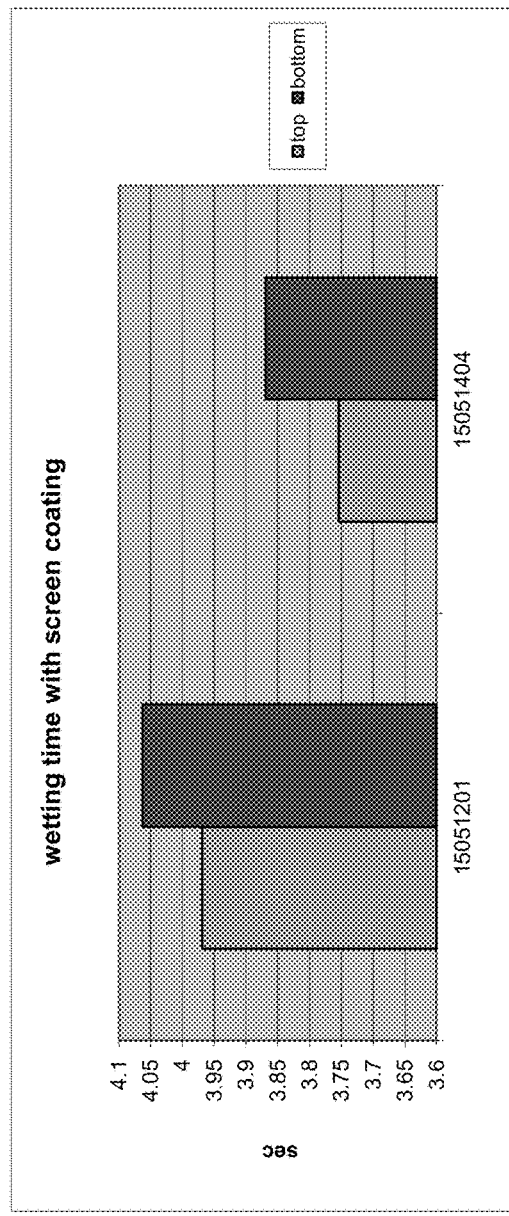
FIG. 57D is a graph illustrating wetting time with screen coating.
Figure 58A:
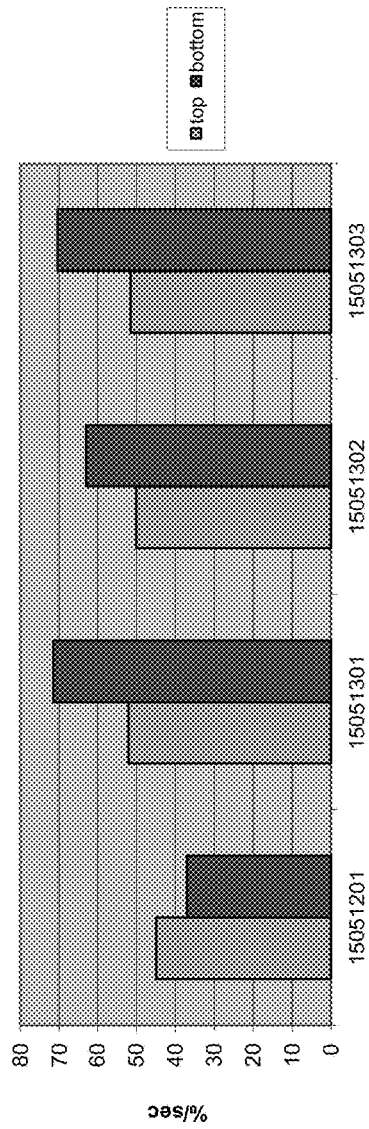
FIG. 58A is a graph illustrating absorption time with spray coating.
Figure 58B:
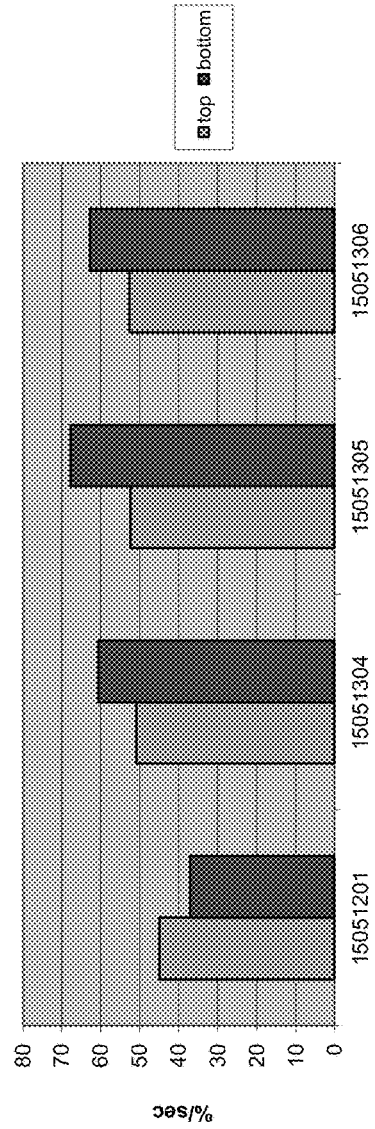
FIG. 58B is a graph illustrating absorption time with stencil coating.
Figure 58C:
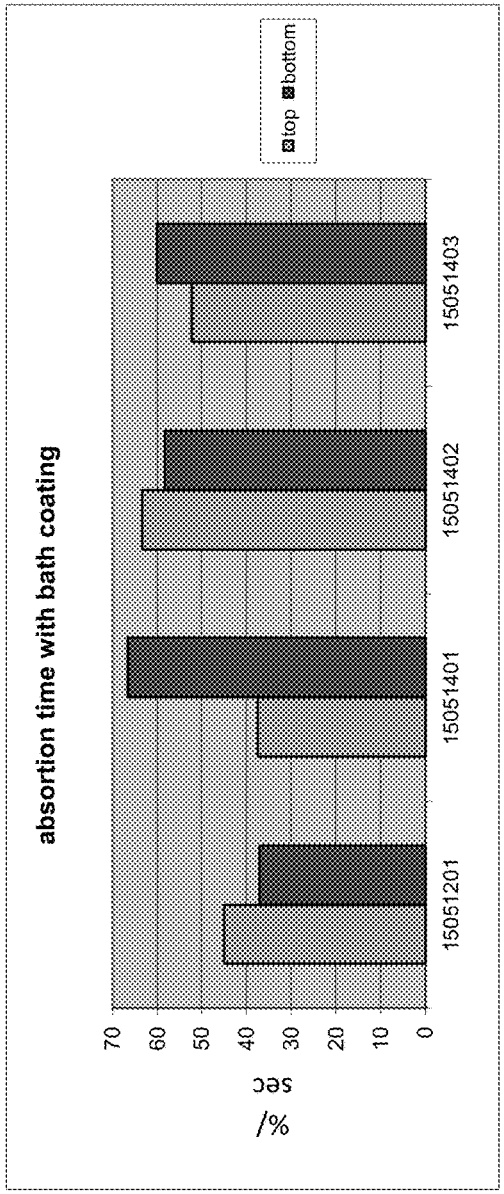
FIG. 58C is a graph illustrating absorption time with bath coating.
Figure 58D:
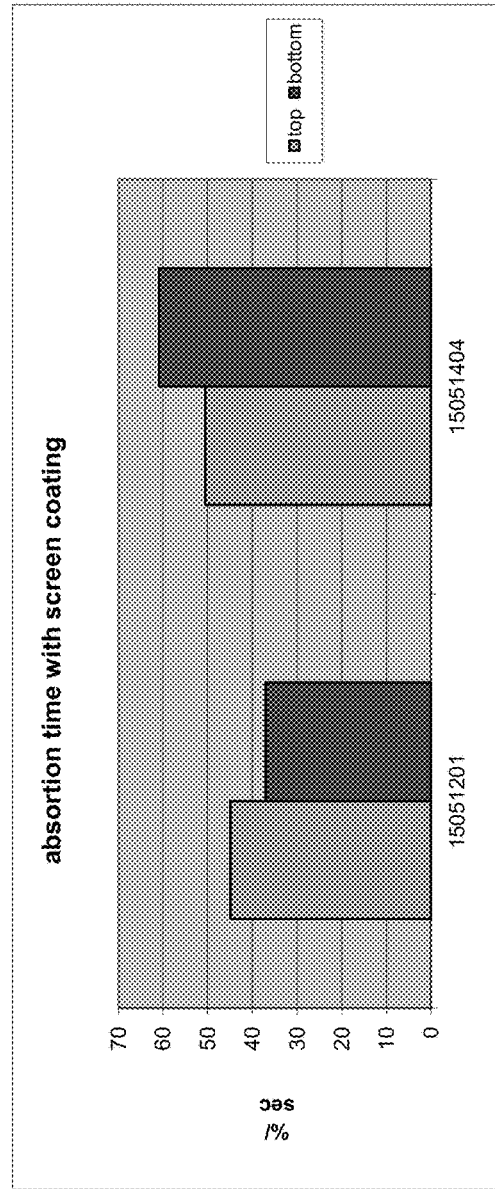
FIG. 58D is a graph illustrating absorption time with screen coating.
Figure 59A:
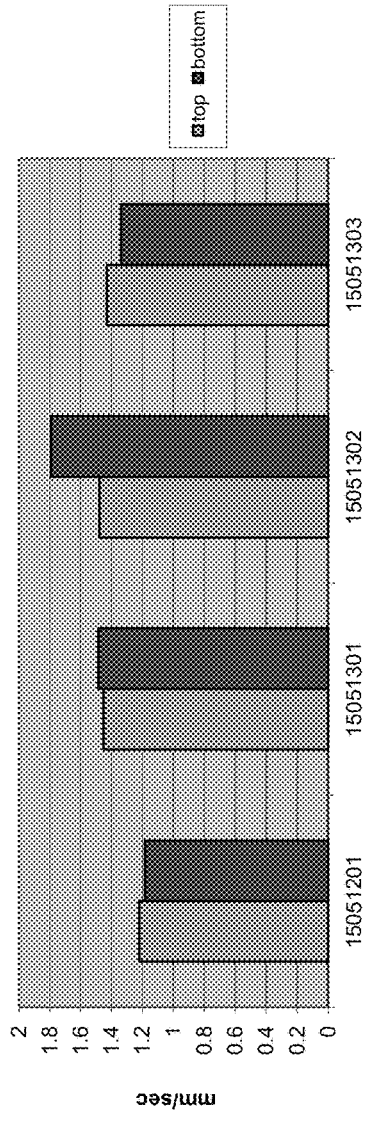
FIG. 59A is a graph illustrating spreading speed with spray coating.
Figure 59B:
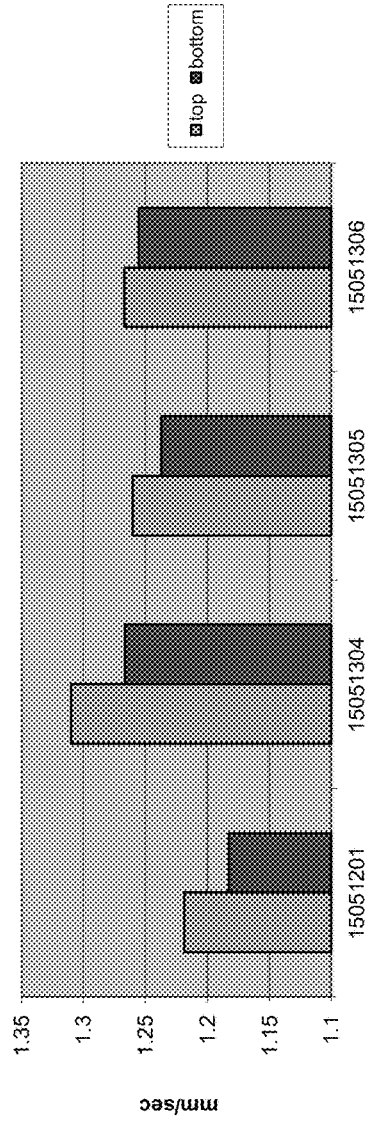
FIG. 59B is a graph illustrating spreading speed with stencil coating.
Figure 59C:
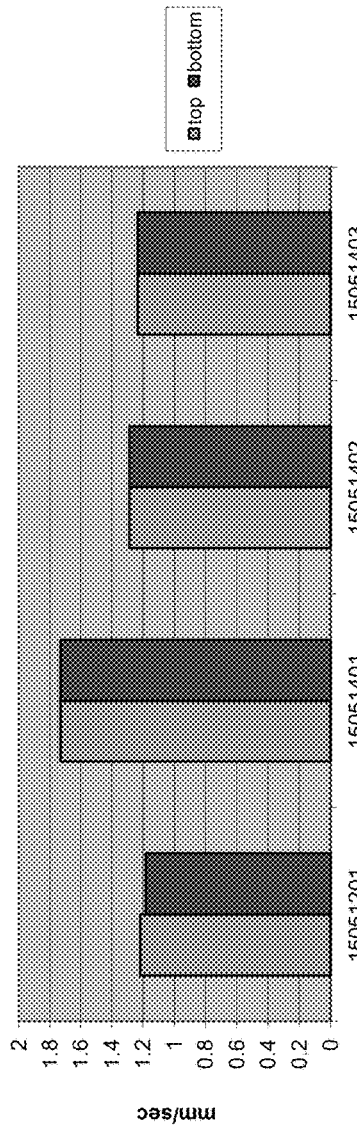
FIG. 59C is a graph illustrating spreading speed with bath coating.
Figure 59D:
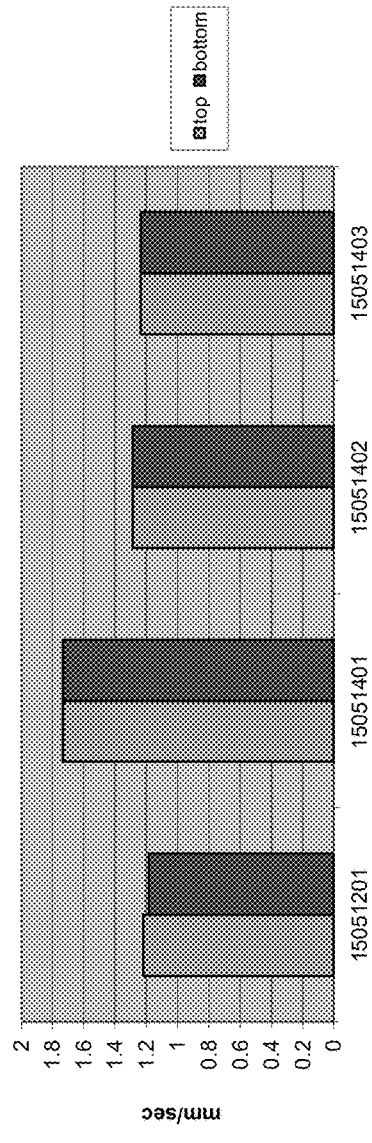
FIG. 59D is a graph illustrating spreading speed with screen coating.
Figure 60C:
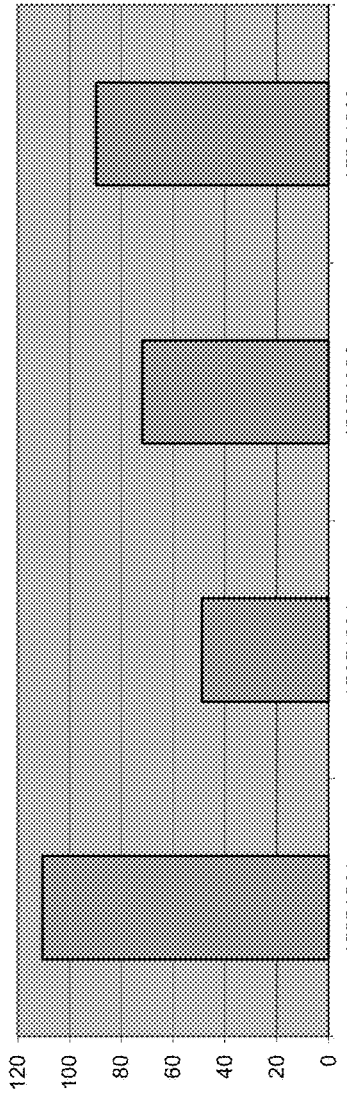
FIG. 60C is a graph illustrating accumulative one way transport index with bath coating.
Figure 60D:
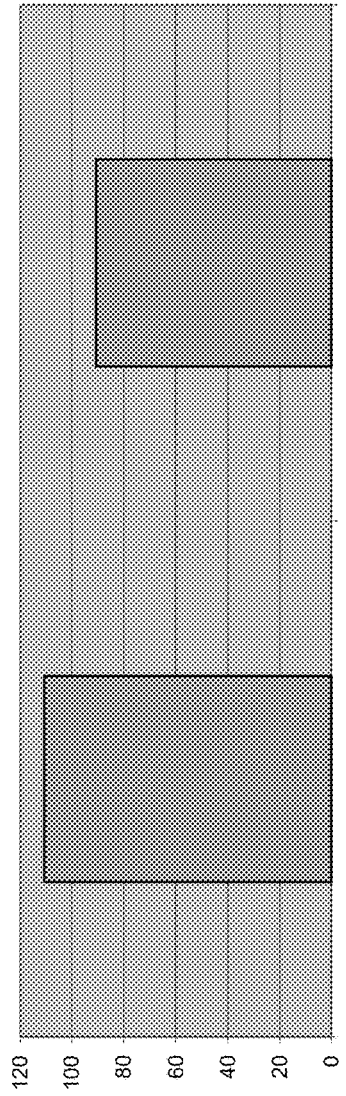
FIG. 60D is a graph illustrating accumulative one way transport index with screen coating.
Figure 61A:
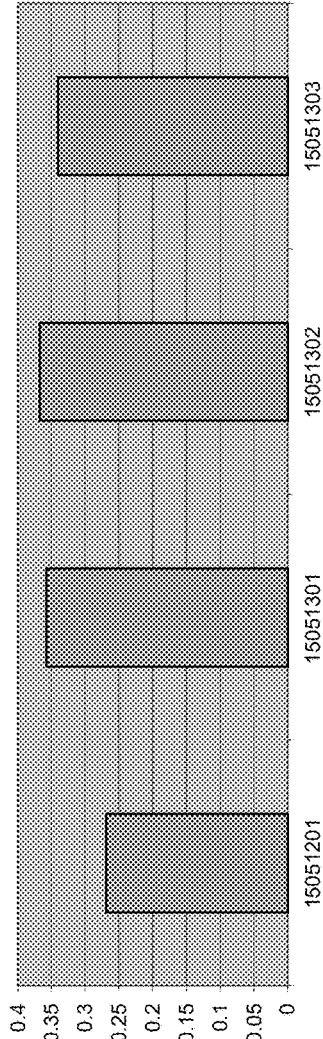
FIG. 61A is a graph illustrating overall moisture management capability with spray coating.
Figure 61B:
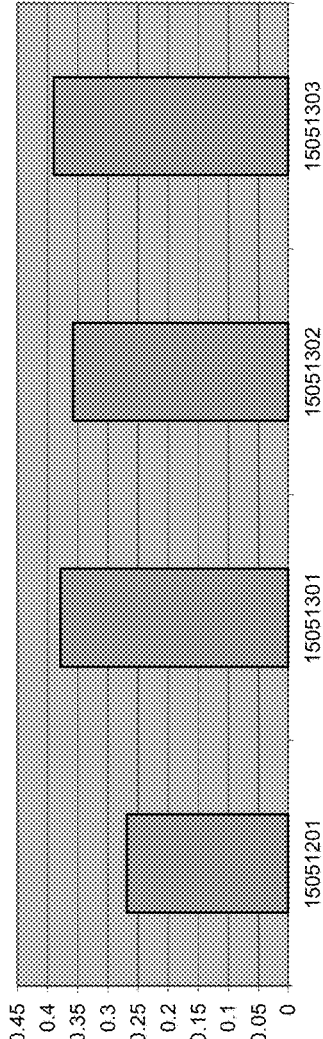
FIG. 61B is a graph illustrating overall moisture management capability with stencil coating.
Figure 61C:
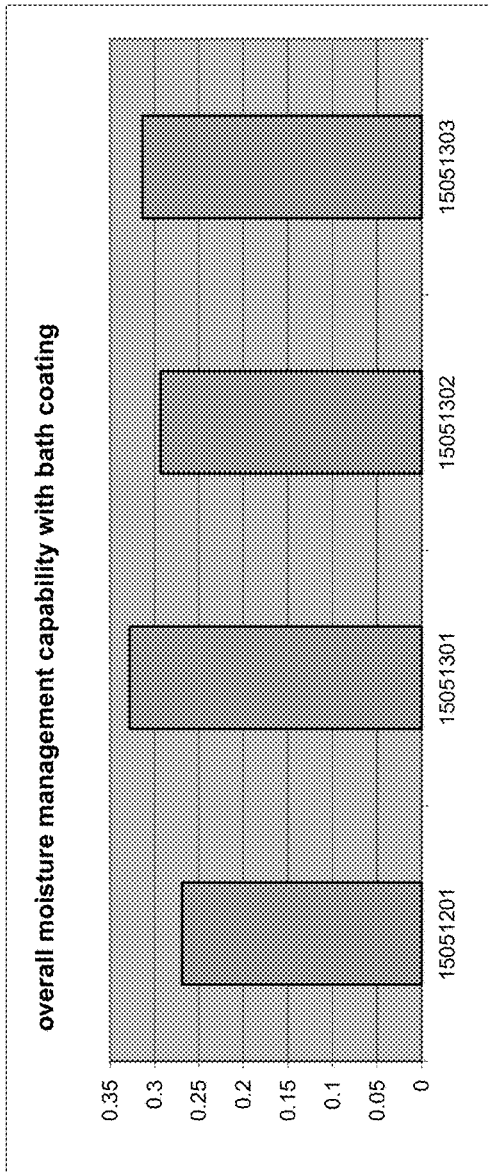
FIG. 61C is a graph illustrating overall moisture management capability with bath coating.
Figure 61D:
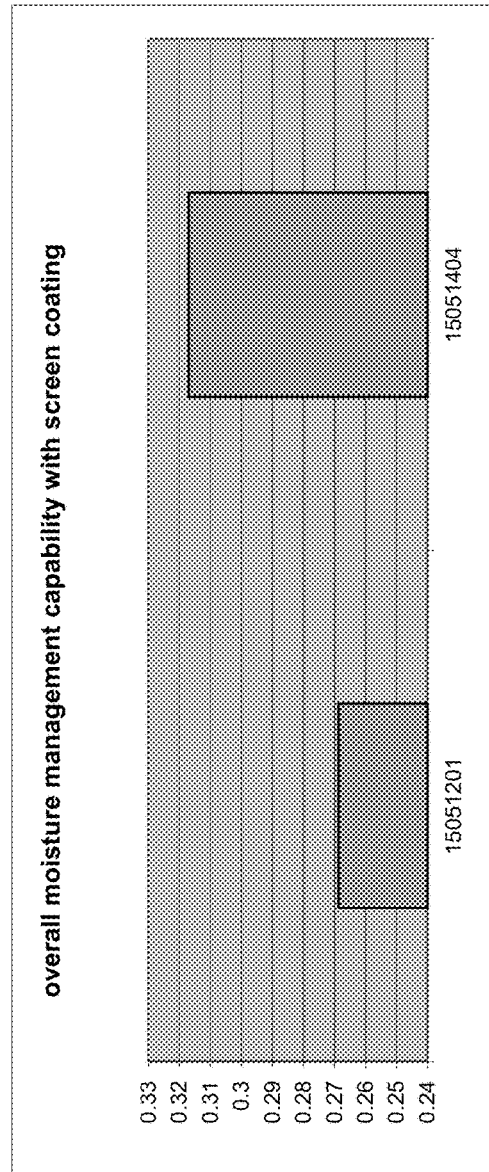
FIG. 61D is a graph illustrating overall moisture management capability with screen coating.
Figure 62A:
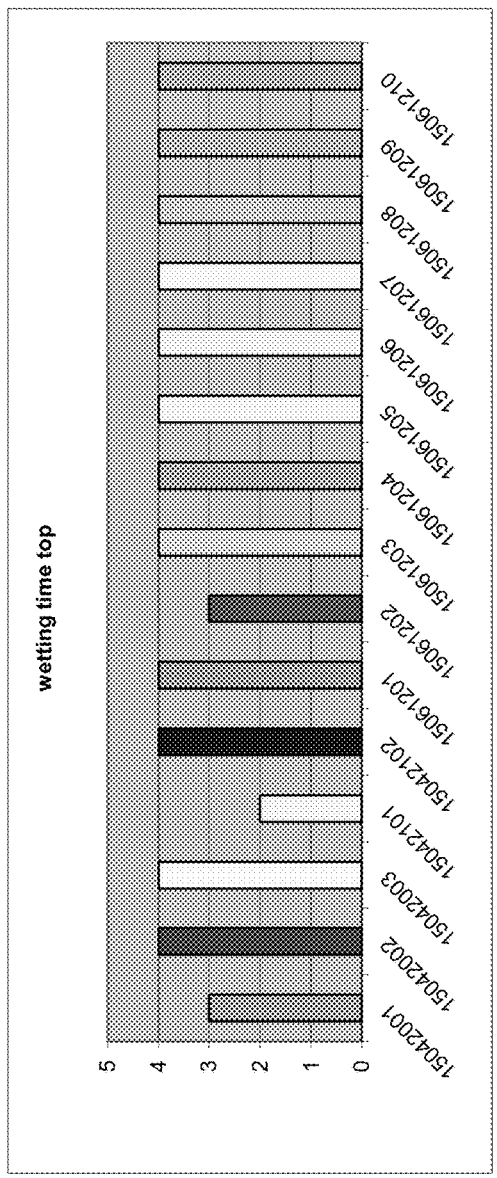
FIG. 62A is a graph illustrating wetting time top.
Figure 62B:
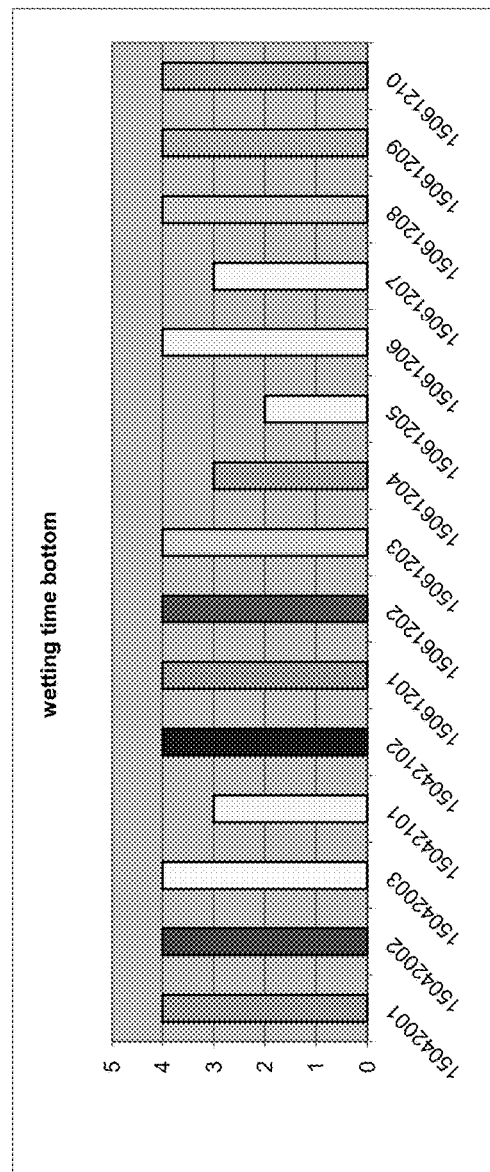
FIG. 62B is a graph illustrating wetting time bottom.
Figure 64A:
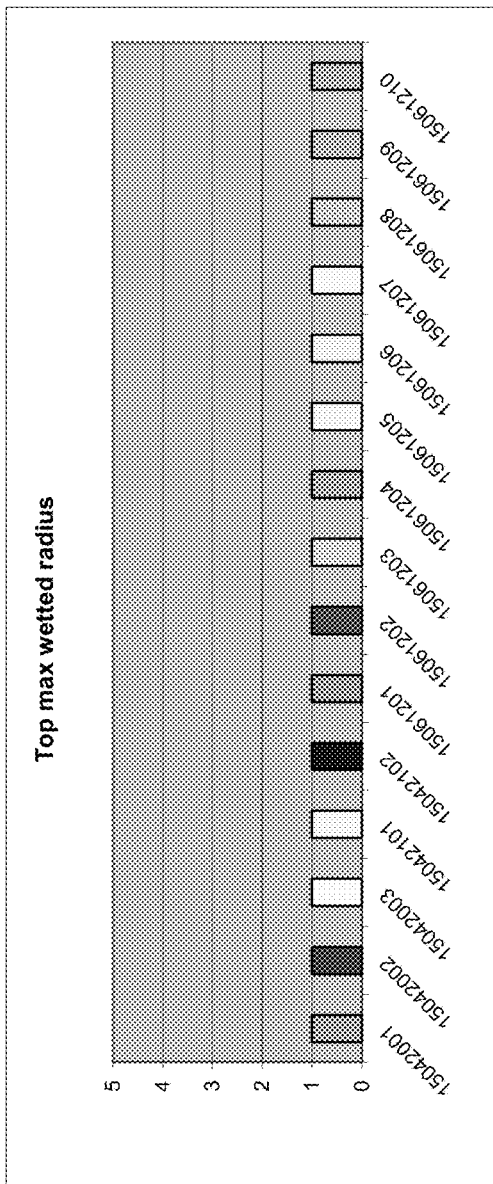
FIG. 64A is a graph illustrating top max wetted radius.
Figure 64B:
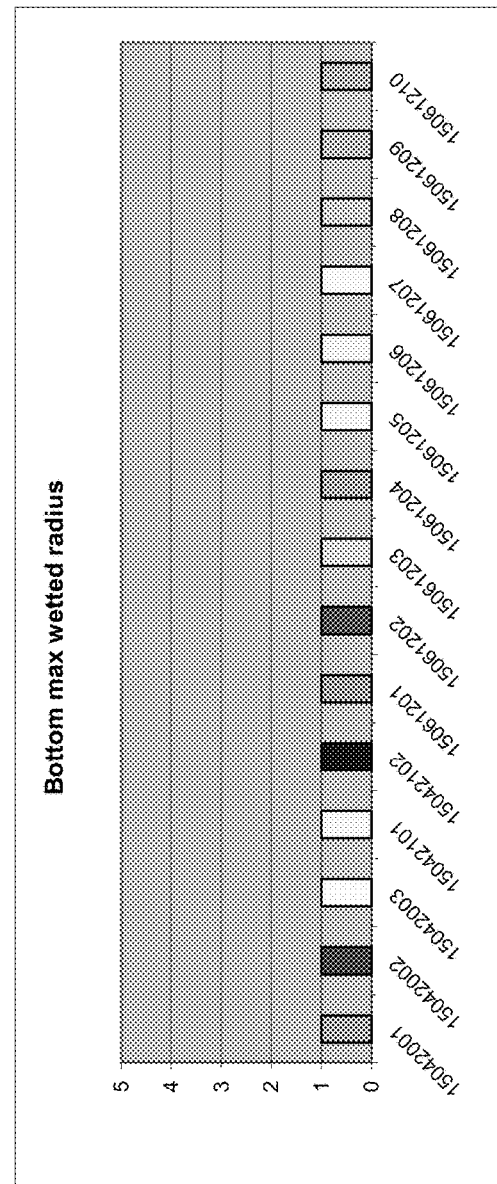
FIG. 64B is a graph illustrating bottom max wetted radius.
Figure 65A:
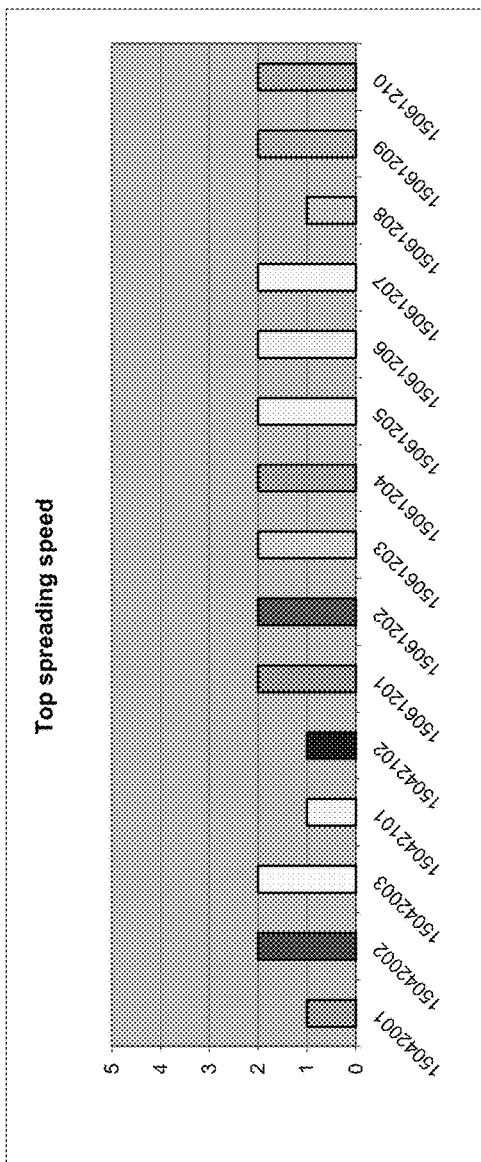
FIG. 65A is a graph illustrating top spreading speed.
Figure 65B:
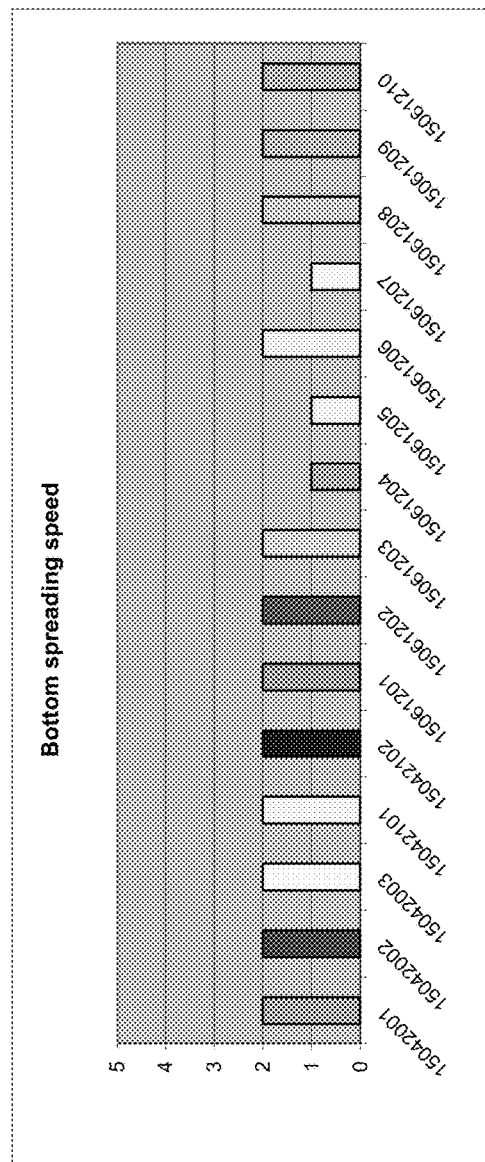
FIG. 65B is a graph illustrating bottom spreading speed.
Figure 66A:
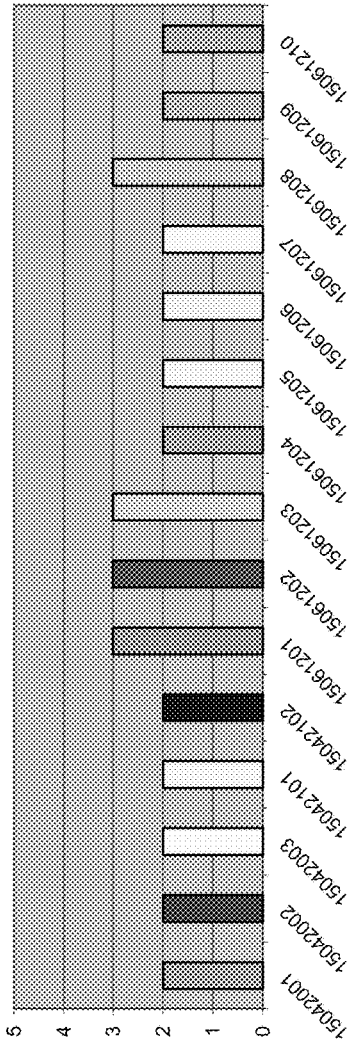
FIG. 66A is a graph illustrating accumulative one-way transport index.
Figure 66B:
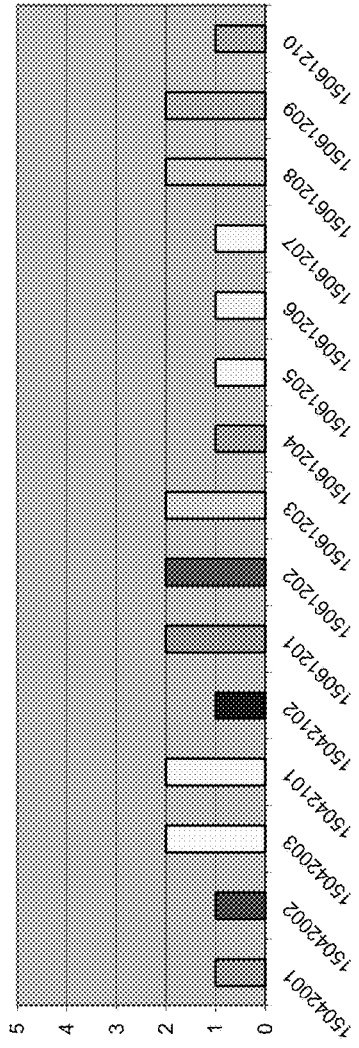
FIG. 66B is a graph illustrating overall moisture management capability.
Figure 67A:
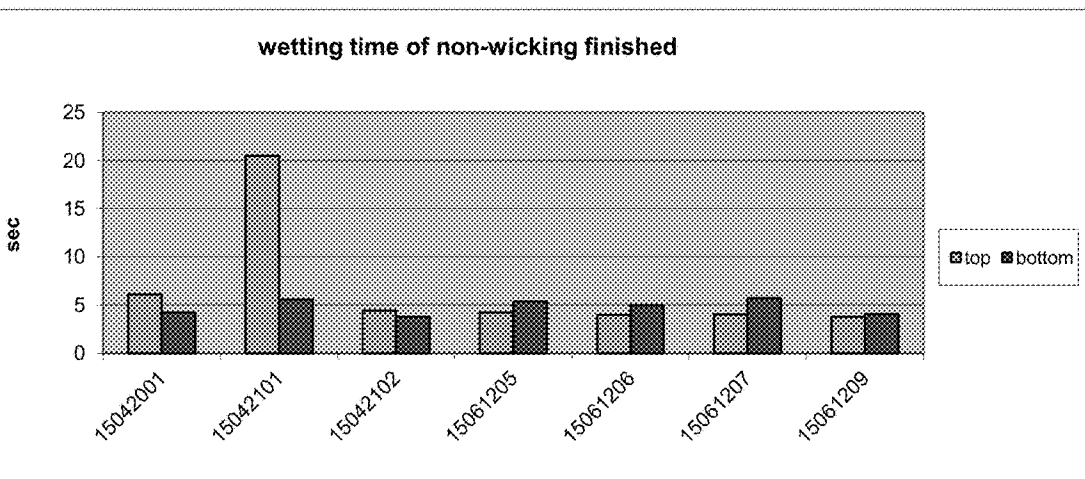
FIG. 67A is a graph illustrating wetting time of non-wicking finished.
Figure 67B:
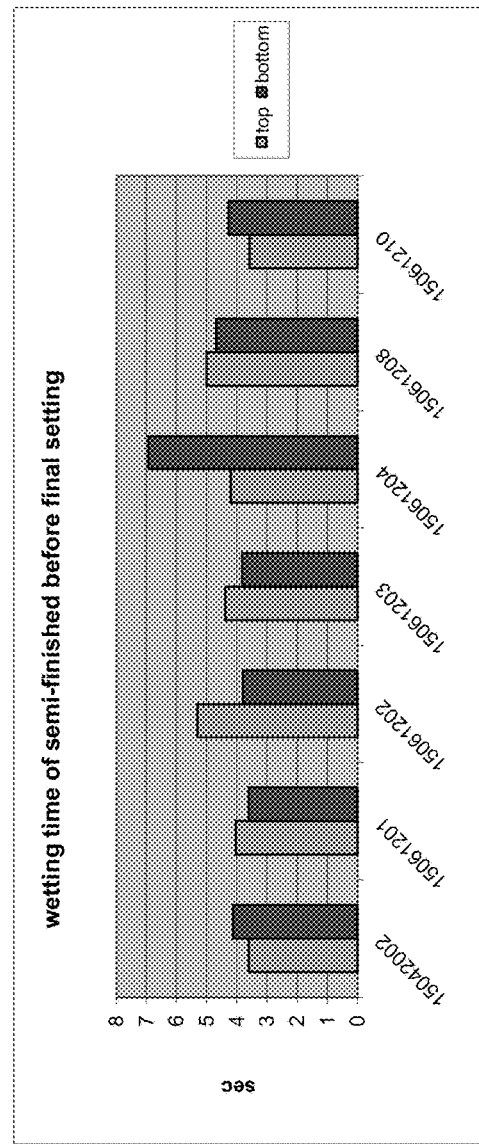
FIG. 67B is a graph illustrating wetting time of semi-finished before final setting.
Figure 68A:
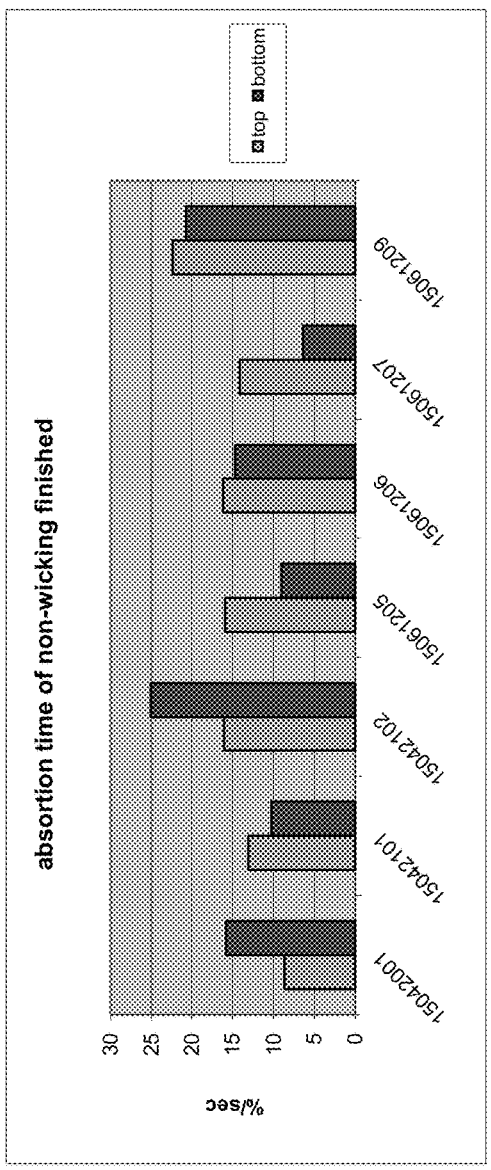
FIG. 68A is a graph illustrating absorption time of non-wicking finished.
Figure 68B:
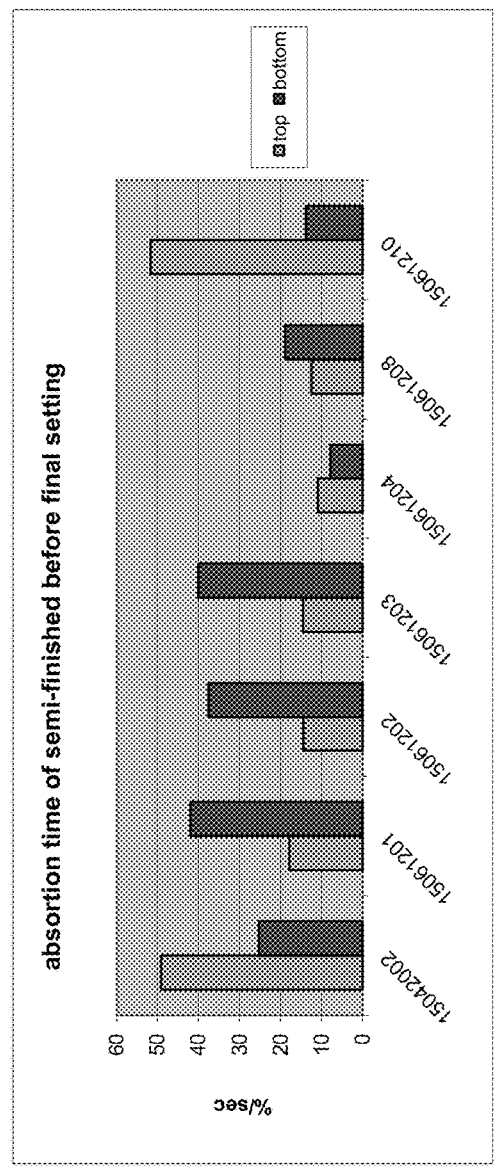
FIG. 68B is a graph illustrating absorption time of semi-finished before final setting.
Figure 69A:
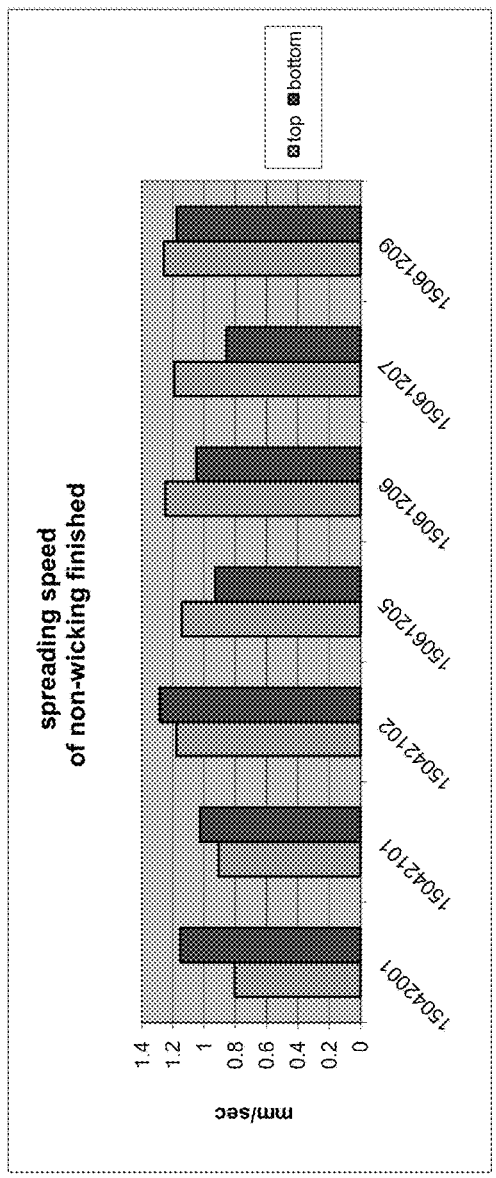
FIG. 69A is a graph illustrating spreading speed of non-wicking finished.
Figure 69B:
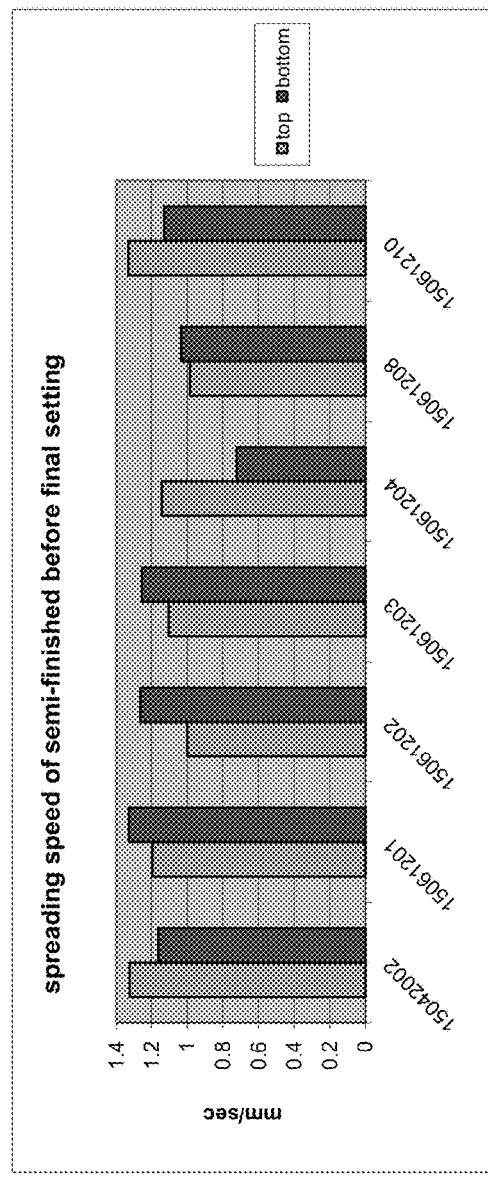
FIG. 69B is a graph illustrating spreading speed of semi-finished before final setting.
Figure 70A:
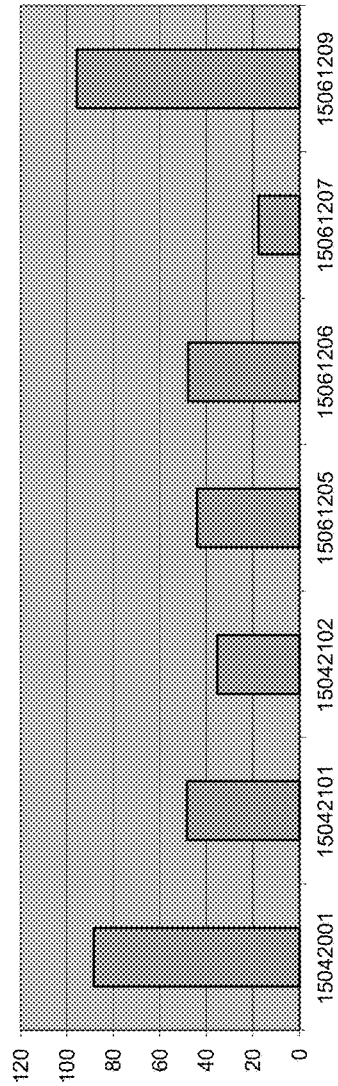
FIG. 70A is a graph illustrating accumulative one way transport index of non-wicking finished.
Figure 70B:
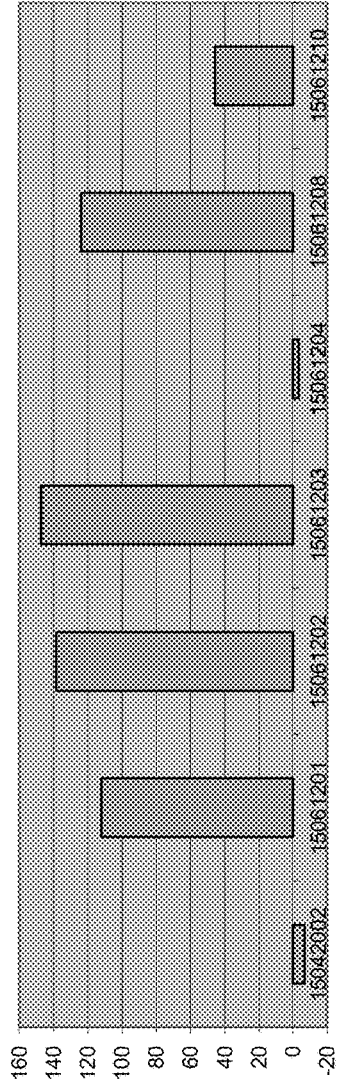
FIG. 70B is a graph illustrating accumulative one way transport index of semi-finished before final setting.
Figure 71A:
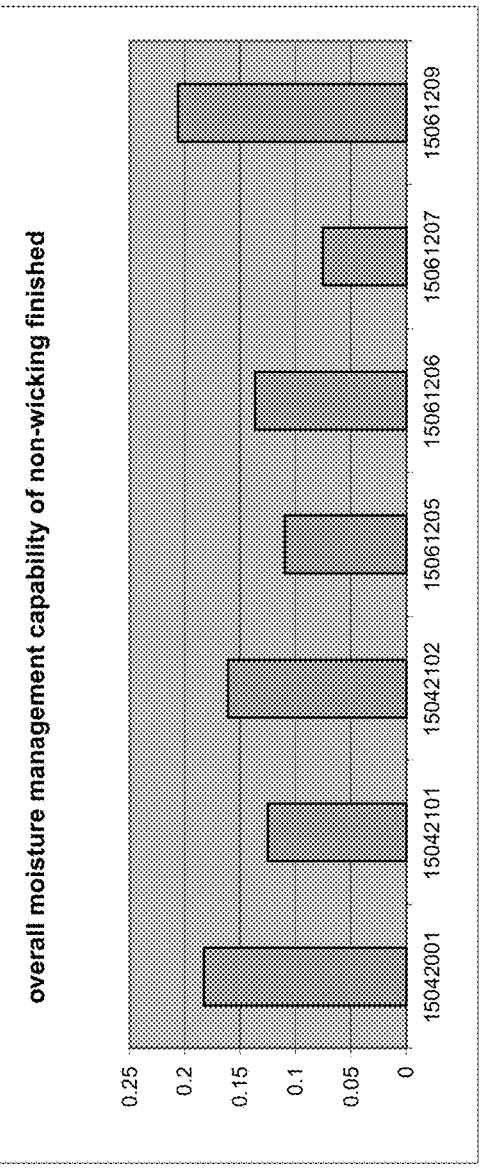
FIG. 71A is a graph illustrating overall moisture management capability of non-wicking finished.
Figure 71B:
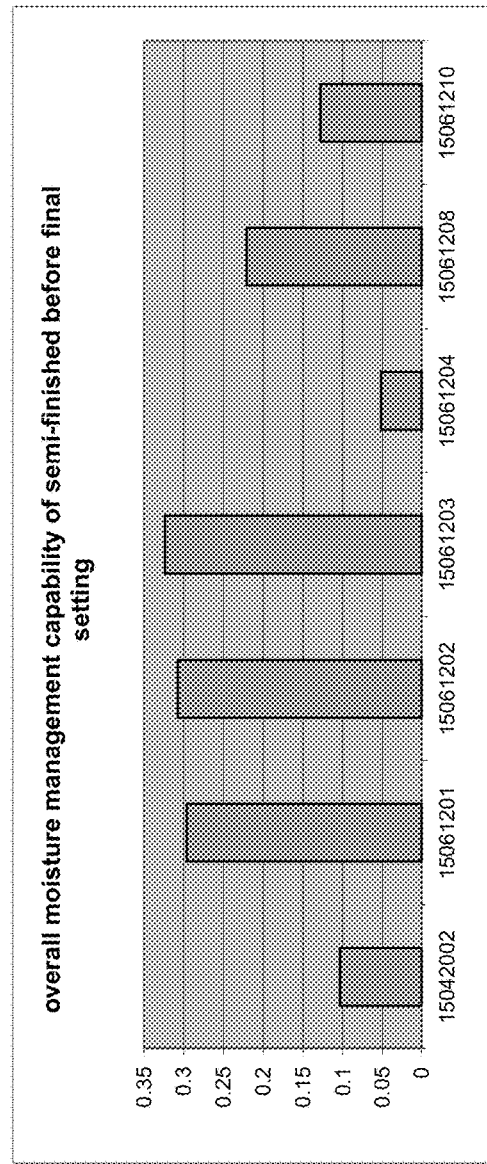
FIG. 71B is a graph illustrating overall moisture management capability of semi-finished before final setting.
Figure 72A:
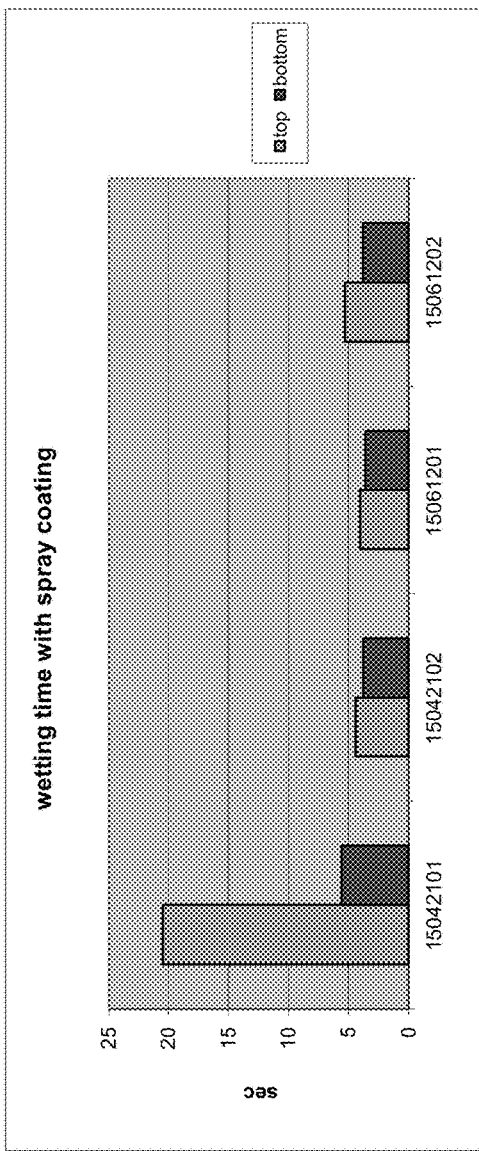
FIG. 72A is a graph illustrating wetting time with spray coating.
Figure 72B:
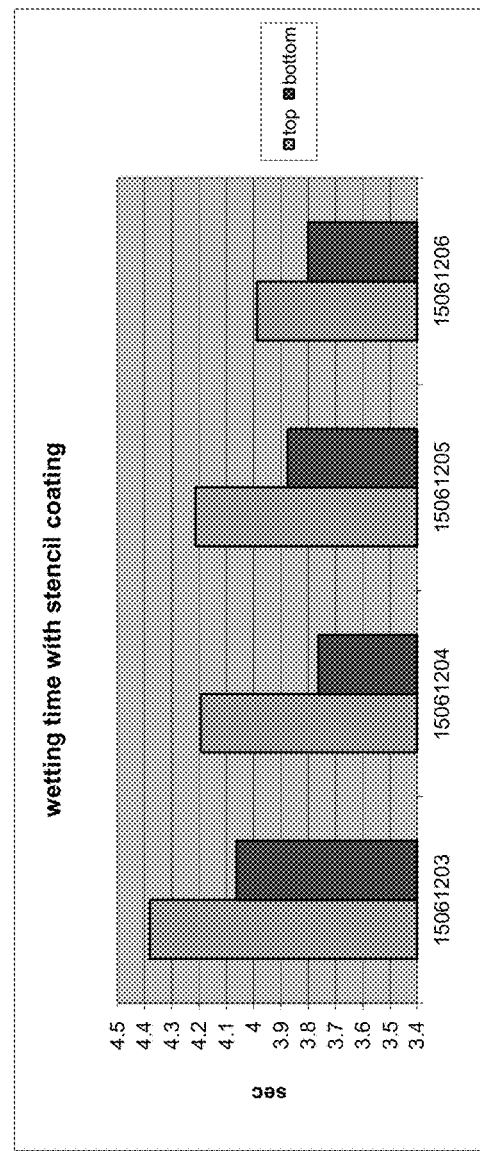
FIG. 72B is a graph illustrating wetting time with stencil coating.
Figure 72C:
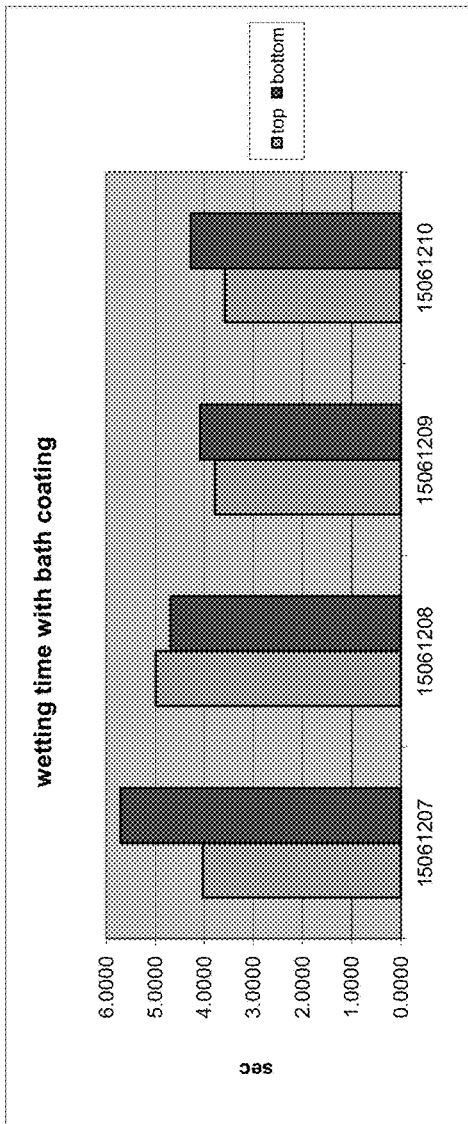
FIG. 72C is a graph illustrating wetting time with bath coating.
Figure 73A:
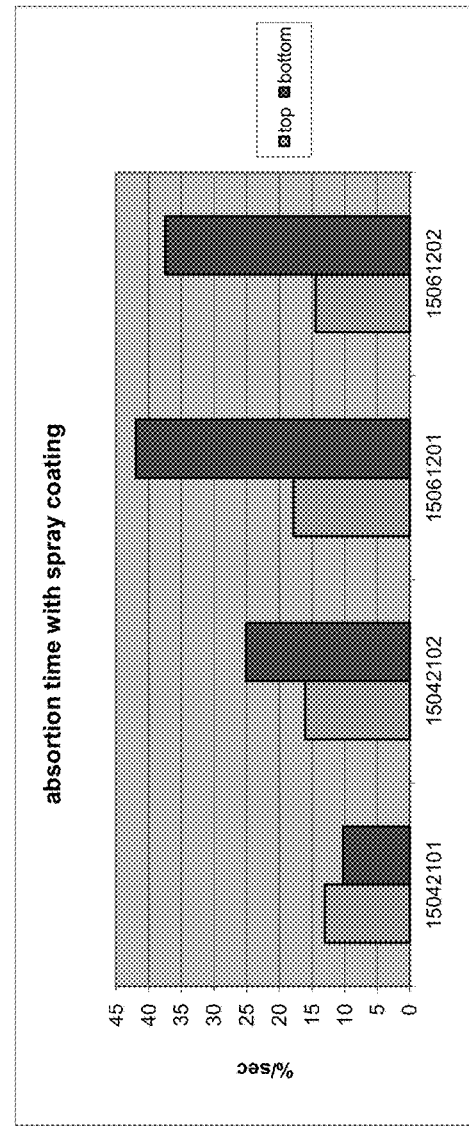
FIG. 73A is a graph illustrating absorption time with spray coating.
Figure 73B:
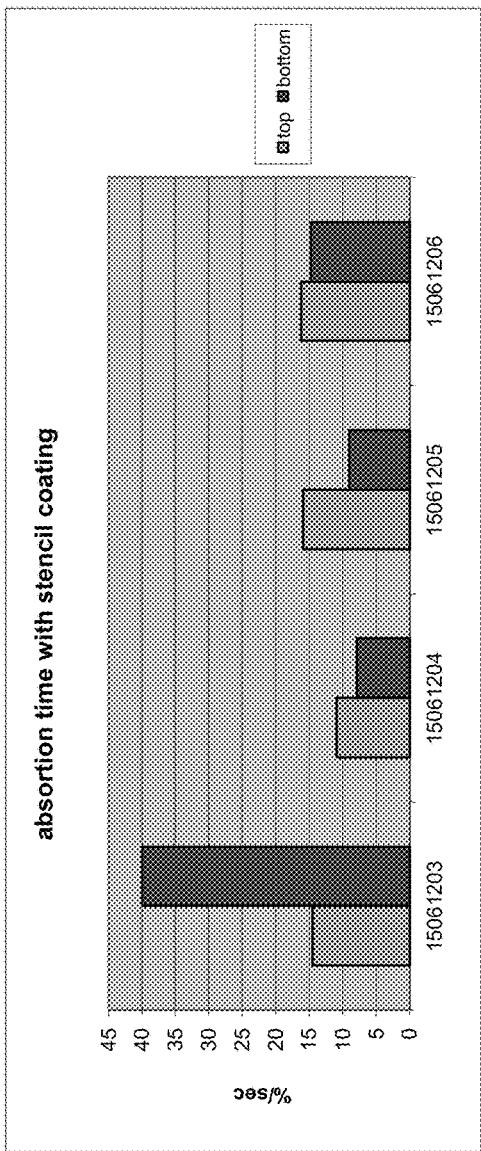
FIG. 73B is a graph illustrating absorption time with stencil coating.
Figure 73C:
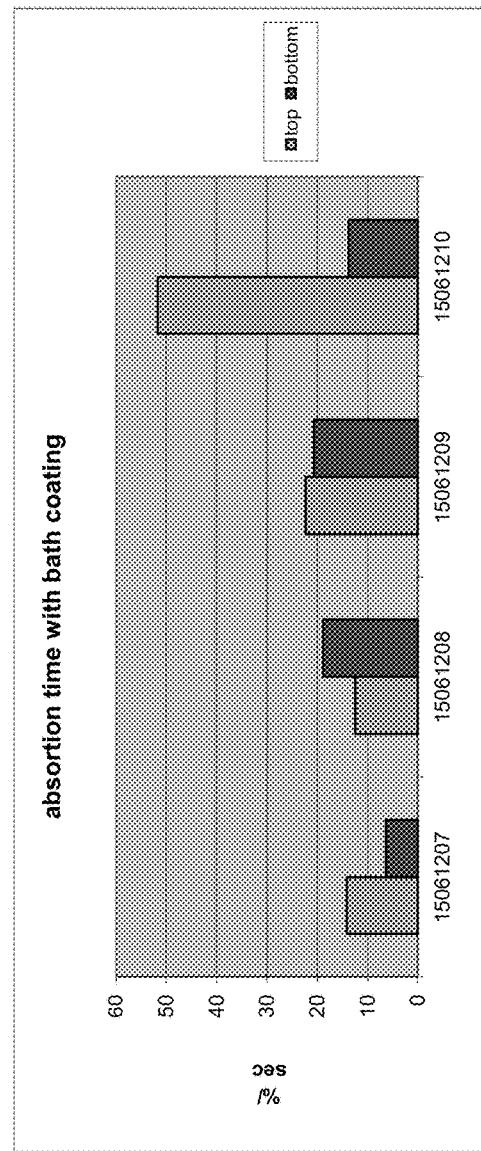
FIG. 73C is a graph illustrating absorption time with bath coating.
Figure 74A:
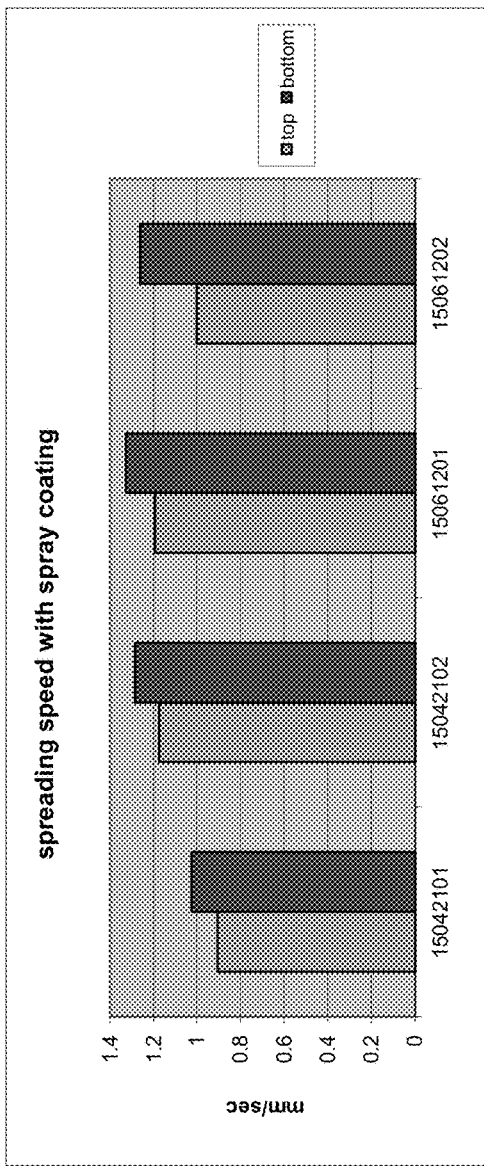
FIG. 74A is a graph illustrating spreading speed with spray coating.
Figure 74B:
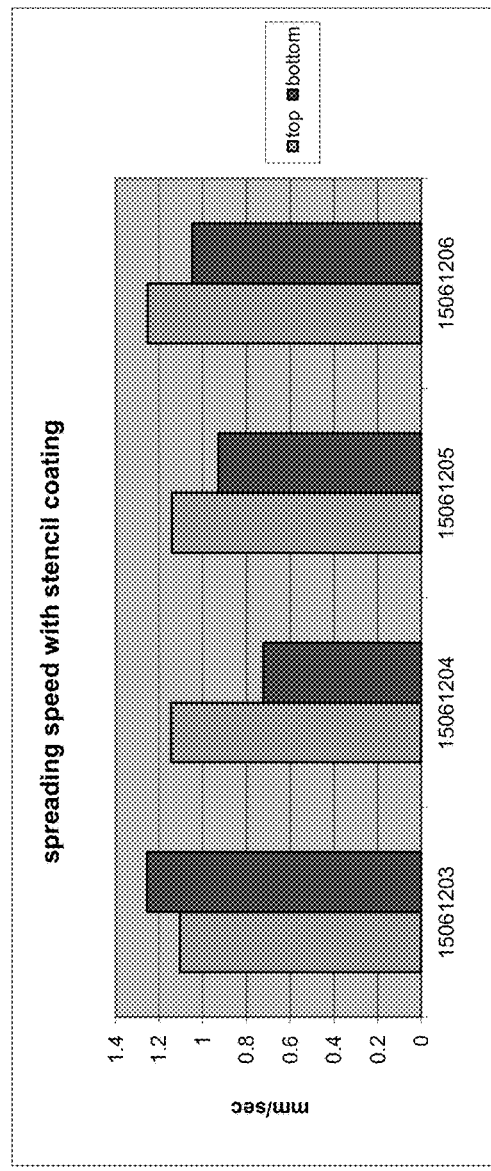
FIG. 74B is a graph illustrating spreading speed with stencil coating.
Figure 74C:
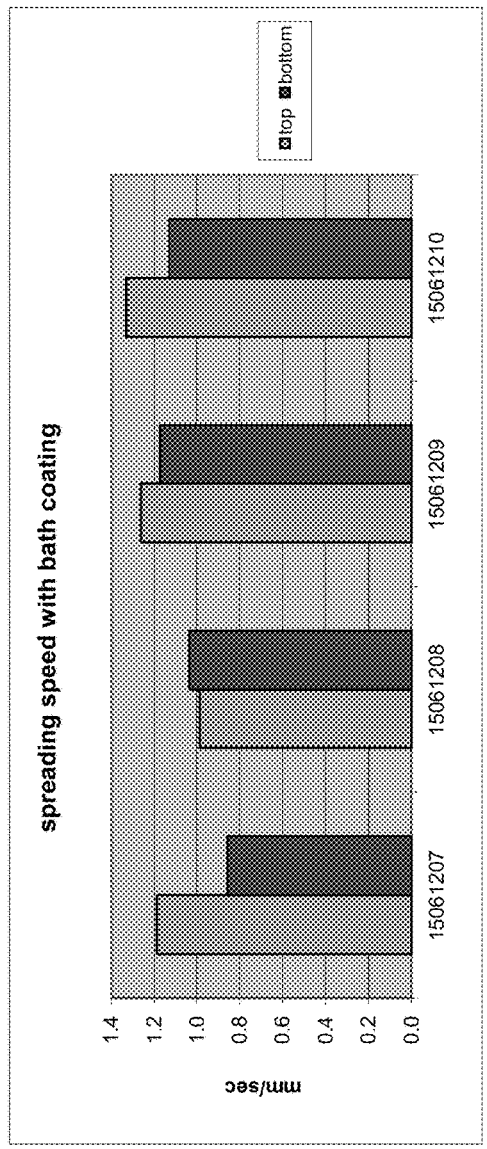
FIG. 74C is a graph illustrating spreading speed with bath coating.
Figure 75A:
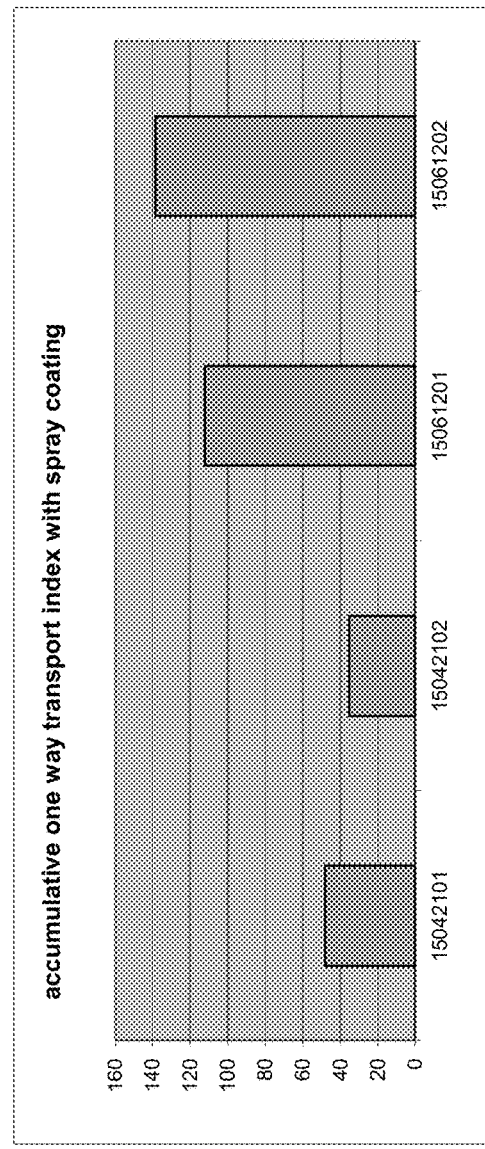
FIG. 75A is a graph illustrating accumulative one way transport index with spray coating.
Figure 75B:
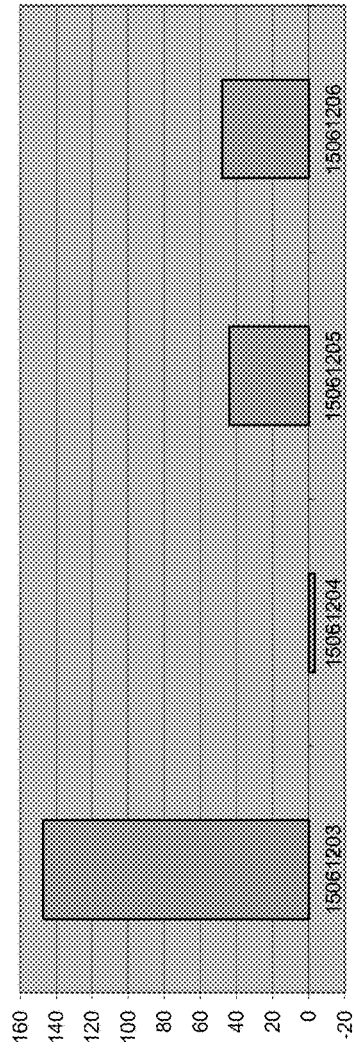
FIG. 75B is a graph illustrating accumulative one way transport index with stencil coating.
Figure 75C:
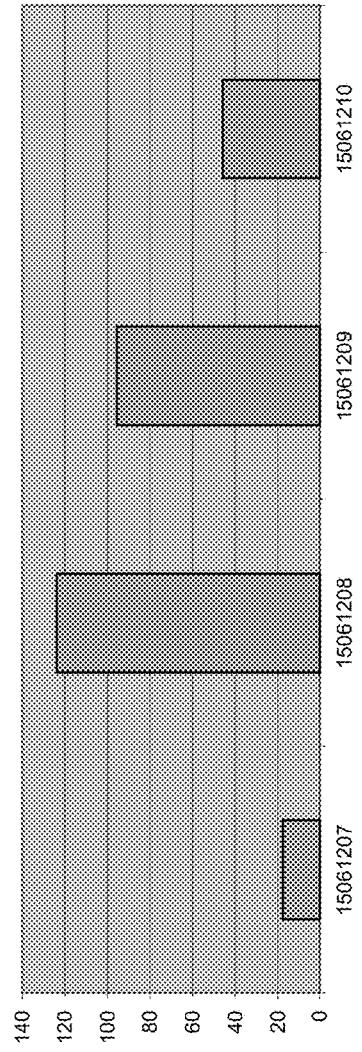
FIG. 75C is a graph illustrating accumulative one way transport index with bath coating.
Figure 76A:
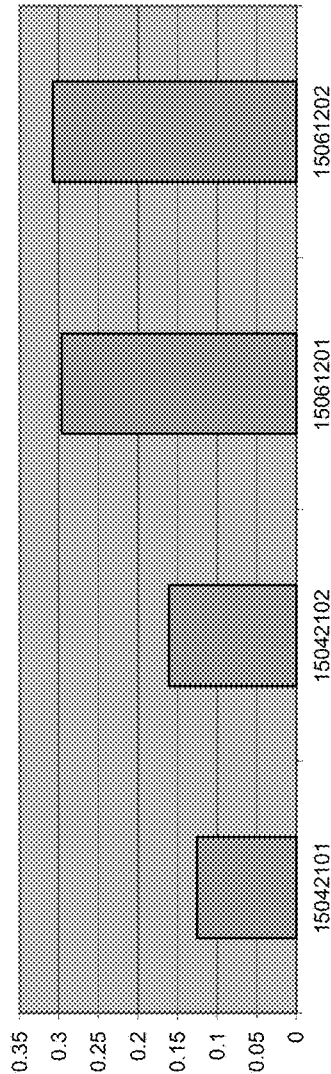
FIG. 76A is a graph illustrating overall moisture management capability with spray coating.
Figure 76B:
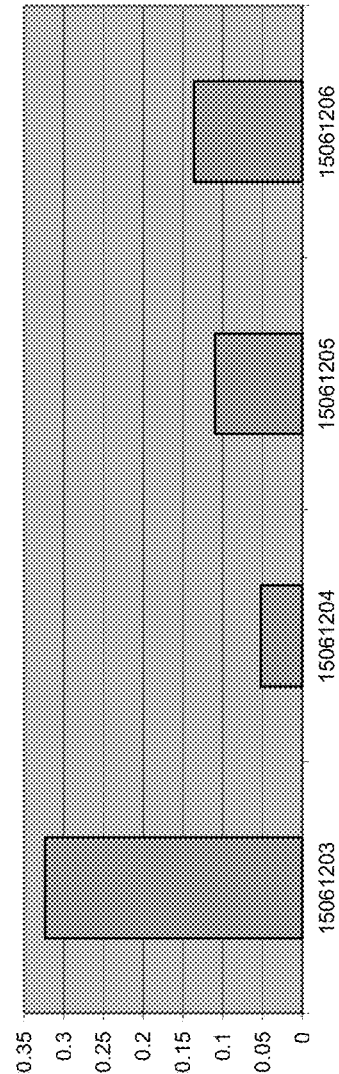
FIG. 76B is a graph illustrating overall moisture management capability with stencil coating.
Figure 76C:
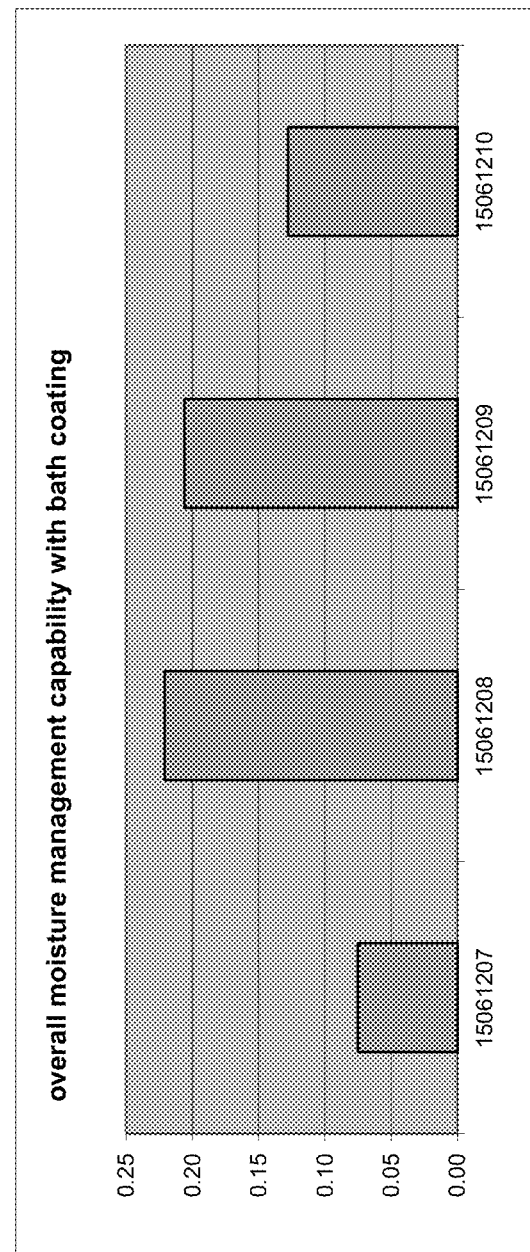
FIG. 76C is a graph illustrating overall moisture management capability with bath coating.
Figure 77A:
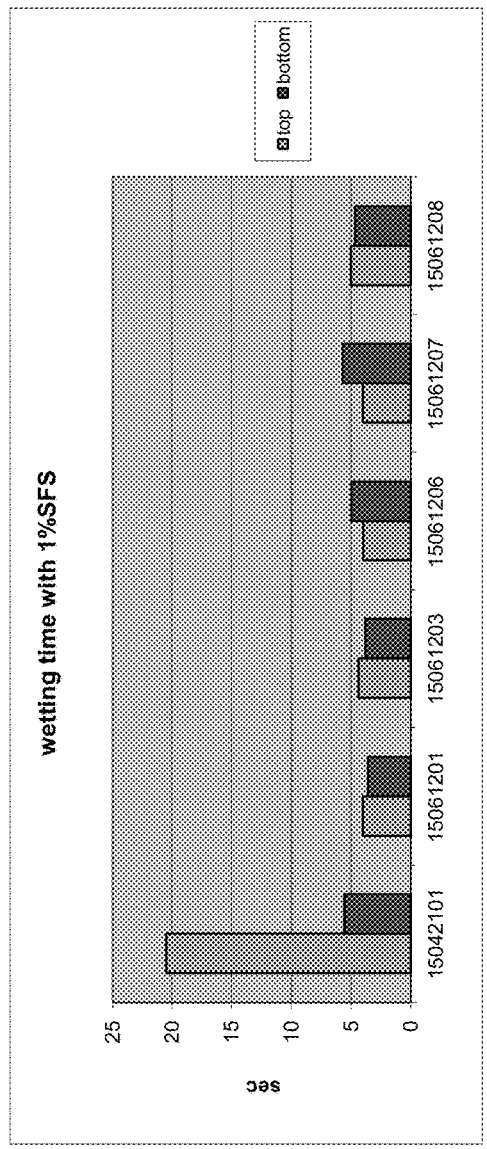
FIG. 77A is a graph illustrating wetting time with 1% SFS.
Figure 77B:
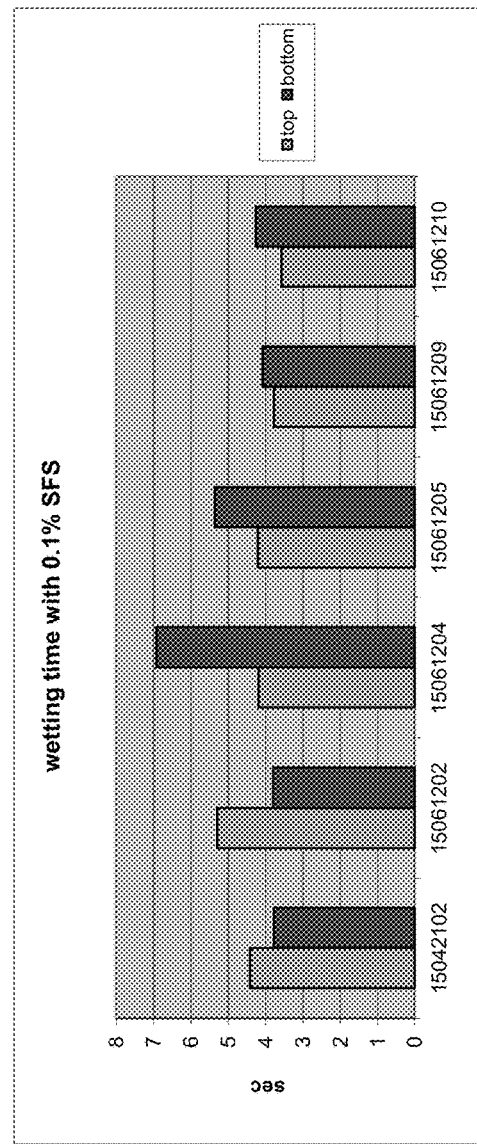
FIG. 77B is a graph illustrating wetting time with 0.1% SFS.
Figure 78A:
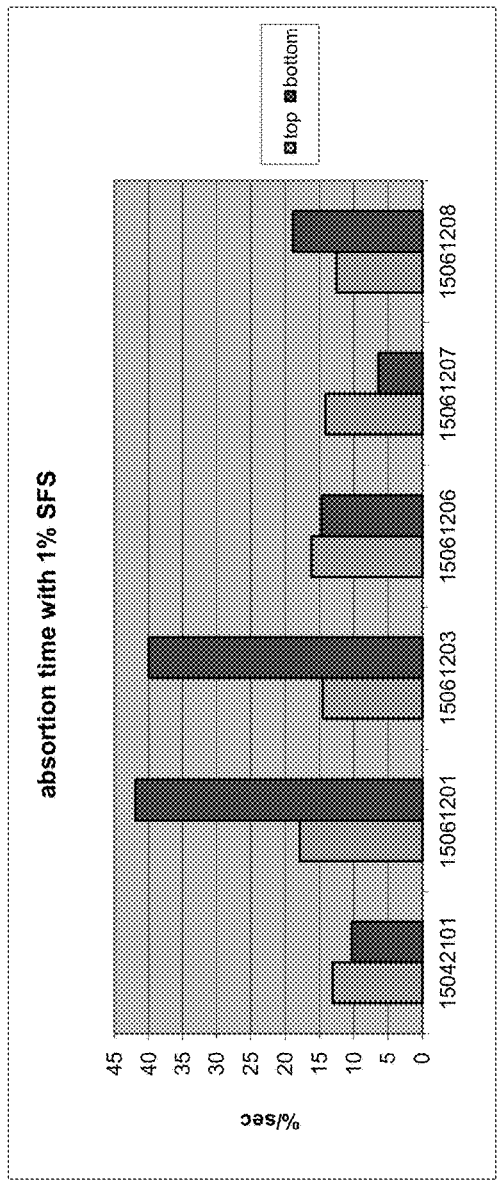
FIG. 78A is a graph illustrating absorption time with 1% SFS.
Figure 78B:
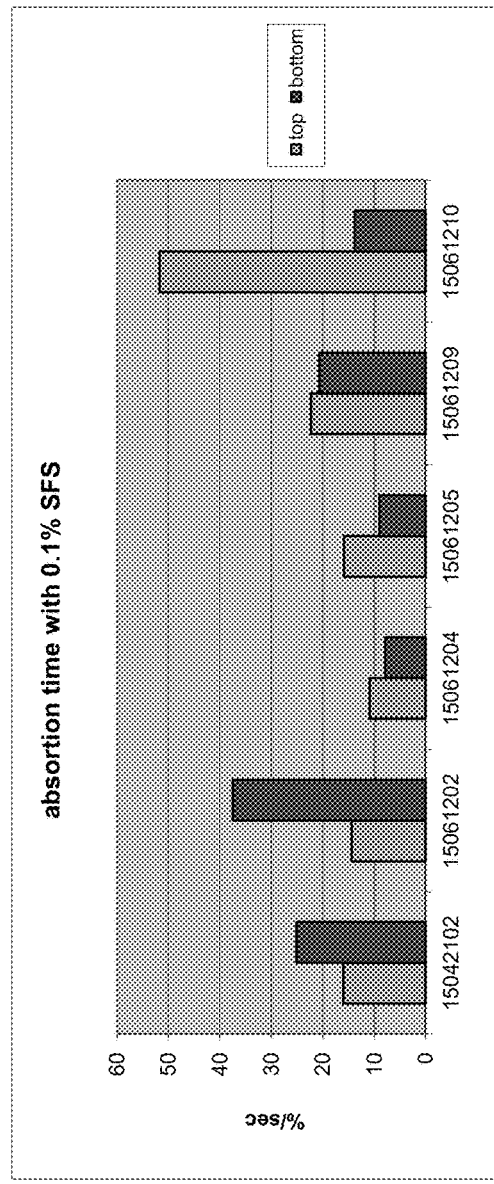
FIG. 78B is a graph illustrating absorption time with 0.1% SFS.
Figure 79A:
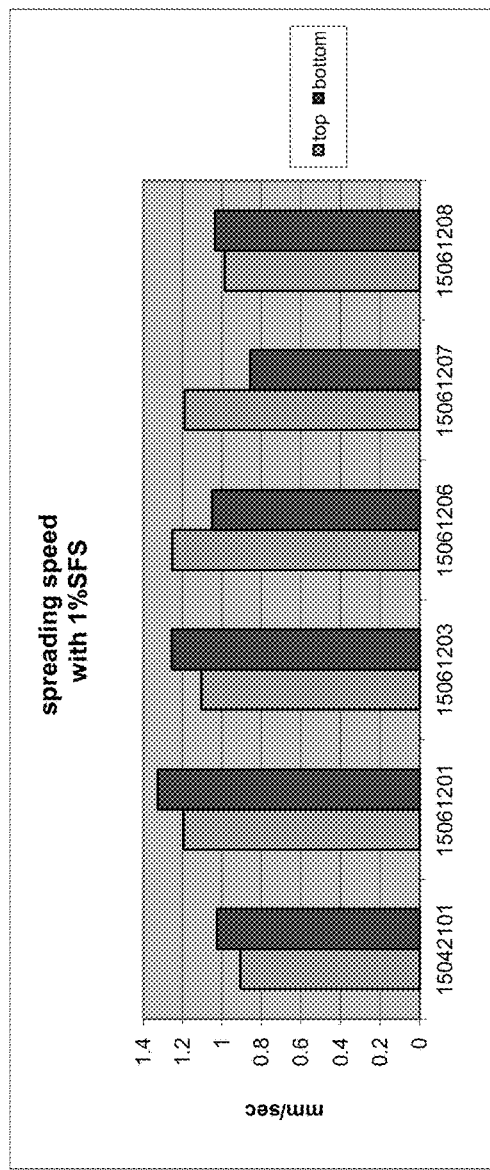
FIG. 79A is a graph illustrating spreading speed with 1% SFS.
Figure 79B:
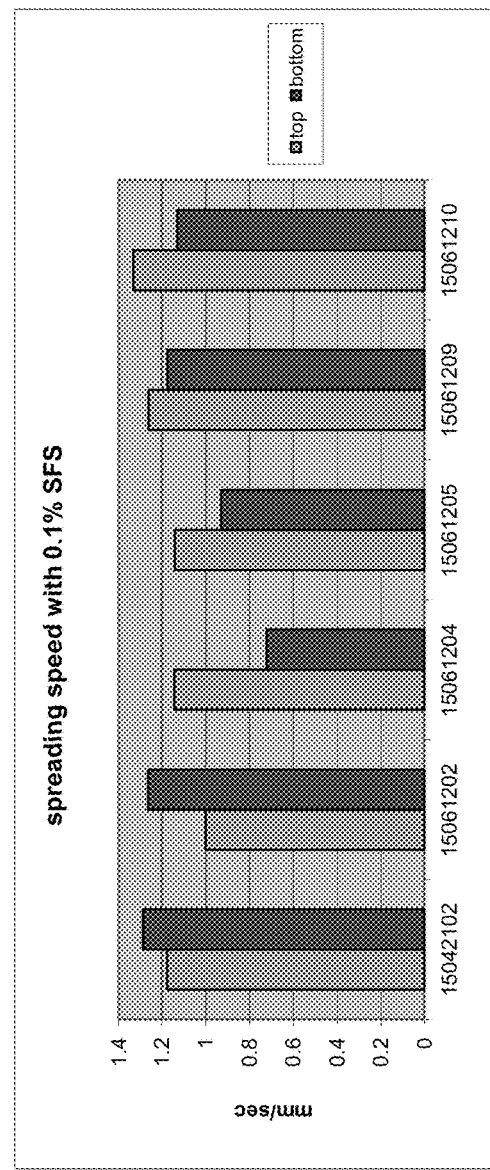
FIG. 79B is a graph illustrating spreading speed with 0.1% SFS.
Figure 80A:
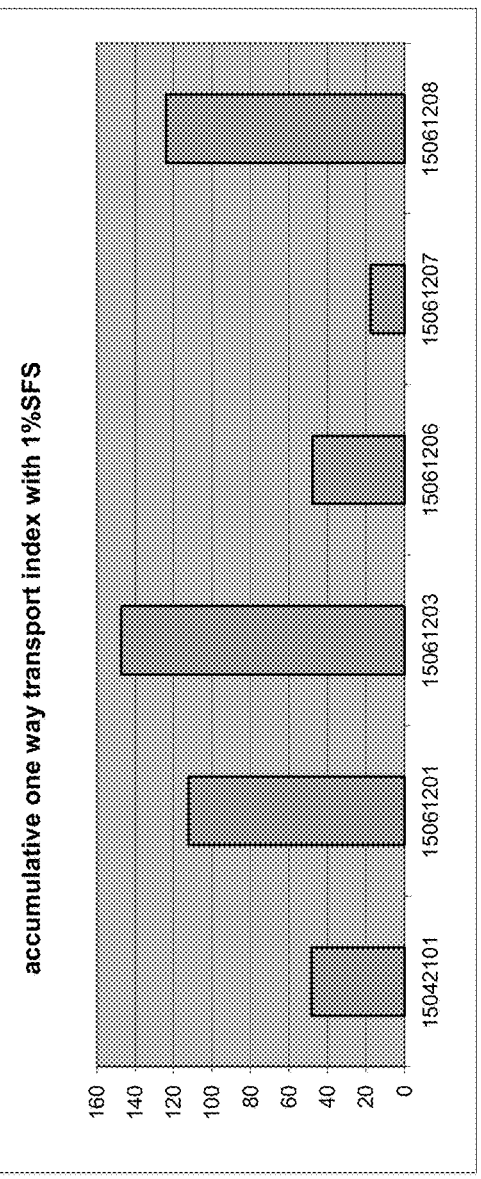
FIG. 80A is a graph illustrating accumulative one way transport index with 1% SFS.
Figure 80B:
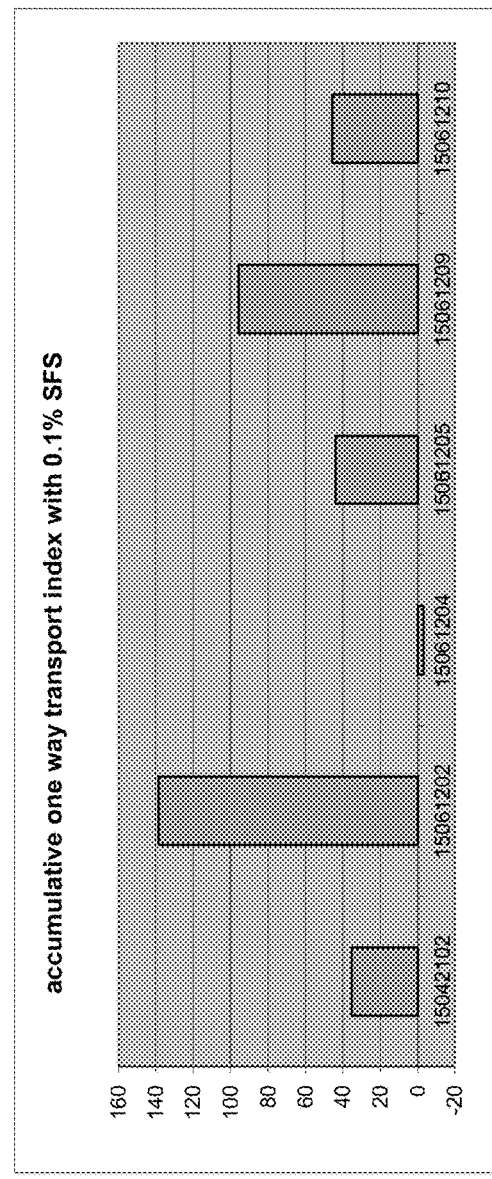
Figure 81A:
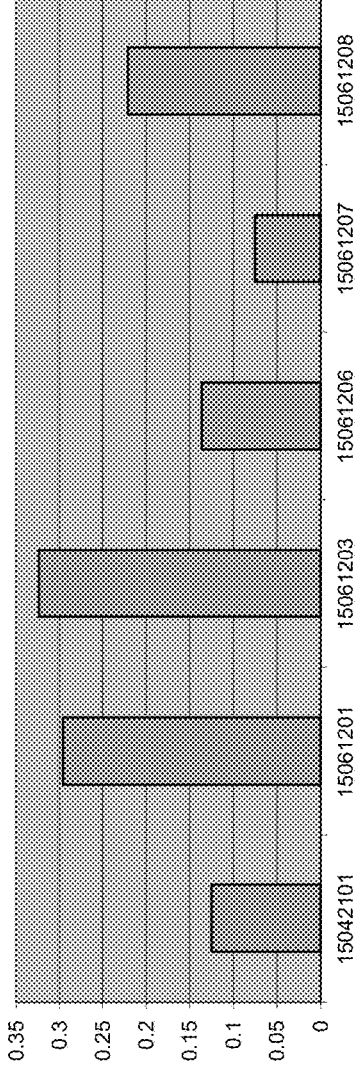
Figure 81B:
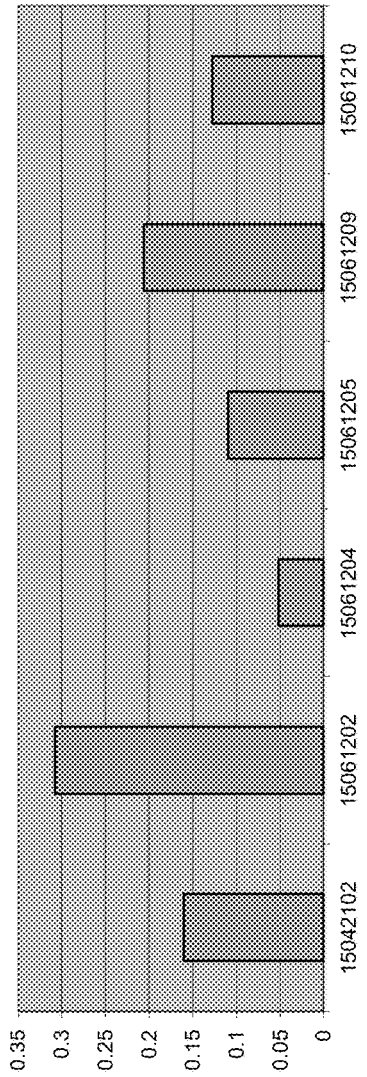
Figure 82A:
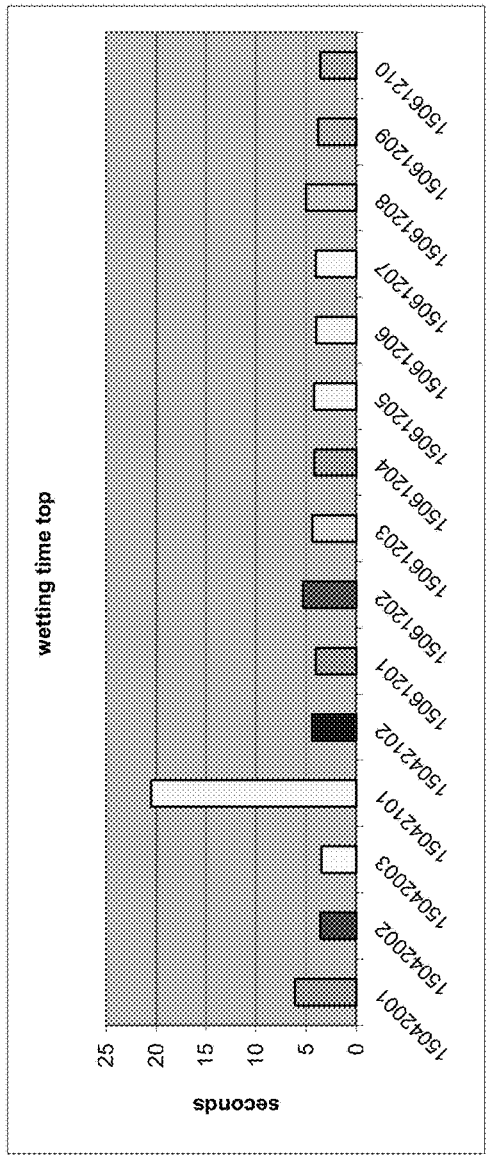
Figure 82B:
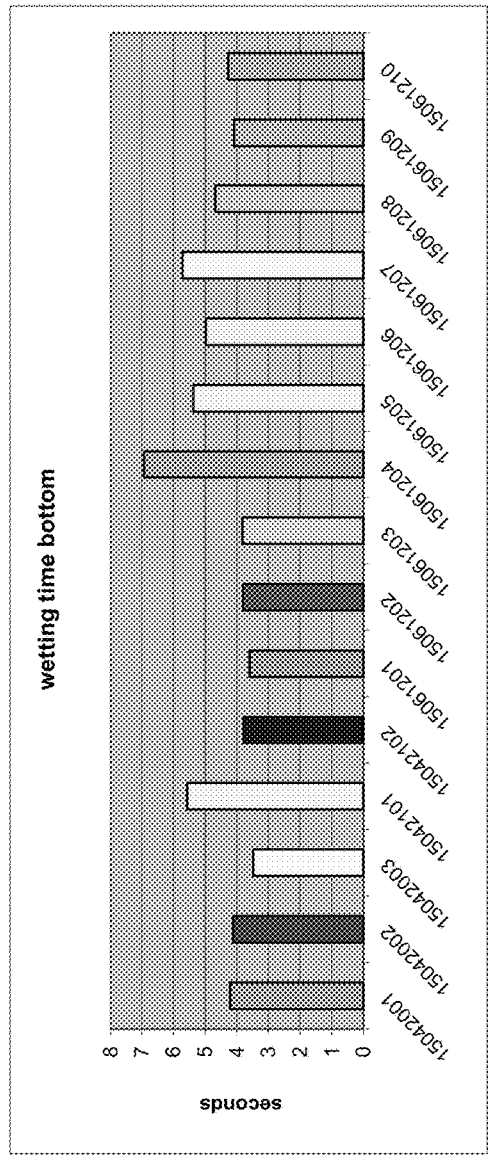
Figure 83A:
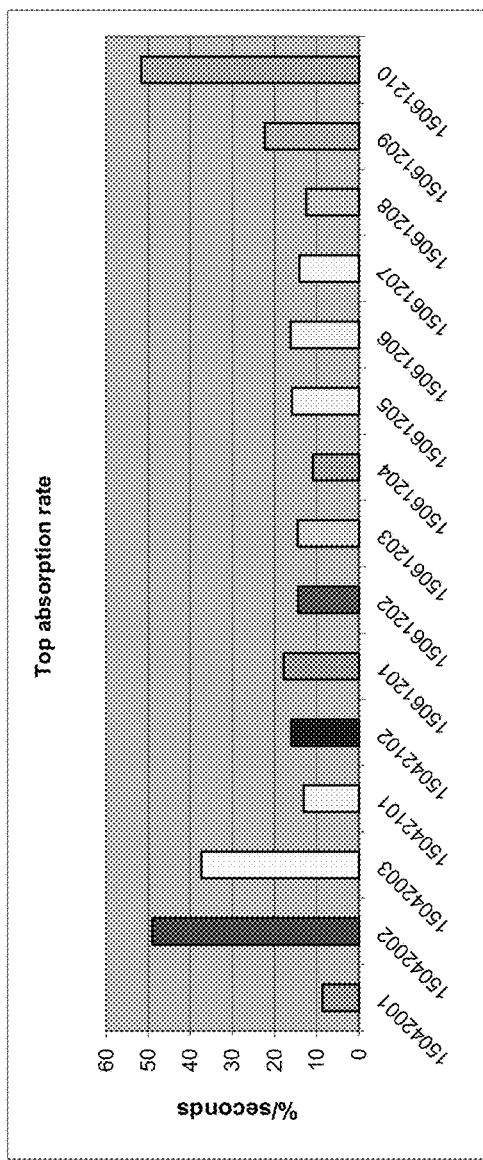
Figure 83B:
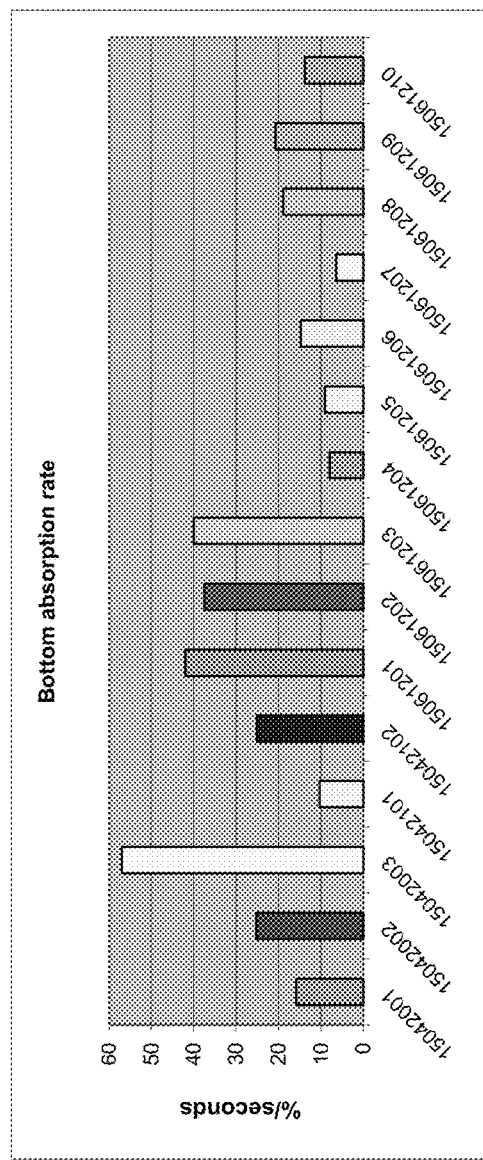
Figure 84A:
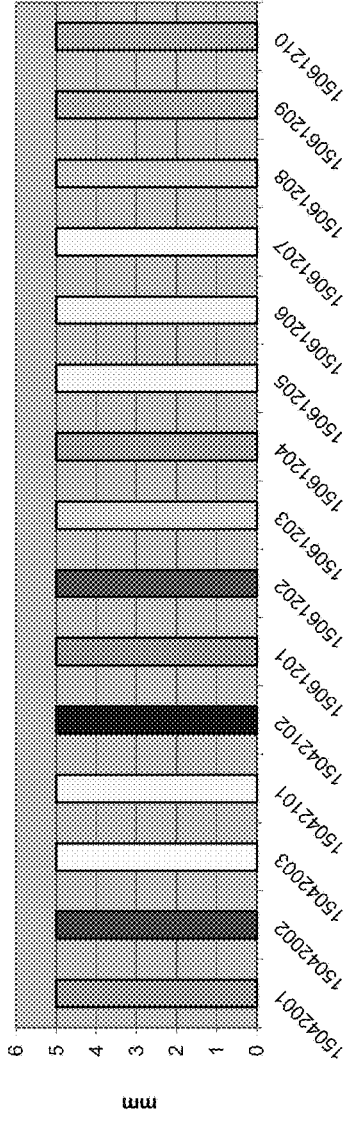
Figure 84B:
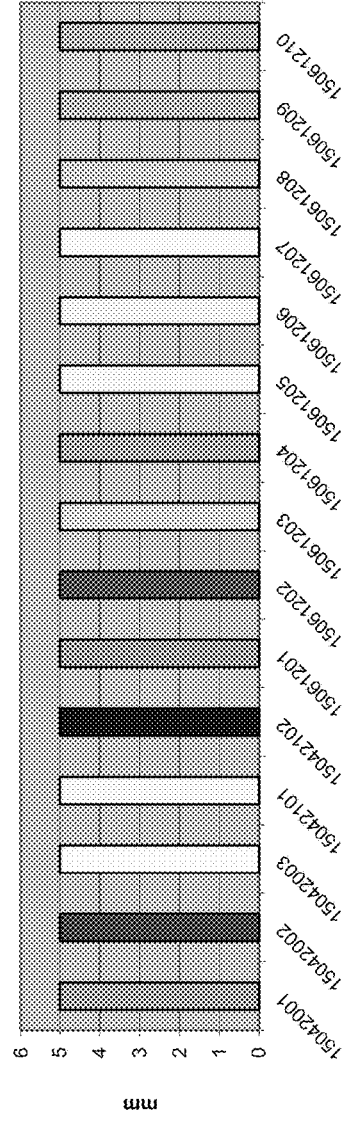
Figure 85A:
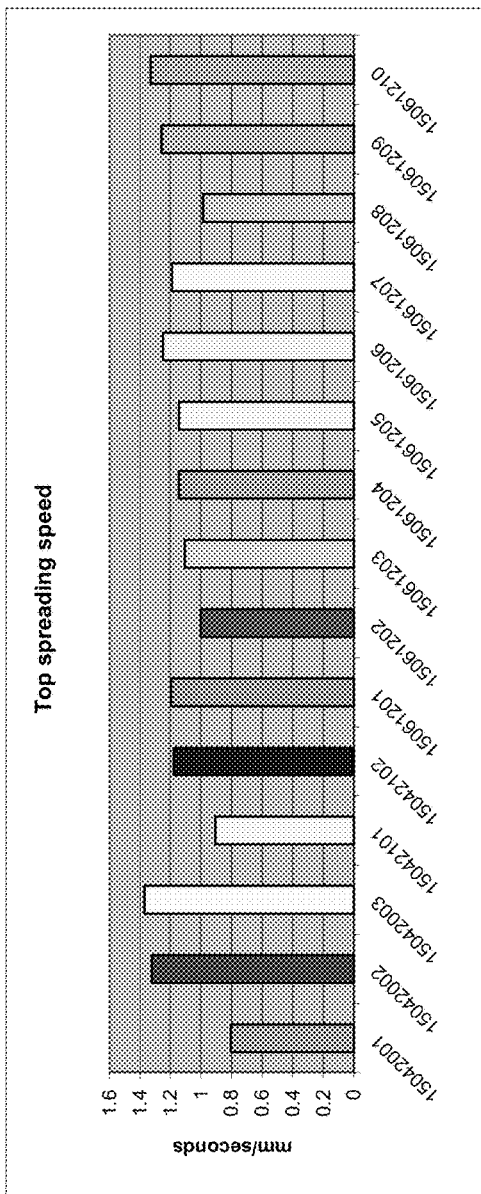
Figure 85B:
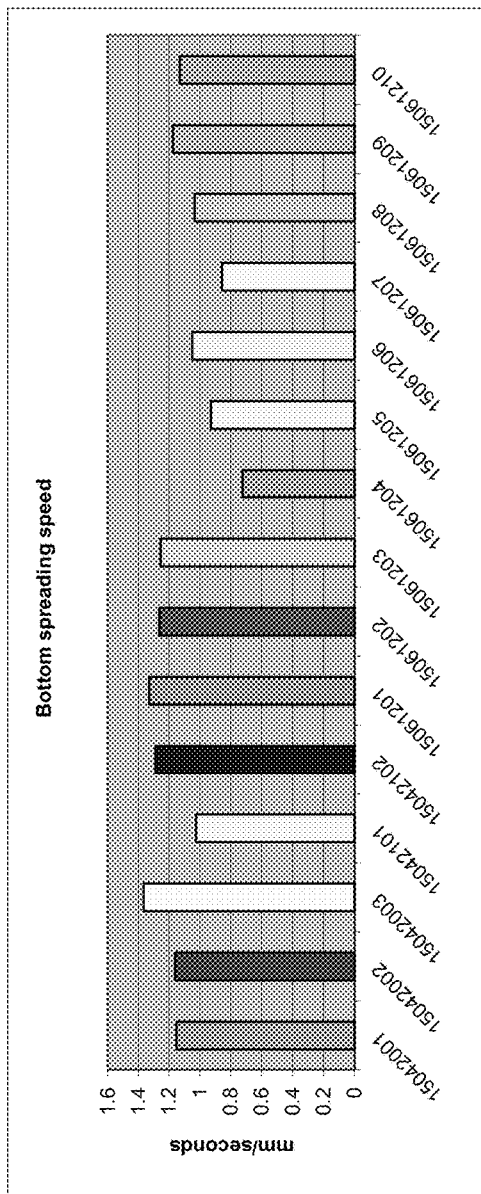

Experiments were carried out to determine the effect of varying the Lithium Bromide (LiBr) temperature when added to silk. FIGS. 48-49 are graphs showing these results, and Tables 10-11 summarize the results. Below is a summary:

No impact on MW or confidence interval (all CI 10500-6500 Da)

Studies illustrated that the temperature of LiBr-silk dissolution, as LiBr is added and begins dissolving, rapidly drops below the original LiBr temperature due to the majority of the mass being silk at room temp

TABLE 10

The effect of Lithium Bromide (LiBr) temperature on molecular weight of silk processed under the conditions of 60 min. Extraction Time., 100° C. Extraction Temperature and 60° C. Oven Dissolution (Oven/Dissolution Time was varied).

| Sample | LiBr Temp (° C.) | Oven Time | Average Mw | Std dev | Confidence Interval | | PD |
|---|---|---|---|---|---|---|---|
| 60 C. LiBr, 1 hr | 60 | 1 | 31700 | | 11931 | 84223 | 2.66 |
| 100 C. LiBr, 1 hr | 100 | 1 | 27907 | 200 | 10735 | 72552 | 2.60 |
| RT LiBr, 4 hr | RT | 4 | 29217 | 1082 | 10789 | 79119 | 2.71 |
| 60 C. LiBr, 4 hr | 60 | 4 | 25578 | 2445 | 9978 | 65564 | 2.56 |
| 80 C. LiBr, 4 hr | 80 | 4 | 26312 | 637 | 10265 | 67441 | 2.56 |

TABLE 10-continued

The effect of Lithium Bromide (LiBr) temperature on molecular weight of silk processed under the conditions of 60 min. Extraction Time., 100° C. Extraction Temperature and 60° C. Oven Dissolution (Oven/Dissolution Time was varied).

| Sample | LiBr Temp (° C.) | Oven Time | Average Mw | Std dev | Confidence Interval | | PD |
|---|---|---|---|---|---|---|---|
| 100 C. LiBr, 4 hr | 100 | 4 | 27681 | 1729 | 11279 | 67931 | 2.45 |
| Boil LiBr, 4 hr | Boil | 4 | 30042 | 1535 | 11183 | 80704 | 2.69 |
| RT LiBr, 6 hr | RT | 6 | 26543 | 1893 | 10783 | 65332 | 2.46 |
| 80 C. LiBr, 6 hr | 80 | 6 | 26353 |  | 10167 | 68301 | 2.59 |
| 100 C. LiBr, 6 hr | 100 | 6 | 27150 | 916 | 11020 | 66889 | 2.46 |

TABLE 11

The effect of Lithium Bromide (LiBr) temperature on molecular weight of silk processed under the conditions of 30 min. Extraction Time, 100° C. Extraction Temperature and 60° C. Oven Dissolution (Oven/Dissolution Time was varied).

| Sample | LiBr Temp (° C.) | Oven Time | Average Mw | Std dev | Confidence Interval | | PD |
|---|---|---|---|---|---|---|---|
| 60 C. LiBr, 4 hr | 60 | 4 | 61956 | 13336 | 21463 | 178847 | 2.89 |
| 80 C. LiBr, 4 hr | 80 | 4 | 59202 | 14027 | 19073 | 183760 | 3.10 |
| 100 C. LiBr, 4 hr | 100 | 4 | 47853 |  | 19757 | 115899 | 2.42 |
| 80 C. LiBr, 6 hr | 80 | 6 | 46824 |  | 18075 | 121292 | 2.59 |
| 100 C. LiBr, 6 hr | 100 | 6 | 55421 | 8991 | 19152 | 160366 | 2.89 |

Experiments were carried out to determine the effect of varying the oven/dissolution temperature. FIGS. 50-54 are graphs showing these results, and Tables 12-16 summarize the results. Below is a summary:

- Oven temperature has less of an effect on 60 min extracted silk than 30 min extracted silk. Without wishing to be bound by theory, it is believed that the 30 min silk is less degraded during extraction and therefore the oven temperature has more of an effect on the larger MW, less degraded portion of the silk.
- For 60° C. vs. 140° C. oven the 30 min extracted silk showed a very significant effect of lower MW at higher oven temp, while 60 min extracted silk had an effect but much less
- The 140° C. oven resulted in a low end in the confidence interval at ~6000 Da

TABLE 12

The effect of oven/dissolution temperature on molecular weight of silk processed under the conditions of 100° C. Extraction Temperature, 30 min. Extraction Time, and 100° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 30 | 60 | 4 | 47853 |  | 19758 | 115900 | 2.42 |
| 30 | 100 | 4 | 40973 | 2632 | 14268 | 117658 | 2.87 |
| 30 | 60 | 6 | 55421 | 8992 | 19153 | 160366 | 2.89 |
| 30 | 100 | 6 | 25604 | 1405 | 10252 | 63943 | 2.50 |

TABLE 13

The effect of oven/dissolution temperature on molecular weight of silk processed under the conditions of 100° C. Extraction Temperature, 60 min. Extraction Time, and 100° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 60 | 60 | 1 | 27908 | 200 | 10735 | 72552 | 2.60 |
| 60 | 100 | 1 | 31520 | 1387 | 11633 | 85407 | 2.71 |
| 60 | 60 | 4 | 27681 | 1730 | 11279 | 72552 | 2.62 |
| 60 | 100 | 4 | 25082 | 1248 | 10520 | 59803 | 2.38 |
| 60 | 60 | 6 | 27150 | 916 | 11020 | 66889 | 2.46 |
| 60 | 100 | 6 | 20980 | 1262 | 10073 | 43695 | 2.08 |

TABLE 14

The effect of oven/dissolution temperature on molecular weight of silk processed under the conditions of 100° C. Extraction Temperature, 60 min. Extraction Time, and 140° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 60 | 60 | 4 | 30042 | 1536 | 11183 | 80705 | 2.69 |
| 60 | 140 | 4 | 15548 |  | 7255 | 33322 | 2.14 |

TABLE 15

The effect of oven/dissolution temperature on molecular weight of silk processed under the conditions of 100° C. Extraction Temperature, 30 min. Extraction Time, and 140° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 30 | 60 | 4 | 49656 | 4580 | 17306 | 142478 | 2.87 |
| 30 | 140 | 4 | 9025 | 1102 | 4493 | 18127 | 2.01 |
| 30 | 60 | 6 | 59383 | 11640 | 17641 | 199889 | 3.37 |
| 30 | 140 | 6 | 13021 | | 5987 | 28319 | 2.17 |

TABLE 16

The effect of oven/dissolution temperature on molecular weight of silk processed under the conditions of 100° C. Extraction Temperature, 60 min. Extraction Time, and 80° C. Lithium Bromide (LiBr) (Oven/Dissolution Time was varied).

| Boil Time | Oven Temp (° C.) | Oven Time | Average Mw | Std dev | Confidence Interval | | PD |
|---|---|---|---|---|---|---|---|
| 60 | 60 | 4 | 26313 | 637 | 10266 | 67442 | 2.56 |
| 60 | 80 | 4 | 30308 | 4293 | 12279 | 74806 | 2.47 |
| 60 | 60 | 6 | 26353 | | 10168 | 68302 | 2.59 |
| 60 | 80 | 6 | 25164 | 238 | 9637 | 65706 | 2.61 |

In an embodiment, when producing a silk gel, an acid is used to help facilitate gelation. In an embodiment, when producing a silk gel that includes a neutral or a basic molecule and/or therapeutic agent, an acid can be added to facilitate gelation. In an embodiment, when producing a silk gel, increasing the pH (making the gel more basic) increases the shelf stability of the gel. In an embodiment, when producing a silk gel, increasing the pH (making the gel more basic) allows for a greater quantity of an acidic molecule to be loaded into the gel.

In an embodiment, natural additives may be added to the silk gel to further stabilize additives. For example, trace elements such as selenium or magnesium or L-methoinine can be used. Further, light-block containers can be added to further increase stability.

In an embodiment, the methods disclosed herein result in a solution with characteristics that can be controlled during manufacturing, including, but not limited to: MW—may be varied by changing extraction and/or dissolution time and temp (e.g., LiBr temperature), pressure, and filtration (e.g., size exclusion chromatography); Structure—removal or cleavage of heavy or light chain of the fibroin protein polymer; Purity—hot water rinse temperature for improved sericin removal or filter capability for improved particulate removal that adversely affects shelf stability of the silk fragment protein mixture solution; Color—the color of the solution can be controlled with, for example, LiBr temp and time; Viscosity; Clarity; and Stability of solution. The resultant pH of the solution is typically about 7 and can be altered using an acid or base as appropriate to storage requirements.

In an embodiment, the above-described SPF mixture solutions may be utilized to coat at least a portion of a fabric which can be used to create a textile. In an embodiment, the above-described SPF mixture solutions may be weaved into yarn that can be used as a fabric in a textile.

Figure 33:
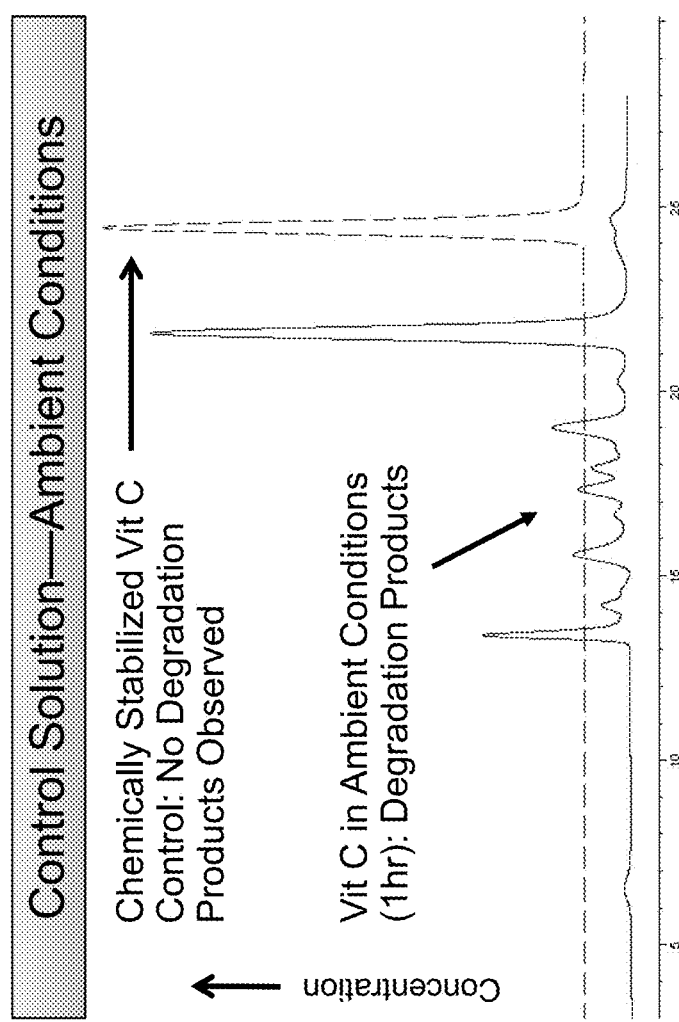
FIG. 33 shows HPLC chromatograms from samples comprising vitamin C.

FIG. 33 shows two HPLC chromatograms from samples comprising vitamin C. The chromatogram shows peaks from (1) a chemically stabilized sample of vitamin C at ambient conditions and (2) a sample of vitamin C taken after 1 hour at ambient conditions without chemical stabilization to prevent oxidation, where degradation products are visible. FIG. 36 is a table summarizing the stability of vitamin C in chemically stabilized solutions.

In some embodiments, a composition of the present disclosure can further include skin penetration enhancers, including, but not limited to, sulfoxides (such as dimethylsulfoxide), pyrrolidones (such as 2-pyrrolidone), alcohols (such as ethanol or decanol), azones (such as laurocapram and 1-dodecylazacycloheptan-2-one), surfactants (including alkyl carboxylates and their corresponding acids such as oleic acid, fluoroalkylcarboxylates and their corresponding acids, alkyl sulfates, alkyl ether sulfates, docusates such as dioctyl sodium sulfosuccinate, alkyl benzene sulfonates, alkyl ether phosphates, and alkyl aryl ether phosphates), glycols (such as propylene glycol), terpenes (such as limonene, p-cymene, geraniol, farnesol, eugenol, menthol, terpineol, carveol, carvone, fenchone, and verbenone), and dimethyl isosorbide.

Following are non-limiting examples of suitable ranges for various parameters in and for preparation of the silk solutions of the present disclosure. The silk solutions of the present disclosure may include one or more, but not necessarily all, of these parameters and may be prepared using various combinations of ranges of such parameters.

In an embodiment, the percent silk in the solution is less than 30%. In an embodiment, the percent silk in the solution is less than 25%. In an embodiment, the percent silk in the solution is less than 20%. In an embodiment, the percent silk in the solution is less than 19%. In an embodiment, the percent silk in the solution is less than 18%. In an embodiment, the percent silk in the solution is less than 17%. In an embodiment, the percent silk in the solution is less than 16%. In an embodiment, the percent silk in the solution is less than 15%. In an embodiment, the percent silk in the solution is less than 14%. In an embodiment, the percent silk in the solution is less than 13%. In an embodiment, the percent silk in the solution is less than 12%. In an embodiment, the percent silk in the solution is less than 11%. In an embodiment, the percent silk in the solution is less than 10%. In an embodiment, the percent silk in the solution is less than 9%. In an embodiment, the percent silk in the solution is less than 8%. In an embodiment, the percent silk in the solution is less than 7%. In an embodiment, the percent silk in the solution is less than 6%. In an embodiment, the percent silk in the solution is less than 5%. In an embodiment, the percent silk in the solution is less than 4%. In an embodiment, the percent silk in the solution is less than 3%. In an embodiment, the percent silk in the solution is less than 2%. In an embodiment, the percent silk in the solution is less than 1%. In an embodiment, the percent silk in the solution is less than 0.9%. In an embodiment, the percent silk in the solution is less than 0.8%. In an embodiment, the percent silk in the solution is less than 0.7%. In an embodiment, the percent silk in the solution is less than 0.6%. In an embodiment, the percent silk in the solution is less than 0.5%. In an embodiment, the percent silk in the solution is less than 0.4%. In an embodiment, the percent silk in the solution is less than 0.3%. In an embodiment, the percent silk in the solution is less than 0.2%. In an embodiment, the percent silk in the solution is less than 0.1%. In an embodiment, the percent silk in the solution is greater than 0.1%. In an embodiment, the percent silk in the solution is greater than 0.2%. In an embodiment, the percent silk in the solution is greater than 0.3%. In an embodiment, the percent silk in the solution is greater than 0.4%. In an embodiment, the percent silk in the solution is greater than 0.5%. In an embodiment, the percent silk in the solution is greater than 0.6%. In an embodiment, the percent silk in the solution is greater than 0.7%. In an embodiment, the percent silk in the solution is greater than 0.8%. In an embodiment, the percent silk in the solution is greater than 0.9%. In an embodiment, the percent silk in the solution is greater than 1%. In an embodiment, the percent silk in the solution is greater than 2%. In an embodiment, the percent silk in the solution is greater than 3%. In an embodiment, the percent silk in the solution is greater than 4%. In an embodiment, the percent silk in the solution is greater than 5%. In an embodiment, the percent silk in the solution is greater than 6%. In an embodiment, the percent silk in the solution is greater than 7%. In an embodiment, the percent silk in the solution is greater than 8%. In an embodiment, the percent silk in the solution is greater than 9%. In an embodiment, the percent silk in the solution is greater than 10%. In an embodiment, the percent silk in the solution is greater than 11%. In an embodiment, the percent silk in the solution is greater than 12%. In an embodiment, the percent silk in the solution is greater than 13%. In an embodiment, the percent silk in the solution is greater than 14%. In an embodiment, the percent silk in the solution is greater than 15%. In an embodiment, the percent silk in the solution is greater than 16%. In an embodiment, the percent silk in the solution is greater than 17%. In an embodiment, the percent silk in the solution is greater than 18%. In an embodiment, the percent silk in the solution is greater than 19%. In an embodiment, the percent silk in the solution is greater than 20%. In an embodiment, the percent silk in the solution is greater than 25%. In an embodiment, the percent silk in the solution is between 0.1% and 30%. In an embodiment, the percent silk in the solution is between 0.1% and 25%. In an embodiment, the percent silk in the solution is between 0.1% and 20%. In an embodiment, the percent silk in the solution is between 0.1% and 15%. In an embodiment, the percent silk in the solution is between 0.1% and 10%. In an embodiment, the percent silk in the solution is between 0.1% and 9%. In an embodiment, the percent silk in the solution is between 0.1% and 8%. In an embodiment, the percent silk in the solution is between 0.1% and 7%. In an embodiment, the percent silk in the solution is between 0.1% and 6.5%. In an embodiment, the percent silk in the solution is between 0.1% and 6%. In an embodiment, the percent silk in the solution is between 0.1% and 5.5%. In an embodiment, the percent silk in the solution is between 0.1% and 5%. In an embodiment, the percent silk in the solution is between 0.1% and 4.5%. In an embodiment, the percent silk in the solution is between 0.1% and 4%. In an embodiment, the percent silk in the solution is between 0.1% and 3.5%. In an embodiment, the percent silk in the solution is between 0.1% and 3%. In an embodiment, the percent silk in the solution is between 0.1% and 2.5%. In an embodiment, the percent silk in the solution is between 0.1% and 2.0%. In an embodiment, the percent silk in the solution is between 0.1% and 2.4%. In an embodiment, the percent silk in the solution is between 0.5% and 5%. In an embodiment, the percent silk in the solution is between 0.5% and 4.5%. In an embodiment, the percent silk in the solution is between 0.5% and 4%. In an embodiment, the percent silk in the solution is between 0.5% and 3.5%. In an embodiment, the percent silk in the solution is between 0.5% and 3%. In an embodiment, the percent silk in the solution is between 0.5% and 2.5%. In an embodiment, the percent silk in the solution is between 1 and 4%. In an embodiment, the percent silk in the solution is between 1 and 3.5%. In an embodiment, the percent silk in the solution is between 1 and 3%. In an embodiment, the percent silk in the solution is between 1 and 2.5%. In an embodiment, the percent silk in the solution is between 1 and 2.4%. In an embodiment, the percent silk in the solution is between 1 and 2%. In an embodiment, the percent silk in the solution is between 20% and 30%. In an embodiment, the percent silk in the solution is between 0.1% and 6%. In an embodiment, the percent silk in the solution is between 6% and 10%. In an embodiment, the percent silk in the solution is between 6% and 8%. In an embodiment, the percent silk in the solution is between 6% and 9%. In an embodiment, the percent silk in the solution is between 10% and 20%. In an embodiment, the percent silk in the solution is between 11% and 19%. In an embodiment, the percent silk in the solution is between 12% and 18%. In an embodiment, the percent silk in the solution is between 13% and 17%. In an embodiment, the percent silk in the solution is between 14% and 16%. In an embodiment, the percent silk in the solution is 2.4%. In an embodiment, the percent silk in the solution is 2.0%.

In an embodiment, the percent sericin in the solution is non-detectable to 30%. In an embodiment, the percent sericin in the solution is non-detectable to 5%. In an embodiment, the percent sericin in the solution is 1%. In an embodiment, the percent sericin in the solution is 2%. In an embodiment, the percent sericin in the solution is 3%. In an embodiment, the percent sericin in the solution is 4%. In an embodiment, the percent sericin in the solution is 5%. In an embodiment, the percent sericin in the solution is 10%. In an embodiment, the percent sericin in the solution is 30%.

In an embodiment, the stability of the LiBr-silk fragment solution is 0 to 1 year. In an embodiment, the stability of the LiBr-silk fragment solution is 0 to 2 years. In an embodiment, the stability of the LiBr-silk fragment solution is 0 to 3 years. In an embodiment, the stability of the LiBr-silk fragment solution is 0 to 4 years. In an embodiment, the stability of the LiBr-silk fragment solution is 0 to 5 years. In an embodiment, the stability of the LiBr-silk fragment solution is 1 to 2 years. In an embodiment, the stability of the LiBr-silk fragment solution is 1 to 3 years. In an embodiment, the stability of the LiBr-silk fragment solution is 1 to 4 years. In an embodiment, the stability of the LiBr-silk fragment solution is 1 to 5 years. In an embodiment, the stability of the LiBr-silk fragment solution is 2 to 3 years. In an embodiment, the stability of the LiBr-silk fragment solution is 2 to 4 years. In an embodiment, the stability of the LiBr-silk fragment solution is 2 to 5 years. In an embodiment, the stability of the LiBr-silk fragment solution is 3 to 4 years. In an embodiment, the stability of the LiBr-silk fragment solution is 3 to 5 years. In an embodiment, the stability of the LiBr-silk fragment solution is 4 to 5 years.

In an embodiment, the stability of a composition of the present disclosure is 10 days to 6 months. In an embodiment, the stability of a composition of the present disclosure is 6 months to 12 months. In an embodiment, the stability of a composition of the present disclosure is 12 months to 18 months. In an embodiment, the stability of a composition of the present disclosure is 18 months to 24 months. In an embodiment, the stability of a composition of the present disclosure is 24 months to 30 months. In an embodiment, the stability of a composition of the present disclosure is 30 months to 36 months. In an embodiment, the stability of a composition of the present disclosure is 36 months to 48 months. In an embodiment, the stability of a composition of the present disclosure is 48 months to 60 months.

In an embodiment, a composition of the present disclosure includes pure silk fibroin-based protein fragments having an average weight average molecular weight ranging from 6 kDa to 16 kDa. In an embodiment, a composition of the present disclosure includes pure silk fibroin-based protein fragments having an average weight average molecular weight ranging from 17 kDa to 38 kDa. In an embodiment, a composition of the present disclosure includes pure silk fibroin-based protein fragments having an average weight average molecular weight ranging from 39 kDa to 80 kDa. In an embodiment, a composition of the present disclosure includes pure silk fibroin-based protein fragments having an average weight average molecular weight ranging from 1 to 5 kDa. In an embodiment, a composition of the present disclosure includes pure silk fibroin-based protein fragments having an average weight average molecular weight ranging from 5 to 10 kDa. In an embodiment, a composition of the present disclosure includes pure silk fibroin-based protein fragments having an average weight average molecular weight ranging from 10 to 15 kDa. In an embodiment, a composition of the present disclosure includes pure silk fibroin-based protein fragments having an average weight average molecular weight ranging from 15 to 20 kDa. In an embodiment, a composition of the present disclosure includes pure silk fibroin-based protein fragments having an average weight average molecular weight ranging from 20 to 25 kDa. In an embodiment, a composition of the present disclosure includes pure silk fibroin-based protein fragments having an average weight average molecular weight ranging from 25 to 30 kDa. In an embodiment, a composition of the present disclosure includes pure silk fibroin-based protein fragments having an average weight average molecular weight ranging from 30 to 35 kDa. In an embodiment, a composition of the present disclosure includes pure silk fibroin-based protein fragments having an average weight average molecular weight ranging from 35 to 40 kDa. In an embodiment, a composition of the present disclosure includes pure silk fibroin-based protein fragments having an average weight average molecular weight ranging from 40 to 45 kDa. In an embodiment, a composition of the present disclosure includes pure silk fibroin-based protein fragments having an average weight average molecular weight ranging from 45 to 50 kDa. In an embodiment, a composition of the present disclosure includes pure silk fibroin-based protein fragments having an average weight average molecular weight ranging from 50 to 55 kDa. In an embodiment, a composition of the present disclosure includes pure silk fibroin-based protein fragments having an average weight average molecular weight ranging from 55 to 60 kDa. In an embodiment, a composition of the present disclosure includes pure silk fibroin-based protein fragments having an average weight average molecular weight ranging from 60 to 65 kDa. In an embodiment, a composition of the present disclosure includes pure silk fibroin-based protein fragments having an average weight average molecular weight ranging from 65 to 70 kDa. In an embodiment, a composition of the present disclosure includes pure silk fibroin-based protein fragments having an average weight average molecular weight ranging from 70 to 75 kDa. In an embodiment, a composition of the present disclosure includes pure silk fibroin-based protein fragments having an average weight average molecular weight ranging from 75 to 80 kDa. In an embodiment, a composition of the present disclosure includes pure silk fibroin-based protein fragments having an average weight average molecular weight ranging from 80 to 85 kDa. In an embodiment, a composition of the present disclosure includes pure silk fibroin-based protein fragments having an average weight average molecular weight ranging from 85 to 90 kDa. In an embodiment, a composition of the present disclosure includes pure silk fibroin-based protein fragments having an average weight average molecular weight ranging from 90 to 95 kDa. In an embodiment, a composition of the present disclosure includes pure silk fibroin-based protein fragments having an average weight average molecular weight ranging from 95 to 100 kDa. In an embodiment, a composition of the present disclosure includes pure silk fibroin-based protein fragments having an average weight average molecular weight ranging from 100 to 105 kDa. In an embodiment, a composition of the present disclosure includes pure silk fibroin-based protein fragments having an average weight average molecular weight ranging from 105 to 110 kDa. In an embodiment, a composition of the present disclosure includes pure silk fibroin-based protein fragments having an average weight average molecular weight ranging from 110 to 115 kDa. In an embodiment, a composition of the present disclosure includes pure silk fibroin-based protein fragments having an average weight average molecular weight ranging from 115 to 120 kDa. In an embodiment, a composition of the present disclosure includes pure silk fibroin-based protein fragments having an average weight average molecular weight ranging from 120 to 125 kDa. In an embodiment, a composition of the present disclosure includes pure silk fibroin-based protein fragments having an average weight average molecular weight ranging from 125 to 130 kDa. In an embodiment, a composition of the present disclosure includes pure silk fibroin-based protein fragments having an average weight average molecular weight ranging from 130 to 135 kDa. In an embodiment, a composition of the present disclosure includes pure silk fibroin-based protein fragments having an average weight average molecular weight ranging from 135 to 140 kDa. In an embodiment, a composition of the present disclosure includes pure silk fibroin-based protein fragments having an average weight average molecular weight ranging from 140 to 145 kDa. In an embodiment, a composition of the present disclosure includes pure silk fibroin-based protein fragments having an average weight average molecular weight ranging from 145 to 150 kDa. In an embodiment, a composition of the present disclosure includes pure silk fibroin-based protein fragments having an average weight average molecular weight ranging from 150 to 155 kDa. In an embodiment, a composition of the present disclosure includes pure silk fibroin-based protein fragments having an average weight average molecular weight ranging from 155 to 160 kDa. In an embodiment, a composition of the present disclosure includes pure silk fibroin-based protein fragments having an average weight average molecular weight ranging from 160 to 165 kDa. I In an embodiment, a composition of the present disclosure includes pure silk fibroin-based protein fragments having an average weight average molecular weight ranging from 165 to 170 kDa. In an embodiment, a composition of the present disclosure includes pure silk fibroin-based protein fragments having an average weight average molecular weight ranging from 170 to 175 kDa. In an embodiment, a composition of the present disclosure includes pure silk fibroin-based protein fragments having an average weight average molecular weight ranging from 175 to 180 kDa. In an embodiment, a composition of the present disclosure includes pure silk fibroin-based protein fragments having an average weight average molecular weight ranging from 180 to 185 kDa. In an embodiment, a composition of the present disclosure includes pure silk fibroin-based protein fragments having an average weight average molecular weight ranging from 185 to 190 kDa. In an embodiment, a composition of the present disclosure includes pure silk fibroin-based protein fragments having an average weight average molecular weight ranging from 190 to 195 kDa. In an embodiment, a composition of the present disclosure includes pure silk fibroin-based protein fragments having an average weight average molecular weight ranging from 195 to 200 kDa. In an embodiment, a composition of the present disclosure includes pure silk fibroin-based protein fragments having an average weight average molecular weight ranging from 200 to 205 kDa. In an embodiment, a composition of the present disclosure includes pure silk fibroin-based protein fragments having an average weight average molecular weight ranging from 205 to 210 kDa. In an embodiment, a composition of the present disclosure includes pure silk fibroin-based protein fragments having an average weight average molecular weight ranging from 210 to 215 kDa. In an embodiment, a composition of the present disclosure includes pure silk fibroin-based protein fragments having an average weight average molecular weight ranging from 215 to 220 kDa. In an embodiment, a composition of the present disclosure includes pure silk fibroin-based protein fragments having an average weight average molecular weight ranging from 220 to 225 kDa. In an embodiment, a composition of the present disclosure includes pure silk fibroin-based protein fragments having an average weight average molecular weight ranging from 225 to 230 kDa. In an embodiment, a composition of the present disclosure includes pure silk fibroin-based protein fragments having an average weight average molecular weight ranging from 230 to 235 kDa. In an embodiment, a composition of the present disclosure includes pure silk fibroin-based protein fragments having an average weight average molecular weight ranging from 235 to 240 kDa. In an embodiment, a composition of the present disclosure includes pure silk fibroin-based protein fragments having an average weight average molecular weight ranging from 240 to 245 kDa. In an embodiment, a composition of the present disclosure includes pure silk fibroin-based protein fragments having an average weight average molecular weight ranging from 245 to 250 kDa. In an embodiment, a composition of the present disclosure includes pure silk fibroin-based protein fragments having an average weight average molecular weight ranging from 250 to 255 kDa. In an embodiment, a composition of the present disclosure includes pure silk fibroin-based protein fragments having an average weight average molecular weight ranging from 255 to 260 kDa. In an embodiment, a composition of the present disclosure includes pure silk fibroin-based protein fragments having an average weight average molecular weight ranging from 260 to 265 kDa. In an embodiment, a composition of the present disclosure includes pure silk fibroin-based protein fragments having an average weight average molecular weight ranging from 265 to 270 kDa. In an embodiment, a composition of the present disclosure includes pure silk fibroin-based protein fragments having an average weight average molecular weight ranging from 270 to 275 kDa. In an embodiment, a composition of the present disclosure includes pure silk fibroin-based protein fragments having an average weight average molecular weight ranging from 275 to 280 kDa. In an embodiment, a composition of the present disclosure includes pure silk fibroin-based protein fragments having an average weight average molecular weight ranging from 280 to 285 kDa. In an embodiment, a composition of the present disclosure includes pure silk fibroin-based protein fragments having an average weight average molecular weight ranging from 285 to 290 kDa. In an embodiment, a composition of the present disclosure includes pure silk fibroin-based protein fragments having an average weight average molecular weight ranging from 290 to 295 kDa. In an embodiment, a composition of the present disclosure includes pure silk fibroin-based protein fragments having an average weight average molecular weight ranging from 295 to 300 kDa. In an embodiment, a composition of the present disclosure includes pure silk fibroin-based protein fragments having an average weight average molecular weight ranging from 300 to 305 kDa. In an embodiment, a composition of the present disclosure includes pure silk fibroin-based protein fragments having an average weight average molecular weight ranging from 305 to 310 kDa. In an embodiment, a composition of the present disclosure includes pure silk fibroin-based protein fragments having an average weight average molecular weight ranging from 310 to 315 kDa. In an embodiment, a composition of the present disclosure includes pure silk fibroin-based protein fragments having an average weight average molecular weight ranging from 315 to 320 kDa. In an embodiment, a composition of the present disclosure includes pure silk fibroin-based protein fragments having an average weight average molecular weight ranging from 320 to 325 kDa. In an embodiment, a composition of the present disclosure includes pure silk fibroin-based protein fragments having an average weight average molecular weight ranging from 325 to 330 kDa. In an embodiment, a composition of the present disclosure includes pure silk fibroin-based protein fragments having an average weight average molecular weight ranging from 330 to 335 kDa. In an embodiment, a composition of the present disclosure includes pure silk fibroin-based protein fragments having an average weight average molecular weight ranging from 35 to 340 kDa. In an embodiment, a composition of the present disclosure includes pure silk fibroin-based protein fragments having an average weight average molecular weight ranging from 340 to 345 kDa. In an embodiment, a composition of the present disclosure includes pure silk fibroin-based protein fragments having an average weight average molecular weight ranging from 345 to 350 kDa.

In an embodiment, a composition of the present disclosure having pure silk fibroin-based protein fragments has a polydispersity ranging from about 1 to about 5.0. In an embodiment, a composition of the present disclosure having pure silk fibroin-based protein fragments has a polydispersity ranging from about 1.5 to about 3.0. In an embodiment, a composition of the present disclosure having pure silk fibroin-based protein fragments has a polydispersity ranging from about 1 to about 1.5. In an embodiment, a composition of the present disclosure having pure silk fibroin-based protein fragments has a polydispersity ranging from about 1.5 to about 2.0. In an embodiment, a composition of the present disclosure having pure silk fibroin-based protein fragments has a polydispersity ranging from about 2.0 to about 2.5. In an embodiment, a composition of the present disclosure having pure silk fibroin-based protein fragments, has a polydispersity ranging from about is 2.0 to about 3.0. In an embodiment, a composition of the present disclosure having pure silk fibroin-based protein fragments, has a polydispersity ranging from about is 2.5 to about 3.0.

In an embodiment, a composition of the present disclosure having pure silk fibroin-based protein fragments has non-detectable levels of LiBr residuals. In an embodiment, the amount of the LiBr residuals in a composition of the present disclosure is between 10 ppm and 1000 ppm. In an embodiment, the amount of the LiBr residuals in a composition of the present disclosure is between 10 ppm and 300 ppm. In an embodiment, the amount of the LiBr residuals in a composition of the present disclosure is less than 25 ppm. In an embodiment, the amount of the LiBr residuals in a composition of the present disclosure is less than 50 ppm. In an embodiment, the amount of the LiBr residuals in a composition of the present disclosure is less than 75 ppm. In an embodiment, the amount of the LiBr residuals in a composition of the present disclosure is less than 100 ppm. In an embodiment, the amount of the LiBr residuals in a composition of the present disclosure is less than 200 ppm. In an embodiment, the amount of the LiBr residuals in a composition of the present disclosure is less than 300 ppm. In an embodiment, the amount of the LiBr residuals in a composition of the present disclosure is less than 400 ppm. In an embodiment, the amount of the LiBr residuals in a composition of the present disclosure is less than 500 ppm. In an embodiment, the amount of the LiBr residuals in a composition of the present disclosure is less than 600 ppm. In an embodiment, the amount of the LiBr residuals in a composition of the present disclosure is less than 700 ppm. In an embodiment, the amount of the LiBr residuals in a composition of the present disclosure is less than 800 ppm. In an embodiment, the amount of the LiBr residuals in a composition of the present disclosure is less than 900 ppm. In an embodiment, the amount of the LiBr residuals in a composition of the present disclosure is less than 1000 ppm. In an embodiment, the amount of the LiBr residuals in a composition of the present disclosure is non-detectable to 500 ppm. In an embodiment, the amount of the LiBr residuals in a composition of the present disclosure is non-detectable to 450 ppm. In an embodiment, the amount of the LiBr residuals in a composition of the present disclosure is non-detectable to 400 ppm. In an embodiment, the amount of the LiBr residuals in a composition of the present disclosure is non-detectable to 350 ppm. In an embodiment, the amount of the LiBr residuals in a composition of the present disclosure is non-detectable to 300 ppm. In an embodiment, the amount of the LiBr residuals in a composition of the present disclosure is non-detectable to 250 ppm. In an embodiment, the amount of the LiBr residuals in a composition of the present disclosure is non-detectable to 200 ppm. In an embodiment, the amount of the LiBr residuals in a composition of the present disclosure is non-detectable to 150 ppm. In an embodiment, the amount of the LiBr residuals in a composition of the present disclosure is non-detectable to 100 ppm. In an embodiment, the amount of the LiBr residuals in a composition of the present disclosure is 100 ppm to 200 ppm. In an embodiment, the amount of the LiBr residuals in a composition of the present disclosure is 200 ppm to 300 ppm. In an embodiment, the amount of the LiBr residuals in a composition of the present disclosure is 300 ppm to 400 ppm. In an embodiment, the amount of the LiBr residuals in a composition of the present disclosure is 400 ppm to 500 ppm.

In an embodiment, a composition of the present disclosure having pure silk fibroin-based protein fragments, has non-detectable levels of $Na_2CO_3$ residuals. In an embodiment, the amount of the $Na_2CO_3$ residuals in a composition of the present disclosure is less than 100 ppm. In an embodiment, the amount of the $Na_2CO_3$ residuals in a composition of the present disclosure is less than 200 ppm. In an embodiment, the amount of the $Na_2CO_3$ residuals in a composition of the present disclosure is less than 300 ppm. In an embodiment, the amount of the $Na_2CO_3$ residuals in a composition of the present disclosure is less than 400 ppm. In an embodiment, the amount of the $Na_2CO_3$ residuals in a composition of the present disclosure is less than 500 ppm. In an embodiment, the amount of the $Na_2CO_3$ residuals in a composition of the present disclosure is less than 600 ppm. In an embodiment, the amount of the $Na_2CO_3$ residuals in a composition of the present disclosure is less than 700 ppm. In an embodiment, the amount of the $Na_2CO_3$ residuals in a composition of the present disclosure is less than 800 ppm. In an embodiment, the amount of the $Na_2CO_3$ residuals in a composition of the present disclosure is less than 900 ppm. In an embodiment, the amount of the $Na_2CO_3$ residuals in a composition of the present disclosure is less than 1000 ppm. In an embodiment, the amount of the $Na_2CO_3$ residuals in a composition of the present disclosure is non-detectable to 500 ppm. In an embodiment, the amount of the $Na_2CO_3$ residuals in a composition of the present disclosure is non-detectable to 450 ppm. In an embodiment, the amount of the $Na_2CO_3$ residuals in a composition of the present disclosure is non-detectable to 400 ppm. In an embodiment, the amount of the $Na_2CO_3$ residuals in a composition of the present disclosure is non-detectable to 350 ppm. In an embodiment, the amount of the $Na_2CO_3$ residuals in a composition of the present disclosure is non-detectable to 300 ppm. In an embodiment, the amount of the $Na_2CO_3$ residuals in a composition of the present disclosure is non-detectable to 250 ppm. In an embodiment, the amount of the $Na_2CO_3$ residuals in a composition of the present disclosure is non-detectable to 200 ppm. In an embodiment, the amount of the $Na_2CO_3$ residuals in a composition of the present disclosure is non-detectable to 150 ppm. In an embodiment, the amount of the $Na_2CO_3$ residuals in a composition of the present disclosure is non-detectable to 100 ppm. In an embodiment, the amount of the $Na_2CO_3$ residuals in a composition of the present disclosure is 100 ppm to 200 ppm. In an embodiment, the amount of the $Na_2CO_3$ residuals in a composition of the present disclosure is 200 ppm to 300 ppm. In an embodiment, the amount of the $Na_2CO_3$ residuals in a composition of the present disclosure is 300 ppm to 400 ppm. In an embodiment, the amount of the $Na_2CO_3$ residuals in a composition of the present disclosure is 400 ppm to 500 ppm.

In an embodiment, the water solubility of pure silk fibroin-based protein fragments of the present disclosure is 50 to 100%. In an embodiment, the water solubility of pure silk fibroin-based protein fragments of the present disclosure is 60 to 100%. In an embodiment, the water solubility of pure silk fibroin-based protein fragments of the present disclosure is 70 to 100%. In an embodiment, the water solubility of pure silk fibroin-based protein fragments of the present disclosure is 80 to 100%. In an embodiment, the water solubility is 90 to 100%. In an embodiment, the silk fibroin-based fragments of the present disclosure are non-soluble in aqueous solutions.

In an embodiment, the solubility of pure silk fibroin-based protein fragments of the present disclosure in organic solutions is 50 to 100%. In an embodiment, the solubility of pure silk fibroin-based protein fragments of the present disclosure in organic solutions is 60 to 100%. In an embodiment, the solubility of pure silk fibroin-based protein fragments of the present disclosure in organic solutions is 70 to 100%. In an embodiment, the solubility of pure silk fibroin-based protein fragments of the present disclosure in organic solutions is 80 to 100%. In an embodiment, the solubility of pure silk fibroin-based protein fragments of the present disclosure in organic solutions is 90 to 100%. In an embodiment, the silk fibroin-based fragments of the present disclosure are non-soluble in organic solutions.

In an embodiment, the extraction temperature during a method of preparing a composition of the present disclosure is greater than 84° C. In an embodiment, the extraction temperature during a method of preparing a composition of the present disclosure is less than 100° C. In an embodiment, the extraction temperature during a method of preparing a composition of the present disclosure is 84° C. to 100° C. In an embodiment, the extraction temperature during a method of preparing a composition of the present disclosure is 84° C. to 94° C. In an embodiment, the extraction temperature during a method of preparing a composition of the present disclosure is 94° C. to 100° C.

The following examples are put forth so as to provide those of ordinary skill in the art with a complete disclosure and description of how to make and use the described embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

There is disclosed a textile that is at least partially surface treated with an aqueous solution of pure silk fibroin-based protein fragments of the present disclosure so as to result in a silk coating on the textile. In an embodiment, the silk coating of the present disclosure is available in a spray can and can be sprayed on any textile by a consumer. In an embodiment, a textile comprising a silk coating of the present disclosure is sold to a consumer. In an embodiment, a textile of the present disclosure is used in constructing action sportswear/apparel, In an embodiment, a silk coating of the present disclosure is positioned on the underlining of apparel. In an embodiment, a silk coating of the present disclosure is positioned on the shell, the lining, or the interlining of apparel. In an embodiment, apparel is partially made from a silk coated textile of the present disclosure and partially made from an uncoated textile. In an embodiment, apparel partially made from a silk coated textile and partially made from an uncoated textile combines an uncoated inert synthetic material with a silk coated inert synthetic material. Examples of inert synthetic material include, but are not limited to, polyester, polyamide, polyaramid, polytetrafluorethylene, polyethylene, polypropylene, polyurethane, silicone, mixtures of polyurethane and polyethylenglycol, ultra-high molecular weight polyethylene, high-performance polyethylene, and mixtures thereof. In an embodiment, apparel partially made from a silk coated textile and partially made from an uncoated textile combines an elastomeric material at least partially covered with a silk coating of the present disclosure. In an embodiment, the percentage of silk to elastomeric material can be varied to achieve desired shrink or wrinkle resistant properties.

In an embodiment, a silk coating of the present disclosure is visible. In an embodiment, a silk coating of the present disclosure positioned on apparel helps control skin temperature. In an embodiment, a silk coating of the present disclosure positioned on apparel helps control fluid transfer away from the skin. In an embodiment, a silk coating of the present disclosure positioned on apparel has a soft feel against the skin decreasing abrasions from fabric on skin. In an embodiment, a silk coating of the present disclosure positioned on a textile has properties that confer at least one of wrinkle resistance, shrinkage resistance, or machine washability to the textile. In an embodiment, a silk coated textile of the present disclosure is 100% machine washable and dry cleanable. In an embodiment, a silk coated textile of the present disclosure is 100% waterproof. In an embodiment, a silk coated textile of the present disclosure is wrinkle resistant. In an embodiment, a silk coated textile of the present disclosure is shrink resistant. In an embodiment, a silk coated textile of the present disclosure has the qualities of being waterproof, breathable, and elastic and possess a number of other qualities which are highly desirable in action sportswear. In an embodiment, a silk coated textile of the present disclosure manufactured from a silk fabric of the present disclosure further includes LYCRA® brand spandex fibers.

In an embodiment, a textile at least partially coated with an aqueous solution of pure silk fibroin-based protein fragments of the present disclosure is a breathable fabric. In an embodiment, a textile at least partially coated with an aqueous solution of pure silk fibroin-based protein fragments of the present disclosure is a water-resistant fabric. In an embodiment, a textile at least partially coated with an aqueous solution of pure silk fibroin-based protein fragments of the present disclosure is a shrink-resistant fabric. In an embodiment, a textile at least partially coated with an aqueous solution of pure silk fibroin-based protein fragments of the present disclosure is a machine-washable fabric. In an embodiment, a textile at least partially coated with an aqueous solution of pure silk fibroin-based protein fragments of the present disclosure is a wrinkle resistant fabric. In an embodiment, textile at least partially coated with an aqueous solution of pure silk fibroin-based protein fragments of the present disclosure provides moisture and vitamins to the skin.

In an embodiment, an aqueous solution of pure silk fibroin-based protein fragments of the present disclosure is used to coat a textile. In an embodiment, the concentration of silk in the solution ranges from about 0.1% to about 20.0%. In an embodiment, the concentration of silk in the solution ranges from about 0.1% to about 15.0%. In an embodiment, the concentration of silk in the solution ranges from about 0.5% to about 10.0%. In an embodiment, the concentration of silk in the solution ranges from about 1.0% to about 5.0%. In an embodiment, an aqueous solution of pure silk fibroin-based protein fragments of the present disclosure is applied directly to a fabric. Alternatively, silk microsphere and any additives may be used for coating a fabric. In an embodiment, additives can be added to an aqueous solution of pure silk fibroin-based protein fragments of the present disclosure before coating (e.g., alcohols) to further enhance material properties. In an embodiment, a silk coating of the present disclosure can have a pattern to optimize properties of the silk on the fabric. In an embodiment, a coating is applied to a fabric under tension and/or lax to vary penetration in to the fabric.

In an embodiment, a silk coating of the present disclosure can be applied at the yarn level, followed by creation of a fabric once the yarn is coated. In an embodiment, an aqueous solution of pure silk fibroin-based protein fragments of the present disclosure can be spun into fibers to make a silk fabric and/or silk fabric blend with other materials known in the apparel industry.

In an embodiment, a method for silk coating a fabric includes immersion of the fabric in any of the aqueous solutions of pure silk fibroin-based protein fragments of the present disclosure. In an embodiment, a method for silk coating a fabric includes spraying. In an embodiment, a method for silk coating a fabric includes chemical vapor deposition. In an embodiment, a method for silk coating a fabric includes electrochemical coating. In an embodiment, a method for silk coating a fabric includes knife coating to spread any of the aqueous solutions of pure silk fibroin-based protein fragments of the present disclosure onto the fabric. The coated fabric may then be air dried, dried under heat/air flow, or cross-linked to the fabric surface. In an embodiment, a drying process includes curing with additives and/or ambient condition.

EXAMPLES

Example 1

Tangential Flow Filtration (TFF) to Remove Solvent from Dissolved Silk Solutions A variety of % silk concentrations have been produced through the use of Tangential Flow Filtration (TFF). In all cases a 1% silk solution was used as the input feed. A range of 750-18,000 mL of 1% silk solution was used as the starting volume. Solution is diafiltered in the TFF to remove lithium bromide. Once below a specified level of residual LiBr, solution undergoes ultrafiltration to increase the concentration through removal of water. See examples below.

7.30% Silk Solution: A 7.30% silk solution was produced beginning with 30 minute extraction batches of 100 g silk cocoons per batch. Extracted silk fibers were then dissolved using 100C 9.3M LiBr in a 100C oven for 1 hour. 100 g of silk fibers were dissolved per batch to create 20% silk in LiBr. Dissolved silk in LiBr was then diluted to 1% silk and filtered through a 5 um filter to remove large debris. 15,500 mL of 1%, filtered silk solution was used as the starting volume/diafiltration volume for TFF. Once LiBr was removed, the solution was ultrafiltered to a volume around 1300 mL. 1262 mL of 7.30% silk was then collected. Water was added to the feed to help remove the remaining solution and 547 mL of 3.91% silk was then collected.

6.44% Silk Solution: A 6.44% silk solution was produced beginning with 60 minute extraction batches of a mix of 25, 33, 50, 75 and 100 g silk cocoons per batch. Extracted silk fibers were then dissolved using 100C 9.3M LiBr in a 100C oven for 1 hour. 35, 42, 50 and 71 g per batch of silk fibers were dissolved to create 20% silk in LiBr and combined. Dissolved silk in LiBr was then diluted to 1% silk and filtered through a 5 um filter to remove large debris. 17,000 mL of 1%, filtered silk solution was used as the starting volume/diafiltration volume for TFF. Once LiBr was removed, the solution was ultrafiltered to a volume around 3000 mL. 1490 mL of 6.44% silk was then collected. Water was added to the feed to help remove the remaining solution and 1454 mL of 4.88% silk was then collected 2.70% Silk Solution: A 2.70% silk solution was produced beginning with 60 minute extraction batches of 25 g silk cocoons per batch. Extracted silk fibers were then dissolved using 100C 9.3M LiBr in a 100C oven for 1 hour. 35.48 g of silk fibers were dissolved per batch to create 20% silk in LiBr. Dissolved silk in LiBr was then diluted to 1% silk and filtered through a 5 um filter to remove large debris. 1000 mL of 1%, filtered silk solution was used as the starting volume/diafiltration volume for TFF. Once LiBr was removed, the solution was ultrafiltered to a volume around 300 mL. 312 mL of 2.7% silk was then collected.

Example 2

Preparation of Silk Gels

TABLE 17

Gel Samples - Silk gel formulations including additives, concentration of silk and additive, gelation conditions and gelation times.

| Sample Name | mL 2% silk solution | Mass Vit C (g) | Ratio silk:VitC | Additive | Amount of additive | Temp/ Treatment | Days to Gelation |
|---|---|---|---|---|---|---|---|
| 1 | 10 | 0.04 | 5:01 | None | None | RT | 8 |
| 2 | 10 | 0.08 | 2.5:1 | None | None | RT | 8 |
| 3 | 10 | 0.2 | 1:01 | None | None | RT | 8 |
| 4 | 10 | 0.4 | 1:02 | None | None | RT | 14 |
| 5 | 10 | 0.8 | 1:04 | None | None | RT | None |
| 6 | 10 | 0.04 | 5:01 | None | None | Fridge | ~39 |
| 7 | 10 | 0.08 | 2.5:1 | None | None | Fridge | ~39 |
| 8 | 10 | 0.2 | 1:01 | None | None | Fridge | ~39 |
| 9 | 10 | 0.4 | 1:02 | None | None | Fridge | None |
| 10 | 10 | 0.8 | 1:04 | None | None | Fridge | None |
| 11 | 10 | 0.2 | 1:01 | None | None | RT/Shake vigorously | 8 |
| O-1 | 10 | 0.04 | 5:01 | None | None | 37 C. Oven | 3 |
| O-2 | 10 | 0.04 | 5:01 | None | None | 50 C. Oven | 2 |
| O-3 | 10 | 0.2 | 1:01 | None | None | 37 C. Oven | 4 |
| O-4 | 10 | 0.2 | 1:01 | None | None | 50 C. Oven | 3 |
| M | 40 | 0.16 | 5:01 | None | None | RT | 5 |
| D | 40 | 0.16 | 5:01 | None | None | RT | 5 |
| E1 | 10 | 0.04 | 5:01 | Vit E | 1 drop | RT | 7 |
| E2 | 10 | 0.04 | 5:01 | Vit E | 3 drops | RT | 7 |
| E3 | 10 | 0 | None | Vit E | 1 drop | RT | None |
| E4 | 10 | 0 | None | Vit E | 3 drops | RT | None |
| L1 | 10 | 0.04 | 5:01 | Lemon | 300 uL | RT | 6 |
| L2 | 10 | 0.04 | 5:01 | Lemon Juice | 300 uL | RT | 6 |
| L3 | 10 | 0.04 | 5:01 | Lemon Juice | 1000 uL | RT | 5 |
| L4 | 10 | 0 | None | Lemon | 300 uL | RT | 6 |
| L5 | 10 | 0 | None | Lemon Juice | 300 uL | RT | 7 |
| Jar 1 | 20 | 0.08 | 5:01 | Lemon Juice | 2000 uL | RT | 5-7 |
| Jar 2 | 5 | 0.02 | 5:01 | Lemongrass Oil | 1 drop | RT | 2-3 |
| R-1 | 10 | 0.04 | 5:01 | Rosemary Oil | 1 drop | RT | 7 |
| T-1 | 10 | 0.04 | 5:01 | None | None | RT/Tube | 7 |

TABLE 17-continued

Gel Samples - Silk gel formulations including additives, concentration of silk and additive, gelation conditions and gelation times.

| Sample Name | mL 2% silk solution | Mass Vit C (g) | Ratio silk:VitC | Additive | Amount of additive | Temp/ Treatment | Days to Gelation |
|---|---|---|---|---|---|---|---|
| RO-1 | 10 | 0.04 | 5:01 | Rose Oil | 1 drop | RT | 6 |
| RO-2 | 10 | None | None | Rose Oil | 1 drop | RT | None |

Ratio of Silk to Vitamin C

Samples 1-10 were used to examine the effect of silk to vitamin C ratio on serum gelation. Samples 1-3 with less vitamin C gelled quicker than samples 4 and 5. All other conditions were kept constant. Samples 6-8 with less vitamin C gelled quicker than samples 9 and 10. All other conditions were kept constant. It is concluded that decreasing the ratio of silk to vitamin C (increasing the amount of vitamin C), will lengthen the time to gel creation. At ratios with small amounts of vitamin C, days to gel creation did not vary greatly.

Physical Stimulation

Samples 3 and 11 were used to examine the effect of physical stimulation on serum gelation. Each sample was prepared under the same conditions. Sample 11 was vigorously shaken for about 3 minutes after addition of vitamin C. Treatment of 3 and 11 was otherwise the same. The shaking resulted in bubbles but did not significantly change gel creation time.

Temperature Treatment

Samples 1, 3, 6, 8, O-1, O-2, O-3, and O-4 were used to examine the effect of temperature treatment on serum gelation time. Samples 1, 6, O-1, and O-2 were identical other than temperature treatment. Samples 3, 8, O-3, and O-4 were identical other than temperature treatment. The two groups differed in silk to vitamin C ratio. Time to serum gelation was directly related to temperature treatment with a higher temperature resulting in quicker serum gelation.

Solution Volume

Samples 1, M and D were used to examine the effect of solution volume on serum gelation time. Samples M and D varied from sample 1 only by an increased solution volume. Samples M and D gelled in 5 days while sample 1 gelled in 8 days. Samples M and D were definitively noticed to be gelled on the day of gelling while sample 1 gelled over a weekend.

Additives

Samples E1, E2, E3, E4, L1, L2, L3, L4, L5, Jar 2, R1, RO-1 and RO-2 were used to examine the effect of additives on serum gelation time. Samples E1-4 contained Vitamin E. Only samples E1 and E2 contained vitamin C and only these two samples gelled. Vitamin E can be added to a solution to become a gel but it appears that another additive may be needed to create a gel. Samples L1-5 contained a form of lemon juice. Samples L1 and L4 had juice directly from a lemon while samples L2, L3 and L5 contained lemon juice from a plastic lemon container. Samples L4 and L5 did not have vitamin C while all others did. All samples gelled showing that lemon juice can create gel on its own. Amount of lemon juice and type of lemon juice had little effect on gelation time. Sample Jar 2 contained lemon grass oil which formed an albumen like substance when initially added. This sample also had vitamin C but gelation time was significantly quicker than with other vitamin C samples. Sample R1 contained rosemary oil, which seemed to be soluble, as well as vitamin C. The sample gelled in a similar time frame to other samples with only vitamin C. Samples RO-1 and RO-2 contained rose oil while only RO-1 had vitamin C. Only RO-1 gelled showing that rose oil will not create a gel quickly on its own. In both cases the rose oil was immiscible and visible as yellow bubbles.

Aqueous silk fibroin-based fragment solution and essential oils are immiscible liquids. In an embodiment, to increase the fragrance of the silk fibroin-based fragment solution, without entrapping oils within the solution, the solution is mixed with the essential oil with the use of a stir bar. The stir bar is rotated at a speed such that some turbulence is observed in the mixture, thus causing contact between the fragrant essential oil and the molecules in solution, adding a scent to the solution. Before casting of product from the solution, mixing may be stopped and the oil allowed to separate to the top of the solution. Dispensing from the bottom fraction of the solution into the final product allows for fragrance without visible essential oil within the final product.

Alternatively, the silk fibroin-based solution and essential oil can be combined with or without additional ingredients and/or an emulsifier to create a composition containing both ingredients.

In an embodiment, mixing of the solution as described above can reduce gelation time if the solution is used to create a gel formulation.

Vessel

Samples T1 and Jar 1 were used to examine the effect of casting vessel on serum gelation time. Jar 1 was cast in a glass jar while T1 was cast in an aluminum tube. Both samples gelled and did not affect serum gel time.

Summary

All treatments of silk solution for gel solution were in a conical tube at room temperature unless otherwise stated. The ratio of silk to vitamin C did affect the ability of a solution to gel as ratios above 1:2 did not gel and a 1:2 ratio took twice as long as other lower ratios (5:1, 2.5:1, 1:1). Temperature affected gel creation time with higher temperatures resulting in quicker gel times. 50° C. treatment gelled in as quick as 2 days, 37° C. treatment gelled in as quick as 3 days, room temperature treatment gelled in 5-8 days and storage in a refrigerator took at least 39 days to gel. The effects of additives on gel creation were dependent on the additive. Vitamin E, Rosemary Oil and Rose Oil all had no effect on gel creation. Each of these additives did not prevent gelation or affect the time to gelation. Each also required the presence of vitamin C to gel. Lemon juice from a fresh lemon, pre-squeezed lemon juice from a plastic lemon container and lemon grass oil did affect gel creation. Without wishing to be bound by theory, it is believed that the lower pH as a result of these additives is the reason the additives had an impact on decreasing gelation time. Both lemon juice types were able to cause gelation without the presence of vitamin C. This occurred in the same number of days as with vitamin C. The lemongrass oil was able to decrease the number of days to gelation to 2-3 days. All additives appeared soluble other than lemongrass oil and rose oil. Rose oil remained in yellow bubbles while the lemongrass oil was partially soluble and formed an albumen like chunk. In an embodiment, oils that are not fully soluble, can still be suspended within the gel as an additive. Physical stimulation by shaking, vessel the solution was cast into and solution volume did not affect gelation time.

TABLE 18

Concentration of vitamin C in various gel formulations.

| Sample Info | Sample Weight (mg) | Concentration of Vitamin C (mg/g) In Sample | Average |
|---|---|---|---|
| Rosemary (Room Temperature storage) | 685.7 | 3.2511 3.2804 | 3.2657 |
| | 638 | 3.3336 3.3332 | 3.3334 |
| Lemongrass (Room Temperature storage) | 646 | 2.8672 2.8868 | 2.877 |
| | 645.5 | 2.9051 2.9052 | 2.9051 |
| Rosemary (Room Temperature; Foil Covered storage) | 645.2 | 3.9063 3.923 | 3.9147 |
| | 649 | 3.9443 3.9305 | 3.9374 |
| Lemongrass (Room Temperature; Foil Covered storage) | 630.1 | 3.8253 3.8295 | 3.8274 |
| | 660.4 | 3.8283 3.8222 | 3.8253 |
| Rosemary (Fridge, Foil Covered storage) | 672.4 | 5.1616 5.1352 | 5.1484 |
| | 616.5 | 5.1984 5.2036 | 5.201 |
| Lemongrass (Fridge, Foil Covered storage) | 640.5 | 5.1871 5.1776 | 5.1824 |
| | 627.7 | 5.2098 5.2154 | 5.2126 |

Example 3

Preparation of Silk Gels

Additional gels may be prepared according to Table 19, Table 20, Table 21, and Table 22.

TABLE 19

Lemongrass Gel

| % Silk Solution | 2% |
|---|---|
| Quantity Vitamin C | 100 mg/15 mL solution |
| Quantity Lemongrass Oil | 20 µL/15 mL solution |

TABLE 20

Rosemary Gel

| % Silk Solution | 2% |
|---|---|
| Quantity Vitamin C | 100 mg/15 mL solution |
| Quantity Rosemary Oil | 20 µL/50 mL solution |

TABLE 21

Lemongrass Gel (50 mL)

| % Silk Solution (60 minute boil, 25 kDA) | 2% |
|---|---|
| Quantity Vitamin C (ascorbyl glucoside) | 12.82 mg/mL solution (641 mg total) |
| Quantity Lemongrass Oil | 1.33 µL/mL solution |
| pH | 4 |

TABLE 22

Rosemary Gel (50 mL)

| % Silk Solution (60 minute boil, 25 kDA) | 2% |
|---|---|
| Quantity Vitamin C (ascorbyl glucoside) | 12.82 mg/mL solution (641 mg total) |
| Quantity Rosemary Oil | 0.8 µL/mL solution |
| pH | 4 |

Gels of the present disclosure can be made with about 0.5% to about 8% silk solutions. Gels of the present disclosure can be made with ascorbyl glucoside at concentrations of about 0.67% to about 15% w/v. Gels of the present disclosure be clear/white in color. Gels of the present disclosure can have a consistency that is easily spread and absorbed by the skin. Gels of the present disclosure can produce no visual residue or oily feel after application. Gels of the present disclosure do not brown over time.

Silk gels with essential oils were prepared by diluting a silk solution of the present disclosure to 2%. Vitamin C was added to the solution and allowed to dissolve. The essential oil was added, stirred and dissolved. The solution was aliquot into jars.

Example 4

Coating Fabrics with Aqueous Silk Solutions

TABLE 23

Silk Solution Characteristics

| Molecular Weight: | 57 kDa | | | |
|---|---|---|---|---|
| Polydispersity: | 1.6 | | | |
| % Silk | 5.0% | 3.0% | 1.0% | 0.5% |
| Process Parameters Extraction | | | | |
| Boil Time: | 30 minutes | | | |
| Boil Temperature: | 100° C. | | | |
| Rinse Temperature: | 60° C. | | | |
| Dissolution | | | | |
| LiBr Temperature: | 100° C. | | | |
| Oven Temperature: | 100° C. | | | |
| Oven Time: | 60 minutes | | | |

TABLE 24

Silk Solution Characteristics

| Molecular Weight: | 25 kDa | | | |
|---|---|---|---|---|
| Polydispersity: | 2.4 | | | |
| % Silk | 5.0% | 3.0% | 1.0% | 0.5% |
| Process Parameters Extraction | | | | |
| Boil Time: | 60 minutes | | | |
| Boil Temperature: | 100° C. | | | |
| Rinse Temperature: | 60° C. | | | |

TABLE 24-continued

Silk Solution Characteristics

Dissolution

| | |
|---|---|
| LiBr Temperature: | 100° C. |
| Oven Temperature: | 100° C. |
| Oven Time: | 60 minutes |

Silk Solution and Silk Gel Application to Fabric and Yarn Samples

Three 50 mm diameter fabric samples from each of three different fabric materials, cotton, polyester, and nylon/LYCRA®, were placed in plastic containers, about 0.3 mL of about 5.8% silk fibroin solution was deposited using a 1 mL syringe and 18 gauge needle on two samples of each material, and allowed to sit for about 1 minute. About 0.3 mL of denatured alcohol (containing methanol and ethanol) was then deposited using a 1 mL syringe and 30 gauge needle on one of the silk-coated samples of each material. In an additional experiment, silk gel with Rosemary Essential Oil (water, silk, ascorbyl glucoside, rosemary essential oil) was collected on a tip and applied to half the length of 2 pieces of 400um tencel yarn. One sample was then wetted with about 0.3 mL alcohol.

Silk Solution Dip Test

Polyester fabric samples were dipped in silk fibroin solutions of varying concentration. Samples were placed in incubator with air flow on foil and allowed to dry at about 22.5° C. for about 15.5 hours. Change in mass before and after silk coating was measured.

TABLE 25

Polyester Fabric Samples with Silk Coatings of the Present Disclosure

| Silk Fibroin Concentration (%) | Starting Mass (g) | Mass after coating (g) | Change (%) | Average Change (%) |
|---|---|---|---|---|
| 1 | 0.25 | 0.26 | +4 | −3% |
|   | 0.30 | 0.27 | −10 |   |
|   | 0.24 | 0.24 | 0 |   |
|   | 0.22 | 0.21 | −5 |   |
| 3 | 0.30 | 0.36 | +20 | 15% |
|   | 0.28 | 0.31 | +11 |   |
|   | 0.29 | 0.33 | +14 |   |
|   | 0.29 | 0.34 | +15 |   |
| 5 | 0.25 | 0.29 | +16 | 16% |
|   | 0.28 | 0.33 | +18 |   |
|   | 0.31 | 0.35 | +13 |   |
|   | 0.27 | 0.31 | +15 |   |

Silk Solution Spray Test

A spray test was performed to verify the handle impact of silk fibroin solution sprayed on polyester fabric. About 0.5% silk fibroin solution was applied to a 4 inch by 4 inch square of polyester fabric using a spray gun from a distance of about 10 inches. Three passes were completed from left to right and from right to left (six passes total). Samples were placed in a 50° C. oven on aluminum foil over a water bath for about 1.5 hours. Methods were repeated with a second polyester fabric sample with an about 5.8% silk fibroin solution spray application. No change in material hand was observed in samples sprayed with either 0.5% or 5.8% solutions. Perceived increase in materials smoothness was observed for samples sprayed with either the 0.5% and 5.8% solutions.

Example 5

Optimized Fabric Coating Processes

The coating processes described in Table 26 were used to produce multiple fabric samples for performance testing, as described in more detail below.

TABLE 26

Coating Processes.

1  Spray
  1.1  Material for coating
    1.1.1  cork board 24" × 36" Hobby Lobby part 132894
    1.1.2  Covered the cork board with polyester interlock fabric
    1.1.3  Saw horse for support
    1.1.4  Several clamps for holding cork panel to saw horse
    1.1.5  Double filter to remove oil residue from compressor and dehumidificaton salt
    1.1.6  Iwata eclipse MP-CS airbrush
    1.1.7  Husky 30.3 liter tank compression system
    1.1.8  Push pin to hold fabric on cork panel Hobby Lobby part #523456
  1.2  Material for preparation
    1.2.1  Scissor
    1.2.2  Ruler
    1.2.3  Balance AWS model Pnx-203
  1.3  Material for drying
    1.3.1  Wolf stove set up at 150° F. maintaining 71-78° C. with fan system.
    1.3.2  Flat baking sheet
    1.3.3  Aluminum foil
    1.3.4  SC 307T thermometer with probe
  1.4  Execution
    1.1.1  lay fabric to be coated on top of cork panel covered with polyester fabric
    1.1.2  secure fabric with pin to the cork panel
    1.1.3  set compressor with oil and humidity filters
    1.1.4  set air pressure supply to 55 psi
    1.1.5  load solution to airbrush gun TABLE 26-continued Coating Processes.

|   |   |   |   |
|---|---|---|---|
| | | 1.1.6 | position airbrush gun approximately 10 inches from board |
| | | 1.1.7 | pull the airbrush gun trigger and over spray 2 inches side to side the fabric to be coated |
| | | 1.1.8 | remove pin from cork panel and place coated fabric on aluminum foil |
| | | 1.1.9 | place coated fabric in oven for 30-60 min at 150° C. |
| 2 | Stencil/Spray | | |
| | 2.1 | Material for coating | |
| | | 2.1.1 | cork board 24" × 36" Hobby Lobby part 132894 |
| | | 2.1.2 | Covered the cork board with polyester interlock fabric |
| | | 2.1.3 | Saw horse for support |
| | | 2.1.4 | Several clamps for holding cork panel to saw horse |
| | | 2.1.5 | Double filter to remove oil residue from compressor and dehumidificaton salt |
| | | 2.1.6 | Iwata eclipse MP-CS airbrush |
| | | 2.1.7 | Husky 30.3 liter tank compression system |
| | | 2.1.8 | Push pin to hold fabric on cork panel Hobby Lobby part #523456 |
| | | 2.1.9 | Stencil pattern SKU#75244 Lincaine 12" × 24" × 0.020" Hobby Lobby |
| | 2.2 | Material for preparation | |
| | | 2.2.1 | Scissor |
| | | 2.2.2 | Ruler |
| | | 2.2.3 | Balance AWS model Pnx-203 |
| | 2.3 | Material for drying | |
| | | 2.3.1 | Wolf stove set up at 150° F. maintaining 71-78° C. with fan system. |
| | | 2.3.2 | Flat baking sheet |
| | | 2.3.3 | Aluminum foil |
| | | 2.3.4 | SC 307T thermometer with probe |
| | 2.4 | Execution | |
| | | 2.4.1 | lay fabric to be coated on top of cork panel covered with polyester fabric |
| | | 2.4.2 | lay stencil pattern on top of fabric |
| | | 2.4.3 | secure stencil with pin to the cork panel |
| | | 2.4.4 | set compressor with oil and humidity filters |
| | | 2.4.5 | set air pressure supply to 55 psi |
| | | 2.4.6 | load solution to airbrush gun |
| | | 2.4.7 | position airbrush gun approximately 10 inches from board |
| | | 2.4.8 | pull the airbrush gun trigger and over spray 2 inches side to side the fabric to be coated |
| | | 2.4.9 | remove pin from cork panel and place coated fabric on aluminum foil |
| | | 2.4.10 | place coated fabric in oven for 30-60 min at 150° C. |
| 3 | Screen print | | |
| | 3.1 | Material for coating | |
| | | 3.1.1 | cork board 24" × 36" Hobby Lobby part 132894 |
| | | 3.1.2 | Covered the cork board with polyester interlock fabric |
| | | 3.1.3 | Saw horse for support |
| | | 3.1.4 | Several clamps for holding cork panel to saw horse |
| | | 3.1.5 | screen print frame 12" × 18" part# 4710 made by Speed Ball |
| | | 3.1.6 | silicon spatula |
| | 3.2 | Material for preparation | |
| | | 3.2.1 | Scissor |
| | | 3.2.2 | Ruler |
| | | 3.2.3 | Balance AWS model Pnx-203 |
| | 3.3 | Material for drying | |
| | | 3.3.1 | Wolf stove set up at 150° F. maintaining 71-78° C. with fan system. |
| | | 3.3.2 | Flat baking sheet |
| | | 3.3.3 | Aluminum foil |
| | | 3.3.4 | SC 307T thermometer with probe |
| | 3.4 | Execution | |
| | | 3.4.1 | lay fabric to be coated on top of cork panel covered with polyester fabric |
| | | 3.4.2 | lay screen print frame on top of fabric |
| | | 3.4.3 | load solution to one edge of the screen print frame |
| | | 3.4.4 | with a silicon spatula move solution across the screen print frame until the entire fabric to be coated surface is covered |
| | | 3.4.5 | remove screen print frame and place coated fabric on aluminum foil |
| | | 3.4.6 | place coated fabric in oven for 30-60 min at 150° C. |
| 4 | Bath | | |
| | 4.1 | Material for coating | |
| | | 4.1.1 | cork board 24" × 36" Hobby Lobby part 132894 |
| | | 4.1.2 | Covered the cork board with polyester interlock fabric |
| | | 4.1.3 | Saw horse for support |
| | | 4.1.4 | Several clamps for holding cork panel to saw horse |
| | | 4.1.5 | Paint tray liner Item #: 170418 Model #: LOWES0-PK170418 at Lowes Hardware |

TABLE 26-continued

Coating Processes.

| | | |
|---|---|---|
| | 4.1.6 | Noodle making machine Imperia model #15-4590 |
| 4.2 | Material for preparation | |
| | 4.2.1 | Scissor |
| | 4.2.2 | Ruler |
| | 4.2.3 | Balance AWS model Pnx-203 |
| 4.3 | Material for drying | |
| | 4.3.1 | Wolf stove set up at 150° F. maintaining 71-78° C. with fan system. |
| | 4.3.2 | Flat baking sheet |
| | 4.3.3 | Aluminum foil |
| | 4.3.4 | SC 307T thermometer with probe |
| 4.4 | Execution | |
| | 4.4.1 | load silk solution inside the paint tray liner well |
| | 4.4.2 | immerse the fabric sample to be coated inside the silk solution until it is all saturated |
| | 4.4.3 | pass the saturated fabric between pressure roller (noodle making machine) to remove any excess solution |
| | 4.4.4 | place coated fabric on aluminum foil |
| | 4.4.5 | place coated fabric in oven for 30-60 min at 150° C. |

The products produced using the coating processes described above were tested for accumulative one way transport capability (or index) and other properties using Association of Textile, Apparel & Materials Professionals (AATCC) test method 195-2012 for the measurement, evaluation, and classification of liquid moisture management properties of textile fabrics. The details of the test methods are available from AATCC, and a synopsis of the methods and calculations is provided here. The absorption rate (ART) (top surface) and (ARB) (bottom surface) is defined as the average speed of liquid moisture absorption for the top and bottom surfaces of the specimen during the initial change of water content during a test. The accumulative one-way transport capability (R) is defined as the difference between the area of the liquid moisture content curves of the top and bottom surfaces of a specimen with respect to time. The bottom surface (B) is defined for testing purposes as the side of the specimen placed down against the lower electrical sensor which is the side of the fabric that would be the outer exposed surface of a garment when it is worn or product when it is used. The top surface (T) for testing purposes is defined as the side of a specimen that, when the specimen is placed on the lower electrical sensor, is facing the upper sensor. This is the side of the fabric that would come in contact with the skin when a garment is worn or when a product is used. The maximum wetted radius (MWRT) and (MWRB) (mm) is defined as the greatest ring radius measured on the top and bottom surfaces. Moisture management is defined, for liquid moisture management testing, as the engineered or inherent transport of aqueous liquids such as perspiration or water (relates to comfort) and includes both liquid and vapor forms of water. The overall (liquid) moisture management capability (OMMC), an index of the overall capability of a fabric to transport liquid moisture as calculated by combining three measured attributes of performance: the liquid moisture absorption rate on the bottom surface (ARB), the one way liquid transport capability (R), and the maximum liquid moisture spreading speed on the bottom surface ($SS_B$). The spreading speed ($SS_i$) is defined as the accumulated rate of surface wetting from the center of the specimen where the test solution is dropped to the maximum wetted radius. The total water content (U) (%) is defined as the sum of the percent water content of the top and bottom surfaces. The wetting time (WTT) (top surface) and (WTB) (bottom surface) is defined as the time in seconds when the top and bottom surfaces of the specimen begin to be wetted after the test is started.

A moisture management tester (MMT) is used to perform the test. The accumulative one way liquid transport capability (R) is calculated as: [Area ($U_B$)−Area ($U_T$)]/total testing time. The OMMC is calculated as: OMMC=$C_1$*$AR_{B\_ndv}$+$C_2$*$R_{nbd}$+$C_3$*$SS_{B\_ndv}$, where $C_1$, $C_2$, and $C_3$ are the weighting values * for $AR_{B\_ndv}$, $R_{ndv}$ and $SS_{B\_ndv}$; ($AR_B$)=absorption rate; (R)=one-way transport capability, and ($SS_B$)=spreading speed. Detailed calculations of these parameters, and other parameters of interest, are provided in AATCC test method 195-2012.

A description of the samples used is given in Table 27.

TABLE 27

Description of samples.

| Sample ID | Description |
|---|---|
| 15051201 | no coating (polyester) |
| 15051301 | 1% silk solution spray coating on 15051201 |
| 15051302 | 0.1% silk solution spray coating on 15051201 |
| 15051303 | 0.05% silk solution spray coating on 15051201 |
| 15051304 | 1% silk solution spray stencil coating on 15051201 |
| 15051305 | 0.1% silk solution spray stencil coating on 15051201 |
| 15051306 | 0.05% silk solution spray stencil coating on 15051201 |
| 15051401 | 1% silk solution bath coating on 15051201 |
| 15051402 | 0.1% silk solution bath coating on 15051201 |
| 15051403 | 0.05% silk solution bath coating on 15051201 |
| 15051404 | PureProC screen print on 15051201 |
| 15042001 | non wicking finished |
| 15042002 | semifinished before final setting |
| 15042003 | with wicking finished |
| 15042101 | non wicking finished (15042001) 1% silk solution spray coating |
| 15042102 | non wicking finished (15042001) 0.1% silk solution spray coating |
| 15061206 | non wicking finished (15042001) 1% silk solution stencil coating |
| 15061207 | non wicking finished (15042001) 1% silk solution bath coating |
| 15061205 | non wicking finished (15042001) 0.1% silk solution stencil coating |
| 15061209 | non wicking finished (15042001) 0.1% silk solution bath coating |
| 15061201 | semifinished before final setting (15042002) 1% silk solution spray coating |
| 15061203 | semifinished before final setting (15042002) 1% silk solution stencil coating |
| 15061208 | semifinished before final setting (15042002) 1% silk solution bath coating |
| 15061202 | semifinished before final setting (15042002) 0.1% silk |

TABLE 27-continued

Description of samples.

| Sample ID | Description |
|---|---|
| | solution spray coating |
| 15061204 | semifinished before final setting (15042002) 0.1% silk solution stencil coating |
| 15061210 | semifinished before final setting (15042002) 0.1% silk solution bath coating |

The results of the tests are depicted in FIG. 57A through FIG. 86B and illustrate the superior performance of silk coated fabric, including superior performance with respect to accumulative one way transport capability (index) and overall moisture management capability.

Example 6

Antimicrobial Properties of Silk Coatings on Fabrics

The antimicrobial properties of silk coatings were testing on four materials: a cotton/LYCRA jersey (15051201), a cotton/LYCRA jersey with 1% silk fibroin solution (sfs) bath coating (15070701), a polyester/LYCRA finish after final setting (15042003), and a polyester/LYCRA semi-finished 1% sfs bath coating (15070702) (wherein LYCRA is the trade name of a polyester-polyurethane copolymer). AATCC test method 100-2012 for the assessment of antibacterial finishes on textile materials was used. The details of the test method are available from AATCC. Briefly, the tests were performed using tryptic soy broth as a growth medium, a sample size of 4 layers, autoclave sterilization, 100 mL Letheen broth with Tween for neutralization, a target inoculation level of 1-2×10$^5$ CFU/mL, 5% nutrient broth as an inoculent carrier and dilution medium, a contact time of 18 to 24 hours, and a temperature of 37 +/−2° C.

The results of the tests are summarized in Table 28 and are depicted in FIG. 87 to FIG. 92, and illustrate the superior antimicrobial performance of the silk-coated fabrics.

TABLE 28

Antimicrobial test results.

| | | Results: cfu/sample | | |
|---|---|---|---|---|
| sample # | bacteria | Zero Contact Time | 24 hr Contact Time | Percent Reduction |
| 15051201 | Staphylococcus aureus ATCC 6538 | 1.23E+05 | 4.90E+06 | −3883.74% |
| | Klebsiella pneumoniae ATCC 4352 | 1.65E+05 | 4.90E+06 | −2869.70% |
| 15070701 | Staphylococcus aureus ATCC 6538 | 1.23E+05 | 4.90E+06 | −3883.74% |
| | Klebsiella pneumoniae ATCC 4352 | 1.65E+05 | 4.90E+06 | −2869.70% |
| 15042003 | Staphylococcus aureus ATCC 6538 | 1.23E+05 | 4.90E+06 | −3883.74% |
| | Klebsiella pneumoniae ATCC 4352 | 1.65E+05 | 4.90E+06 | −2869.70% |
| 15070702 | Staphylococcus aureus ATCC 6538 | 1.23E+05 | 1.03E+04 | 91.63% |

TABLE 28-continued

Antimicrobial test results.

| | | Results: cfu/sample | | |
|---|---|---|---|---|
| sample # | bacteria | Zero Contact Time | 24 hr Contact Time | Percent Reduction |
| | Klebsiella pneumoniae ATCC 4352 | 1.65E+05 | 2.33E+05 | −40.91% |

Example 7

Methods of Preparing Fabrics with Silk Coatings

A method for preparing an aqueous solution of pure silk fibroin-based protein fragments having an average weight average molecular weight ranging from about 6 kDa to about 16 kDa includes the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight ranging from about 6 kDa to about 16 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide.

A method for preparing an aqueous solution of pure silk fibroin-based protein fragments having an average weight average molecular weight ranging from about 17 kDa to about 38 kDa includes the steps of: adding a silk source to a boiling (100° C.) aqueous solution of sodium carbonate for a treatment time of between about 30 minutes to about 60 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, wherein the aqueous solution of silk protein fragments comprises sodium carbonate residuals of between about 10 ppm and about 100 ppm, wherein the aqueous solution of pure silk fibroin-based protein fragments comprises fragments having an average weight average molecular weight ranging from about 17 kDa to about 38 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide.

A method for preparing an aqueous solution of pure silk fibroin-based protein fragments having an average weight average molecular weight ranging from about 39 kDa to about 80 kDa, includes the steps of: adding a silk source to a boiling (100° C.) aqueous solution of sodium carbonate for a treatment time of about 30 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, sodium carbonate residuals of between about 10 ppm and about 100 ppm, fragments having an average weight average molecular weight ranging from about 40 kDa to about 65 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide.

Example 8

Characterization of Silk Coatings on Polyester

A summary of the results from studies of silk coatings on polyester are given in Table 29 and Table 30. The results shown in FIG. 93 and FIG. 94 illustrate that the accumulative one way transport index and OMMC performance is maintained even at 60 wash cycles. Additional test results are shown in FIG. 95 to FIG. 102. The antimicrobial performance of the silk coated polyester fabrics are maintained to 25 to 50 washing cycles, as shown in FIG. 103 to FIG. 104. The results illustrate the surprising improvement in moisture management properties, as well as the surprising result that the improved properties survive many wash cycles.

TABLE 29

Test results for semifinished polyester with 1% silk solution coating.

Testing Results: Semifinished polyester with 1% silk solution coating

| Number of Washes | Raw Data: | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Overall Moisture Management Capability OMMC |
|---|---|---|---|---|---|---|---|---|---|---|---|
| 0 Cycles | Mean | 5.63 | 3.95 | 7.24 | 28.73 | 5 | 5 | 0.90 | 1.22 | 133.26 | 0.27 |
|  | S. Deviation | 1.20 | 0.38 | 1.46 | 8.62 | 0 | 0 | 0.20 | 0.12 | 34.81 | 0.06 |
|  | CV | 0.21 | 0.10 | 0.20 | 0.30 | 0 | 0 | 0.22 | 0.09 | 0.26 | 0.21 |
| 10 Cycles | Mean | 23.87 | 7.96 | 4.82 | 8.55 | 5 | 5 | 0.46 | 0.68 | 144.84 | 0.22 |
|  | S. Deviation | 31.51 | 3.30 | 0.84 | 2.94 | 0 | 0 | 0.28 | 0.23 | 27.71 | 0.03 |
|  | CV | 1.32 | 0.41 | 0.17 | 0.34 | 0 | 0 | 0.61 | 0.33 | 0.19 | 0.14 |
| 25 Cycles | Mean | 6.09 | 4.59 | 7.36 | 17.22 | 5 | 5 | 0.83 | 1.05 | 124.05 | 0.22 |
|  | S. Deviation | 1.61 | 0.44 | 2.98 | 3.28 | 0 | 0 | 0.17 | 0.09 | 11.70 | 0.02 |
|  | CV | 0.26 | 0.10 | 0.40 | 0.19 | 0 | 0 | 0.20 | 0.09 | 0.09 | 0.09 |
| 50 Cycles | Mean | 25.20 | 11.64 | 6.84 | 7.80 | 5 | 5 | 0.39 | 0.53 | 58.81 | 0.13 |
|  | S. Deviation | 28.06 | 6.36 | 3.38 | 5.70 | 0 | 0 | 0.30 | 0.27 | 26.56 | 0.03 |
|  | CV | 1.11 | 0.55 | 0.49 | 0.73 | 0 | 0 | 0.77 | 0.51 | 0.45 | 0.25 |

TABLE 30

Test results for wicking finished polyester without silk coating.

Testing Results: Wicking Finished Polyester

| Number of Washes | Raw Data: | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Over all Moisture Management Capability OMMC |
|---|---|---|---|---|---|---|---|---|---|---|---|
| 0 Cycles | Mean | 3.46 | 3.48 | 37.30 | 56.90 | 5 | 5 | 1.37 | 1.36 | 62.37 | 0.29 |
|  | S. Deviation | 0.07 | 0.04 | 12.89 | 10.24 | 0 | 0 | 0.02 | 0.02 | 9.74 | 0.03 |
|  | CV | 0.02 | 0.01 | 0.35 | 0.18 | 0 | 0 | 0.02 | 0.01 | 0.16 | 0.12 |
| 25 Cycles | Mean | 6.69 | 6.71 | 7.23 | 6.89 | 5 | 5 | 0.75 | 0.76 | 30.40 | 0.09 |
|  | S. Deviation | 1.48 | 1.92 | 1.27 | 2.74 | 0 | 0 | 0.13 | 0.19 | 16.22 | 0.02 |
|  | CV | 0.22 | 0.29 | 0.18 | 0.40 | 0 | 0 | 0.17 | 0.25 | 0.53 | 0.20 |
| 50 Cycles | Mean | 11.27 | 8.46 | 6.70 | 9.35 | 5 | 5 | 0.54 | 0.65 | 31.21 | 0.09 |
|  | S. Deviation | 6.57 | 3.53 | 1.45 | 5.21 | 0 | 0 | 0.23 | 0.25 | 18.26 | 0.03 |
|  | CV | 0.58 | 0.42 | 0.22 | 0.56 | 0 | 0 | 0.44 | 0.38 | 0.59 | 0.30 |

Example 9

Characterization of Silk Coatings on Polyester Fabrics

Scanning electron microscopy (SEM) analysis was performed using a Hitachi S-4800 field-emission SEM (FE-SEM) operated at 2 kV accelerating voltage. Pieces from each sample were sectioned using a razor blade and placed on carbon adhesive tape mounted on aluminum SEM stubs. A coating of iridium approximately 2 nm thick was applied via sputter deposition in order to minimize the buildup of surface charge.

The samples used in the SEM study are described in Table 31. SEM micrographs for fabric samples are shown in FIG. 105 to FIG. 167.

TABLE 31

Fabric samples tested by scanning electron microscopy and optical profilometry.

| Sample ID | Fabric | Silk solution for coating/treatment (average molecular weight, Da) | Silk coating/treatment method using silk fibroin solution (sfs) |
|---|---|---|---|
| FAB-10-SPRAY-B | Semi-finished UA R20904012 | 41,576 | spray with 1% sfs |
| FAB-01-SPRAY-B | Semi-finished UA R20904012 | 41,576 | spray with 0.1% sfs |
| FAB-10-STEN-B | Semi-finished UA R20904012 | 41,576 | stencil spray with 1% sfs |
| FAB-10-BATH-B | Semi-finished UA R20904012 | 41,576 | bath with 1% sfs |
| FAB-01-BATH-B | Semi-finished UA R20904012 | 41,576 | bath with 0.1% sfs |
| FAB-01-SPRAY-C | Semi-finished UA R20904012 | 10,939 | spray with 0.1% sfs |
| FAB-01-STEN-C | Semi-finished UA R20904012 | 10,939 | stencil spray with 0.1% sfs |
| FAB-10-BATH-C | Semi-finished UA R20904012 | 10,939 | bath with 1% sfs |

The fabric SEM results show that the silk solution has very clearly been deposited along and between individual polyester fibers. The use of 0.1% silk solution results in less coating than 1.0% silk solution. The use of a bath for 0.1% silk solution, with an average molecular weight of 41 kDa, results in uniform coating along fibers with large, smooth features. The use of a spray with a 0.1% silk solution, with an average molecular weight of 41 kDa, in coating along fibers as well as connected, webbed coating between fibers. The use of a spray for 0.1% silk solution, with an average molecular weight of 11 kDa, results in uniform coating along fibers with small, spotted/ribbed features. The use of a stencil for 0.1% silk solution, with an average molecular weight of 11 kDa, results in coating along fibers that has clear edges and delineation between coated and non coated sides. The use of a bath for 1.0% silk solution, with an average molecular weight of 41 kDa, results in thick coating along fibers as well as thick connected, webbed coating between fibers. The use of a bath for 1.0% silk solution, with an average molecular weight of 11 kDa, results in coating along all sides of individual fibers. Coating appears uniform on surface with many single point extrusions. The use of a spray for 1.0% silk solution, with an average molecular weight of 41 kDa, results in coating along fibers as well as connected, webbed coating between fibers, which was thicker than that observed using 0.1% silk solution. The use of a stencil for 1.0% silk solution, with an average molecular weight of 41 kDa, results in coating along fibers and between fibers, and the coating appears well organized.

The SEM results demonstrate that the silk coating has been applied as an even, thin, uniform coating to the fibers of the fabric. This illustrates the surprising result that the silk coating was applied to the fibers without the use of any additives or cross-linking, using a water based delivery system.

Example 10

Characterization of Silk Coatings on Polyester Films

The film samples are described in Table 32. The SEM images from these films are shown in FIG. 168 to FIG. 237.

TABLE 32

Film samples tested by scanning electron microscopy and optical profilometry.

| Sample identifier | Polyester substrate material | Silk solution for coating/treatment (average molecular weight, Da) | Silk coating/ treatment method using silk fibroin solution (sfs) |
|---|---|---|---|
| FIL-10-SPRAY-B-01MYL | 0.01 Mylar | 41,576 | spray with 1% sfs |
| FIL-01-SPRAY-B-01MYL | 0.01 Mylar | 41,576 | spray with 0.1% sfs |
| FIL-01-SPRAY-B-007MEL | 0.007 Melinex | 41,576 | spray with 0.1% sfs |
| FIL-01-SPRAY-C-01MYL | 0.01 Mylar | 10,939 | spray with 0.1% sfs |
| FIL-01-STEN-B-01MYL | 0.01 Mylar | 41,576 | stencil spray with 0.1% sfs |
| FIL-01-STEN-C-01MYL | 0.01 Mylar | 10,939 | stencil spray with 0.1% sfs |
| FIL-10-BATH-B-01MYL | 0.01 Mylar | 41,576 | bath with 1% sfs |
| FIL-10-BATH-B-007MEL | 0.007 Melinex | 41,576 | bath with 1% sfs |
| FIL-10-BATH-C-01MYL | 0.01 Mylar | 10,939 | bath with 1% sfs |
| FIL-01-BATH-B-01MYL | 0.01 Mylar | 41,576 | bath with 0.1% sfs |

The results show that the silk coatings are applied uniformly. Little to no variation is observed in the characteristics or topology of the coated polyester films. Surprisingly, the coating is even, uniform, and thin. Furthermore, surprising, the silk coated the fibers without any additives or cross-linking using a water-based system.

Optical profiling was carried out using a Zygo New View 6200 optical profilometer. Two locations on each sample were randomly selected and measured with 10× magnification. The results are shown in FIG. 241 to FIG. 264. The results indicate that the silk-coated samples have a homogeneous deposition of silk fibroin. Surface roughness features observed in the control are visible after silk coating on Mylar films, which is consistent with the presence of a relatively thin silk film that is forming a conformal coating on Mylar. The results substantiate the uniformity of the coating, and demonstrate that silk can be stenciled into discrete locations.

Contact profilometry was performed and the cross-sectioned samples were examined by SEM. Results are shown in FIG. 265 to FIG. 268. For sample FIL-10-SPRAY-B-10MYL, the thickness ranged from approximately 260 nm to 850 nm in 4 locations analyzed. For sample FIL-10-BATH-B-01MYL, the coating ranged from approximately 140 nm to 400 nm in 4 locations. SEM images from cross-sections show similar trends, with one location on sample FIL-10-SPRAY-B-10MYL having a cross-section that measures approximately 500 nm and one on FIL-10-BATH-B-01MYL measuring approximately 180 nm.

Example 11

Preparation of Silk Fibroin Solutions with Higher Molecular Weights

The preparation of silk fibroin solutions with higher molecular weights is given in Table 33.

TABLE 33

Preparation and properties of silk fibroin solutions.

| Sample Name | Extraction Time (mins) | Extraction Temp (° C.) | LiBr Temp (° C.) | Oven/Sol'n Temp | Average weight average molecular weight (kDa) | Average polydispersity |
|---|---|---|---|---|---|---|
| Group A TFF | 60 | 100 | 100 | 100° C. oven | 34.7 | 2.94 |
| Group A DIS | 60 | 100 | 100 | 100° C. oven | 44.7 | 3.17 |
| Group B TFF | 60 | 100 | 100 | 100° C. sol'n | 41.6 | 3.07 |
| Group B DIS | 60 | 100 | 100 | 100° C. sol'n | 44.0 | 3.12 |
| Group C TFF | 60 | 100 | 140 | 140° C. sol'n | 10.9 | 3.19 |
| Group C DIS | 60 | 100 | 140 | 140° C. sol'n | | |
| Group D DIS | 30 | 90 | 60 | 60° C. sol'n | 129.7 | 2.56 |
| Group D FIL | 30 | 90 | 60 | 60° C. sol'n | 144.2 | 2.73 |
| Group E DIS | 15 | 100 | RT | 60° C. sol'n | 108.8 | 2.78 |
| Group E FIL | 15 | 100 | RT | 60° C. sol'n | 94.8 | 2.62 |

Example 12

Silk Coatings on Natural Fabrics

The coating of natural fabric with silk fibroin solutions and the resulting properties are illustrated in Table 34, Table 35, FIG. 269, and FIG. 270. The results demonstrate that silk fibroin solutions can coat cotton-Lyrca natural fabrics including LUON and POWER LUXTREME.

TABLE 34

Silk fibroin coated fabrics.

| Legend | Fabric |
|---|---|
| 15072201 | Power Luxtreme RT1211362 |
| 15072202 | Luon RT20602020 |
| 15072301 | Power Luxtreme RT1211362 (15072201) 1% silk solution spray coating |
| 15072302 | Luon RT20602020 (15072202) 1% silk solution spray coating |
| 15072303 | Power Luxtreme RT1211362 (15072201) 0.1% silk solution spray coating |
| 15072304 | Luon RT20602020 (15072202) 0.1% silk solution spray coating |
| 15072305 | Power Luxtreme RT1211362 (15072201) 1% silk solution stencil coating |
| 15072306 | Luon RT20602020 (15072202) 1% silk solution stencil coating |
| 15072307 | Power Luxtreme RT1211362 (15072201) 0.1% silk solution stencil coating |
| 15072308 | Luon RT20602020 (15072202) 0.1% silk solution stencil coating |
| 15072309 | Power Luxtreme RT1211362 (15072201) 1% silk solution bath coating |
| 15072310 | Luon RT20602020 (15072202) 1% silk solution bath coating |
| 15072311 | Power Luxtreme RT1211362 (15072201) 0.1% silk solution bath coating |
| 15072312 | Luon RT20602020 (15072202) 0.1% silk solution bath coating |

TABLE 35

Test results for silk fibroin coated fabrics.

| Raw Data: | | Wetting Time Top (sec) | Wetting Time Bottom (sec) | Top Absorption Rate (%/sec) | Bottom Absorption Rate (%/sec) | Top Max Wetted Radius (mm) | Bottom Max Wetted Radius (mm) | Top Spreading Speed (mm/sec) | Bottom Spreading Speed (mm/sec) | Accumulative One-Way Transport index(%) | Over all Moisture Management Capability OMMC |
|---|---|---|---|---|---|---|---|---|---|---|---|
| 15072201 | Mean | 64.3786 | 3.4072 | 8.8123 | 8.60494 | 5 | 5 | 0.15038 | 1.41686 | 151.65248 | 0.25898 |
| 15072202 | Mean | 25.1786 | 28.1922 | 5.4636 | 6.195 | 5 | 5 | 0.218 | 0.4244 | 80.9572 | 0.1529 |
| 15072301 | Mean | 16.7172 | 12.2804 | 21.9859 | 33.6196 | 5 | 5 | 0.4304 | 0.4906 | 143.6659 | 0.2808 |
| 15072302 | Mean | 25.8898 | 41.5026 | 6.16512 | 8.70282 | 5 | 5 | 0.23336 | 0.1791 | 44.06124 | 0.10704 |
| 15072303 | Mean | 42.152 | 4.7268 | 7.9114 | 19.3725 | 4 | 5 | 0.3261 | 1.364 | 370.2757 | 0.5297 |
| 15072304 | Mean | 78.4746 | 34.3138 | 5.01486 | 6.63212 | 5 | 5 | 0.0661 | 0.38728 | 94.97976 | 0.16848 |
| 15072305 | Mean | 36.1954 | 17.2038 | 6.27158 | 6.25526 | 5 | 5 | 0.18872 | 0.89046 | 139.73478 | 0.23052 |
| 15072306 | Mean | 78.4746 | 34.3138 | 5.01486 | 6.63212 | 5 | 5 | 0.0661 | 0.38728 | 94.97976 | 0.16848 |
| 15072307 | Mean | 36.195 | 17.2038 | 6.2716 | 6.2553 | 5 | 5 | 0.1887 | 0.8905 | 139.7348 | 0.2305 |
| 15072308 | Mean | 57.335 | 25.7588 | 5.6432 | 6.4437 | 5 | 5 | 0.1274 | 0.6389 | 117.3573 | 0.1995 |
| 15072309 | Mean | 54.1384 | 9.2662 | 4.01594 | 9.11064 | 5 | 5 | 0.09398 | 0.85306 | 267.0755 | 0.36724 |
| 15072310 | Mean | 28.4544 | 13.6658 | 6.8844 | 7.8956 | 5 | 5 | 0.3059 | 0.5111 | 104.5035 | 0.1794 |
| 15072311 | Mean | 5.1292 | 4.4738 | 8.8047 | 13.0277 | 5 | 5 | 0.9486 | 1.1702 | 246.6729 | 0.3597 |
| 15072312 | Mean | 6.8516 | 9.4722 | 11.0684 | 11.7268 | 5 | 5 | 0.7394 | 0.5794 | 73.4005 | 0.1461 |

All patents, patent applications, and published references cited herein are hereby incorporated by reference in their entirety. While the methods of the present disclosure have been described in connection with the specific embodiments thereof, it will be understood that it is capable of further modification. Further, this application is intended to cover any variations, uses, or adaptations of the methods of the present disclosure, including such departures from the present disclosure as come within known or customary practice in the art to which the methods of the present disclosure pertain.

We claim:

1. An article comprising a fiber or yarn having a coating, wherein the coating comprises silk based proteins or fragments thereof having an average weight average molecular weight selected from about 5 to about 10 kDa, about 6 kDa to about 16 kDa, about 17 kDa to about 38 kDa, about 39 kDa to about 80 kDa, about 60 to about 100 kDa, or about 80 kDa to about 144 kDa,
   wherein the silk based proteins or fragments thereof have a polydispersity of between about 1.5 and about 3.0, and
   wherein the silk based proteins or protein fragments thereof, prior to coating the fiber or yarn, do not spontaneously or gradually gelate and do not visibly change in color or turbidity when in a solution for at least 10 days.

2. The article of claim 1, wherein the article is a fabric.

3. The article of claim 1, wherein the silk based proteins or fragments thereof comprise silk fibroin fragments having about 0.01% (w/w) to about 10% (w/w) sericin.

4. The article of claim 1, wherein the silk based proteins or fragments thereof are selected from the group consisting of natural silk based proteins or fragments thereof, recombinant silk based proteins or fragments thereof, and combinations thereof.

5. The article of claim 4, wherein the silk based proteins or fragments thereof are natural silk based proteins or fragments thereof that are selected from the group consisting of spider silk based proteins or fragments thereof, silkworm silk based proteins or fragments thereof, and combinations thereof.

6. The article of claim 5, wherein the natural silk based proteins or fragments are silkworm silk based proteins or fragments thereof, and the silkworm silk based proteins or fragments thereof is *Bombyx mori* silk based proteins or fragments thereof.

7. The article of claim 1, wherein the coating comprises a copolymer.

8. The article of claim 1, wherein the fiber or yarn is selected from the group consisting of natural fiber or yarn, synthetic fiber or yarn, or combinations thereof.

9. The article of claim 8, wherein the fiber or yarn is natural fiber or yarn selected from the group consisting of alpaca fleece, alpaca wool, *lama* fleece, *lama* wool, cotton, cashmere, sheep fleece, sheep wool, and combinations thereof.

10. The article of claim 8, wherein the fiber or yarn is synthetic fiber or yarn selected from the group consisting of polyester, nylon, polyester-polyurethane copolymer, and combinations thereof.

11. The article of claim 2, wherein the fabric exhibits an improved property, wherein the improved property is an accumulative one-way moisture transport index selected from the group consisting of greater than 40%, greater than 60%, greater than 80%, greater than 100%, greater than 120%, greater than 140%, greater than 160%, and greater than 180%.

12. The article of claim 2, wherein the fabric exhibits an improved property, wherein the improved property is an accumulative one way transport capability increase relative to uncoated fabric selected from the group consisting of 1.2 fold, 1.5 fold, 2.0 fold, and 3.0 fold.

13. The article of claim 2, wherein the fabric exhibits an improved property, wherein the improved property is an overall moisture management capability selected from the group consisting of greater than 0.05, greater than 0.10, greater than 0.15, greater than 0.20, greater than 0.25, greater than 0.30, greater than 0.35, greater than 0.40, greater than 0.50, greater than 0.60, greater than 0.70, and greater than 0.80.

14. The article of claim 13, wherein the improved property is determined after a period of machine washing cycles selected from the group consisting of 5 cycles, 10 cycles, 25 cycles, and 50 cycles.

15. The article of claim 2, wherein the fabric exhibits substantially no increase in microbial growth after a number of machine washing cycles selected from the group consisting of 5 cycles, 10 cycles, 25 cycles, and 50 cycles.

16. The article of claim 15, wherein the microbial growth is microbial growth of a microbe selected from the group consisting of *Staphylococcus aureus, Klebisiella pneumoniae*, and combinations thereof.

17. The article of claim 16, wherein the microbial growth is reduced by a percentage selected from the group consisting of 50%, 100%, 500%, 1000%, 2000%, and 3000% compared to an uncoated fabric.

18. The article of claim 2, wherein the coating is applied to the fabric at the fiber level prior to forming the fabric.

19. The article of claim 2, wherein the coating is applied to the fabric at the fabric level.

20. The article of claim 19, wherein the fabric is bath coated.

21. The article of claim 19, wherein the fabric is spray coated.

22. The article of claim 19, wherein the fabric is coated with a stencil.

23. The article of claim 19, wherein the coating is applied to at least one side of the fabric using a method selected from the group consisting of a bath coating process, a spray coating process, a stencil process, a silk-foam based process, and a roller-based process.

24. The article of claim 1, wherein the coating has a thickness of about 5 nm to about 500 nm.

25. The article of claim 1, wherein the coating has a thickness selected from the group consisting of about 5 nm, about 10 nm, about 15 nm, about 20 nm, about 25 nm, about 50 nm, about 100 nm, about 200 nm, about 500 nm, about 1 μm, about 5 μm, about 10 μm, and about 20 μm.

26. The article of claim 2, wherein the coating is adsorbed on the fabric.

27. The article of claim 2, wherein the coating is attached to the fabric through chemical, enzymatic, thermal, or irradiative cross-linking.

28. The article of claim 19, wherein the hand of the coated fabric is improved relative to an uncoated fabric.

29. The article of claim 28, wherein the hand of the coated fabric that is improved is selected from the group consisting of softness, crispness, dryness, silkiness, and combinations thereof.

30. An article comprising:
a synthetic fiber or yarn; and
a coating comprising silk based proteins or fragments thereof having an average weight average molecular weight selected from about 5 kDa to about 144 kDa and a polydispersity ranging from 1 to about 5.0,
wherein the article is a fabric, and
wherein the silk based proteins or protein fragments, prior to coating the fabric, do not spontaneously or gradually gelate and do not visibly change in color or turbidity when in a solution for at least 10 days.

31. The article of claim 30, wherein the synthetic fiber or yarn comprises polyester.

32. The article of claim 30, wherein the synthetic fiber or yarn comprises polyamide.

33. The article of claim 30, wherein the synthetic fiber or yarn comprises polyaramid.

34. The article of claim 30, wherein the synthetic fiber or yarn comprises polytetrafluorethylene.

35. The article of claim 30, wherein the synthetic fiber or yarn comprises polyethylene.

36. The article of claim 30, wherein the synthetic fiber or yarn comprises polypropylene.

37. The article of claim 30, wherein the synthetic fiber or yarn comprises polyurethane.

38. The article of claim 30, wherein the synthetic fiber or yarn comprises nylon.

39. The article of claim 30, wherein the synthetic fiber or yarn comprises polyester-polyurethane copolymer.

40. The article of claim 30, wherein the silk based proteins or fragments thereof comprise silk fibroin fragments having about 0.01% (w/w) to about 10% (w/w) sericin.

41. The article of claim 30, wherein the silk based proteins or fragments thereof are selected from the group consisting of natural silk based proteins or fragments thereof, recombinant silk based proteins or fragments thereof, and combinations thereof.

42. The article of claim 30, wherein the silk based proteins or fragments thereof are natural silk based proteins or fragments thereof that are selected from the group consisting of spider silk based proteins or fragments thereof, silkworm silk based proteins or fragments thereof, and combinations thereof.

43. The article of claim 42, wherein the natural silk based proteins or fragments are silkworm silk based proteins or fragments thereof, and the silkworm silk based proteins or fragments thereof is *Bombyx mori* silk based proteins or fragments thereof.

44. The article of claim 30, wherein the silk based proteins or protein fragments thereof have an average weight average molecular weight range selected from about 5 to about 10 kDa, about 6 kDa to about 16 kDa, about 17 kDa to about 38 kDa, about 39 kDa to about 80 kDa, about 60 to about 100 kDa, or about 80 kDa to about 144 kDa, wherein the silk based proteins or fragments thereof have a polydispersity of between about 1.5 and about 3.0.

45. The article of claim 30, wherein the coating is applied to the fabric at the fiber level prior to forming the fabric.

46. The article of claim 30, wherein the coating is applied to the fabric at the fabric level.

47. The article of claim 30, wherein the hand of the coated fabric is improved relative to an uncoated fabric.

48. The article of claim 47, wherein the hand of the coated fabric that is improved is selected from the group consisting of softness, crispness, dryness, silkiness, and combinations thereof.

\* \* \* \* \*